(12) United States Patent
Narayanan et al.

(10) Patent No.: US 11,549,017 B2
(45) Date of Patent: Jan. 10, 2023

(54) NIR TO SWIR FLUORESCENT COMPOUNDS FOR IMAGING AND DETECTION

(71) Applicant: PERKINELMER HEALTH SCIENCES, INC., Waltham, MA (US)

(72) Inventors: Nara Narayanan, Westford, MA (US); Kevin Groves, Arlington, MA (US); Guojie Ho, Sudbury, MA (US)

(73) Assignee: PerkinElmer Health Sciences, Inc., Waltham, MA (US)

(*) Notice: Subject to any disclaimer, the term of this patent is extended or adjusted under 35 U.S.C. 154(b) by 80 days.

(21) Appl. No.: 16/124,639

(22) Filed: Sep. 7, 2018

(65) Prior Publication Data
US 2019/0100654 A1 Apr. 4, 2019

Related U.S. Application Data

(60) Provisional application No. 62/565,263, filed on Sep. 29, 2017.

(51) Int. Cl.

| | | |
|---|---|---|
| A61K 51/00 | (2006.01) |
| A61M 36/14 | (2006.01) |
| C09B 23/16 | (2006.01) |
| A61P 35/00 | (2006.01) |
| C07D 403/14 | (2006.01) |
| C07D 409/08 | (2006.01) |
| C07D 209/90 | (2006.01) |
| C07D 403/08 | (2006.01) |
| C07D 401/08 | (2006.01) |
| C07D 333/74 | (2006.01) |
| A61K 49/00 | (2006.01) |
| A61K 51/04 | (2006.01) |
| C07D 209/92 | (2006.01) |
| C07D 333/50 | (2006.01) |
| C09B 1/00 | (2006.01) |
| G01N 33/58 | (2006.01) |

(52) U.S. Cl.
CPC .......... *C09B 23/16* (2013.01); *A61K 49/0052* (2013.01); *A61K 49/0058* (2013.01); *A61K 51/0431* (2013.01); *A61K 51/0434* (2013.01); *A61K 51/0446* (2013.01); *A61K 51/0497* (2013.01); *A61P 35/00* (2018.01); *C07D 209/90* (2013.01); *C07D 209/92* (2013.01); *C07D 333/50* (2013.01); *C07D 333/74* (2013.01); *C07D 401/08* (2013.01); *C07D 403/08* (2013.01); *C07D 403/14* (2013.01); *C07D 409/08* (2013.01); *C09B 1/002* (2013.01); *C09B 1/005* (2013.01); *C09B 23/166* (2013.01); *G01N 33/582* (2013.01)

(58) Field of Classification Search
CPC ............ A61K 49/0052; A61K 49/0058; A61K 51/0431; A61K 51/0434; A61K 51/0446; A61K 51/0497; A61P 35/00; C07D 209/90; C07D 290/92; C07D 333/50; C07D 333/74; C07D 401/08; C07D 403/08; C07D 403/14; C07D 409/08; C09B 1/002; C09B 1/005; C09B 23/166; C09B 23/19; G01N 33/582

See application file for complete search history.

(56) References Cited

U.S. PATENT DOCUMENTS

| | | | |
|---|---|---|---|
| 7,488,468 B1* | 2/2009 | Miwa .................. | C09B 23/0008 424/9.6 |
| 8,227,621 B2* | 7/2012 | Peng | |
| 8,329,915 B2 | 12/2012 | Moawia et al. | |
| 8,628,753 B2* | 1/2014 | Murthy ................ | C09B 23/086 424/9.6 |
| 9,097,667 B2* | 8/2015 | Mao ....................... | C09B 57/02 |
| 2009/0124792 A1* | 5/2009 | Achilefu ................ | C22B 11/04 530/391.3 |
| 2010/0197937 A1 | 8/2010 | Minami et al. | |
| 2013/0101513 A1* | 4/2013 | Yang ................... | G01N 33/5091 424/9.1 |
| 2016/0244614 A1 | 8/2016 | Cheng et al. | |

FOREIGN PATENT DOCUMENTS

| | | |
|---|---|---|
| EP | 2940082 A1 | 11/2015 |
| WO | 2012054749 A1 | 4/2012 |
| WO | 2016081813 A1 | 5/2016 |

OTHER PUBLICATIONS

Kanofsky et al. (Photochem. Photobiol. 2000, 71,361-368).*
Mujumdar et al. (Bioconj. Chem. 1996, 7, 356-362).*
Narayanan et al. (J. Org. Chem. 1995, 60, p. 2391-2395).*
Tam, et al., Organic Letters, 2010; vol. 12; No. 15; pp. 3340-3343.
M A Kudinova et al:"alpha-Pyrylotetracarbocyani Nes", Chemistry of Heterocyclic Compounds, Nov. 1983 (Nov. 1983), pp. 1241-1241, XP055526730,Retrieved from the Internet:URL:https://link.springer.com/content/pdf/10.1007/BF00515369.pdf [retrieved on Nov. 26, 2018]compound IIIb.

(Continued)

*Primary Examiner* — Michael G. Hartley
*Assistant Examiner* — Melissa J Perreira
(74) *Attorney, Agent, or Firm* — Dinsmore & Shohl LLP; Weston R. Gould

(57) ABSTRACT

This disclosure provides a family of compounds that absorb and fluoresce in the short wave infrared region (SWIR, optionally 1000 nm to 1300 nm), including hydrophilic compounds that exhibit absorption and emission spectral profiles in aqueous solutions substantially similar to those observed in organic solvents such as methanol or DMSO. The compounds can be chemically linked to biomolecules including proteins, nucleic acids, and therapeutic small molecules. The compounds are useful for imaging in a variety of medical, biological and diagnostic applications, including SWIR in vivo imaging of regions of interest within a mammal.

42 Claims, 12 Drawing Sheets

(56) References Cited

OTHER PUBLICATIONS

Takanori Suzuki et al: "Preparation, Properties,and X-ray Structures of Bis (I0-methyl-9-methyleneacridan)-type Electron Donors with a Thiophene, Bithiophene, or Terthiophene Skeleton: Redox Switching of Thiophene—Thienoquinoid Structure Accompanied by UV-vis-NIR Electrochromic Response", Chemistry Letters,vol. 42, No. 9,Sep. 5, 2013 (Sep. 5, 2013), pp. 1004-1006, XP055526880, Japan ISSN: 0366-7022, DOI:10.1246/cl .130401 compounds 1-4.

N P Vasilenko et al: "Symmetrical Dyes-Derivatives of Naphtho [1,8-b,c]Thiophene",1987, XP055535754, Retrieved from the Internet:URL: https://link.springer.com/content/pdf/10.1007/BF00762000.pdf [retrieved on Dec. 18, 2018] compound III.

Maged Henary et al : "Functionalization of benzo [c,d ] indole system for the synthesis of visible and near-infrared dyes", Journal of Heterocyclic Chemistry, vol. 46, No. 1, 2009, pp. 84-87,XP055535744, US ISSN: 0022-152X, DOI:10.1002/jhet.39 compounds 8, 10, 14, 15.

International Search Report for PCT/US2018/049921 dated Jan. 10, 2019.

\* cited by examiner

NIR TO SWIR FLUORESCENT COMPOUNDS FOR IMAGING AND DETECTION

CROSS REFERENCE TO RELATED APPLICATIONS

This application depends from and claims priority to U.S. Provisional Application No. 62/565,263 filed Sep. 29, 2017, the entire contents of which are incorporated herein by reference.

FIELD

This disclosure related to methods for the production of fluorescent compounds and their use for detection or imaging in vitro, ex vivo or in vivo.

BACKGROUND

Optical imaging with fluorescent molecules is a powerful imaging modality with significant advantages over other modalities both in vitro and in vivo. Dyes that fluoresce in the far red to near-infrared (NIR) region (650-900 nm) have been widely employed for in vivo imaging due to the superior penetration of light through tissue at these wavelengths relative to shorter wavelength visible or UV light which is strongly absorbed. NIR dyes also absorb and emit far outside of the typical range of tissue autofluorescence, making them extremely well suited for in vitro imaging of tissues and cells. However, NIR imaging still suffers compromised image resolution, especially at greater imaging depths, due to the inherent light scattering properties of tissue or other turbid media. The magnitude of scattering by turbid media such as tissue is substantially diminished at longer SWIR wavelengths of light, e.g. 900-1700 nm which can be detected by recently available InGaAs based cameras and detectors. More specifically, within this region there are particular windows of excitation and emission that may result in optimal image quality. However, the lack of availability of materials that absorb and/or emit light in this region and are also suitable for adaptation to in vitro or in vivo imaging applications has hobbled the advancement of SWIR imaging of biological targets.

Known SWIR fluorescent materials include organic fluorochromes, such as IR-1048 and IR-1061, and nanomaterials such as carbon nanotubes, quantum dots and rare-earth nanocomposites. However, most known SWIR organic fluorochromes have little to no water solubility, a property necessary for broad in vivo use due to distribution and excretion properties, and nanoparticles generally show poor in vivo targeting qualities due to large size, high non-specific accumulation, poor clearance properties and potential toxicity. These properties also render these materials poorly suited for translation into clinical use, where rapid clearance is required to reduce the risk of toxicity due to long term exposure. There exists an urgent need for novel fluorescent materials with SWIR absorbance and/or emission profiles for the development of new biological diagnostic and clinical imaging applications. Suitable materials with strong absorption in the SWIR region could also have extended application into SWIR mediated photoacoustic imaging and photodynamic therapy. Moreover, the ability to synthesize molecules whose optical absorbance and emission properties that align with specific optimal windows for deep tissue or in vivo imaging would enable precise tuning of imaging parameters with the potential for significant advancement in the field of optical imaging.

SUMMARY

The following summary is provided to facilitate an understanding of some of the innovative features unique to the present disclosure and is not intended to be a full description. A full appreciation of the various aspects of the disclosure can be gained by taking the entire specification, claims, drawings, and abstract as a whole.

Provided are methods for the production of fluorescent compositions. The compositions generally contain a fluorescent dye (referred to as a "fluorochrome") which can absorb and/or emit light in the near infrared (NIR) to shortwave infrared (SWIR) region of the electromagnetic spectrum (approximately 700 nm to approximately 2500 nm, optionally from 900 nm to 1700 nm). The compositions are optionally bound or conjugated to other molecules or materials, that may be used in various medical, diagnostic and biological applications including but not limited to detection or imaging in vitro, ex vivo or in vivo.

The present disclosure is directed to fluorescent compounds based on polymethine bridged heterocycles that absorb and or emit light in the near infrared (NIR) to shortwave infrared (SWIR) regions of the electromagnetic spectrum (approximately 700 nm to approximately 2500 nm, preferably from 900 nm to 1700 nm). The compounds generally contain multiple substituents, such as sulfonates, aryl sulfonates, $C_1$ to $C_{24}$ alkyl sulfonates, taurine, carboxylates, alkylammonium, polyethylene glycol or other hydrophillic groups that confer solubility and compatibility with biological environments or assay conditions or improve optical properties of the fluorochrome. The compounds optionally have the capability to be linked, coupled or otherwise bound to other molecules, oligonucleotides, DNAs, RNAs, PNAs, siRNAs, peptides, proteins, antibodies, nanoparticles, viruses, cells, or tissues through one or more linking or binding substituents. The compounds, on their own or linked to other molecules, can be used for detection, fluorescence imaging (in vitro, ex vivo, or in vivo), photoacoustic imaging, microscopy, cytometry, immunoassays, diagnostics, photothermal therapy, or other chemical, biological, or medical applications. The fluorescent dyes can be used in fluorescence of imaging whole animals in NIR to SWIR wavelengths. In other aspects, the present disclosure provides methods for the production of compounds bearing various combinations of suitable substituents. The disclosure also provides methods and ranges for optimal imaging of tissues and whole animals in the NIR to SWIR regions.

In certain embodiments, the disclosure comprises fluorescent compounds having a general structure according to (Formula I):

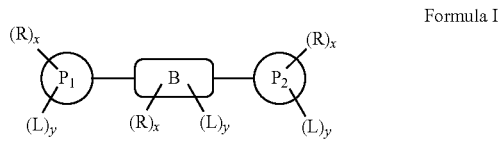

Formula I wherein $P_1$ and $P_2$ are heterocyclic moieties as described below; B is a conjugated bridge as described below; R is, independently for each occurrence, a substituent; L is a linker or linking group; and x and y are, for each occurrence, integers from 0 to 15.

In certain embodiments, provided are fluorescent compounds having a general structure according to Formula II:

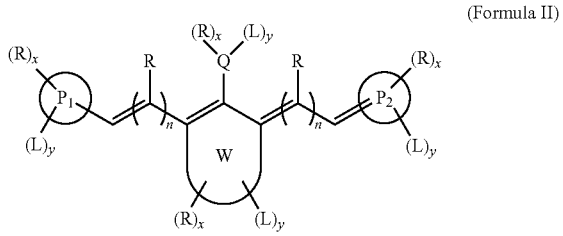

(Formula II)

wherein $P_1$ and $P_2$ are heterocyclic moieties; B (from Formula I) includes a polymethine bridge (depicted in this position in Formula II) where Q is a hydrogen, halogen, alkyl, aryl, heteroaryl, hydroxyl, alkoxy, aryloxy, alkylthio, arylthio, nitrogen, silicon, boron, carboxy, cyano, ester, amine, amide, or derivative thereof; W is absent or represents a cyclic, bicyclic, polycyclic, carbocyclic, heterocyclic group; and throughout the molecule R is, independently for each occurrence, absent or a substituent; L is a linker or linking group capable of forming covalent bonds to other molecules or bearing a reactive group capable of forming such bonds; and x, y and n are, independently for each occurrence, integers from 0 to 15.

BRIEF DESCRIPTION OF THE DRAWINGS

The aspects set forth in the drawings as provided herein are illustrative and exemplary in nature and not intended to limit the subject matter defined by the claims. The following detailed description and disclosure can be understood when read in conjunction with the following drawings where like structure is indicated with like reference numerals and in which:

DETAILED DESCRIPTION

Figure 1:
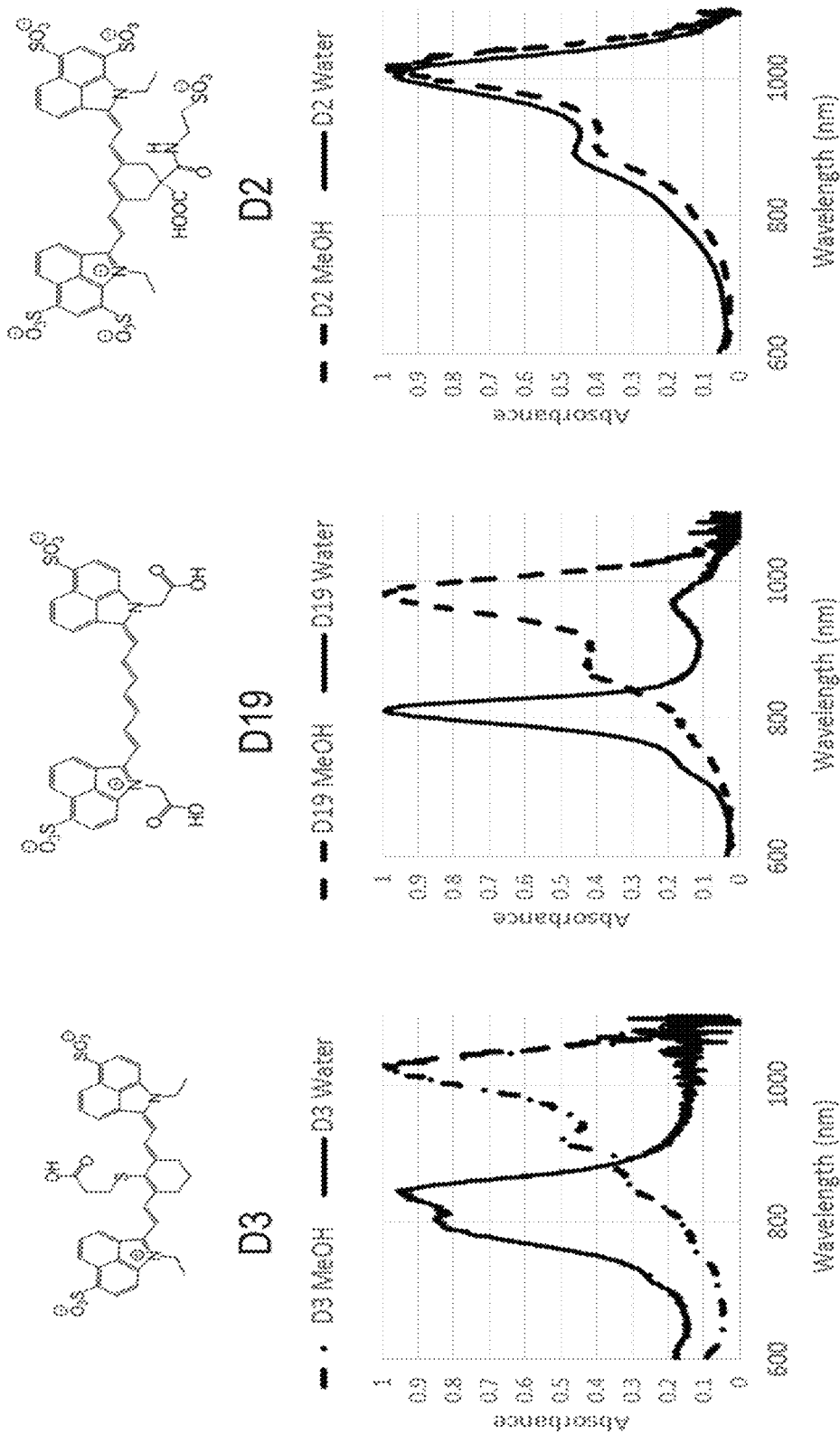
FIG. 1 illustrates absorbance spectra of various compounds according to aspects as provided herein in water or methanol.

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the processes or compositions are described as an order of individual steps or using specific materials, it is appreciated that steps or materials may be interchangeable such that the description of the invention may include multiple parts or steps arranged in many ways as is readily appreciated by one of ordinary skill in the art.

It will be understood that, although the terms "first," "second," "third," etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, "a first element," "component," "region," "layer," or "section" discussed below could be termed a second (or other) element, component, region, layer, or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

The present disclosure provides a family of fluorochrome compounds (e.g., dyes) that absorb and/or emit light having a wavelength in the range from about 700 nm to about 2500 nm, optionally in the range from about 900 nm to about 1700 nm. In certain embodiments, the dyes absorb and/or emit light having a wavelength in the range from about 750 nm to about 1550 nm, from about 950 nm to about 1350 nm, or from about 1000 nm to about 1250 nm. The fluorochrome compounds or certain conjugates or derivatives thereof can, in some instances, be conjugated to other molecules or biomolecules and are particularly useful in a variety of in vitro and in vivo imaging applications.

Generally, the fluorochromes of this disclosure can be represented by the formula $P_1$—B—$P_2$, wherein $P_1$ and $P_2$ each represent conjugated heterocyclic or heteroaromatic moieties and B represents a bridging functionality between $P_1$ and $P_2$, such as a polymethine bridge consisting of conjugated double bonded methylene chains, conjugated aryl or heteroaryl groups, thiadiazole, benzothiadiazole, bisbenzothiadiazole, or combinations thereof with suitable substituents.

In certain embodiments, the provided compounds (e.g., imaging compounds) comprises fluorescent compounds having a general structure according to (Formula I):

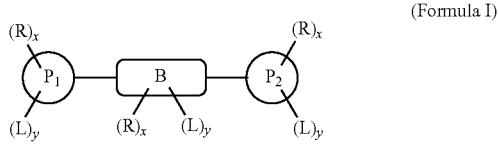

(Formula I)

wherein $P_1$ and $P_2$ are heterocyclic or heteroaromatic or polycyclic moieties such as an acridine or acridinium moiety, a pyrylium or thiopyrylium moiety, and indole, benzindole or benz[c,d]indole moiety, naphtho thiophene moiety such as a 1,8-naphtho thiophene moiety, or related structures and salts thereof; B is a conjugated bridging moiety, optionally a polymethine bridge including or consisting of conjugated double bonded methylene chains, conjugated aryl or heteroaryl groups, thiadiazole, benzothiadiazole, bisbenzothiadiazole, or other structures as described herein and combinations thereof; R is, independently for each occurrence, a substituent optionally as described herein; L is a linker or linking group bound to or capable of forming bonds to other molecules, optionally drugs, peptides, proteins, antibodies, cells or tissues, or bearing a reactive group capable of forming such bonds as described herein; and x and y are, for each occurrence, integers from 0 to 15.

In some embodiments, the compounds provided herein may be fluorescent compounds having a general structure according to Formula II:

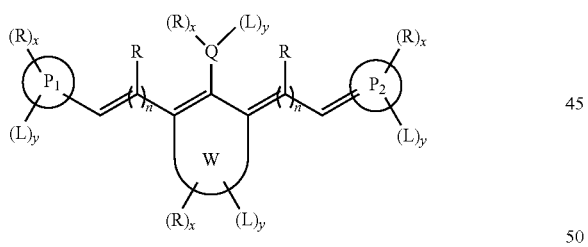

(Formula II)

wherein $P_1$ and $P_2$ are heterocyclic or heteroaromatic or polycyclic moieties such as an acridine or acridinium moiety, a pyrylium or thiopyrylium moiety, and indole, benzindole or benz[c,d]indole moiety, naphtho thiophene moiety, or related structures and salts thereof, optionally as described herein; the conjugated bridging moiety (B in Formula I) is optionally a polymethine bridge that includes conjugated double bonded methylene chains, conjugated aryl or heteroaryl groups, thiadiazole, benzothiadiazole, bisbenzothiadiazole, or other structures optionally as described herein, and combinations thereof; Q is a hydrogen, halogen, alkyl, aryl, heteroaryl, hydroxyl, alkoxy, aryloxy, alkylthio, arylthio, nitrogen, silicon, boron, carboxy, cyano, ester, amine, amide, L or derivative thereof as described below; W is absent or represents a cyclic, bicyclic, polycyclic, carbocyclic, or heterocyclic group or derivative thereof optionally as described below; R is, independently for each occurrence, absent or a substituent optionally as described herein; L is a linker or linking group bound to or capable of forming bonds to other molecules, such as drugs, peptides, proteins, antibodies, cells or tissues, or bearing a reactive group capable of forming such bonds optionally as described herein; and x, y and n are, independently for each occurrence, integers from 0 to 15.

I. Definitions

As used herein the term "biomolecule" is any molecule the general structure of which may be found in a living organism. The definition of biomolecule illustratively includes fragments of any polymeric molecule the general structure of which may be found in a living organism. Illustrative examples of fragments include a peptide or amino acid fragment of a protein or a nucleic acid or oligonucleotide as a fragment of a nucleic acid molecule (e.g., DNA, RNA). Illustrative examples of a biomolecule include a protein, peptide, antibody, carbohydrate, lipid, amino acid, nucleic acid, nucleotide, among others.

II. Fluorochrome Compounds

In certain embodiments, the bridge B of Formula I corresponds to one of the formulae shown in Table 1a below:

TABLE 1a

| Bridge # | Structure |
|---|---|
| B1 | 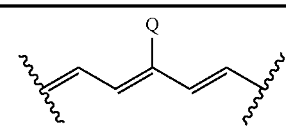 |
| B2 | 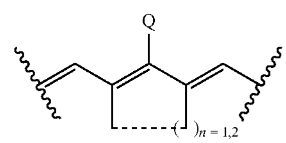 |
| B3 | 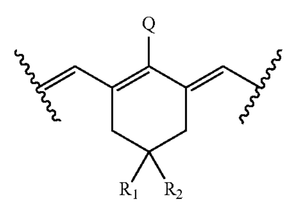 |
| B4 | 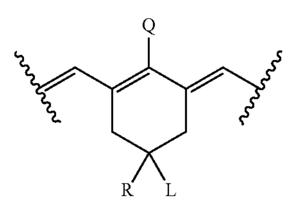 |
| B5 | 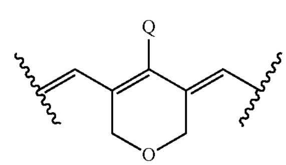 |

TABLE 1a-continued

| Bridge # | Structure |
|---|---|
| B6 | 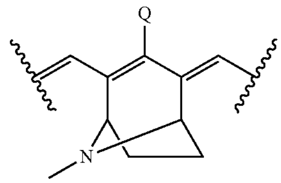 |
| B7 | 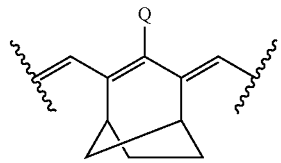 |
| B8 | 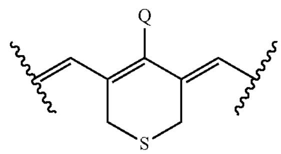 |
| B9 | 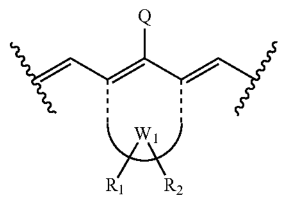 |
| B10 | 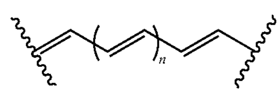 |
| B11 | 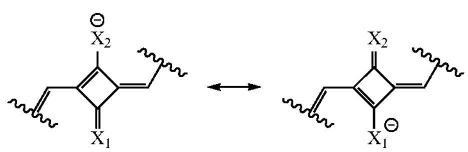 |
| B12 | 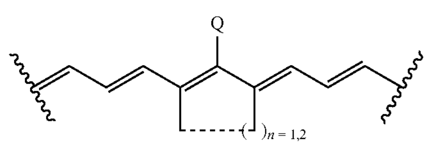 |
| B13 | 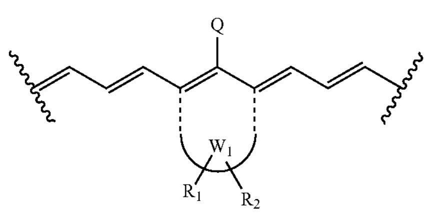 |
| B14 | 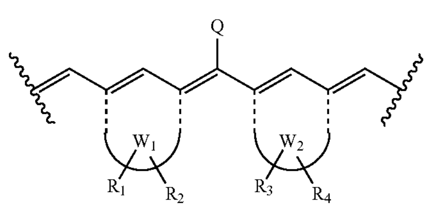 |

TABLE 1a-continued

| Bridge # | Structure |
|---|---|
| B15 | 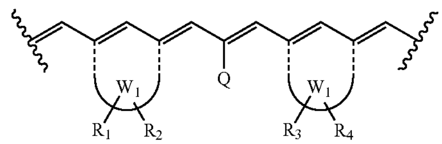 |
| B16 | 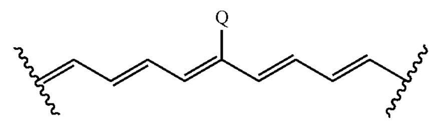 |
| B17 | 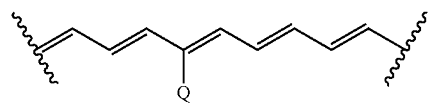 |
| B18 | 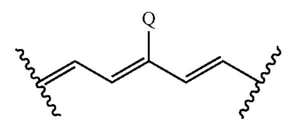 |
| B19 | 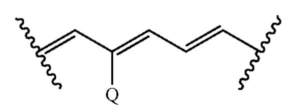 |
| B20 | | wherein Q, $X_1$, $X_2$, R, $R_1$-$R_4$, L, $W_1$, and $W_2$ are as defined herein for formula I or II.

In certain embodiments, the bridge B of Formula I corresponds to one of the formulae shown in Table 1b below, or salts thereof.

TABLE 1b

| Bridge # | Structure |
|---|---|
| B30 | 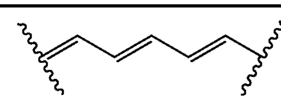 |
| B31 | 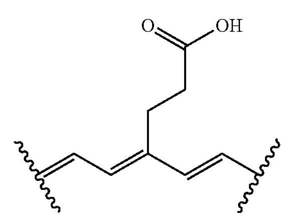 [SMILES: */C=C/C(=C/C=*)CCC(=O)O] |
| B32 | 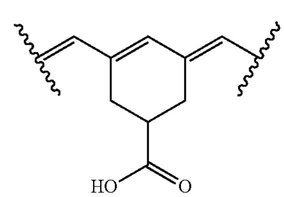 [SMILES: */C=C1/C=C(C=*)CC(C(=O)O)C1] |

TABLE 1b-continued

| Bridge # | Structure |
|---|---|
| B33 | (cyclohexane bridge with carboxylic acid and amide-CH2CH2-SO3H) |
| B34 | (cyclohexane bridge with -S-CH2CH2-COOH) |
| B35 | (bicyclic bridge with -S-CH2CH2-COOH) |
| B36 | (cyclopentane bridge with -S-CH2CH2-COOH) |
| B37 | (cyclohexene bridge with -S-phenyl-CH2-COOH) |
| B38 | (cyclopentene bridge with -S-phenyl-CH2-COOH) |
| B39 | (bicyclic bridge with -S-phenyl-CH2-COOH) |

End groups (P):

In certain embodiments, $P_1$ and $P_2$ may, each independently, correspond to one of the formulae shown in Table 2a below:

TABLE 2a

| P # | Structure |
|---|---|
| P3 | (acridinium structure with $R_1$ on $N^+$, $R_2$, $R_3$, $R_4$, $R_5$ substituents) |
| P4 | (quinolinium fused cyclopentane structure with $R_1$ on $N^+$, $R_2$, $R_3$, $R_4$, $R_5$, $R_6$ substituents, n = 1, 2) |

TABLE 2a-continued

| P # | Structure |
|---|---|
| P5 | (structure) |
| P6 | (structure) |
| P7 | (structure) |
| P8 | (structure) |
| P9 | (structure) |
| P10 | (structure) |
| P11 | (structure) |
| P12 | (structure) |
| P13 | (structure) |

TABLE 2a-continued

| P # | Structure |
|---|---|
| P14 | (structure) |
| P15 | (structure) |
| P16 | (structure) |
| P17 | (structure) |
| P18 | (structure) |
| P19 | (structure) |
| P20 | (structure) |
| P21 | (structure) |
| P22 | (structure) |

TABLE 2a-continued

| P # | Structure |
|---|---|
| P23 | (structure with pyridinium core, substituents $R_1$–$R_{11}$) |
| P24 | (quinolinium structure with substituents $R_1$–$R_{10}$) |
| P25 | (pyridinium structure with substituents $R_1$–$R_{11}$) |
| P26 | (cyclopenta-fused pyridinium structure with substituents $R_1$–$R_{11}$, with $)_{1,2}$) |

Wherein X, Y, Z, R, $R_1$-$R_{12}$, Q, and $W_1$-$W_4$ are as defined herein for formula I or II.

Heteroaryl Substituents X, Y and Z

A compound as provided herein optionally includes one or more heterocycles. A heterocycle optionally includes one or more substituents X, Y, or Z. Illustrative examples of heterocycles of P1 or P2 including one or more substituents X, Y, or Z are illustrated but not limited to those presented in Table 2a. In certain embodiments, X, Y, and Z are, independently, O, S, N, P, Si, C, or (C=C). It is understood that each of X, Y, and Z, if capable, may bear additional substituents, including but not limited to H, $C_{1-24}$ alkyl, $C_{1-24}$ dialkyl, aryl, aryl sulfonate, $C_1$ to $C_{24}$ alkyl sulfonate, arylsulfonate, halogen, nitro, hydroxyl, N-alkyl, O-alkyl, S-alkyl, N-aryl, among others. It is further understood that substitution of X, Y, and Z may impart a net charge that would be paired as a salt with a suitable counterion or exist as an inner-salt (zwitterion) with another group within the same molecule.

In certain embodiments, $P_1$ and $P_2$ may, each independently, correspond to one of the formulae shown in Table 2b below, or salts thereof.

TABLE 2b

| P # | Structure |
|---|---|
| P30 | (benzo[cd]indolium with $O_3S^-$ and propyl-$SO_3H$ N-substituent) |
| P31 | (benzo[cd]indolium with $O_3S^-$ and N-ethyl) |
| P32 | (benzo[cd]indolium with $O_3S^-$ and propyl-$SO_3H$ N-substituent) |

TABLE 2b-continued
| P # | Structure |
|---|---|
| P33 | 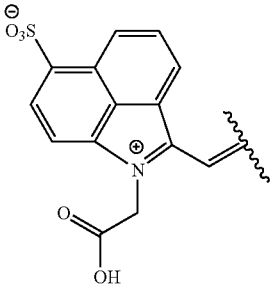 |
| P34 | 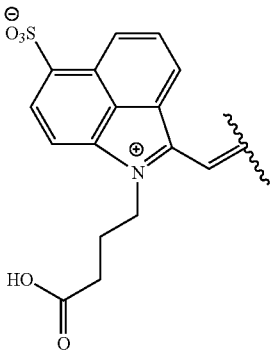 |
| P35 | 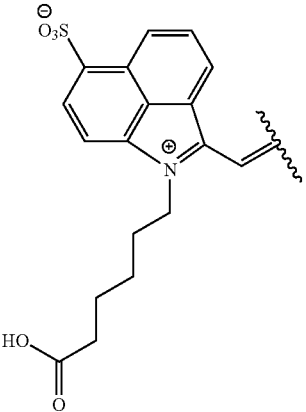 |
| P36 | 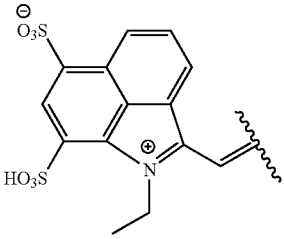 |
| P37 | 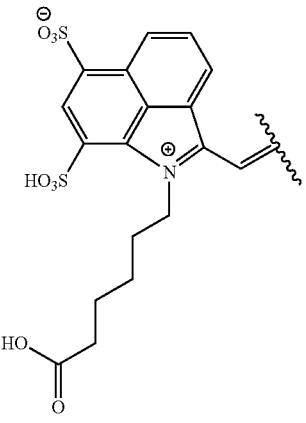 |
| P38 | 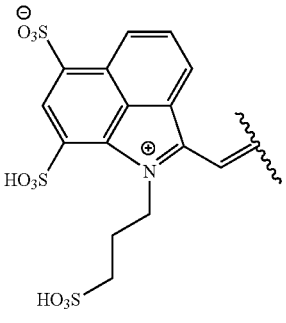 |
| P39 | 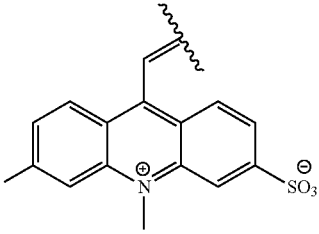 |
| P40 | 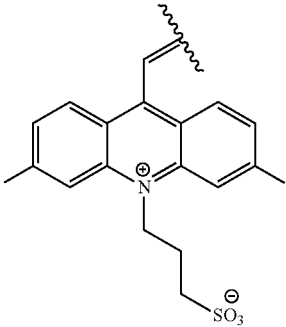 |

TABLE 2b-continued
| P # | Structure |
|---|---|
| P41 | 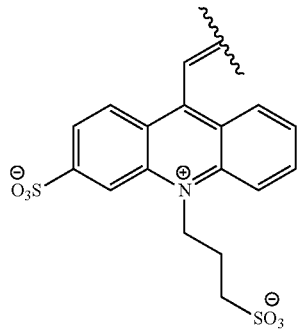 |
| P42 | 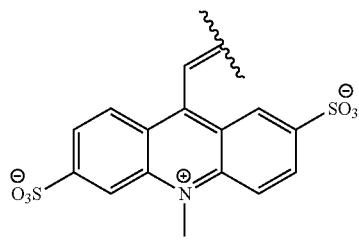 |
| P43 | 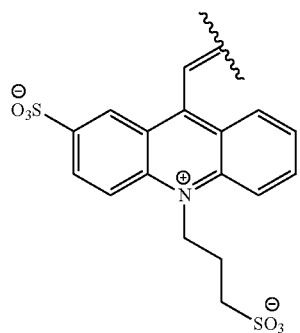 |
| P44 | 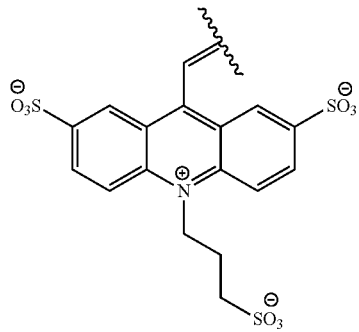 |
| P45 | 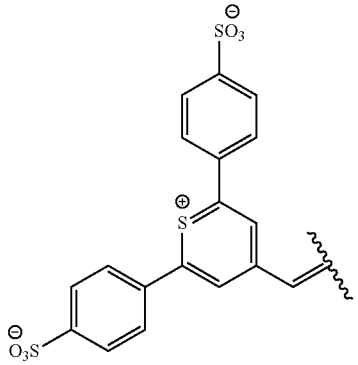 |
| P46 | 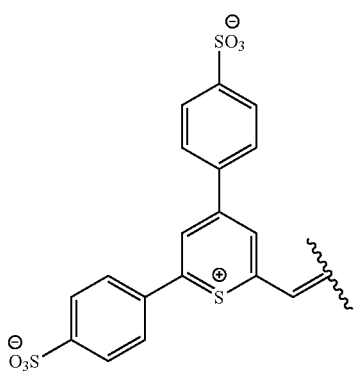 |
| P47 | 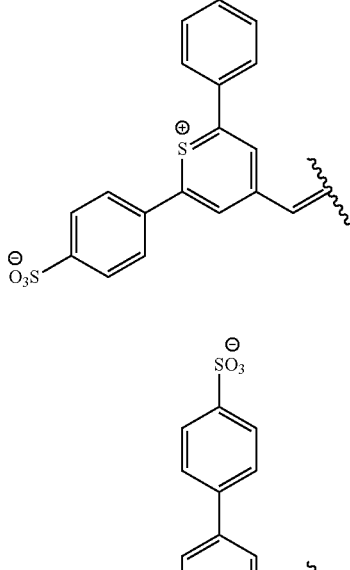 |
| P48 | 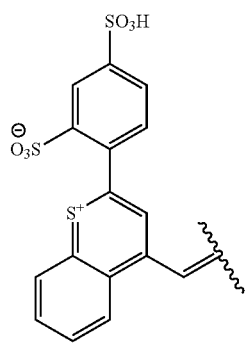 |

TABLE 2b-continued

| P # | Structure |
|---|---|
| P49 | 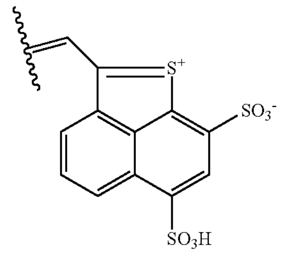 |
| P50 | 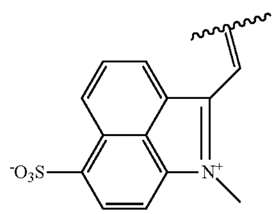 |
| P51 | 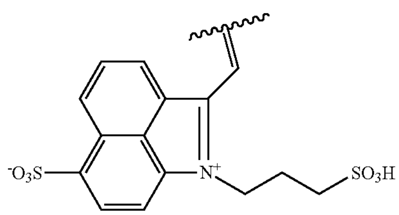 |
| P52 | 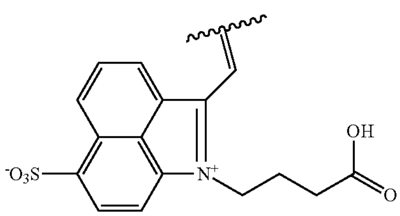 |
| P53 | 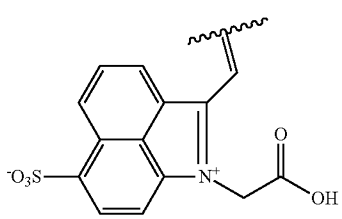 |

Q Substituents:

In certain embodiments of the disclosure, Q in any of the formulae provided herein is a hydrogen, $C_1$-$C_{24}$ alkyl, aryl, heteroaryl, polyaryl, phenyl, thienyl, furanyl, pyridyl, pyridinium, halogen, substituted or unsubstituted S-alkyl, substituted or unsubstituted S-aryl, substituted or unsubstituted O-alkyl, substituted or unsubstituted O-aryl, substituted or unsubstituted N-alkyl, substituted or unsubstituted N-aryl, cyano, trifluoromethyl, azidoaryl, boronic acid, boronic ester, or other. In other aspects, Q is further substituted with one or more R groups or L linking groups, as defined herein.

W (Rings):

In certain embodiments, W and $W_1$-$W_4$ are, independently, absent or cyclic groups containing aliphatic or aromatic carbon, nitrogen, oxygen, sulfur, or silicon forming a 4 to 9 membered ring, optionally with further substituents. In other aspects, W or any one or more of $W_1$-$W_4$ represent fused aromatic or heteroaromatic groups, optionally further substituted with one or more R groups or L groups as defined herein. In other aspects, W or any one or more of $W_1$-$W_4$ represent bicyclic, tricyclic or polycyclic, heterocyclic, heterobicyclic, or polyheterocyclic moieties.

R Substituents:

In various embodiments, substituents R, $R_1$, $R_2$, $R_3$, $R_4$, $R_5$, $R_6$, $R_7$, $R_8$, $R_9$, $R_{10}$, $R_{11}$, and $R_{12}$ each independently are absent or can represent hydrogen, substituted or unsubstituted $C_1$ to $C_{24}$ alkyl, substituted or unsubstituted alkylaryl, substituted or unsubstituted aryl, substituted or unsubstituted heteroaryl, substituted or unsubstituted alkenyl, substituted or unsubstituted alkynyl, sulfonate, aryl sulfonate, $C_1$ to $C_{24}$ alkyl sulfonate, taurine, carboxylate, amine, alkylamine, dialkylamine, arylamine, alkylarylamine, di(sulfoalkyl)amine, alkylammonium, arylammonium, sulfonamide, halogen, hydroxy, amide, nitro, cyano, azide, O-alkyl, S-alkyl, silyl, trialkylsilyl, O-silyl, haloalkyl, alkylsulfhydryl, trifluoromethyl, hydrazide, amino acid, or peptide.

L Linkers:

In various aspects of the disclosure, L is absent or is a linker moiety or linking group covalently or non-covalently bound to or capable of forming covalent or non-covalent bonds to other molecules, such as drugs, peptides, proteins, antibodies, nucleic acids, carbohydrates, lipids, biomolecules, nanoparticles, membranes, cells or tissues. In some aspects, L may bear a reactive group capable of forming such bonds, optionally bearing a functional group such as a carboxylate, carboxyalkyl, maleimide, alkyl ester, aryl ester, succinimidyl ester, amine, carbamate, carboxamide, propargyl, azidoalkyl, isocyanate, isothiocyanate, sulfonyl chloride, pentafluorophenyl ester, acyl fluoride, acyl chloride, acyl azide, tyramide, cinnamamide, hydroxycinammamide, aldehyde, ketone, phosphoramidite, phthalamido, biotin or other group that can be linked, bound or conjugated to a molecule, drug, biomolecule, peptide, protein nanoparticle, cell, tissue, etc.

In some aspects the linking, conjugation or binding of a molecule to L is performed separately prior to use for imaging, detection, diagnostic, assay or other purposes. In other aspects, the binding or conjugation to L occurs in situ, optionally during imaging, detection, diagnostic or other assay or application, such as in a microtiter plate, in cell culture, on a microscope slide, in a cuvette, in an imager, on the surface of a tissue, or in vivo in a living animal. In some aspects, the binding is mediated by the action of an enzyme. In some aspects, the enzyme is horseradish peroxidase. In some aspects, the linking is irreversible. In other aspects, the linking is reversible. In other aspects, the linking is reversible upon exposure to a reversing or dissociating reagent, or by changing temperature, pH, or ionic strength, or by exposure to light, heat, microwaves, ultrasound, metal ions, enzymes, or catalysts.

In some embodiments, L may be selected from the formulae shown in Table 3, wherein E is carbon, nitrogen, sulfur, oxygen, silicon or phosphorus; F is carboxylate, carboxyalkyl, maleimide, alkyl ester, aryl ester, succinimidyl ester, amine, carbamate, carboxamide, propargyl, azidoalkyl, isocyanate, isothiocyanate, sulfonyl chloride, pentafluorophenyl ester, acyl fluoride, acyl chloride, acyl azide, tyramide, cinnamamide, hydroxycinammamide, aldehyde, ketone, phosphoramidite, phthalamido, biotin; and n is an integer between 0 and 100.

TABLE 3

| Linker (L) | Structure |
|---|---|
| L1 | 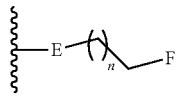 |
| L2 | 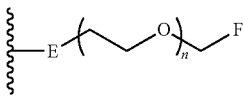 |
| L3 | 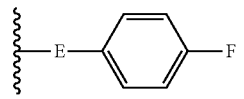 |
| L4 | 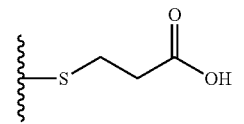 [SMILES: *SCCC(=O)O] |
| L5 | 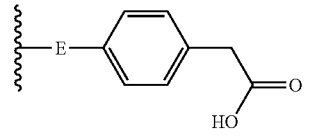 |
| L6 | 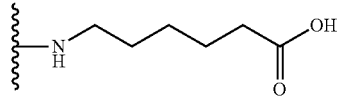 [SMILES: *NCCCCCC(=O)O] |
| L7 | 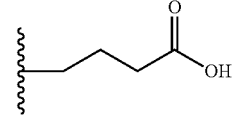 [SMILES: *CCCC(=O)O] |
| L8 | 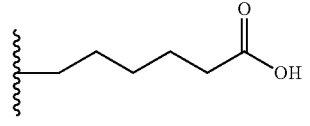 |
| L9 | 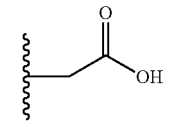 [SMILES: *CC(=O)O] |

TABLE 3-continued

| Linker (L) | Structure |
|---|---|
| L10 | 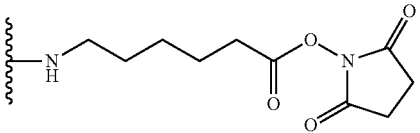 [SMILES: *NCCCCCC(=O)ON1C(=O)CCC1=O] |
| L11 | 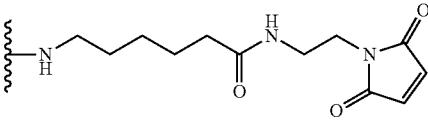 [SMILES: *NCCCCCC(=O)NCCN1C(=O)C=CC1=O] |
| L12 | 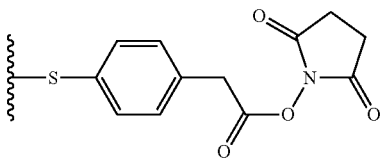 [SMILES: *Sc1ccc(CC(=O)ON2C(=O)CCC2=O)cc1] |
| L13 | 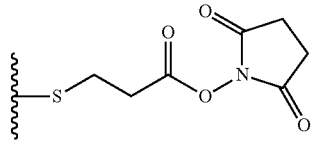 [SMILES: *SCCC(=O)ON1C(=O)CCC1=O] |
| L14 | 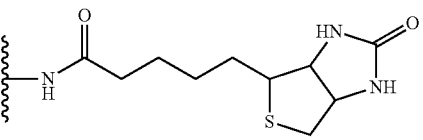 [SMILES: *NC(=O)CCCCC1SCC2NC(=O)NC21] |

In certain aspects, the fluorochrome compounds as provided herein are as defined in Table 4.

In certain aspects of the disclosure, $P_1$ and $P_2$ represent substituted benz[c,d]indole moieties. In certain aspects of the disclosure, $P_1$ and $P_2$ represent substituted benz[c,d]indole moieties optionally as illustrated in Table 4 as D1 to D20.

In certain aspects of the disclosure, $P_1$ and $P_2$ represent substituted acridine or acridinium moieties. Optionally, $P_1$ and $P_2$ represent substituted acridine or acridinium moieties optionally as illustrated in Table 4 as D51 to D59.

In certain aspects of the disclosure, $P_1$ and $P_2$ represent substituted thiopyrylium or pyrylium moieties. Optionally, $P_1$ and $P_2$ represent substituted thiopyrylium or pyrylium moieties optionally as illustrated in Table 4 as D21 to D50 and D60 to D64.

TABLE 4
Exemplary compounds according to this disclosure.
D1
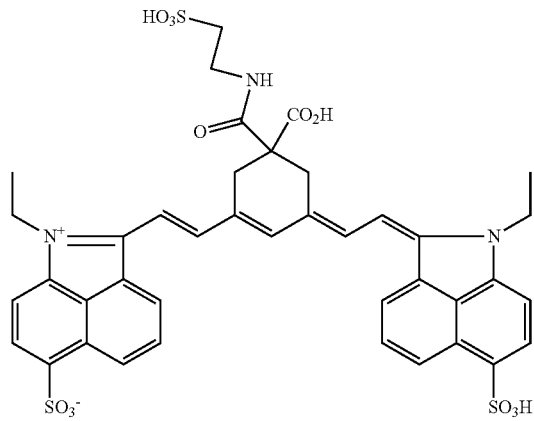
D2
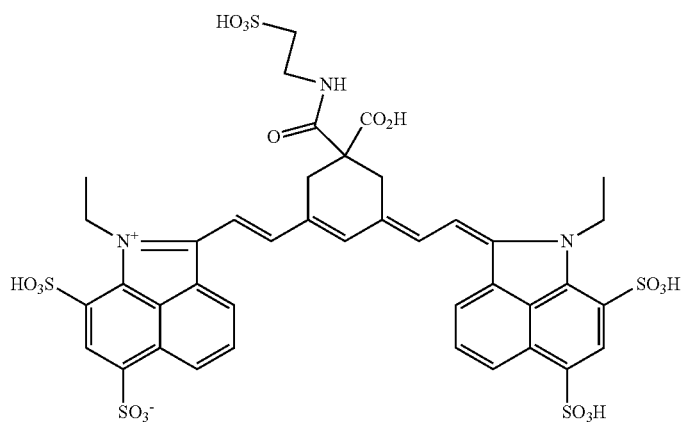
D3
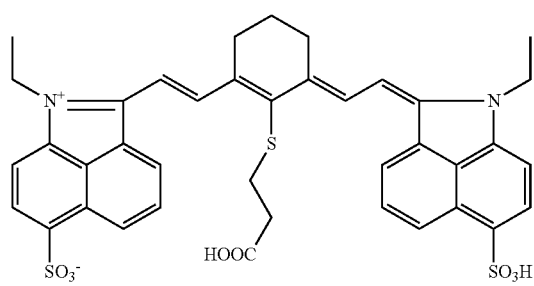
D4
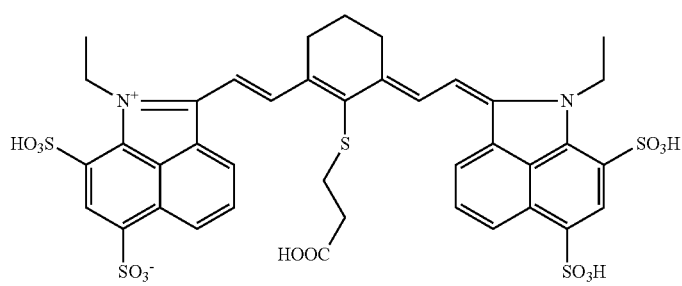

TABLE 4-continued
Exemplary compounds according to this disclosure.
D5
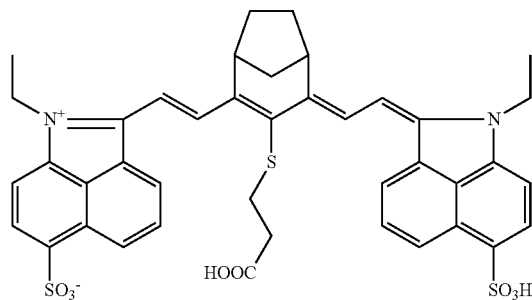
D6
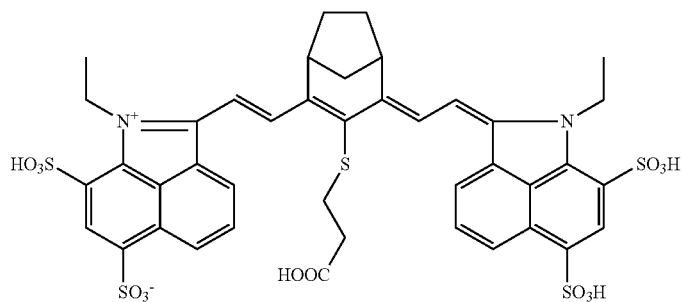
D7
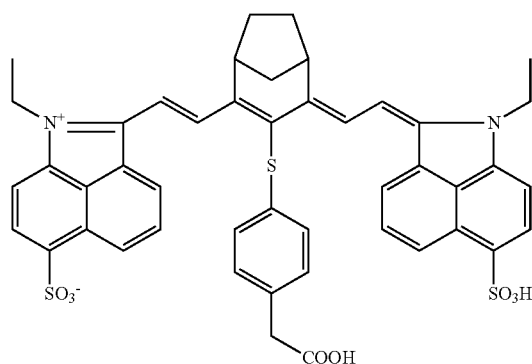
D8
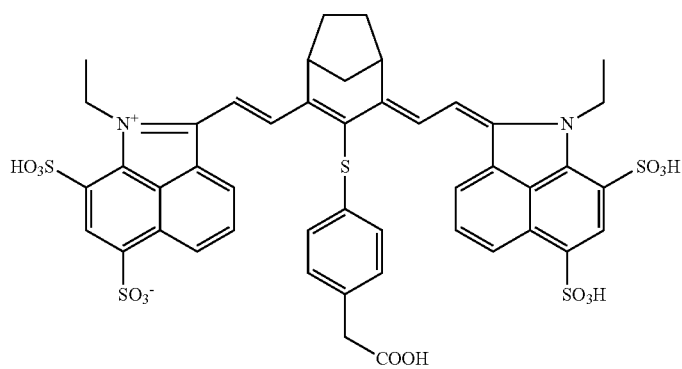

TABLE 4-continued
Exemplary compounds according to this disclosure.
D9
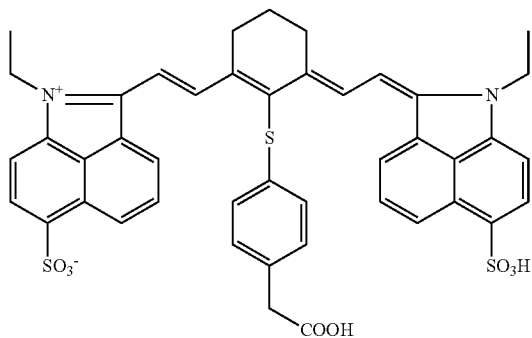
D10
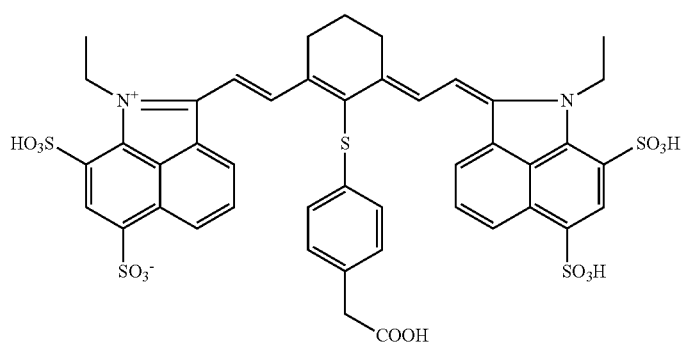
D11
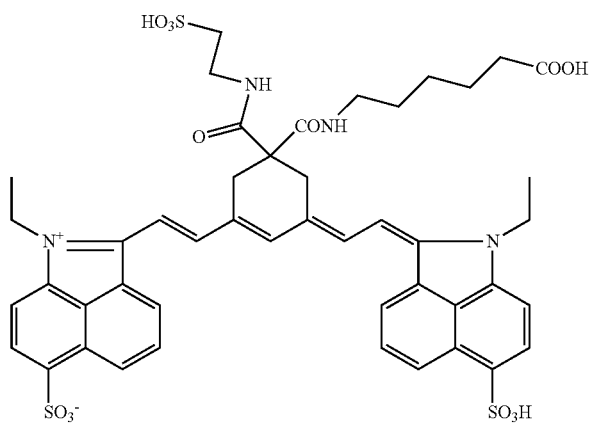
D12
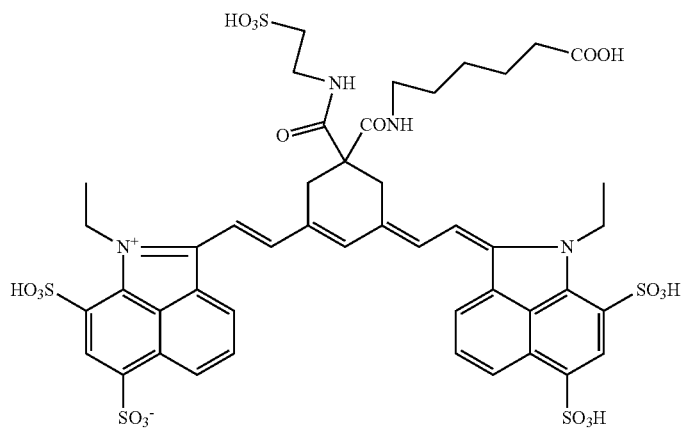

TABLE 4-continued
Exemplary compounds according to this disclosure.
D13 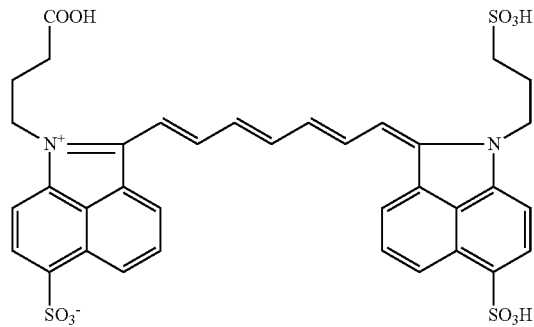
D14 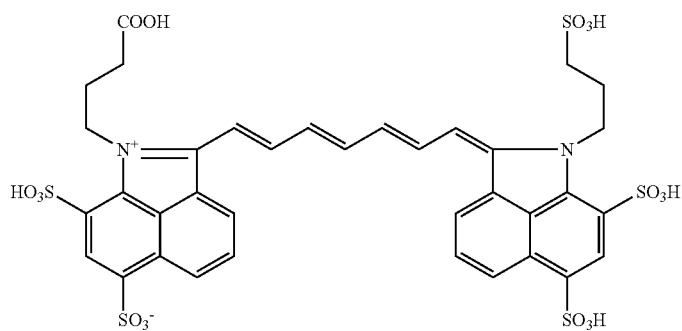
D15 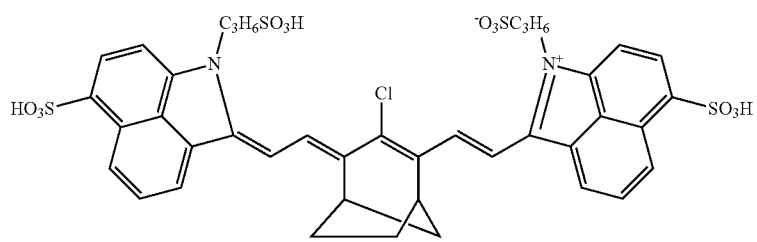
D16 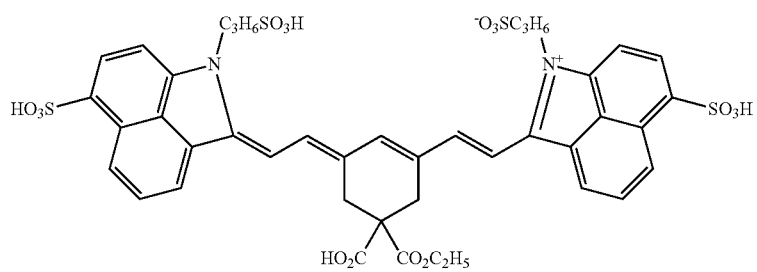
D17 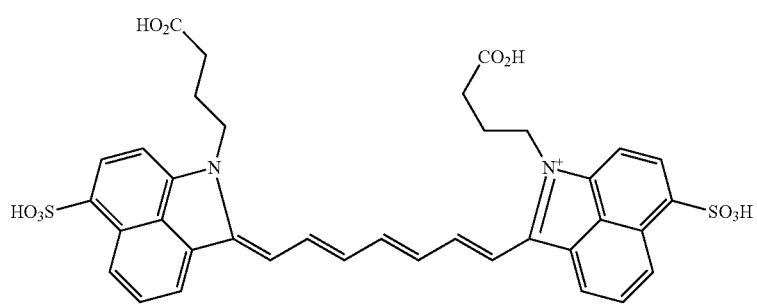 [SMILES: O=C(O)CCCn1\c(=C/C=C/C=C/C=C/C2=[N+](CCCC(=O)O)c3ccc(S(=O)(=O)O)c4cccc2c34)c2cccc3c(S(=O)(=O)O)ccc1c32]

TABLE 4-continued
Exemplary compounds according to this disclosure.
D18 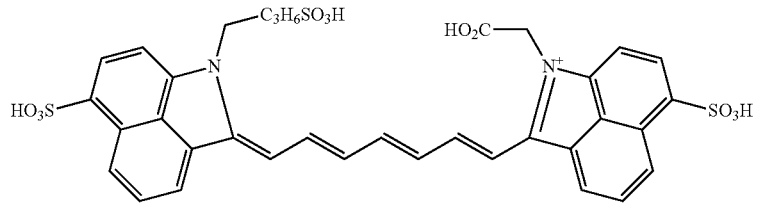
D19 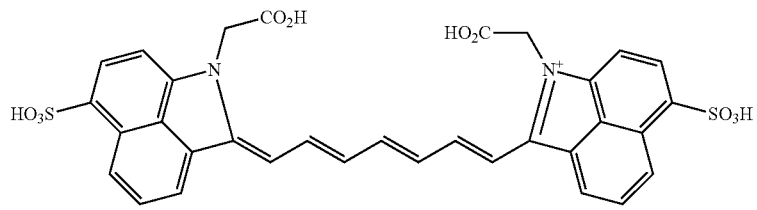 [SMILES: O=C(O)Cn1\c(=C/C=C/C=C/C=C/C2=[N+](CC(=O)O)c3ccc(S(=O)(=O)O)c4cccc2c34)c2cccc3c(S(=O)(=O)O)ccc1c32]
D20 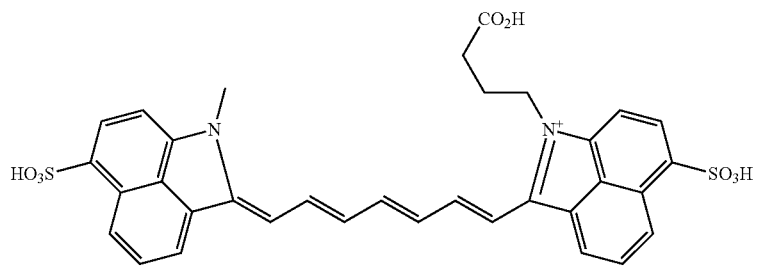 [SMILES: Cn1\c(=C/C=C/C=C/C=C/C2=[N+](CCCC(=O)O)c3ccc(S(=O)(=O)O)c4cccc2c34)c2cccc3c(S(=O)(=O)O)ccc1c32]
D21 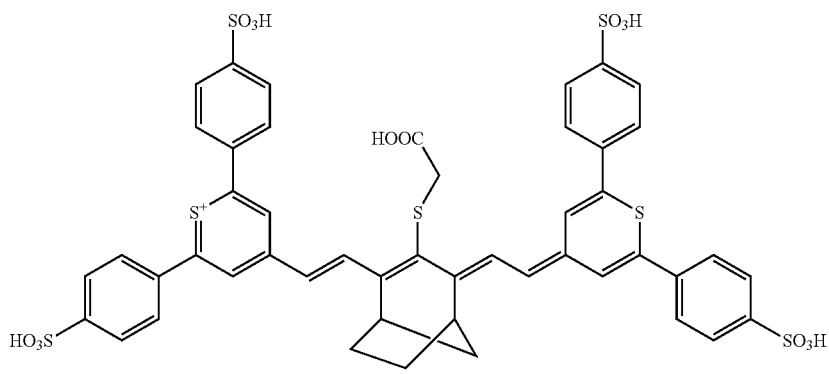 [SMILES: O=C(O)CSC1=C(/C=C/c2cc(-c3ccc(S(=O)(=O)O)cc3)[s+]c(-c3ccc(S(=O)(=O)O)cc3)c2)C2CCC(C2)/C1=C\C=C1C=C(c2ccc(S(=O)(=O)O)cc2)SC(c2ccc(S(=O)(=O)O)cc2)=C1]
D22 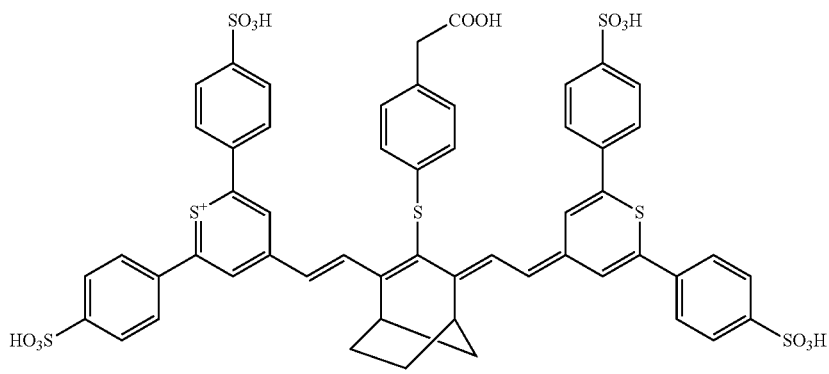 [SMILES: O=C(O)Cc1ccc(SC2=C(/C=C/c3cc(-c4ccc(S(=O)(=O)O)cc4)[s+]c(-c4ccc(S(=O)(=O)O)cc4)c3)C3CCC(C3)/C2=C\C=C2C=C(c3ccc(S(=O)(=O)O)cc3)SC(c3ccc(S(=O)(=O)O)cc3)=C2)cc1]

TABLE 4-continued
Exemplary compounds according to this disclosure.
D23
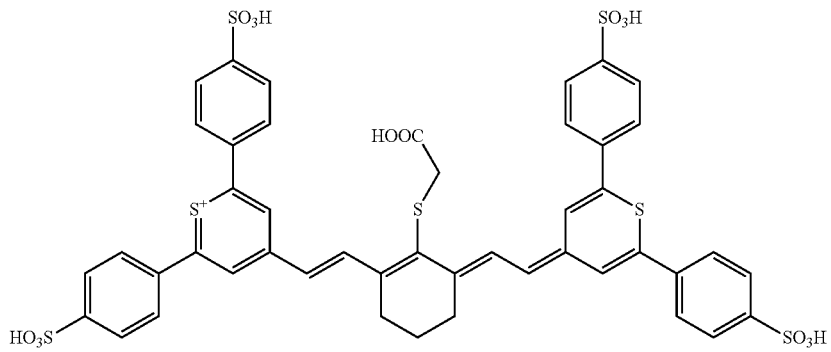 [SMILES: O=C(O)CSC1=C(/C=C/c2cc(-c3ccc(S(=O)(=O)O)cc3)[s+]c(-c3ccc(S(=O)(=O)O)cc3)c2)CCC/C1=C\C=C1C=C(c2ccc(S(=O)(=O)O)cc2)SC(c2ccc(S(=O)(=O)O)cc2)=C1]
D24
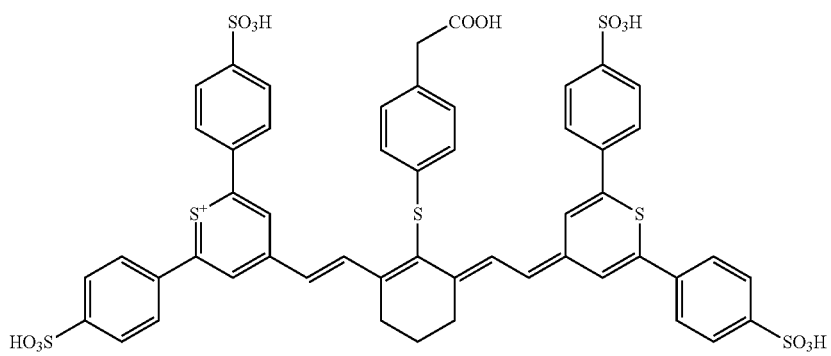 [SMILES: O=C(O)Cc1ccc(SC2=C(/C=C/c3cc(-c4ccc(S(=O)(=O)O)cc4)[s+]c(-c4ccc(S(=O)(=O)O)cc4)c3)CCC/C2=C\C=C2C=C(c3ccc(S(=O)(=O)O)cc3)SC(c3ccc(S(=O)(=O)O)cc3)=C2)cc1]
D25
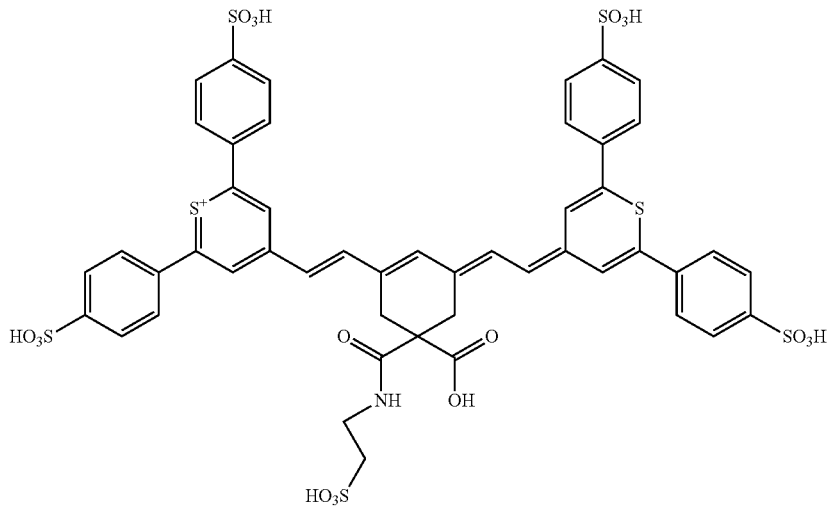 [SMILES: O=C(O)C1(C(=O)NCCS(=O)(=O)O)CC(/C=C/c2cc(-c3ccc(S(=O)(=O)O)cc3)[s+]c(-c3ccc(S(=O)(=O)O)cc3)c2)=CC(=C/C=C2C=C(c3ccc(S(=O)(=O)O)cc3)SC(c3ccc(S(=O)(=O)O)cc3)=C2)/C1]

TABLE 4-continued
Exemplary compounds according to this disclosure.
D26
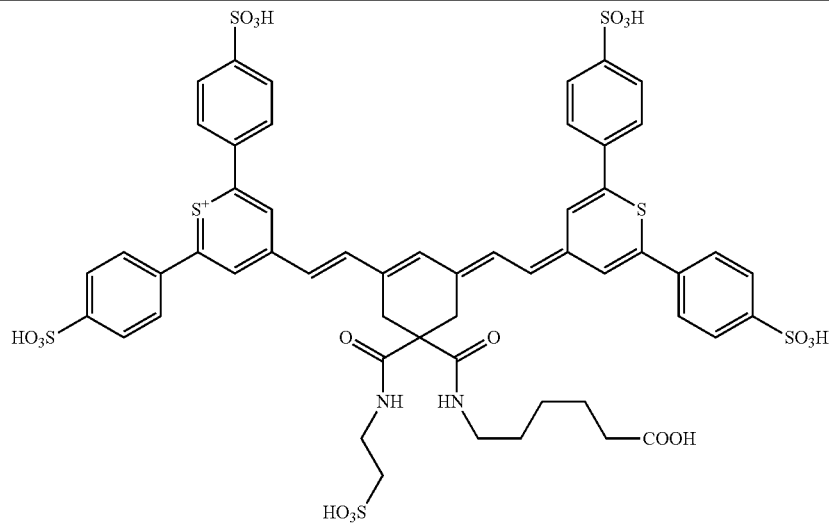
D27
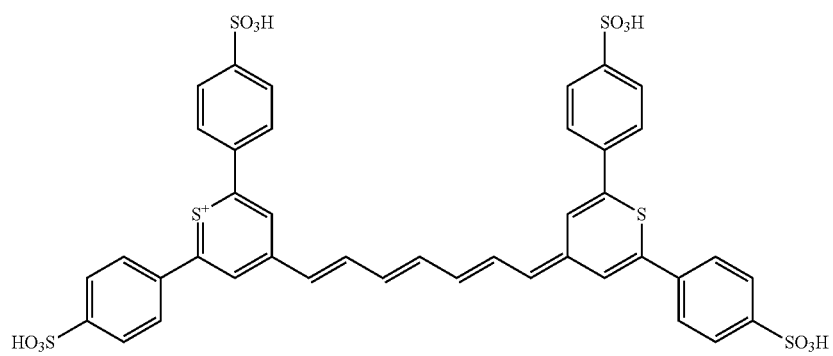 [SMILES: O=S(=O)(O)c1ccc(C2=CC(=C/C=C/C=C/C=C/c3cc(-c4ccc(S(=O)(=O)O)cc4)[s+]c(-c4ccc(S(=O)(=O)O)cc4)c3)C=C(c3ccc(S(=O)(=O)O)cc3)S2)cc1]
D28
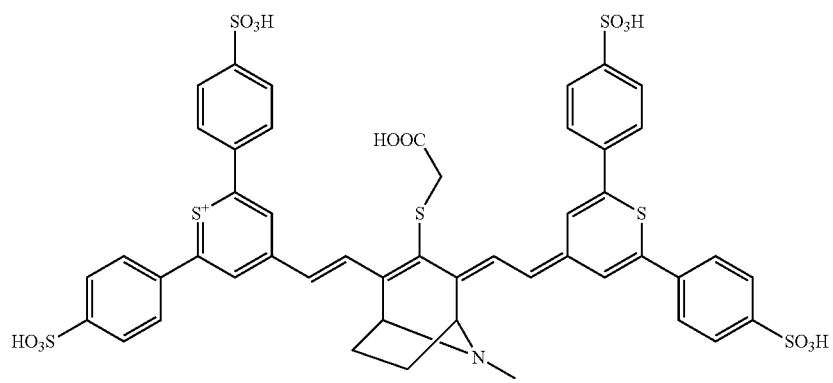 [SMILES: CN1C2CCC1/C(=C\C=C1C=C(c3ccc(S(=O)(=O)O)cc3)SC(c3ccc(S(=O)(=O)O)cc3)=C1)C(SCC(=O)O)=C2/C=C/c1cc(-c2ccc(S(=O)(=O)O)cc2)[s+]c(-c2ccc(S(=O)(=O)O)cc2)c1]
D29
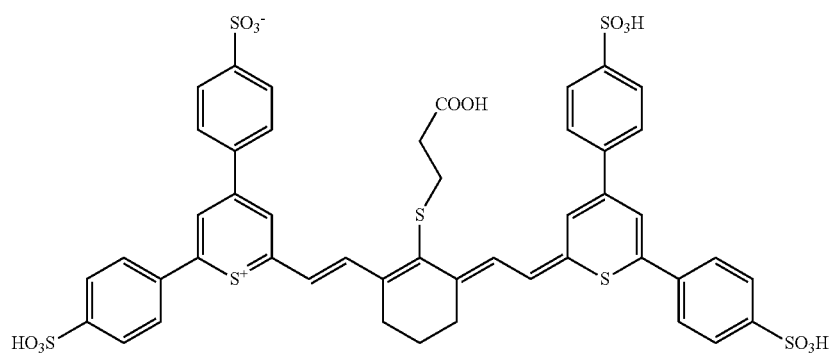

TABLE 4-continued
Exemplary compounds according to this disclosure.
D30
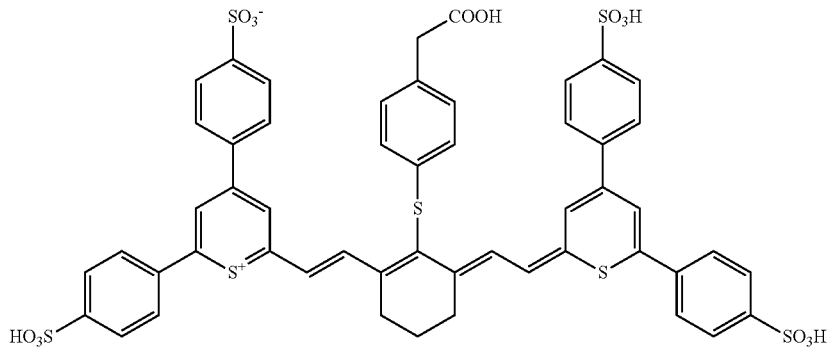
D31
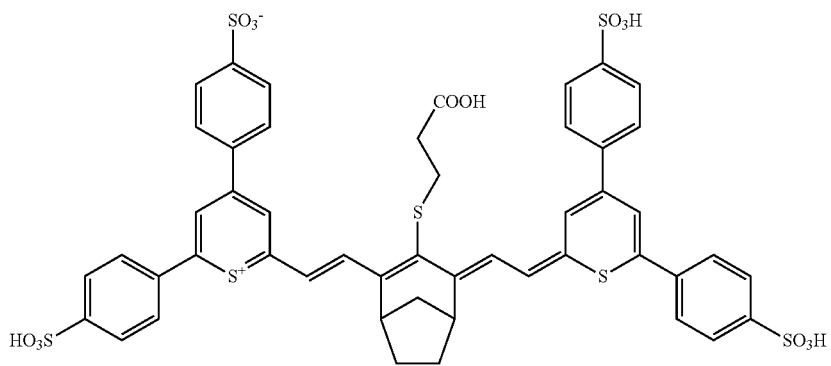
D32
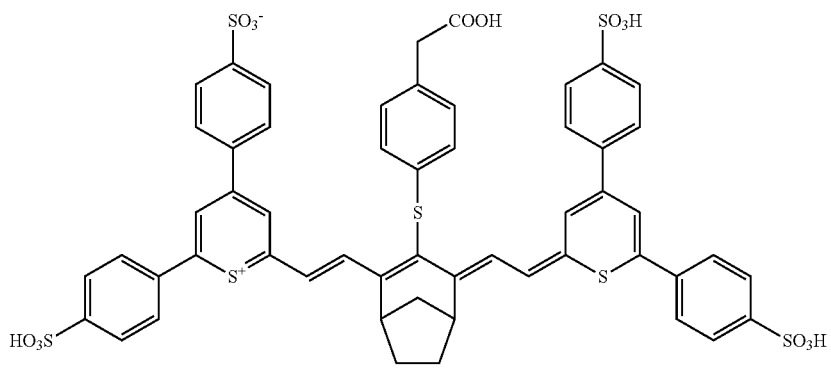
D33
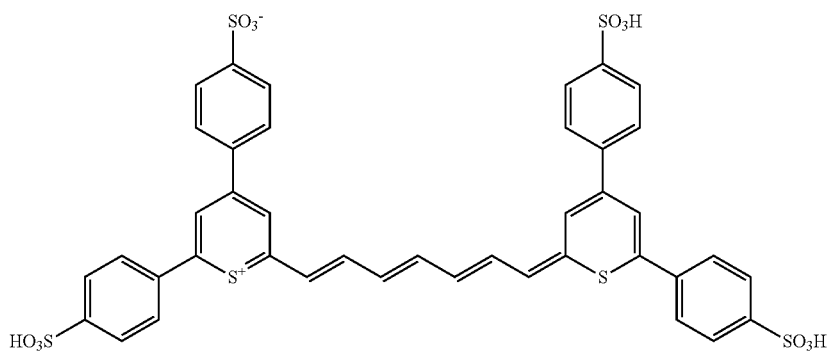

TABLE 4-continued
Exemplary compounds according to this disclosure.
D34 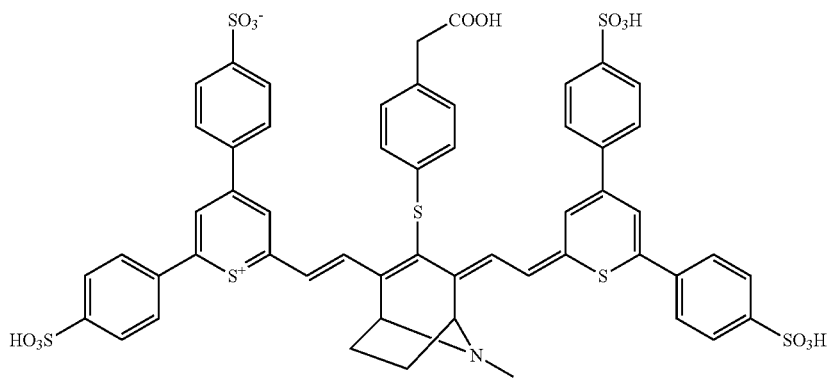
D35 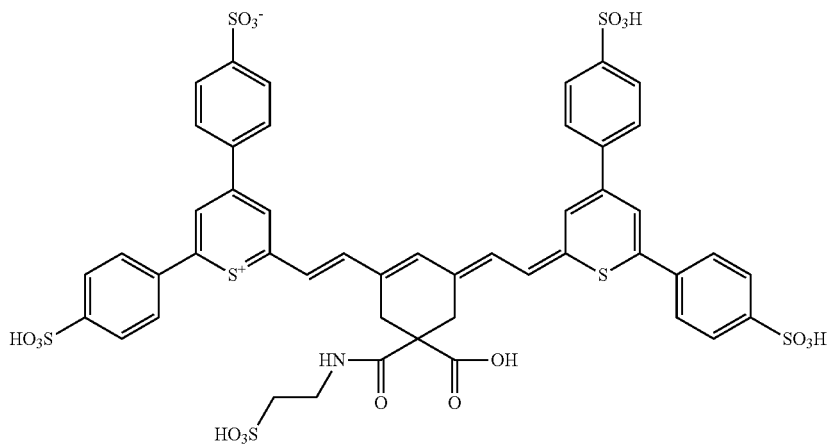
D36 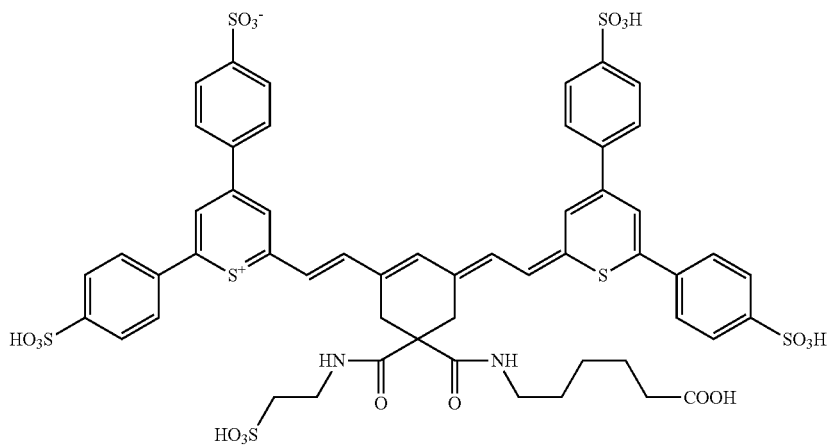
D37 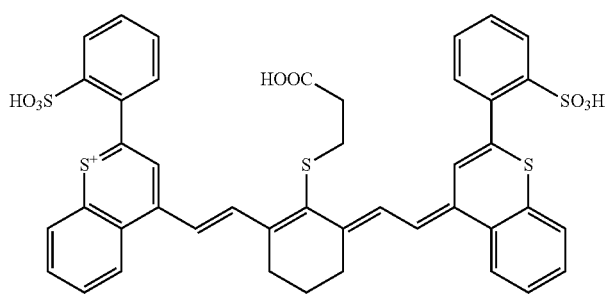 [SMILES: O=C(O)CCSC1=C(/C=C/c2cc(-c3ccccc3S(=O)(=O)O)[s+]c3ccccc23)CCC/C1=C\C=C1/C=C(c2ccccc2S(=O)(=O)O)Sc2ccccc21]

TABLE 4-continued
Exemplary compounds according to this disclosure.
D38 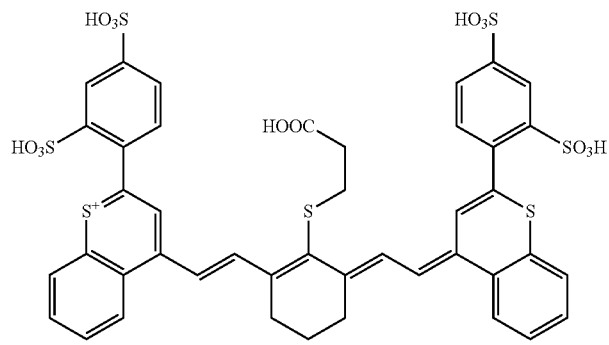 [SMILES: O=C(O)CCSC1=C(/C=C/c2cc(-c3ccc(S(=O)(=O)O)cc3S(=O)(=O)O)[s+]c3ccccc23)CCC/C1=C\C=C1/C=C(c2ccc(S(=O)(=O)O)cc2S(=O)(=O)O)Sc2ccccc21]
D39 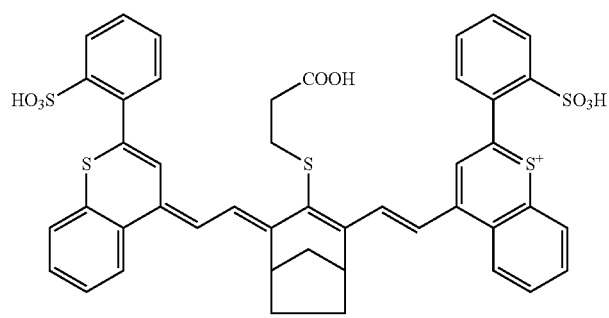 [SMILES: O=C(O)CCSC1=C(/C=C/c2cc(-c3ccccc3S(=O)(=O)O)[s+]c3ccccc23)C2CCC(C2)/C1=C\C=C1/C=C(c2ccccc2S(=O)(=O)O)Sc2ccccc21]
D40 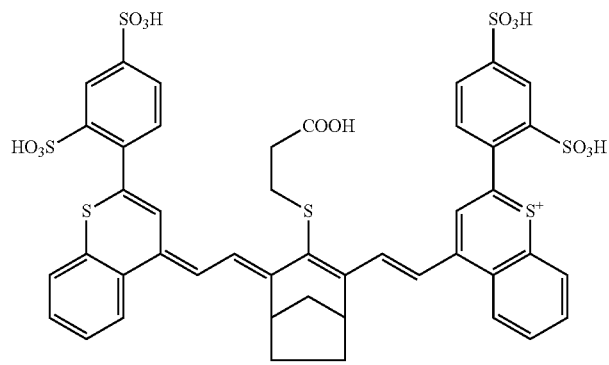
D41 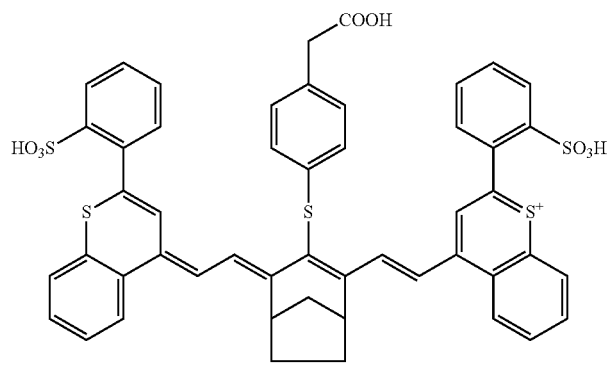

TABLE 4-continued
Exemplary compounds according to this disclosure.
D42
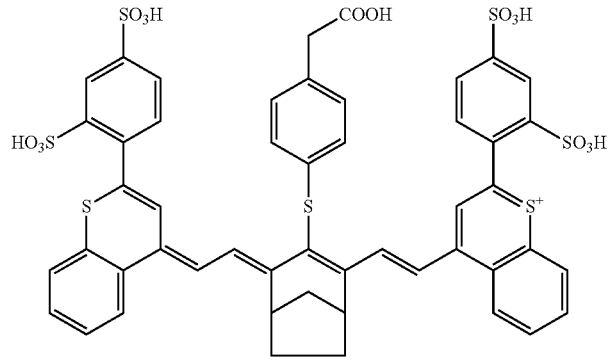 [SMILES: O=C(O)Cc1ccc(SC2=C(/C=C/c3cc(-c4ccc(S(=O)(=O)O)cc4S(=O)(=O)O)[s+]c4ccccc34)C3CCC(C3)/C2=C\C=C2/C=C(c3ccc(S(=O)(=O)O)cc3S(=O)(=O)O)Sc3ccccc32)cc1]
D43
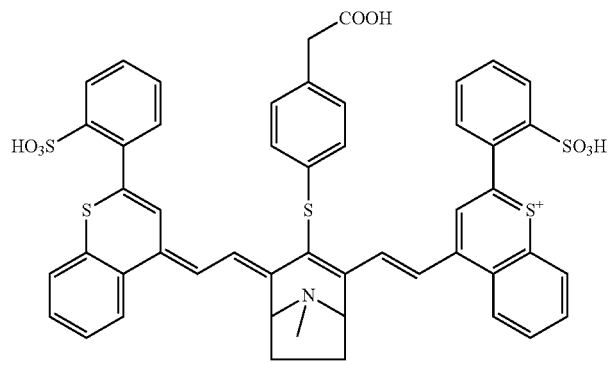 [SMILES: CN1C2CCC1/C(=C\C=C1/C=C(c3ccccc3S(=O)(=O)O)Sc3ccccc31)C(Sc1ccc(CC(=O)O)cc1)=C2/C=C/c1cc(-c2ccccc2S(=O)(=O)O)[s+]c2ccccc12]
D44
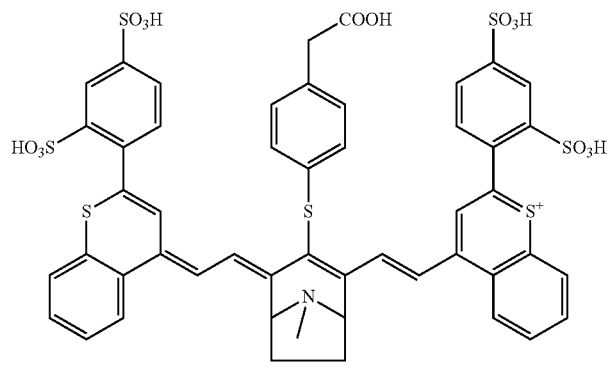 [SMILES: CN1C2CCC1/C(=C\C=C1/C=C(c3ccc(S(=O)(=O)O)cc3S(=O)(=O)O)Sc3ccccc31)C(Sc1ccc(CC(=O)O)cc1)=C2/C=C/c1cc(-c2ccc(S(=O)(=O)O)cc2S(=O)(=O)O)[s+]c2ccccc12]
D45
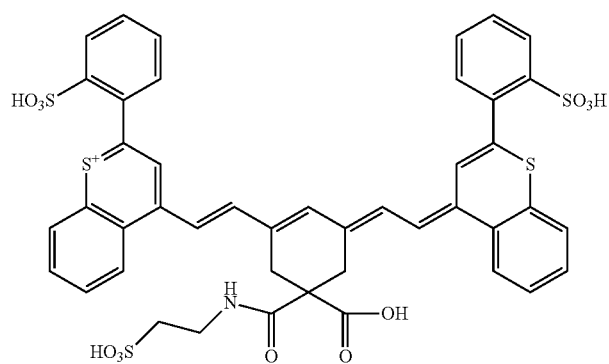 [SMILES: O=C(O)C1(C(=O)NCCS(=O)(=O)O)CC(/C=C/c2cc(-c3ccccc3S(=O)(=O)O)[s+]c3ccccc23)=CC(=C/C=C2\C=C(c3ccccc3S(=O)(=O)O)Sc3ccccc32)/C1]

TABLE 4-continued
Exemplary compounds according to this disclosure.
D46
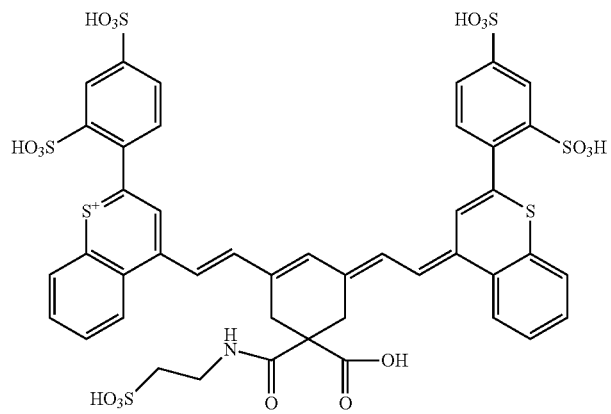 [SMILES: O=C(O)C1(C(=O)NCCS(=O)(=O)O)CC(/C=C/c2cc(-c3ccc(S(=O)(=O)O)cc3S(=O)(=O)O)[s+]c3ccccc23)=CC(=C/C=C2\C=C(c3ccc(S(=O)(=O)O)cc3S(=O)(=O)O)Sc3ccccc32)/C1]
D47
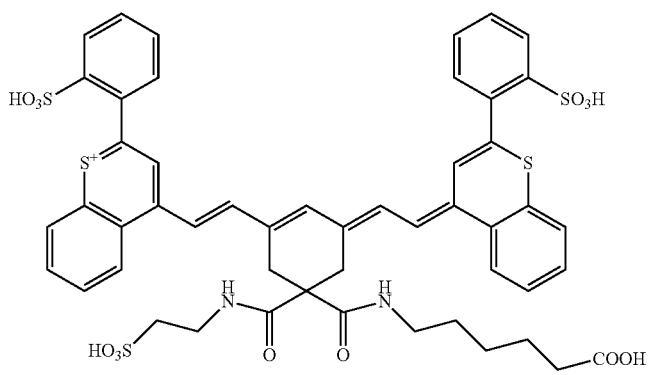 [SMILES: O=C(O)CCCCCNC(=O)C1(C(=O)NCCS(=O)(=O)O)CC(/C=C/c2cc(-c3ccccc3S(=O)(=O)O)[s+]c3ccccc23)=CC(=C/C=C2\C=C(c3ccccc3S(=O)(=O)O)Sc3ccccc32)/C1]
D48
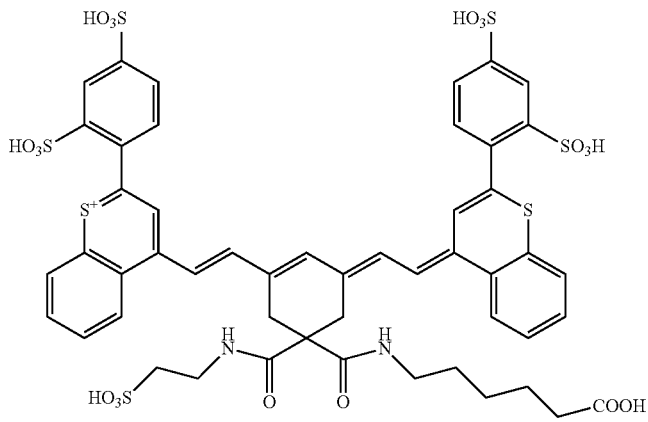 [SMILES: O=C(O)CCCCCNC(=O)C1(C(=O)NCCS(=O)(=O)O)CC(/C=C/c2cc(-c3ccc(S(=O)(=O)O)cc3S(=O)(=O)O)[s+]c3ccccc23)=CC(=C/C=C2\C=C(c3ccc(S(=O)(=O)O)cc3S(=O)(=O)O)Sc3ccccc32)/C1]
D49
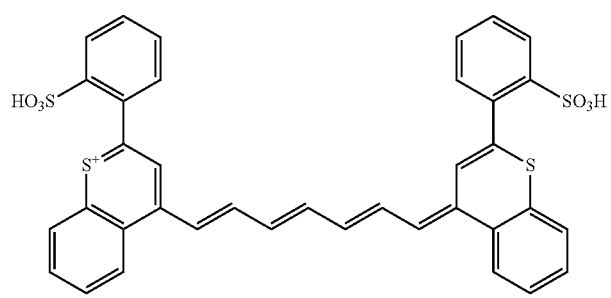 [SMILES: O=S(=O)(O)c1ccccc1C1=C\C(=C/C=C/C=C/C=C/c2cc(-c3ccccc3S(=O)(=O)O)[s+]c3ccccc23)c2ccccc2S1]

TABLE 4-continued
Exemplary compounds according to this disclosure.
D50
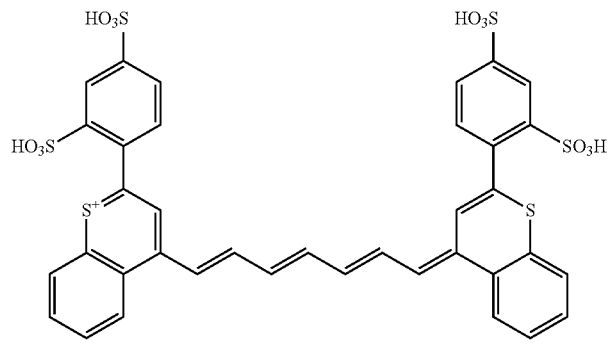 [SMILES: O=S(=O)(O)c1ccc(C2=C\C(=C/C=C/C=C/C=C/c3cc(-c4ccc(S(=O)(=O)O)cc4S(=O)(=O)O)[s+]c4ccccc34)c3ccccc3S2)c(S(=O)(=O)O)c1]
D51
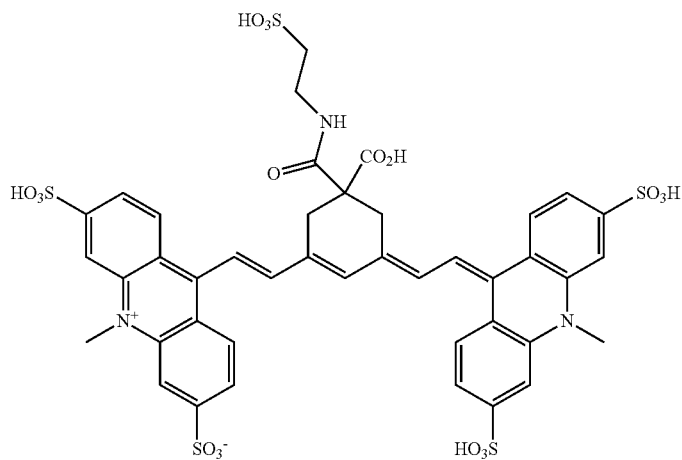
D52
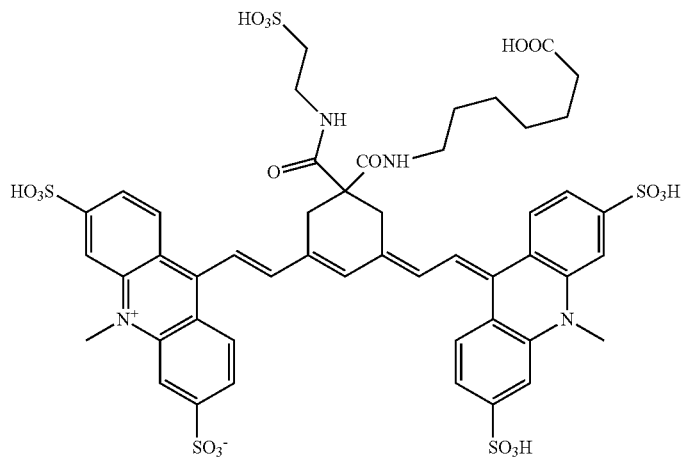
D53
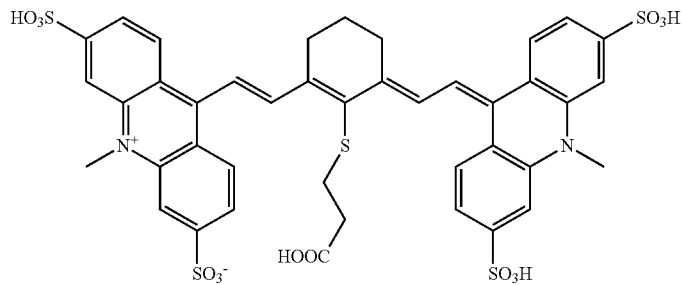

TABLE 4-continued
Exemplary compounds according to this disclosure.
D54
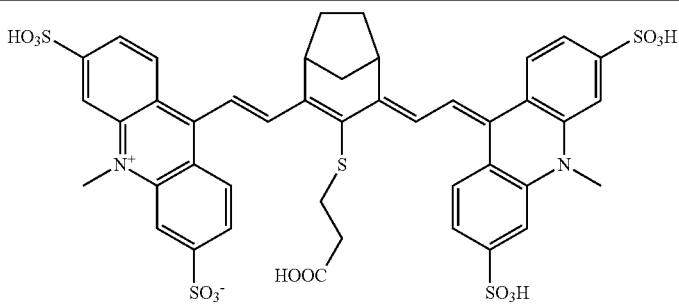
D55
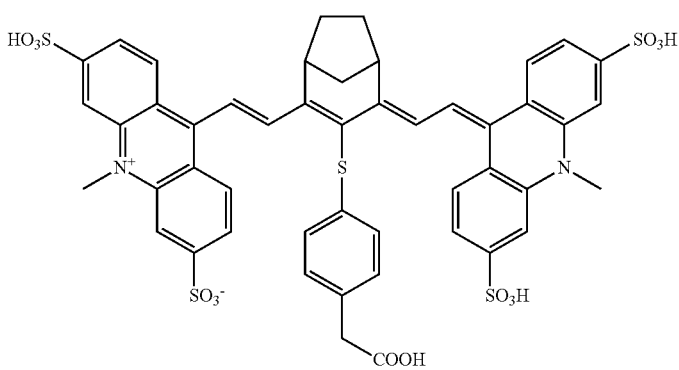
D56
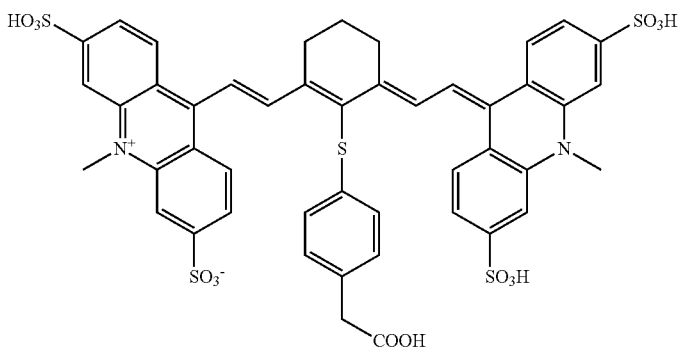
D57
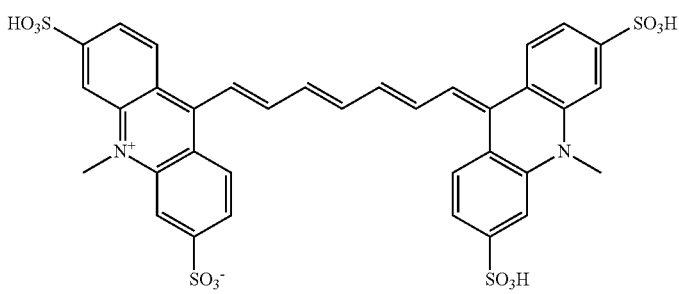
D58
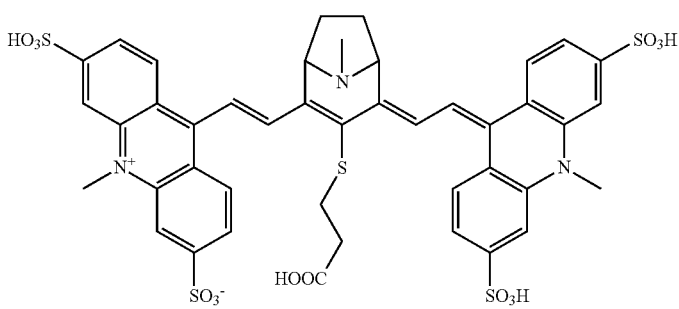

TABLE 4-continued
Exemplary compounds according to this disclosure.
D59
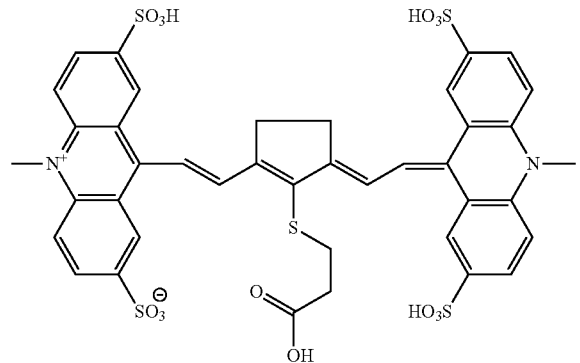
D60
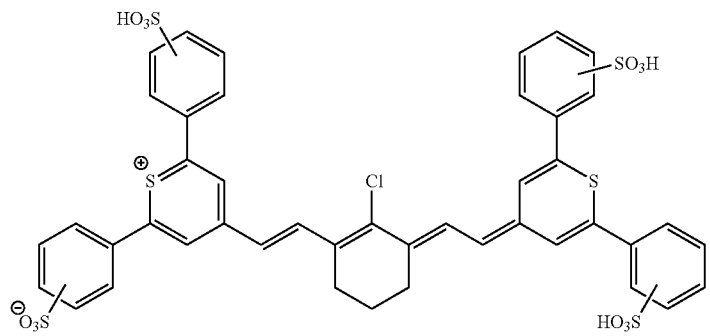
D61
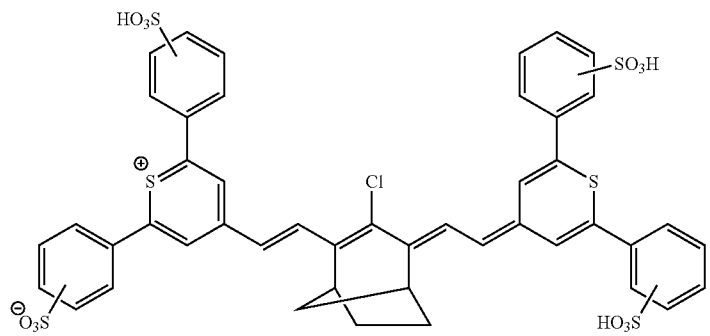
D62
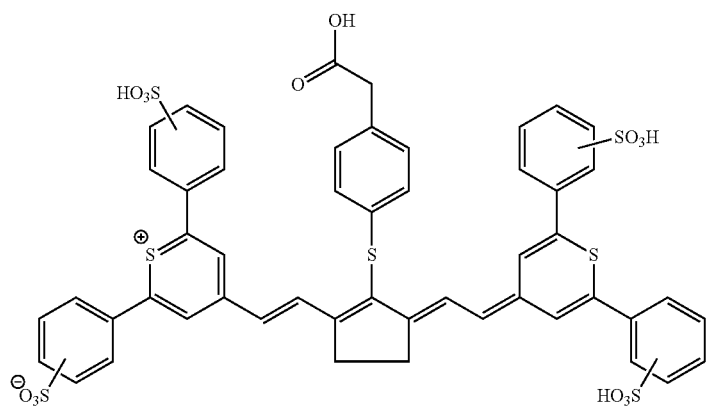

TABLE 4-continued
Exemplary compounds according to this disclosure.
D63
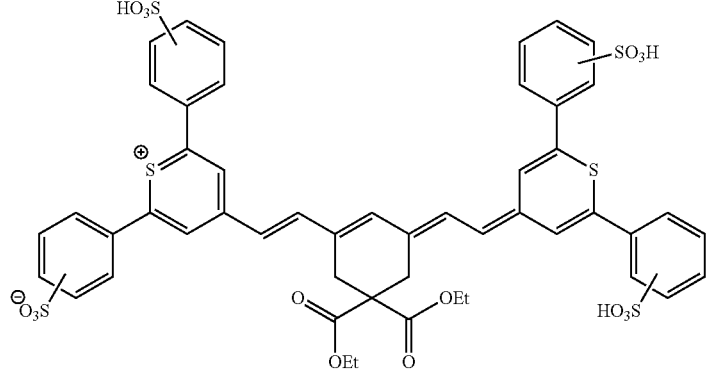
D64
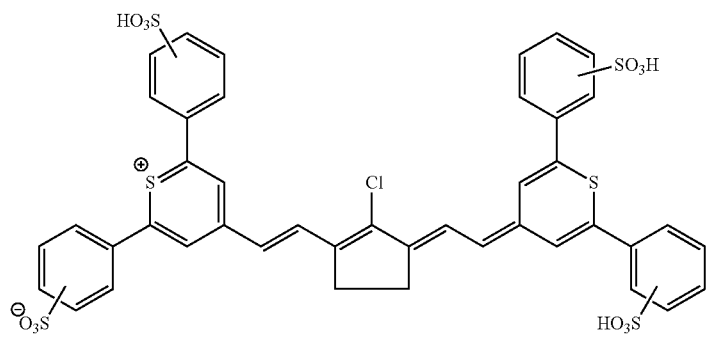
D65
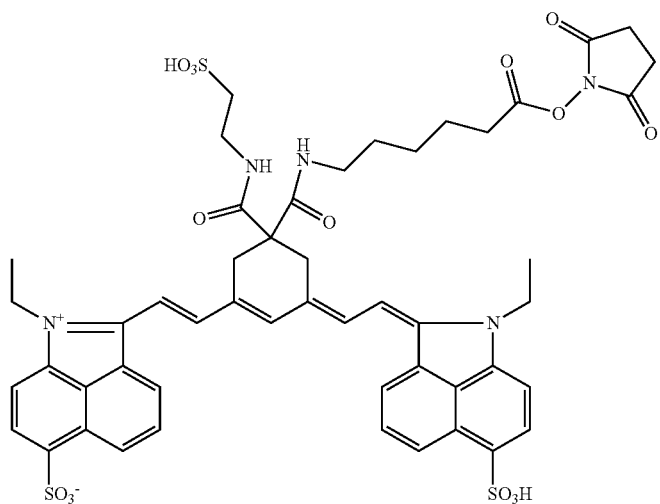

TABLE 4-continued
Exemplary compounds according to this disclosure.
D66
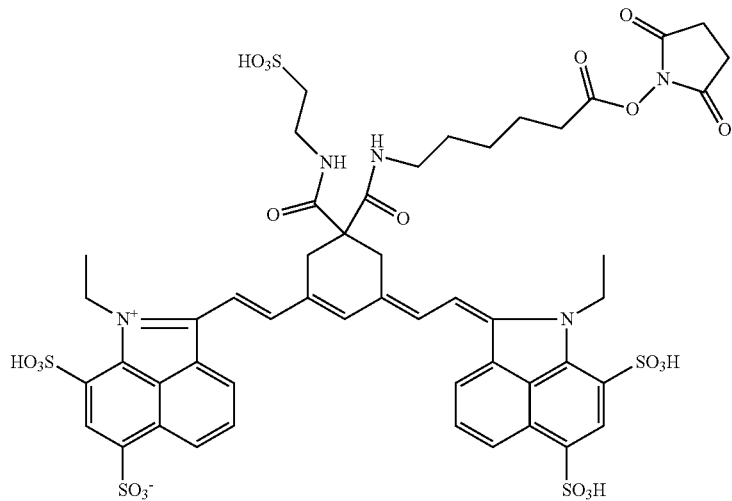
D67
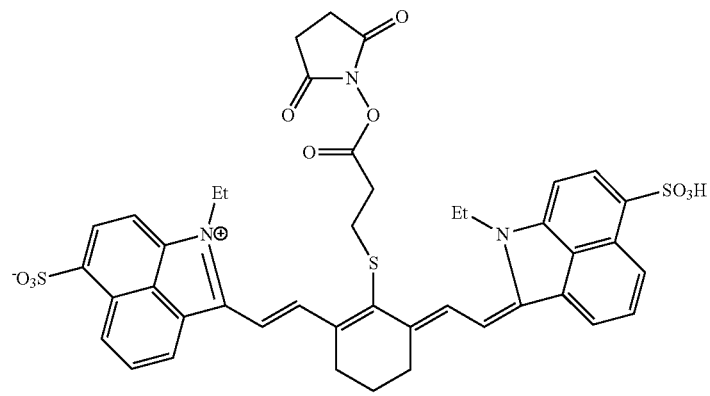
D68
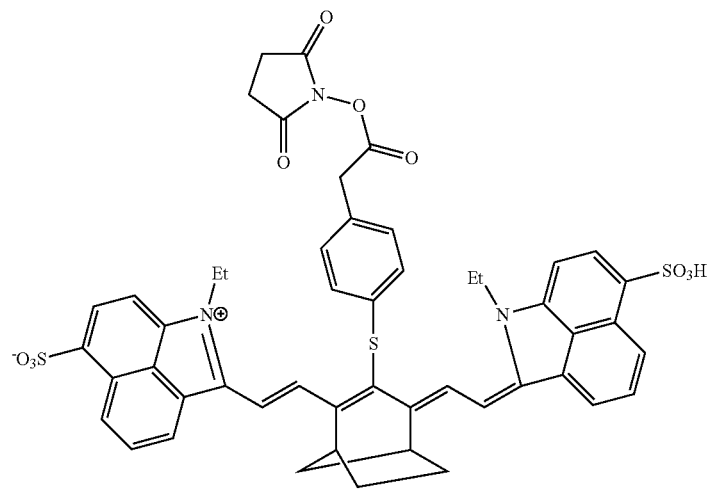

TABLE 4-continued
Exemplary compounds according to this disclosure.
D69
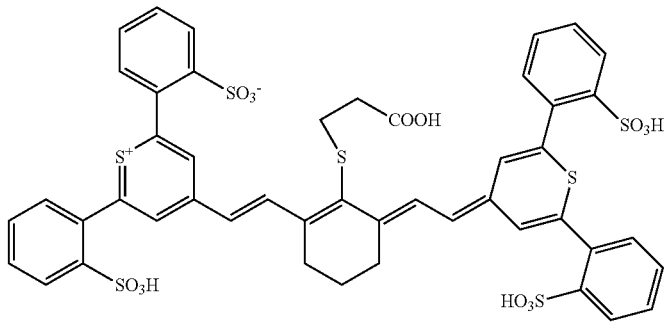
D70
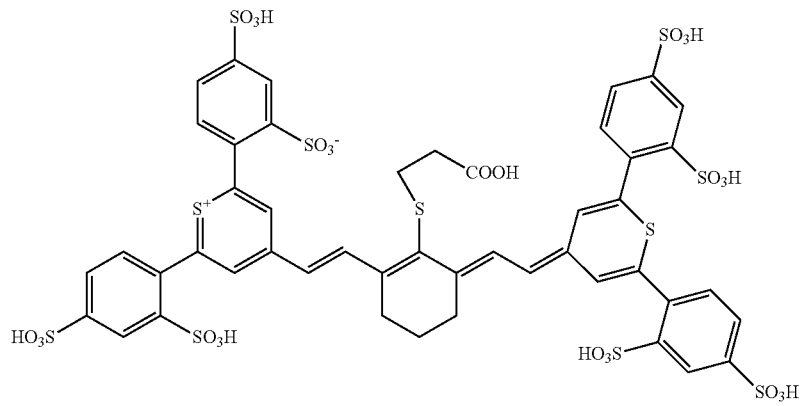
D71
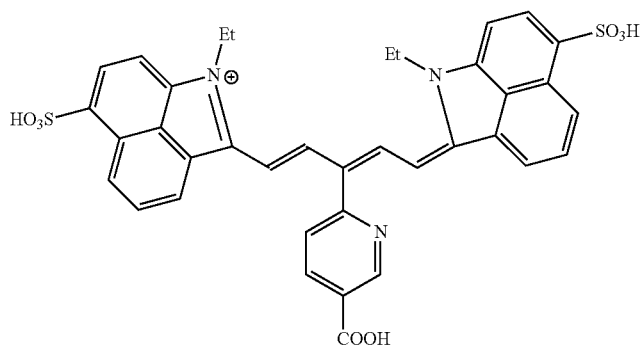 [SMILES: CCn1\c(=C/C=C(/C=C/C2=[N+](CC)c3ccc(S(=O)(=O)O)c4cccc2c34)c2ccc(C(=O)O)cn2)c2cccc3c(S(=O)(=O)O)ccc1c32]
D73
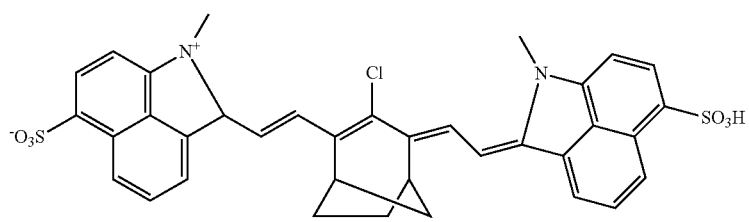

TABLE 4-continued
Exemplary compounds according to this disclosure.
D74
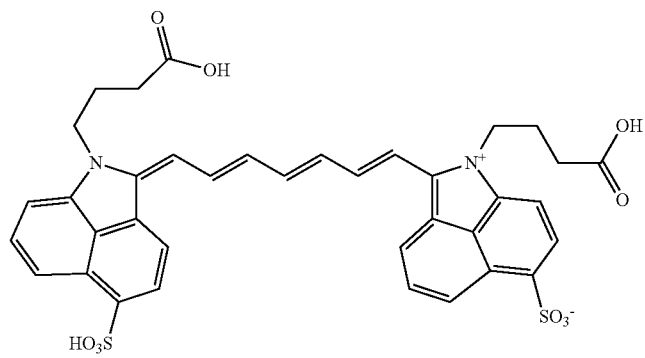
D75
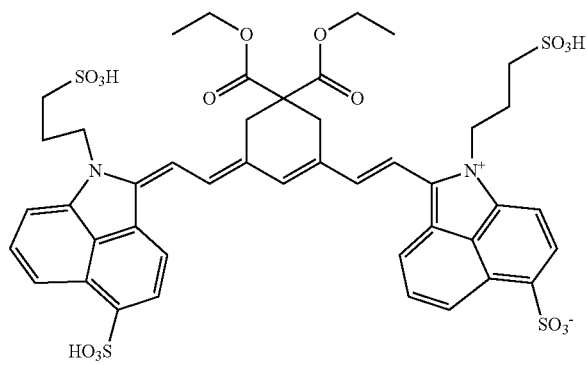
D76
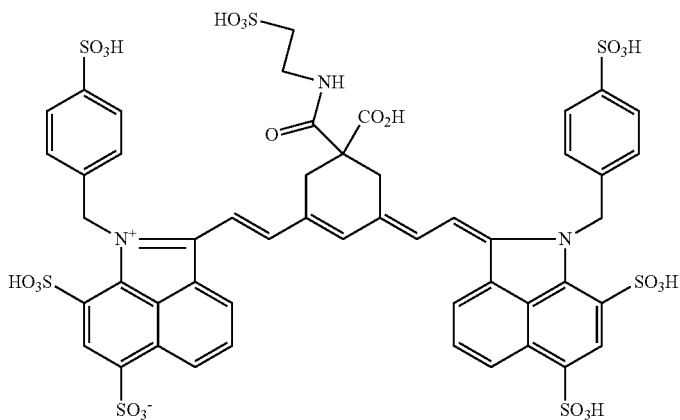
D77
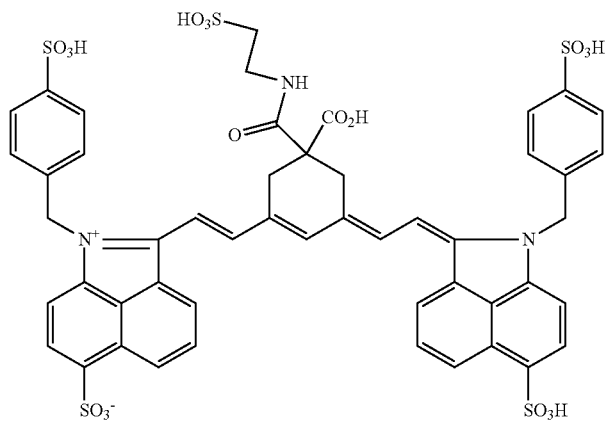

TABLE 4-continued
Exemplary compounds according to this disclosure.
D78
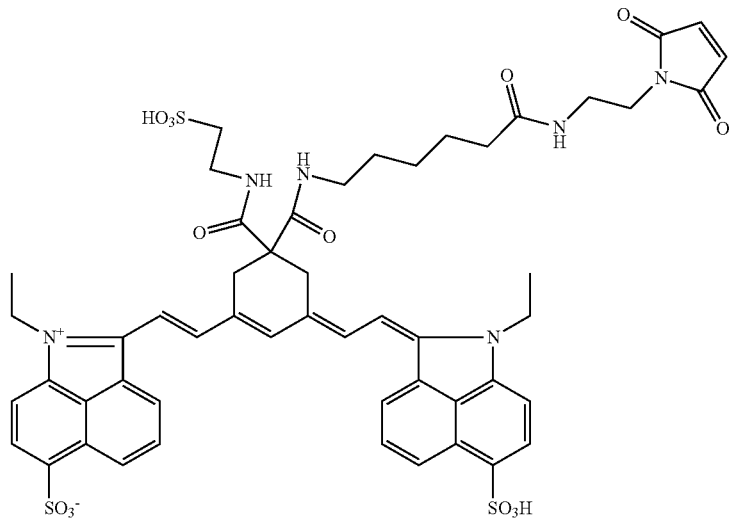
D79
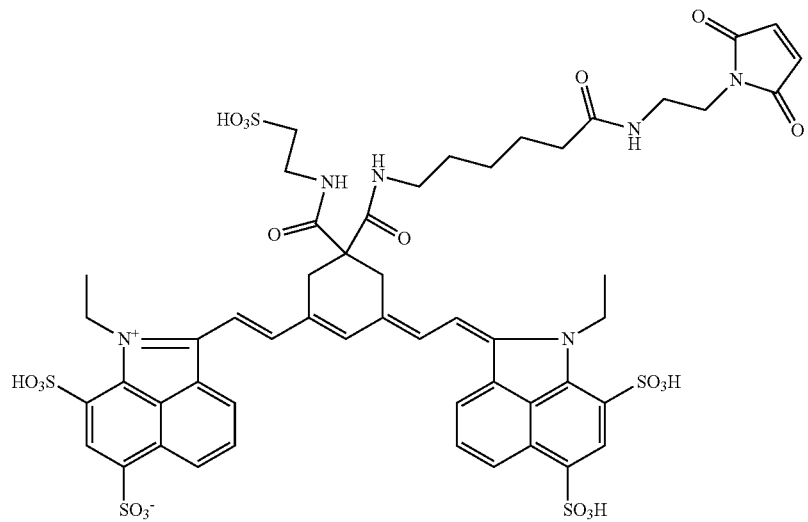
D80
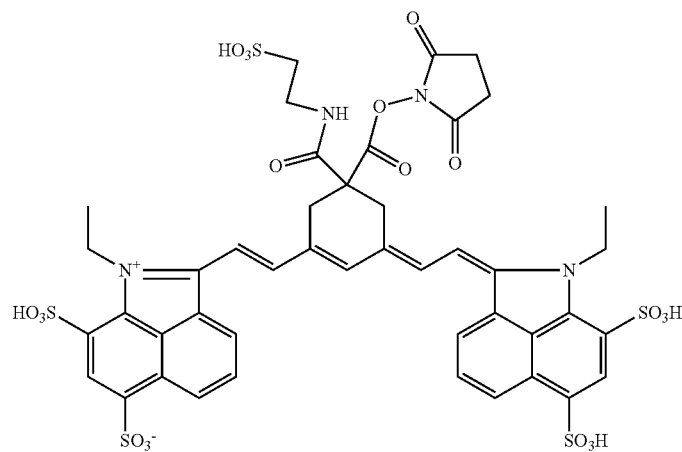

TABLE 4-continued
Exemplary compounds according to this disclosure.
D81
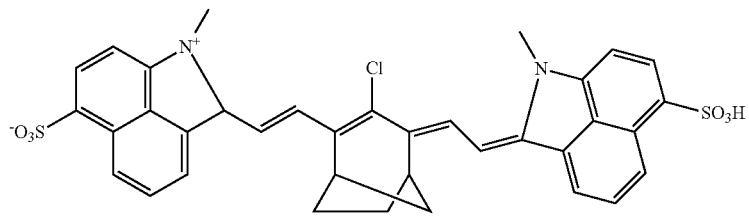
D82
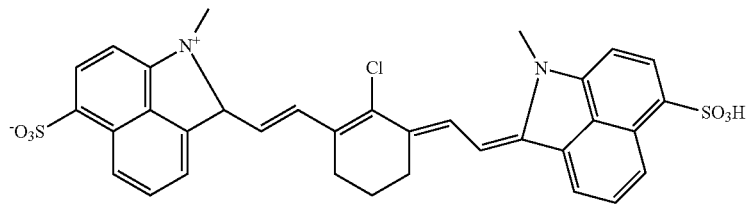
D85
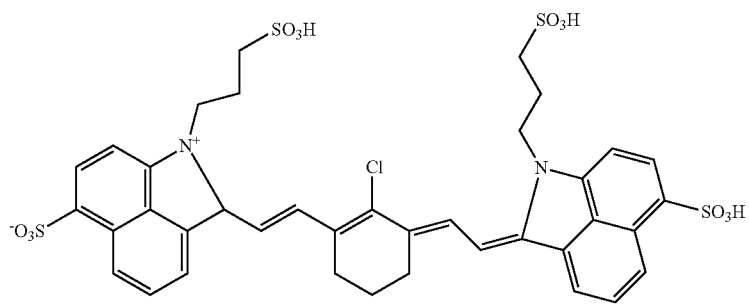
Other exemplary dyes are shown in Table 4B:
TABLE 4B
Additional exemplary compounds according to this disclosure.
D72
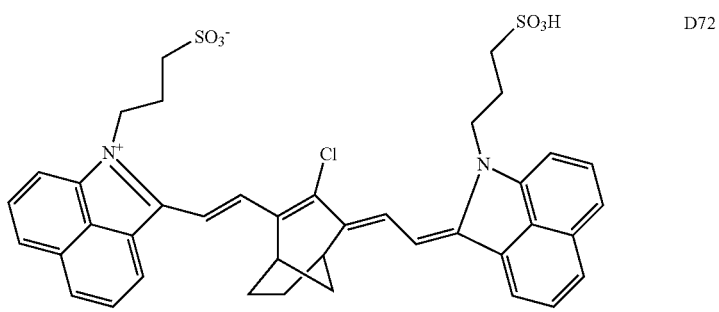
D84
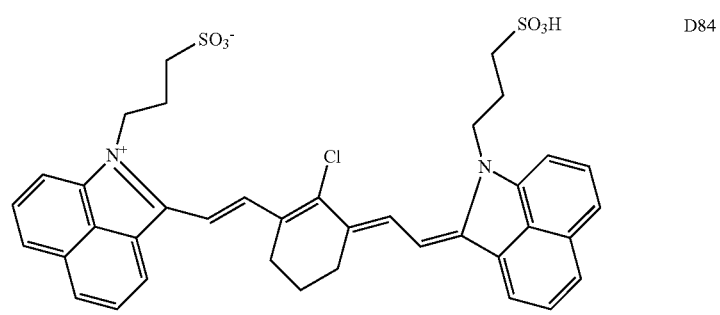

TABLE 4B-continued

Additional exemplary compounds according to this disclosure.

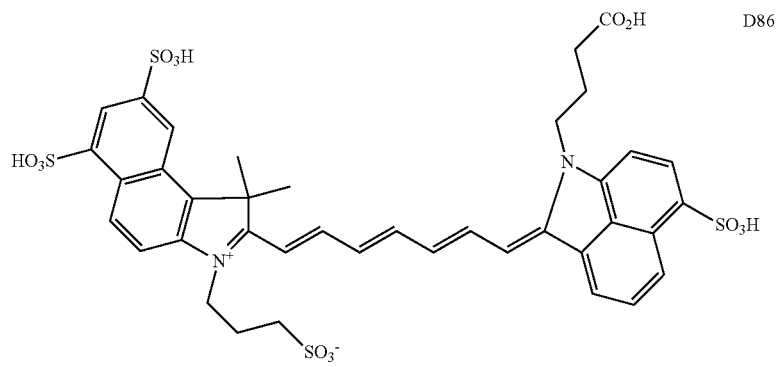
D86

TABLE 5

Exemplary compounds according to this disclosure.

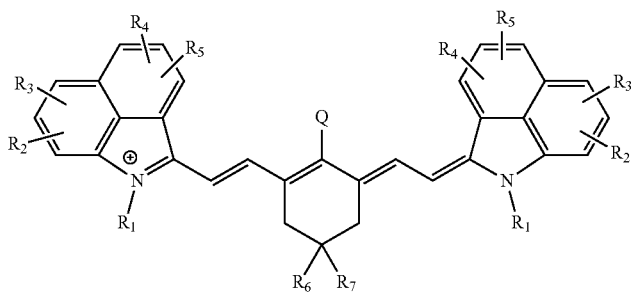

Q = H & VARIATION IN $R_6$, $R_7$

| No | $R_1$ | X | $R_2$ | $R_3$ | $R_4$ | $R_5$ | $R_6$ | Y | $R_7$ | Z | Q |
|---|---|---|---|---|---|---|---|---|---|---|---|
| T5-1 | $(CH_2)_{1-12}$ | H | $SO_3H$ | H | $SO_3H$ | H | COOY | $(CH_2)_{1-6}H$ | CONH-Z | $(CH_2)_{1-6}SO_3H$ | H |
| T5-2 | $(CH_2)_{1-12}$ | $SO_3H$ | H | H | H | H | COOY | $(CH_2)_{1-6}H$ | CONH-Z | $(CH_2)_{1-6}SO_3H$ | H |
| T5-3 | $(CH_2)_{1-12}$ X | H | $SO_3H$ | $SO_3H$ | H | H | COOY | $(CH_2)_{1-6}H$ | CONH-Z | $(CH_2)_{1-6}SO_3H$ | H |
| T5-4 | $(CH_2)_{1-12}$ X | H | H | H | $SO_3H$ | $SO_3H$ | COOY | $(CH_2)_{1-6}H$ | CONH-Z | $(CH_2)_{1-6}SO_3H$ | H |
| T5-5 | $(CH_2)_{1-12}$ X | $SO_3H$ | H | H | $SO_3H$ | $SO_3H$ | COOY | $(CH_2)_{1-6}H$ | CONH-Z | $(CH_2)_{1-6}SO_3H$ | H |
| T5-6 | $(CH_2)_{1-12}$ X | $SO_3H$ | $SO_3H$ | $SO_3H$ | H | H | COOY | $(CH_2)_{1-6}H$ | CONH-Z | $(CH_2)_{1-6}SO_3H$ | H |
| T5-7 | $(CH_2)_{1-12}$ X | $SO_3H$ | $SO_3H$ | $SO_3H$ | $SO_3H$ | $SO_3H$ | COOY | $(CH_2)_{1-6}H$ | CONH-Z | $(CH_2)_{1-6}SO_3H$ | H |
| T5-8 | $(CH_2)_{1-12}$ X | H | $SO_3H$ | H | $SO_3H$ | H | COOY | H | CONH-Z | $(CH_2)_{1-6}SO_3H$ | H |
| T5-9 | $(CH_2)_{1-12}$ X | $SO_3H$ | H | H | H | H | COOY | H | CONH-Z | $(CH_2)_{1-6}SO_3H$ | H |
| T5-10 | $(CH_2)_{1-12}$ X | H | $SO_3H$ | $SO_3H$ | H | H | COOY | H | CONH-Z | $(CH_2)_{1-6}SO_3H$ | H |
| T5-11 | $(CH_2)_{1-12}$ X | H | H | H | $SO_3H$ | $SO_3H$ | COOY | H | CONH-Z | $(CH_2)_{1-6}SO_3H$ | H |
| T5-12 | $(CH_2)_{1-12}$ X | $SO_3H$ | H | H | $SO_3H$ | $SO_3H$ | COOY | H | CONH-Z | $(CH_2)_{1-6}SO_3H$ | H |
| T5-13 | $(CH_2)_{1-12}$ X | $SO_3H$ | $SO_3H$ | $SO_3H$ | H | H | COOY | H | CONH-Z | $(CH_2)_{1-6}SO_3H$ | H |
| T5-14 | $(CH_2)_{1-12}$ X | $SO_3H$ | $SO_3H$ | $SO_3H$ | $SO_3H$ | $SO_3H$ | COOY | H | CONH-Z | $(CH_2)_{1-6}SO_3H$ | H |
| T5-15 | $(CH_2)_{1-12}$ X | H | $SO_3H$ | H | $SO_3H$ | H | COOY | NSuccinimidyl | CONH-Z | $(CH_2)_{1-6}SO_3H$ | H |
| T5-16 | $(CH_2)_{1-12}$ X | $SO_3H$ | H | H | H | H | COOY | NSuccinimidyl | CONH-Z | $(CH_2)_{1-6}SO_3H$ | H |
| T5-17 | $(CH_2)_{1-12}$ X | H | $SO_3H$ | $SO_3H$ | H | H | COOY | NSuccinimidyl | CONH-Z | $(CH_2)_{1-6}SO_3H$ | H |
| T5-18 | $(CH_2)_{1-12}$ X | H | H | H | $SO_3H$ | $SO_3H$ | COOY | NSuccinimidyl | CONH-Z | $(CH_2)_{1-6}SO_3H$ | H |
| T5-19 | $(CH_2)_{1-12}$ X | $SO_3H$ | H | H | $SO_3H$ | $SO_3H$ | COOY | NSuccinimidyl | CONH-Z | $(CH_2)_{1-6}SO_3H$ | H |
| T5-20 | $(CH_2)_{1-12}$ X | $SO_3H$ | $SO_3H$ | $SO_3H$ | H | H | COOY | NSuccinimidyl | CONH-Z | $(CH_2)_{1-6}SO_3H$ | H |
| T5-21 | $(CH_2)_{1-12}$ X | $SO_3H$ | $SO_3H$ | $SO_3H$ | $SO_3H$ | $SO_3H$ | COOY | NSuccinimidyl | CONH-Z | $(CH_2)_{1-6}SO_3H$ | H |
| T5-22 | $(CH_2)_{1-12}$ X | H | $SO_3H$ | H | $SO_3H$ | H | CONH—Y | $(CH_2)_{1-6}COOH$ | CONH-Z | $(CH_2)_{1-6}SO_3H$ | H |
| T5-23 | $(CH_2)_{1-12}$ X | $SO_3H$ | H | H | H | H | CONH—Y | $(CH_2)_{1-6}COOH$ | CONH-Z | $(CH_2)_{1-6}SO_3H$ | H |
| T5-24 | $(CH_2)_{1-12}$ X | H | $SO_3H$ | $SO_3H$ | H | H | CONH—Y | $(CH_2)_{1-6}COOH$ | CONH-Z | $(CH_2)_{1-6}SO_3H$ | H |
| T5-25 | $(CH_2)_{1-12}$ X | H | H | H | $SO_3H$ | $SO_3H$ | CONH—Y | $(CH_2)_{1-6}COOH$ | CONH-Z | $(CH_2)_{1-6}SO_3H$ | H |
| T5-26 | $(CH_2)_{1-12}$ X | $SO_3H$ | H | H | $SO_3H$ | $SO_3H$ | CONH—Y | $(CH_2)_{1-6}COOH$ | CONH-Z | $(CH_2)_{1-6}SO_3H$ | H |
| T5-27 | $(CH_2)_{1-12}$ X | $SO_3H$ | $SO_3H$ | $SO_3H$ | H | H | CONH—Y | $(CH_2)_{1-6}COOH$ | CONH-Z | $(CH_2)_{1-6}SO_3H$ | H |
| T5-28 | $(CH_2)_{1-12}$ X | $SO_3H$ | $SO_3H$ | $SO_3H$ | $SO_3H$ | $SO_3H$ | CONH—Y | $(CH_2)_{1-6}COOH$ | CONH-Z | $(CH_2)_{1-6}SO_3H$ | H |
| T5-29 | $(CH_2)_{1-12}$ X | H | $SO_3H$ | H | $SO_3H$ | H | CONH—Y | $(CH_2)_{1-6}COO$—SU | CONH-Z | $(CH_2)_{1-6}SO_3H$ | H |
| T5-30 | $(CH_2)_{1-12}$ X | $SO_3H$ | H | H | H | H | CONH—Y | $(CH_2)_{1-6}COO$—SU | CONH-Z | $(CH_2)_{1-6}SO_3H$ | H |
| T5-31 | $(CH_2)_{1-12}$ X | H | $SO_3H$ | $SO_3H$ | H | H | CONH—Y | $(CH_2)_{1-6}COO$—SU | CONH-Z | $(CH_2)_{1-6}SO_3H$ | H |
| T5-32 | $(CH_2)_{1-12}$ X | H | H | H | $SO_3H$ | $SO_3H$ | CONH—Y | $(CH_2)_{1-6}COO$—SU | CONH-Z | $(CH_2)_{1-6}SO_3H$ | H |
| T5-33 | $(CH_2)_{1-12}$ X | $SO_3H$ | H | H | $SO_3H$ | $SO_3H$ | CONH—Y | $(CH_2)_{1-6}COO$—SU | CONH-Z | $(CH_2)_{1-6}SO_3H$ | H |
| T5-34 | $(CH_2)_{1-12}$ X | $SO_3H$ | $SO_3H$ | $SO_3H$ | H | H | CONH—Y | $(CH_2)_{1-6}COO$—SU | CONH-Z | $(CH_2)_{1-6}SO_3H$ | H |
| T5-35 | $(CH_2)_{1-12}$ X | $SO_3H$ | $SO_3H$ | $SO_3H$ | $SO_3H$ | $SO_3H$ | CONH—Y | $(CH_2)_{1-6}COO$—SU | CONH-Z | $(CH_2)_{1-6}SO_3H$ | H |

TABLE 5-continued

Exemplary compounds according to this disclosure.

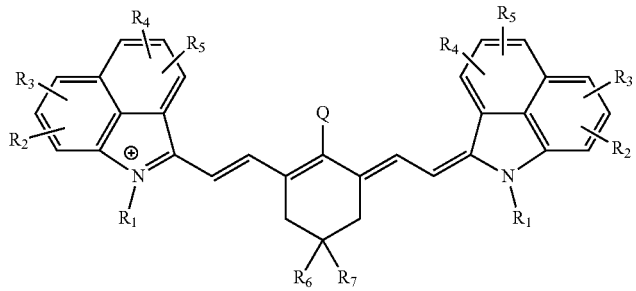

Q = H & VARIATION IN R6, R7

| No | R1 | X | R2 | R3 | R4 | R5 | R6 | Y | R7 | Z | Q |
|---|---|---|---|---|---|---|---|---|---|---|---|
| T5-36 | $(CH_2)_{1-12}$ X | H | $SO_3H$ | H | $SO_3H$ | H | CONH—Y | $(CH_2)_{1-6}$CO—Mal | CONH-Z | $(CH_2)_{1-6}SO_3H$ | H |
| T5-37 | $(CH_2)_{1-12}$ X | $SO_3H$ | H | H | H | H | CONH—Y | $(CH_2)_{1-6}$CO—Mal | CONH-Z | $(CH_2)_{1-6}SO_3H$ | H |
| T5-38 | $(CH_2)_{1-12}$ X | $SO_3H$ | $SO_3H$ | H | H | H | CONH—Y | $(CH_2)_{1-6}$CO—Mal | CONH-Z | $(CH_2)_{1-6}SO_3H$ | H |
| T5-39 | $(CH_2)_{1-12}$ X | H | H | H | $SO_3H$ | $SO_3H$ | CONH—Y | $(CH_2)_{1-6}$CO—Mal | CONH-Z | $(CH_2)_{1-6}SO_3H$ | H |
| T5-40 | $(CH_2)_{1-12}$ X | $SO_3H$ | H | H | $SO_3H$ | $SO_3H$ | CONH—Y | $(CH_2)_{1-6}$CO—Mal | CONH-Z | $(CH_2)_{1-6}SO_3H$ | H |
| T5-41 | $(CH_2)_{1-12}$ X | $SO_3H$ | $SO_3H$ | $SO_3H$ | H | H | CONH—Y | $(CH_2)_{1-6}$CO—Mal | CONH-Z | $(CH_2)_{1-6}SO_3H$ | H |
| T5-42 | $(CH_2)_{1-12}$ X | $SO_3H$ | $SO_3H$ | $SO_3H$ | $SO_3H$ | $SO_3H$ | CONH—Y | $(CH_2)_{1-6}$CO—Mal | CONH-Z | $(CH_2)_{1-6}SO_3H$ | H |
| T5-43 | $(CH_2)_{1-6}$ Ph-$SO_3H$ | $SO_3H$ | H | $SO_3H$ | H | H | CONH—Y | $(CH_2)_{1-6}$COOH | CONH-Z | $(CH_2)_{1-6}SO_3H$ | H |
| T5-44 | $(CH_2)_{1-6}$ Ph-$SO_3H$ | H | H | H | H | H | CONH—Y | $(CH_2)_{1-6}$COOH | CONH-Z | $(CH_2)_{1-6}SO_3H$ | H |
| T5-45 | $(CH_2)_{1-6}$ Ph-$SO_3H$ | $SO_3H$ | $SO_3H$ | H | H | H | CONH—Y | $(CH_2)_{1-6}$COOH | CONH-Z | $(CH_2)_{1-6}SO_3H$ | H |
| T5-46 | $(CH_2)_{1-6}$ Ph-$SO_3H$ | H | H | H | $SO_3H$ | $SO_3H$ | CONH—Y | $(CH_2)_{1-6}$COOH | CONH-Z | $(CH_2)_{1-6}SO_3H$ | H |
| T5-47 | $(CH_2)_{1-6}$ Ph-$SO_3H$ | $SO_3H$ | H | H | $SO_3H$ | $SO_3H$ | CONH—Y | $(CH_2)_{1-6}$COOH | CONH-Z | $(CH_2)_{1-6}SO_3H$ | H |
| T5-48 | $(CH_2)_{1-6}$ Ph-$SO_3H$ | $SO_3H$ | $SO_3H$ | $SO_3H$ | H | H | CONH—Y | $(CH_2)_{1-6}$COOH | CONH-Z | $(CH_2)_{1-6}SO_3H$ | H |
| T5-49 | $(CH_2)_{1-6}$ Ph-$SO_3H$ | $SO_3H$ | $SO_3H$ | $SO_3H$ | $SO_3H$ | $SO_3H$ | CONH—Y | $(CH_2)_{1-6}$COOH | CONH-Z | $(CH_2)_{1-6}SO_3H$ | H |
| T5-50 | $(CH_2)_{1-6}$ Ph-$SO_3H$ | $SO_3H$ | H | $SO_3H$ | H | H | CONH—Y | $(CH_2)_{1-6}$CO—SU | CONH-Z | $(CH_2)_{1-6}SO_3H$ | H |
| T5-51 | $(CH_2)_{1-6}$ Ph-$SO_3H$ | H | H | H | H | H | CONH—Y | $(CH_2)_{1-6}$CO—SU | CONH-Z | $(CH_2)_{1-6}SO_3H$ | H |
| T5-52 | $(CH_2)_{1-6}$ Ph-$SO_3H$ | $SO_3H$ | $SO_3H$ | H | H | H | CONH—Y | $(CH_2)_{1-6}$CO—SU | CONH-Z | $(CH_2)_{1-6}SO_3H$ | H |
| T5-53 | $(CH_2)_{1-6}$ Ph-$SO_3H$ | H | H | H | $SO_3H$ | $SO_3H$ | CONH—Y | $(CH_2)_{1-6}$CO—SU | CONH-Z | $(CH_2)_{1-6}SO_3H$ | H |
| T5-54 | $(CH_2)_{1-6}$ Ph-$SO_3H$ | $SO_3H$ | H | H | $SO_3H$ | $SO_3H$ | CONH—Y | $(CH_2)_{1-6}$CO—SU | CONH-Z | $(CH_2)_{1-6}SO_3H$ | H |
| T5-55 | $(CH_2)_{1-6}$ Ph-$SO_3H$ | $SO_3H$ | $SO_3H$ | $SO_3H$ | H | H | CONH—Y | $(CH_2)_{1-6}$CO—SU | CONH-Z | $(CH_2)_{1-6}SO_3H$ | H |
| T5-56 | $(CH_2)_{1-6}$ Ph-$SO_3H$ | $SO_3H$ | $SO_3H$ | $SO_3H$ | $SO_3H$ | $SO_3H$ | CONH—Y | $(CH_2)_{1-6}$CO—SU | CONH-Z | $(CH_2)_{1-6}SO_3H$ | H |
| T5-57 | $(CH_2)_{1-6}$ Ph-$SO_3H$ | $SO_3H$ | H | $SO_3H$ | H | H | CONH—Y | $(CH_2)_{1-6}$CO—Mal | CONH-Z | $(CH_2)_{1-6}SO_3H$ | H |
| T5-58 | $(CH_2)_{1-6}$ Ph-$SO_3H$ | H | H | H | H | H | CONH—Y | $(CH_2)_{1-6}$CO—Mal | CONH-Z | $(CH_2)_{1-6}SO_3H$ | H |
| T5-59 | $(CH_2)_{1-6}$ Ph-$SO_3H$ | $SO_3H$ | $SO_3H$ | H | H | H | CONH—Y | $(CH_2)_{1-6}$CO—Mal | CONH-Z | $(CH_2)_{1-6}SO_3H$ | H |
| T5-60 | $(CH_2)_{1-6}$ Ph-$SO_3H$ | H | H | H | $SO_3H$ | $SO_3H$ | CONH—Y | $(CH_2)_{1-6}$CO—Mal | CONH-Z | $(CH_2)_{1-6}SO_3H$ | H |
| T5-61 | $(CH_2)_{1-6}$ Ph-$SO_3H$ | $SO_3H$ | H | H | $SO_3H$ | $SO_3H$ | CONH—Y | $(CH_2)_{1-6}$CO—Mal | CONH-Z | $(CH_2)_{1-6}SO_3H$ | H |
| T5-62 | $(CH_2)_{1-6}$ Ph-$SO_3H$ | $SO_3H$ | $SO_3H$ | $SO_3H$ | H | H | CONH—Y | $(CH_2)_{1-6}$CO—Mal | CONH-Z | $(CH_2)_{1-6}SO_3H$ | H |
| T5-63 | $(CH_2)_{1-6}$ Ph-$SO_3H$ | $SO_3H$ | $SO_3H$ | $SO_3H$ | $SO_3H$ | $SO_3H$ | CONH—Y | $(CH_2)_{1-6}$CO—Mal | CONH-Z | $(CH_2)_{1-6}SO_3H$ | H |

OSu = N-Hydroxysuccinimidyl; MAL = N-(2-(N-maleimido)-ethyl)-amide

TABLE 6

Exemplary compounds according to this disclosure.

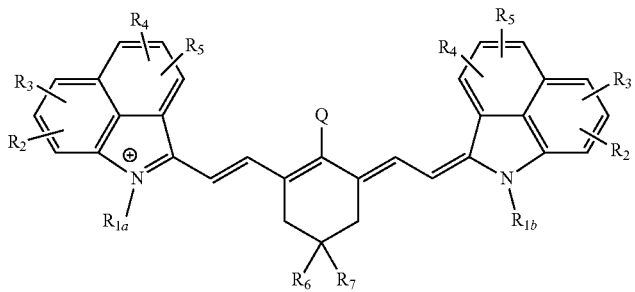

Variation in Q when R6 = R7 = H

| No | R1a = $(CH_2)_{1-12}$— | R1b = $(CH_2)_{1-12}$— | R2 | R3 | R4 | R5 | R6 | Y | R7 | Z | Q |
|---|---|---|---|---|---|---|---|---|---|---|---|
| T6-1 | COOH | $SO_3H$ | $SO_3H$ | H | $SO_3H$ | H | H | H | — | | H |
| T6-2 | COOH | $SO_3H$ | H | H | H | H | H | H | | | H |
| T6-3 | COOH | $SO_3H$ | $SO_3H$ | $SO_3H$ | H | H | H | H | | | H |

TABLE 6-continued

Exemplary compounds according to this disclosure.

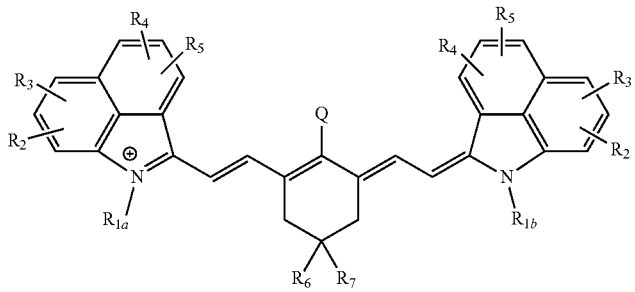

Variation in Q when $R_6 = R_7 = H$

| No | R1a = $(CH_2)_{1-12}$— | R1b = $(CH_2)_{1-12}$— | $R_2$ | $R_3$ | $R_4$ | $R_5$ | $R_6$ | Y | $R_7$ | Z | Q |
|---|---|---|---|---|---|---|---|---|---|---|---|
| T6-4 | COOH | H | H | H | $SO_3H$ | $SO_3H$ | H | | H | | H |
| T6-5 | COOH | $SO_3H$ | H | H | $SO_3H$ | $SO_3H$ | H | | H | | H |
| T6-6 | COOH | H | $SO_3H$ | $SO_3H$ | H | H | H | | H | | H |
| T6-7 | COOH | $SO_3H$ | $SO_3H$ | $SO_3H$ | $SO_3H$ | $SO_3H$ | H | | H | | H |
| T6-8 | COOH | $SO_3H$ | $SO_3H$ | H | $SO_3H$ | H | H | | H | — | Cl |
| T6-9 | COOH | $SO_3H$ | H | H | H | H | H | | H | | Cl |
| T6-10 | COOH | $SO_3H$ | $SO_3H$ | $SO_3H$ | H | H | H | | H | | Cl |
| T6-11 | COOH | H | H | H | $SO_3H$ | $SO_3H$ | H | | H | | Cl |
| T6-12 | COOH | $SO_3H$ | H | H | $SO_3H$ | $SO_3H$ | H | | H | | Cl |
| T6-13 | COOH | H | $SO_3H$ | $SO_3H$ | H | H | H | | H | | Cl |
| T6-14 | COOH | $SO_3H$ | $SO_3H$ | $SO_3H$ | $SO_3H$ | $SO_3H$ | H | | H | | Cl |
| T6-15 | COOH | $SO_3H$ | $SO_3H$ | H | $SO_3H$ | H | H | | H | — | $S(CH_2)_{1-6}SO_3H$ |
| T6-16 | COOH | $SO_3H$ | H | H | H | H | H | | H | | $S(CH_2)_{1-6}SO_3H$ |
| T6-17 | COOH | $SO_3H$ | $SO_3H$ | $SO_3H$ | H | H | H | | H | | $S(CH_2)_{1-6}SO_3H$ |
| T6-18 | COOH | H | H | H | $SO_3H$ | $SO_3H$ | H | | H | | $S(CH_2)_{1-6}SO_3H$ |
| T6-19 | COOH | $SO_3H$ | H | H | $SO_3H$ | $SO_3H$ | H | | H | | $S(CH_2)_{1-6}SO_3H$ |
| T6-20 | COOH | H | $SO_3H$ | $SO_3H$ | H | H | H | | H | | $S(CH_2)_{1-6}SO_3H$ |
| T6-21 | COOH | $SO_3H$ | $SO_3H$ | $SO_3H$ | $SO_3H$ | $SO_3H$ | H | | H | | $S(CH_2)_{1-6}SO_3H$ |
| T6-22 | CO—OSU | $SO_3H$ | $SO_3H$ | H | $SO_3H$ | H | H | | H | — | $S(CH_2)_{1-6}SO_3H$ |
| T6-23 | CO—OSU | $SO_3H$ | H | H | H | H | H | | H | | $S(CH_2)_{1-6}SO_3H$ |
| T6-24 | CO—OSU | $SO_3H$ | $SO_3H$ | $SO_3H$ | H | H | H | | H | | $S(CH_2)_{1-6}SO_3H$ |
| T6-25 | CO—OSU | H | H | H | $SO_3H$ | $SO_3H$ | H | | H | | $S(CH_2)_{1-6}SO_3H$ |
| T6-26 | CO—OSU | $SO_3H$ | H | H | $SO_3H$ | $SO_3H$ | H | | H | | $S(CH_2)_{1-6}SO_3H$ |
| T6-27 | CO—OSU | H | $SO_3H$ | $SO_3H$ | H | H | H | | H | | $S(CH_2)_{1-6}SO_3H$ |
| T6-28 | CO—OSU | $SO_3H$ | $SO_3H$ | $SO_3H$ | $SO_3H$ | $SO_3H$ | H | | H | | $S(CH_2)_{1-6}SO_3H$ |
| T6-29 | COOH | $SO_3H$ | $SO_3H$ | H | $SO_3H$ | H | H | | H | — | S-Ph-$SO_3H$ |
| T6-30 | COOH | $SO_3H$ | H | H | H | H | H | | H | | S-Ph-$SO_3H$ |
| T6-31 | COOH | $SO_3H$ | $SO_3H$ | $SO_3H$ | H | H | H | | H | | S-Ph-$SO_3H$ |
| T6-32 | COOH | H | H | H | $SO_3H$ | $SO_3H$ | H | | H | | S-Ph-$SO_3H$ |
| T6-33 | COOH | $SO_3H$ | H | H | $SO_3H$ | $SO_3H$ | H | | H | | S-Ph-$SO_3H$ |
| T6-34 | COOH | H | $SO_3H$ | $SO_3H$ | H | H | H | | H | | S-Ph-$SO_3H$ |
| T6-35 | COOH | $SO_3H$ | $SO_3H$ | $SO_3H$ | $SO_3H$ | $SO_3H$ | H | | H | | S-Ph-$SO_3H$ |
| T6-36 | CO—OSU | $SO_3H$ | $SO_3H$ | H | $SO_3H$ | H | H | | H | — | S-Ph-$SO_3H$ |
| T6-37 | CO—OSU | $SO_3H$ | H | H | H | H | H | | H | | S-Ph-$SO_3H$ |
| T6-38 | CO—OSU | $SO_3H$ | $SO_3H$ | $SO_3H$ | H | H | H | | H | | S-Ph-$SO_3H$ |
| T6-39 | CO—OSU | H | H | H | $SO_3H$ | $SO_3H$ | H | | H | | S-Ph-$SO_3H$ |
| T6-40 | CO—OSU | $SO_3H$ | H | H | $SO_3H$ | $SO_3H$ | H | | H | | S-Ph-$SO_3H$ |
| T6-41 | CO—OSU | H | $SO_3H$ | $SO_3H$ | H | H | H | | H | | S-Ph-$SO_3H$ |
| T6-42 | CO—OSU | $SO_3H$ | $SO_3H$ | $SO_3H$ | $SO_3H$ | $SO_3H$ | H | | H | | S-Ph-$SO_3H$ |
| T6-43 | CO—MAL | $SO_3H$ | $SO_3H$ | H | $SO_3H$ | H | H | | H | — | S-Ph-$SO_3H$ |
| T6-44 | CO—MAL | $SO_3H$ | H | H | H | H | H | | H | | S-Ph-$SO_3H$ |
| T6-45 | CO—MAL | $SO_3H$ | $SO_3H$ | $SO_3H$ | H | H | H | | H | | S-Ph-$SO_3H$ |
| T6-46 | CO—MAL | H | H | H | $SO_3H$ | $SO_3H$ | H | | H | | S-Ph-$SO_3H$ |
| T6-47 | CO—MAL | $SO_3H$ | H | H | $SO_3H$ | $SO_3H$ | H | | H | | S-Ph-$SO_3H$ |
| T6-48 | CO—MAL | H | $SO_3H$ | $SO_3H$ | H | H | H | | H | | S-Ph-$SO_3H$ |
| T6-49 | CO—MAL | $SO_3H$ | $SO_3H$ | $SO_3H$ | $SO_3H$ | $SO_3H$ | H | | H | | S-Ph-$SO_3H$ |
| T6-50 | COOH | $SO_3H$ | $SO_3H$ | H | $SO_3H$ | H | H | | H | — | $S(CH_2)_{1-6}SO_3H$ |
| T6-51 | COOH | $SO_3H$ | H | H | H | H | H | | H | | $S(CH_2)_{1-6}SO_3H$ |
| T6-52 | COOH | $SO_3H$ | $SO_3H$ | $SO_3H$ | H | H | H | | H | | $S(CH_2)_{1-6}SO_3H$ |
| T6-53 | COOH | H | H | H | $SO_3H$ | $SO_3H$ | H | | H | | $S(CH_2)_{1-6}SO_3H$ |
| T6-54 | COOH | $SO_3H$ | H | H | $SO_3H$ | $SO_3H$ | H | | H | | $S(CH_2)_{1-6}SO_3H$ |
| T6-55 | COOH | H | $SO_3H$ | $SO_3H$ | H | H | H | | H | | $S(CH_2)_{1-6}SO_3H$ |
| T6-56 | COOH | $SO_3H$ | $SO_3H$ | $SO_3H$ | $SO_3H$ | $SO_3H$ | H | | H | | $S(CH_2)_{1-6}SO_3H$ |
| T6-57 | CO—OSU | $SO_3H$ | $SO_3H$ | H | $SO_3H$ | H | H | | H | — | $S(CH_2)_{1-6}SO_3H$ |
| T6-58 | CO—OSU | $SO_3H$ | H | H | H | H | H | | H | | $S(CH_2)_{1-6}SO_3H$ |
| T6-59 | CO—OSU | $SO_3H$ | $SO_3H$ | $SO_3H$ | H | H | H | | H | | $S(CH_2)_{1-6}SO_3H$ |
| T6-60 | CO—OSU | H | H | H | $SO_3H$ | $SO_3H$ | H | | H | | $S(CH_2)_{1-6}SO_3H$ |
| T6-61 | CO—OSU | $SO_3H$ | H | H | $SO_3H$ | $SO_3H$ | H | | H | | $S(CH_2)_{1-6}SO_3H$ |

TABLE 6-continued

Exemplary compounds according to this disclosure.

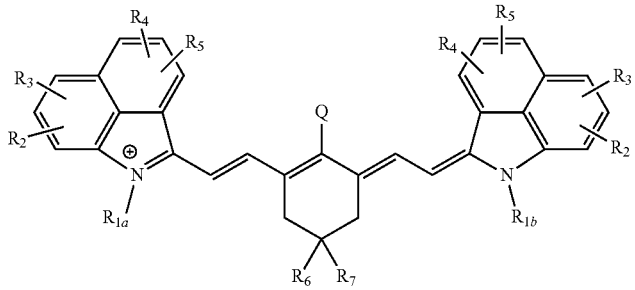

Variation in Q when $R_6 = R_7 = H$

| No | R1a = (CH$_2$)$_{1-12}$— | R1b = (CH$_2$)$_{1-12}$— | R$_2$ | R$_3$ | R$_4$ | R$_5$ | R$_6$ | Y | R$_7$ | Z | Q |
|---|---|---|---|---|---|---|---|---|---|---|---|
| T6-62 | CO—OSU | H | SO$_3$H | SO$_3$H | H | H | H |  | H |  | S(CH$_2$)$_{1-6}$SO$_3$H |
| T6-63 | CO—OSU | SO$_3$H | SO$_3$H | SO$_3$H | SO$_3$H | SO$_3$H | H |  | H |  | S(CH$_2$)$_{1-6}$SO$_3$H |
| T6-64 | COOH | SO$_3$H | SO$_3$H | H | SO$_3$H | H | H |  | H | — | O-Ph-SO$_3$H |
| T6-65 | COOH | SO$_3$H | H | H | H | H | H |  | H |  | O-Ph-SO$_3$H |
| T6-66 | COOH | SO$_3$H | SO$_3$H | SO$_3$H | H | H | H |  | H |  | O-Ph-SO$_3$H |
| T6-67 | COOH | H | H | H | SO$_3$H | SO$_3$H | H |  | H |  | O-Ph-SO$_3$H |
| T6-68 | COOH | SO$_3$H | H | H | SO$_3$H | SO$_3$H | H |  | H |  | O-Ph-SO$_3$H |
| T6-69 | COOH | H | SO$_3$H | SO$_3$H | H | H | H |  | H |  | O-Ph-SO$_3$H |
| T6-70 | COOH | SO$_3$H | SO$_3$H | SO$_3$H | SO$_3$H | SO$_3$H | H |  | H |  | O-Ph-SO$_3$H |
| T6-71 | CO—OSU | SO$_3$H | SO$_3$H | H | SO$_3$H | H | H |  | H | — | O-Ph-SO$_3$H |
| T6-72 | CO—OSU | SO$_3$H | H | H | H | H | H |  | H |  | O-Ph-SO$_3$H |
| T6-73 | CO—OSU | SO$_3$H | SO$_3$H | SO$_3$H | H | H | H |  | H |  | O-Ph-SO$_3$H |
| T6-74 | CO—OSU | H | H | H | SO$_3$H | SO$_3$H | H |  | H |  | O-Ph-SO$_3$H |
| T6-75 | CO—OSU | SO$_3$H | H | H | SO$_3$H | SO$_3$H | H |  | H |  | O-Ph-SO$_3$H |
| T6-76 | CO—OSU | H | SO$_3$H | SO$_3$H | H | H | H |  | H |  | O-Ph-SO$_3$H |
| T6-77 | CO—OSU | SO$_3$H | SO$_3$H | SO$_3$H | SO$_3$H | SO$_3$H | H |  | H |  | O-Ph-SO$_3$H |
| T6-78 | CO—MAL | SO$_3$H | SO$_3$H | H | SO$_3$H | H | H |  | H | — | O-Ph-SO$_3$H |
| T6-79 | CO—MAL | SO$_3$H | H | H | H | H | H |  | H |  | O-Ph-SO$_3$H |
| T6-80 | CO—MAL | SO$_3$H | SO$_3$H | SO$_3$H | H | H | H |  | H |  | O-Ph-SO$_3$H |
| T6-81 | CO—MAL | H | H | H | SO$_3$H | SO$_3$H | H |  | H |  | O-Ph-SO$_3$H |
| T6-82 | CO—MAL | SO$_3$H | H | H | SO$_3$H | SO$_3$H | H |  | H |  | O-Ph-SO$_3$H |
| T6-83 | CO—MAL | H | SO$_3$H | SO$_3$H | H | H | H |  | H |  | O-Ph-SO$_3$H |
| T6-84 | CO—MAL | SO$_3$H | SO$_3$H | SO$_3$H | SO$_3$H | SO$_3$H | H |  | H |  | O-Ph-SO$_3$H |
| T6-85 | SO$_3$H | SO$_3$H | SO$_3$H | H | SO$_3$H | H | H |  | H | — | Cl |
| T6-86 | SO$_3$H | SO$_3$H | H | H | H | H | H |  | H |  | Cl |
| T6-87 | SO$_3$H | SO$_3$H | SO$_3$H | SO$_3$H | H | H | H |  | H |  | Cl |
| T6-88 | SO$_3$H | SO$_3$H | H | H | SO$_3$H | SO$_3$H | H |  | H |  | Cl |
| T6-89 | SO$_3$H | SO$_3$H | H | H | SO$_3$H | SO$_3$H | H |  | H |  | Cl |
| T6-90 | SO$_3$H | SO$_3$H | SO$_3$H | SO$_3$H | H | H | H |  | H |  | Cl |
| T6-91 | SO$_3$H | SO$_3$H | SO$_3$H | SO$_3$H | SO$_3$H | SO$_3$H | H |  | H |  | Cl |
| T6-92 | SO$_3$H | SO$_3$H | SO$_3$H | H | SO$_3$H | H | H |  | H | — | S(CH$_2$)$_{1-6}$COOH |
| T6-93 | SO$_3$H | SO$_3$H | H | H | H | H | H |  | H |  | S(CH$_2$)$_{1-6}$COOH |
| T6-94 | SO$_3$H | SO$_3$H | SO$_3$H | SO$_3$H | H | H | H |  | H |  | S(CH$_2$)$_{1-6}$COOH |
| T6-95 | SO$_3$H | SO$_3$H | H | H | SO$_3$H | SO$_3$H | H |  | H |  | S(CH$_2$)$_{1-6}$COOH |
| T6-96 | SO$_3$H | SO$_3$H | H | H | SO$_3$H | SO$_3$H | H |  | H |  | S(CH$_2$)$_{1-6}$COOH |
| T6-97 | SO$_3$H | SO$_3$H | SO$_3$H | SO$_3$H | H | H | H |  | H |  | S(CH$_2$)$_{1-6}$COOH |
| T6-98 | SO$_3$H | SO$_3$H | SO$_3$H | SO$_3$H | SO$_3$H | SO$_3$H | H |  | H |  | S(CH$_2$)$_{1-6}$COOH |
| T6-99 | SO$_3$H | SO$_3$H | SO$_3$H | H | SO$_3$H | H | H |  | H | — | S(CH$_2$)$_{1-6}$CO—OSU |
| T6-100 | SO$_3$H | SO$_3$H | H | H | H | H | H |  | H |  | S(CH$_2$)$_{1-6}$CO—OSU |
| T6-101 | SO$_3$H | SO$_3$H | SO$_3$H | SO$_3$H | H | H | H |  | H |  | S(CH$_2$)$_{1-6}$CO—OSU |
| T6-102 | SO$_3$H | SO$_3$H | H | H | SO$_3$H | SO$_3$H | H |  | H |  | S(CH$_2$)$_{1-6}$CO—OSU |
| T6-103 | SO$_3$H | SO$_3$H | H | H | SO$_3$H | SO$_3$H | H |  | H |  | S(CH$_2$)$_{1-6}$CO—OSU |
| T6-104 | SO$_3$H | SO$_3$H | SO$_3$H | SO$_3$H | H | H | H |  | H |  | S(CH$_2$)$_{1-6}$CO—OSU |
| T6-105 | SO$_3$H | SO$_3$H | SO$_3$H | SO$_3$H | SO$_3$H | SO$_3$H | H |  | H |  | S(CH$_2$)$_{1-6}$CO—OSU |
| T6-106 | SO$_3$H | SO$_3$H | SO$_3$H | H | SO$_3$H | H | H |  | H | — | S(CH$_2$)$_{1-6}$CO—MAL |
| T6-107 | SO$_3$H | SO$_3$H | H | H | H | H | H |  | H |  | S(CH$_2$)$_{1-6}$CO—MAL |
| T6-108 | SO$_3$H | SO$_3$H | SO$_3$H | SO$_3$H | H | H | H |  | H |  | S(CH$_2$)$_{1-6}$CO—MAL |
| T6-109 | SO$_3$H | SO$_3$H | H | H | SO$_3$H | SO$_3$H | H |  | H |  | S(CH$_2$)$_{1-6}$CO—MAL |
| T6-110 | SO$_3$H | SO$_3$H | H | H | SO$_3$H | SO$_3$H | H |  | H |  | S(CH$_2$)$_{1-6}$CO—MAL |
| T6-111 | SO$_3$H | SO$_3$H | SO$_3$H | SO$_3$H | H | H | H |  | H |  | S(CH$_2$)$_{1-6}$CO—MAL |
| T6-112 | SO$_3$H | SO$_3$H | SO$_3$H | SO$_3$H | SO$_3$H | SO$_3$H | H |  | H |  | S(CH$_2$)$_{1-6}$CO—MAL |
| T6-113 | SO$_3$H | SO$_3$H | SO$_3$H | H | SO$_3$H | H | H |  | H | — | S-Ph-(CH$_2$)$_{0-6}$COOH |
| T6-114 | SO$_3$H | SO$_3$H | H | H | H | H | H |  | H |  | S-Ph-(CH$_2$)$_{0-6}$COOH |
| T6-115 | SO$_3$H | SO$_3$H | SO$_3$H | SO$_3$H | H | H | H |  | H |  | S-Ph-(CH$_2$)$_{0-6}$COOH |
| T6-116 | SO$_3$H | SO$_3$H | H | H | SO$_3$H | SO$_3$H | H |  | H |  | S-Ph-(CH$_2$)$_{0-6}$COOH |
| T6-117 | SO$_3$H | SO$_3$H | H | H | SO$_3$H | SO$_3$H | H |  | H |  | S-Ph-(CH$_2$)$_{0-6}$COOH |
| T6-118 | SO$_3$H | SO$_3$H | SO$_3$H | SO$_3$H | H | H | H |  | H |  | S-Ph-(CH$_2$)$_{0-6}$COOH |
| T6-119 | SO$_3$H | SO$_3$H | SO$_3$H | SO$_3$H | SO$_3$H | SO$_3$H | H |  | H |  | S-Ph-(CH$_2$)$_{0-6}$COOH |

TABLE 6-continued

Exemplary compounds according to this disclosure.

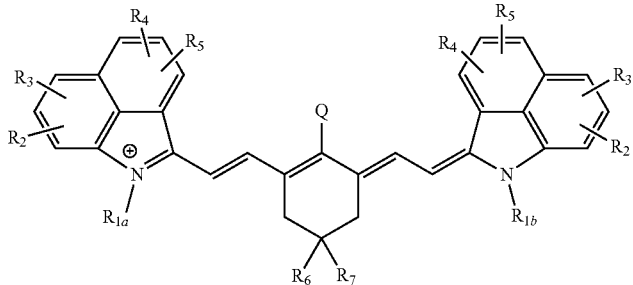

Variation in Q when R₆ = R₇ = H

| No | R1a = (CH₂)₁₋₁₂— | R1b = (CH₂)₁₋₁₂— | R₂ | R₃ | R₄ | R₅ | R₆ | Y | R₇ | Z | Q |
|---|---|---|---|---|---|---|---|---|---|---|---|
| T6-120 | SO₃H | SO₃H | SO₃H | H | SO₃H | H | H | | H | — | S-Ph-(CH₂)₀₋₆CO—OSU |
| T6-121 | SO₃H | SO₃H | H | H | H | H | H | | H | | S-Ph-(CH₂)₀₋₆CO—OSU |
| T6-122 | SO₃H | SO₃H | SO₃H | SO₃H | H | H | H | | H | | S-Ph-(CH₂)₀₋₆CO—OSU |
| T6-123 | SO₃H | SO₃H | H | H | SO₃H | SO₃H | H | | H | | S-Ph-(CH₂)₀₋₆CO—OSU |
| T6-124 | SO₃H | SO₃H | H | H | SO₃H | SO₃H | H | | H | | S-Ph-(CH₂)₀₋₆CO—OSU |
| T6-125 | SO₃H | SO₃H | SO₃H | SO₃H | H | H | H | | H | | S-Ph-(CH₂)₀₋₆CO—OSU |
| T6-126 | SO₃H | SO₃H | SO₃H | SO₃H | SO₃H | SO₃H | H | | H | | S-Ph-(CH₂)₀₋₆CO—OSU |
| T6-127 | SO₃H | SO₃H | SO₃H | H | SO₃H | H | H | | H | — | S-Ph-(CH₂)₀₋₆CO—MAL |
| T6-128 | SO₃H | SO₃H | H | H | H | H | H | | H | | S-Ph-(CH₂)₀₋₆CO—MAL |
| T6-129 | SO₃H | SO₃H | SO₃H | SO₃H | H | H | H | | H | | S-Ph-(CH₂)₀₋₆CO—MAL |
| T6-130 | SO₃H | SO₃H | H | H | SO₃H | SO₃H | H | | H | | S-Ph-(CH₂)₀₋₆CO—MAL |
| T6-131 | SO₃H | SO₃H | H | H | SO₃H | SO₃H | H | | H | | S-Ph-(CH₂)₀₋₆CO—MAL |
| T6-132 | SO₃H | SO₃H | SO₃H | SO₃H | H | H | H | | H | | S-Ph-(CH₂)₀₋₆CO—MAL |
| T6-133 | SO₃H | SO₃H | SO₃H | SO₃H | SO₃H | SO₃H | H | | H | | S-Ph-(CH₂)₀₋₆CO—MAL |
| T6-134 | SO₃H | SO₃H | SO₃H | H | SO₃H | H | H | | H | — | O-Ph-(CH₂)₀₋₆COOH |
| T6-135 | SO₃H | SO₃H | H | H | H | H | H | | H | | O-Ph-(CH₂)₀₋₆COOH |
| T6-136 | SO₃H | SO₃H | SO₃H | SO₃H | H | H | H | | H | | O-Ph-(CH₂)₀₋₆COOH |
| T6-137 | SO₃H | SO₃H | H | H | SO₃H | SO₃H | H | | H | | O-Ph-(CH₂)₀₋₆COOH |
| T6-138 | SO₃H | SO₃H | H | H | SO₃H | SO₃H | H | | H | | O-Ph-(CH₂)₀₋₆COOH |
| T6-139 | SO₃H | SO₃H | SO₃H | SO₃H | H | H | H | | H | | O-Ph-(CH₂)₀₋₆COOH |
| T6-140 | SO₃H | SO₃H | SO₃H | SO₃H | SO₃H | SO₃H | H | | H | | O-Ph-(CH₂)₀₋₆COOH |
| T6-141 | SO₃H | SO₃H | SO₃H | H | SO₃H | H | H | | H | — | O-Ph-(CH₂)₀₋₆CO—OSU |
| T6-142 | SO₃H | SO₃H | H | H | H | H | H | | H | | O-Ph-(CH₂)₀₋₆CO—OSU |
| T6-143 | SO₃H | SO₃H | SO₃H | SO₃H | H | H | H | | H | | O-Ph-(CH₂)₀₋₆CO—OSU |
| T6-144 | SO₃H | SO₃H | H | H | SO₃H | SO₃H | H | | H | | O-Ph-(CH₂)₀₋₆CO—OSU |
| T6-145 | SO₃H | SO₃H | H | H | SO₃H | SO₃H | H | | H | | O-Ph-(CH₂)₀₋₆CO—OSU |
| T6-146 | SO₃H | SO₃H | SO₃H | SO₃H | H | H | H | | H | | O-Ph-(CH₂)₀₋₆CO—OSU |
| T6-147 | SO₃H | SO₃H | SO₃H | SO₃H | SO₃H | SO₃H | H | | H | | O-Ph-(CH₂)₀₋₆CO—OSU |
| T6-148 | SO₃H | SO₃H | SO₃H | H | SO₃H | H | H | | H | — | O-Ph-(CH₂)₀₋₆CO—MAL |
| T6-149 | SO₃H | SO₃H | H | H | H | H | H | | H | | O-Ph-(CH₂)₀₋₆CO—MAL |
| T6-150 | SO₃H | SO₃H | SO₃H | SO₃H | H | H | H | | H | | O-Ph-(CH₂)₀₋₆CO—MAL |
| T6-151 | SO₃H | SO₃H | H | H | SO₃H | SO₃H | H | | H | | O-Ph-(CH₂)₀₋₆CO—MAL |
| T6-152 | SO₃H | SO₃H | H | H | SO₃H | SO₃H | H | | H | | O-Ph-(CH₂)₀₋₆CO—MAL |
| T6-153 | SO₃H | SO₃H | SO₃H | SO₃H | H | H | H | | H | | O-Ph-(CH₂)₀₋₆CO—MAL |
| T6-154 | SO₃H | SO₃H | SO₃H | SO₃H | SO₃H | SO₃H | H | | H | | O-Ph-(CH₂)₀₋₆CO—MAL |

OSu = N-Hydroxysuccinimidyl; MAL = N-(2-(N-maleimido)-ethyl)-amide

TABLE 7

Exemplary compounds according to this disclosure.

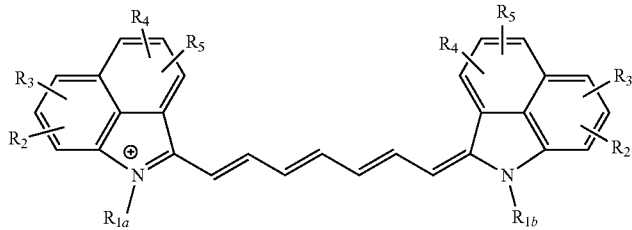

No ring on the bridge; Q, R$_6$, and R$_7$ absent

| No | R$_{1a}$ = (CH$_2$)$_{1-12}$— | R$_{1b}$ = (CH$_2$)$_{1-12}$— | R$_2$ | R$_3$ | R$_4$ | R$_5$ |
|---|---|---|---|---|---|---|
| T7-1 | COOH | SO$_3$H | SO$_3$H | H | SO$_3$H | H |
| T7-2 | COOH | SO$_3$H | H | H | H | H |
| T7-3 | COOH | SO$_3$H | SO$_3$H | SO$_3$H | H | H |
| T7-4 | COOH | H | H | H | SO$_3$H | SO$_3$H |
| T7-5 | COOH | SO$_3$H | H | H | SO$_3$H | SO$_3$H |
| T7-6 | COOH | H | SO$_3$H | SO$_3$H | H | H |
| T7-7 | COOH | SO$_3$H | SO$_3$H | SO$_3$H | SO$_3$H | SO$_3$H |
| T7-8 | CO—OSU | SO$_3$H | SO$_3$H | H | SO$_3$H | H |
| T7-9 | CO—OSU | SO$_3$H | H | H | H | H |
| T7-10 | CO—OSU | SO$_3$H | SO$_3$H | SO$_3$H | H | H |
| T7-11 | CO—OSU | H | H | H | SO$_3$H | SO$_3$H |
| T7-12 | CO—OSU | SO$_3$H | H | H | SO$_3$H | SO$_3$H |
| T7-13 | CO—OSU | H | SO$_3$H | SO$_3$H | H | H |
| T7-14 | CO—OSU | SO$_3$H | SO$_3$H | SO$_3$H | SO$_3$H | SO$_3$H |
| T7-15 | CO—MAL | SO$_3$H | SO$_3$H | H | SO$_3$H | H |
| T7-16 | CO—MAL | SO$_3$H | H | H | H | H |
| T7-17 | CO—MAL | SO$_3$H | SO$_3$H | SO$_3$H | H | H |
| T7-18 | CO—MAL | H | H | H | SO$_3$H | SO$_3$H |
| T7-19 | CO—MAL | SO$_3$H | H | H | SO$_3$H | SO$_3$H |
| T7-20 | CO—MAL | H | SO$_3$H | SO$_3$H | H | H |
| T7-21 | CO—MAL | SO$_3$H | SO$_3$H | SO$_3$H | SO$_3$H | SO$_3$H |

OSu = N-Hydroxysuccinimidyl; MAL = N-(2-(N-maleimido)-ethyl)-amide

TABLE 8

Exemplary compounds according to this disclosure.
Napthothiophene based SWIR Dyes

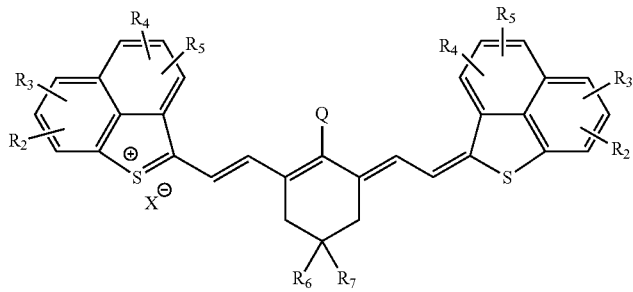

R$_1$ absent Q = H & VARIATION IN R$_6$, R$_7$

| No | R$_2$ | R$_3$ | R$_4$ | R$_5$ | R$_6$ | Y | R$_7$ | Z | Q |
|---|---|---|---|---|---|---|---|---|---|
| T8-1 | SO$_3$H | H | SO$_3$H | H | COOY | (CH$_2$)$_{1-6}$H | CONH-Z | (CH$_2$)$_{1-6}$SO$_3$H | H |
| T8-2 | H | H | H | H | COOY | (CH$_2$)$_{1-6}$H | CONH-Z | (CH$_2$)$_{1-6}$SO$_3$H | H |
| T8-3 | SO$_3$H | SO$_3$H | H | H | COOY | (CH$_2$)$_{1-6}$H | CONH-Z | (CH$_2$)$_{1-6}$SO$_3$H | H |
| T8-4 | H | H | SO$_3$H | SO$_3$H | COOY | (CH$_2$)$_{1-6}$H | CONH-Z | (CH$_2$)$_{1-6}$SO$_3$H | H |
| T8-5 | SO$_3$H | SO$_3$H | SO$_3$H | SO$_3$H | COOY | (CH$_2$)$_{1-6}$H | CONH-Z | (CH$_2$)$_{1-6}$SO$_3$H | H |
| T8-6 | SO$_3$H | H | SO$_3$H | H | COOY | H | CONH-Z | (CH$_2$)$_{1-6}$SO$_3$H | H |
| T8-7 | H | H | H | H | COOY | H | CONH-Z | (CH$_2$)$_{1-6}$SO$_3$H | H |
| T8-8 | SO$_3$H | SO$_3$H | H | H | COOY | H | CONH-Z | (CH$_2$)$_{1-6}$SO$_3$H | H |
| T8-9 | H | H | SO$_3$H | SO$_3$H | COOY | H | CONH-Z | (CH$_2$)$_{1-6}$SO$_3$H | H |
| T8-10 | SO$_3$H | SO$_3$H | SO$_3$H | SO$_3$H | COOY | H | CONH-Z | (CH$_2$)$_{1-6}$SO$_3$H | H |

TABLE 8-continued

Exemplary compounds according to this disclosure.
Napthothiophene based SWIR Dyes

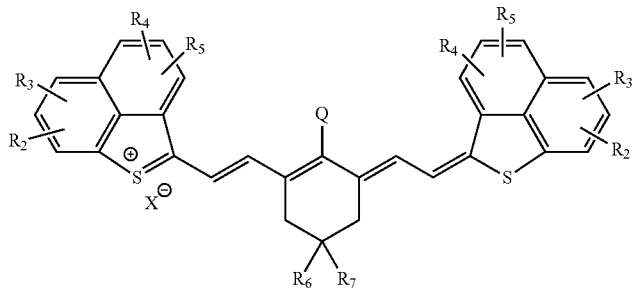

$R_1$ absent Q = H & VARIATION IN $R_6$, $R_7$

| No | $R_2$ | $R_3$ | $R_4$ | $R_5$ | $R_6$ | Y | $R_7$ | Z | Q |
|---|---|---|---|---|---|---|---|---|---|
| T8-11 | $SO_3H$ | H | $SO_3H$ | H | COOY | N-Succinimidyl | CONH-Z | $(CH_2)_{1-6}SO_3H$ | H |
| T8-12 | H | H | H | H | COOY | N-Succinimidyl | CONH-Z | $(CH_2)_{1-6}SO_3H$ | H |
| T8-13 | $SO_3H$ | $SO_3H$ | H | H | COOY | N-Succinimidyl | CONH-Z | $(CH_2)_{1-6}SO_3H$ | H |
| T8-14 | H | H | $SO_3H$ | $SO_3H$ | COOY | N-Succinimidyl | CONH-Z | $(CH_2)_{1-6}SO_3H$ | H |
| T8-15 | $SO_3H$ | $SO_3H$ | $SO_3H$ | $SO_3H$ | COOY | N-Succinimidyl | CONH-Z | $(CH_2)_{1-6}SO_3H$ | H |
| T8-16 | $SO_3H$ | H | $SO_3H$ | H | CONH—Y | $(CH_2)_{1-6}COOH$ | CONH-Z | $(CH_2)_{1-6}SO_3H$ | H |
| T8-17 | H | H | H | H | CONH—Y | $(CH_2)_{1-6}COOH$ | CONH-Z | $(CH_2)_{1-6}SO_3H$ | H |
| T8-18 | $SO_3H$ | $SO_3H$ | H | H | CONH—Y | $(CH_2)_{1-6}COOH$ | CONH-Z | $(CH_2)_{1-6}SO_3H$ | H |
| T8-19 | H | H | $SO_3H$ | $SO_3H$ | CONH—Y | $(CH_2)_{1-6}COOH$ | CONH-Z | $(CH_2)_{1-6}SO_3H$ | H |
| T8-20 | $SO_3H$ | $SO_3H$ | $SO_3H$ | $SO_3H$ | CONH—Y | $(CH_2)_{1-6}COOH$ | CONH-Z | $(CH_2)_{1-6}SO_3H$ | H |
| T8-21 | $SO_3H$ | H | $SO_3H$ | H | CONH—Y | $(CH_2)_{1-6}CO$—OSu | CONH-Z | $(CH_2)_{1-6}SO_3H$ | H |
| T8-22 | H | H | H | H | CONH—Y | $(CH_2)_{1-6}CO$—OSu | CONH-Z | $(CH_2)_{1-6}SO_3H$ | H |
| T8-23 | $SO_3H$ | $SO_3H$ | H | H | CONH—Y | $(CH_2)_{1-6}CO$—OSu | CONH-Z | $(CH_2)_{1-6}SO_3H$ | H |
| T8-24 | H | H | $SO_3H$ | $SO_3H$ | CONH—Y | $(CH_2)_{1-6}CO$—OSu | CONH-Z | $(CH_2)_{1-6}SO_3H$ | H |
| T8-25 | $SO_3H$ | $SO_3H$ | $SO_3H$ | $SO_3H$ | CONH—Y | $(CH_2)_{1-6}CO$—OSu | CONH-Z | $(CH_2)_{1-6}SO_3H$ | H |
| T8-26 | $SO_3H$ | H | $SO_3H$ | H | CONH—Y | $(CH_2)_{1-6}CO$—Mal | CONH-Z | $(CH_2)_{1-6}SO_3H$ | H |
| T8-27 | H | H | H | H | CONH—Y | $(CH_2)_{1-6}CO$—Mal | CONH-Z | $(CH_2)_{1-6}SO_3H$ | H |
| T8-28 | $SO_3H$ | $SO_3H$ | H | H | CONH—Y | $(CH_2)_{1-6}CO$—Mal | CONH-Z | $(CH_2)_{1-6}SO_3H$ | H |
| T8-29 | H | H | $SO_3H$ | $SO_3H$ | CONH—Y | $(CH_2)_{1-6}CO$—Mal | CONH-Z | $(CH_2)_{1-6}SO_3H$ | H |
| T8-30 | $SO_3H$ | $SO_3H$ | $SO_3H$ | $SO_3H$ | CONH—Y | $(CH_2)_{1-6}CO$—Mal | CONH-Z | $(CH_2)_{1-6}SO_3H$ | H |

OSu = N-Hydroxysuccinimidyl; MAL = N-(2-(N-maleimido)-ethyl)-amide

TABLE 9

Examplary compounds according to this disclosure.

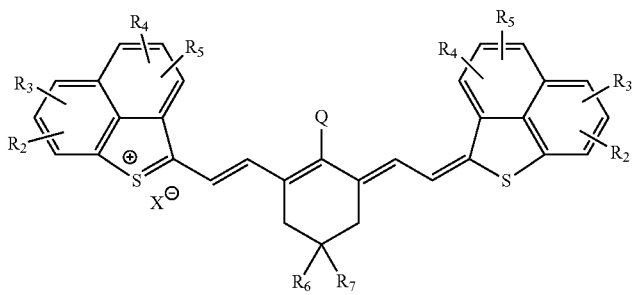

Variation in Q when $R_6 = R_7 = H$

| No | $R_2$ | $R_3$ | $R_4$ | $R_5$ | $R_6$ | $R_7$ | Q |
|---|---|---|---|---|---|---|---|
| T9-1 | $SO_3H$ | $SO_3H$ | $SO_3H$ | H | $SO_3H$ | H | H | Cl |
| T9-2 | $SO_3H$ | $SO_3H$ | $SO_3H$ | H | H | H | H | Cl |
| T9-3 | $SO_3H$ | $SO_3H$ | $SO_3H$ | $SO_3H$ | H | H | H | Cl |
| T9-4 | $SO_3H$ | $SO_3H$ | H | H | $SO_3H$ | $SO_3H$ | H | Cl |
| T9-5 | $SO_3H$ | $SO_3H$ | $SO_3H$ | $SO_3H$ | $SO_3H$ | $SO_3H$ | H | Cl |
| T9-6 | $SO_3H$ | $SO_3H$ | $SO_3H$ | H | $SO_3H$ | H | H | $S(CH_2)_{1-6}COOH$ |
| T9-7 | $SO_3H$ | $SO_3H$ | $SO_3H$ | H | H | H | H | $S(CH_2)_{1-6}COOH$ |
| T9-8 | $SO_3H$ | $SO_3H$ | $SO_3H$ | $SO_3H$ | H | H | H | $S(CH_2)_{1-6}COOH$ |
| T9-9 | $SO_3H$ | $SO_3H$ | H | H | $SO_3H$ | $SO_3H$ | H | $S(CH_2)_{1-6}COOH$ |
| T9-10 | $SO_3H$ | $SO_3H$ | $SO_3H$ | $SO_3H$ | $SO_3H$ | $SO_3H$ | H | $S(CH_2)_{1-6}COOH$ |
| T9-11 | $SO_3H$ | $SO_3H$ | $SO_3H$ | H | $SO_3H$ | H | H | $S(CH_2)_{1-6}CO$—OSu |

TABLE 9-continued

Examplary compounds according to this disclosure.

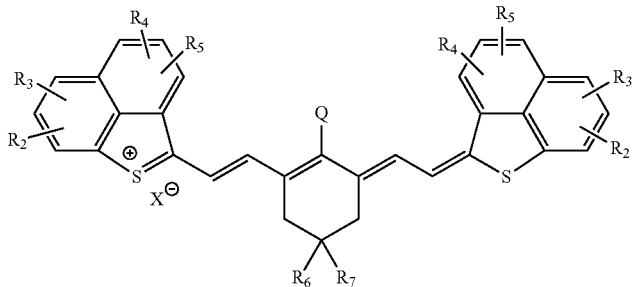

Variation in Q when $R_6 = R_7 = H$

| No | | | $R_2$ | $R_3$ | $R_4$ | $R_5$ | $R_6$ | $R_7$ | Q |
|---|---|---|---|---|---|---|---|---|---|
| T9-12 | $SO_3H$ | $SO_3H$ | H | H | H | H | H | H | $S(CH_2)_{1-6}CO$—OSu |
| T9-13 | $SO_3H$ | $SO_3H$ | $SO_3H$ | $SO_3H$ | H | H | H | H | $S(CH_2)_{1-6}CO$—OSu |
| T9-14 | $SO_3H$ | $SO_3H$ | H | H | $SO_3H$ | $SO_3H$ | H | H | $S(CH_2)_{1-6}CO$—OSu |
| T9-15 | $SO_3H$ | $SO_3H$ | $SO_3H$ | $SO_3H$ | $SO_3H$ | $SO_3H$ | H | H | $S(CH_2)_{1-6}CO$—OSu |
| T9-16 | $SO_3H$ | $SO_3H$ | $SO_3H$ | H | $SO_3H$ | H | H | H | $S(CH_2)_{1-6}CO$—MAL |
| T9-17 | $SO_3H$ | $SO_3H$ | H | H | H | H | H | H | $S(CH_2)_{1-6}CO$—MAL |
| T9-18 | $SO_3H$ | $SO_3H$ | $SO_3H$ | $SO_3H$ | H | H | H | H | $S(CH_2)_{1-6}CO$—MAL |
| T9-19 | $SO_3H$ | $SO_3H$ | H | H | $SO_3H$ | $SO_3H$ | H | H | $S(CH_2)_{1-6}CO$—MAL |
| T9-20 | $SO_3H$ | $SO_3H$ | $SO_3H$ | $SO_3H$ | $SO_3H$ | $SO_3H$ | H | H | $S(CH_2)_{1-6}CO$—MAL |
| T9-21 | $SO_3H$ | $SO_3H$ | $SO_3H$ | H | $SO_3H$ | H | H | H | S-Ph-$(CH_2)_{0-6}$COOH |
| T9-22 | $SO_3H$ | $SO_3H$ | H | H | H | H | H | H | S-Ph-$(CH_2)_{0-6}$COOH |
| T9-23 | $SO_3H$ | $SO_3H$ | $SO_3H$ | $SO_3H$ | H | H | H | H | S-Ph-$(CH_2)_{0-6}$COOH |
| T9-24 | $SO_3H$ | $SO_3H$ | H | H | $SO_3H$ | $SO_3H$ | H | H | S-Ph-$(CH_2)_{0-6}$COOH |
| T9-25 | $SO_3H$ | $SO_3H$ | $SO_3H$ | $SO_3H$ | $SO_3H$ | $SO_3H$ | H | H | S-Ph-$(CH_2)_{0-6}$COOH |
| T9-26 | $SO_3H$ | $SO_3H$ | $SO_3H$ | H | $SO_3H$ | H | H | H | S-Ph-$(CH_2)_{0-6}CO$—OSu |
| T9-27 | $SO_3H$ | $SO_3H$ | H | H | H | H | H | H | S-Ph-$(CH_2)_{0-6}CO$—OSu |
| T9-28 | $SO_3H$ | $SO_3H$ | $SO_3H$ | $SO_3H$ | H | H | H | H | S-Ph-$(CH_2)_{0-6}CO$—OSu |
| T9-29 | $SO_3H$ | $SO_3H$ | H | H | $SO_3H$ | $SO_3H$ | H | H | S-Ph-$(CH_2)_{0-6}CO$—OSu |
| T9-30 | $SO_3H$ | $SO_3H$ | $SO_3H$ | $SO_3H$ | $SO_3H$ | $SO_3H$ | H | H | S-Ph-$(CH_2)_{0-6}CO$—OSu |
| T9-31 | $SO_3H$ | $SO_3H$ | $SO_3H$ | H | $SO_3H$ | H | H | H | S-Ph-$(CH_2)_{0-6}CO$—MAL |
| T9-32 | $SO_3H$ | $SO_3H$ | H | H | H | H | H | H | S-Ph-$(CH_2)_{0-6}CO$—MAL |
| T9-33 | $SO_3H$ | $SO_3H$ | $SO_3H$ | $SO_3H$ | H | H | H | H | S-Ph-$(CH_2)_{0-6}CO$—MAL |
| T9-34 | $SO_3H$ | $SO_3H$ | H | H | $SO_3H$ | $SO_3H$ | H | H | S-Ph-$(CH_2)_{0-6}CO$—MAL |
| T9-35 | $SO_3H$ | $SO_3H$ | $SO_3H$ | $SO_3H$ | $SO_3H$ | $SO_3H$ | H | H | S-Ph-$(CH_2)_{0-6}CO$—MAL |
| T9-36 | $SO_3H$ | $SO_3H$ | $SO_3H$ | H | $SO_3H$ | H | H | H | O-Ph-$(CH_2)_{0-6}$COOH |
| T9-37 | $SO_3H$ | $SO_3H$ | H | H | H | H | H | H | O-Ph-$(CH_2)_{0-6}$COOH |
| T9-38 | $SO_3H$ | $SO_3H$ | $SO_3H$ | $SO_3H$ | H | H | H | H | O-Ph-$(CH_2)_{0-6}$COOH |
| T9-39 | $SO_3H$ | $SO_3H$ | H | H | $SO_3H$ | $SO_3H$ | H | H | O-Ph-$(CH_2)_{0-6}$COOH |
| T9-40 | $SO_3H$ | $SO_3H$ | $SO_3H$ | $SO_3H$ | $SO_3H$ | $SO_3H$ | H | H | O-Ph-$(CH_2)_{0-6}$COOH |
| T9-41 | $SO_3H$ | $SO_3H$ | $SO_3H$ | H | $SO_3H$ | H | H | H | O-Ph-$(CH_2)_{0-6}CO$—OSu |
| T9-42 | $SO_3H$ | $SO_3H$ | H | H | H | H | H | H | O-Ph-$(CH_2)_{0-6}CO$—OSu |
| T9-43 | $SO_3H$ | $SO_3H$ | $SO_3H$ | $SO_3H$ | H | H | H | H | O-Ph-$(CH_2)_{0-6}CO$—OSu |
| T9-44 | $SO_3H$ | $SO_3H$ | $SO_3H$ | $SO_3H$ | H | H | H | H | O-Ph-$(CH_2)_{0-6}CO$—OSu |
| T9-45 | $SO_3H$ | $SO_3H$ | $SO_3H$ | $SO_3H$ | $SO_3H$ | $SO_3H$ | H | H | O-Ph-$(CH_2)_{0-6}CO$—OSu |
| T9-46 | $SO_3H$ | $SO_3H$ | $SO_3H$ | H | $SO_3H$ | H | H | H | O-Ph-$(CH_2)_{0-6}CO$—MAL |
| T9-47 | $SO_3H$ | $SO_3H$ | H | H | H | H | H | H | O-Ph-$(CH_2)_{0-6}CO$—MAL |
| T9-48 | $SO_3H$ | $SO_3H$ | $SO_3H$ | $SO_3H$ | H | H | H | H | O-Ph-$(CH_2)_{0-6}CO$—MAL |
| T9-49 | $SO_3H$ | $SO_3H$ | H | H | $SO_3H$ | $SO_3H$ | H | H | O-Ph-$(CH_2)_{0-6}CO$—MAL |
| T9-50 | $SO_3H$ | $SO_3H$ | $SO_3H$ | $SO_3H$ | $SO_3H$ | $SO_3H$ | H | H | O-Ph-$(CH_2)_{0-6}CO$—MAL |

OSu = N-Hydroxysuccinimidyl; MAL = N-(2-(N-maleimido)-ethyl)-amide

TABLE 10
Examplary compounds according to this disclosure.
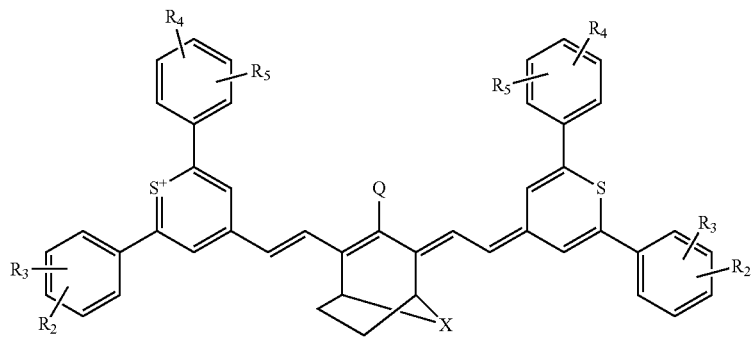
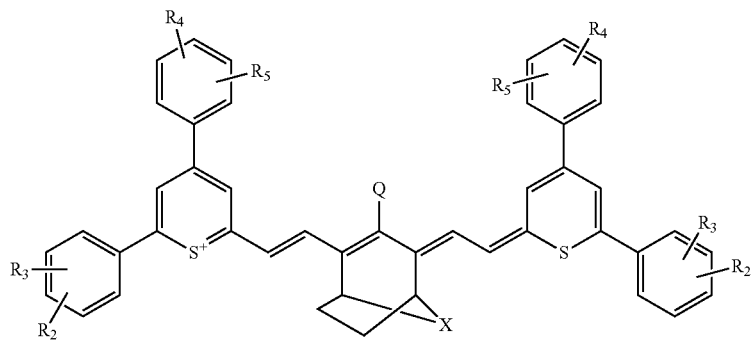
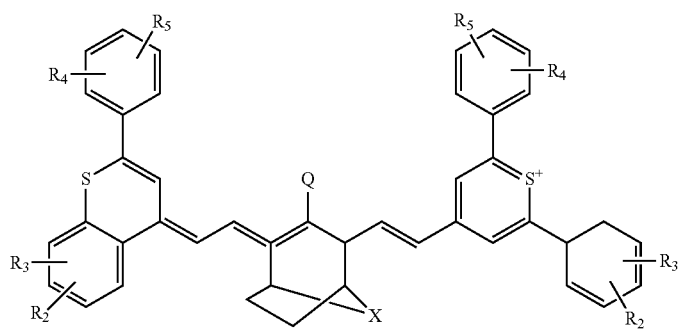
X = CH₂ or N—CH₃
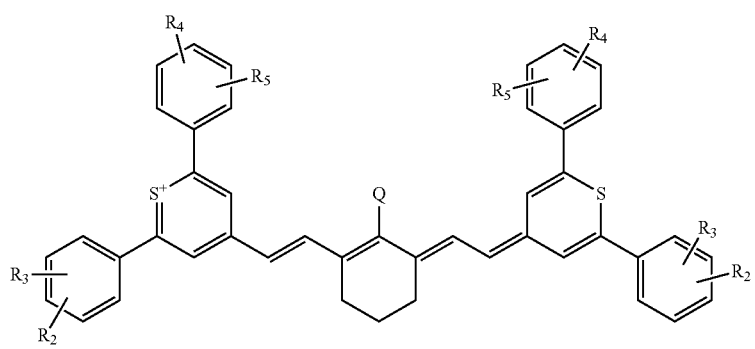

TABLE 10-continued

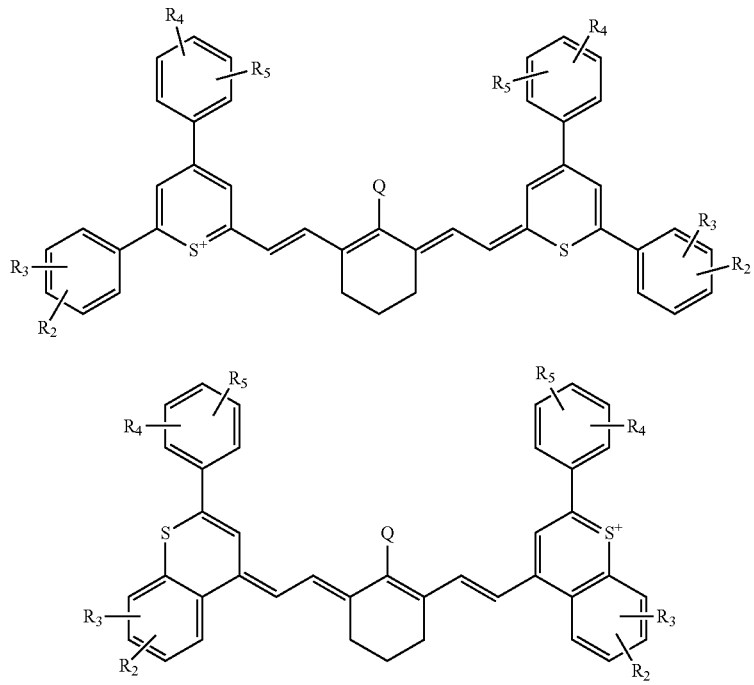

| No | R₂ | R₃ | R₄ | R₅ | Q |
|---|---|---|---|---|---|
| T10-1 | SO₃H | H | SO₃H | H | Cl |
| T10-2 | H | H | SO₃H | SO₃H | Cl |
| T10-3 | SO₃H | SO₃H | H | H | Cl |
| T10-4 | SO₃H | SO₃H | SO₃H | SO₃H | Cl |
| T10-5 | H | SO₃H | H | SO₃H | Cl |
| T10-6 | SO₃H | H | SO₃H | H | S(CH₂)₁₋₆COOH |
| T10-7 | H | H | SO₃H | SO₃H | S(CH₂)₁₋₆COOH |
| T10-8 | SO₃H | SO₃H | H | H | S(CH₂)₁₋₆COOH |
| T10-9 | SO₃H | SO₃H | SO₃H | SO₃H | S(CH₂)₁₋₆COOH |
| T10-10 | H | SO₃H | H | SO₃H | S(CH₂)₁₋₆COOH |
| T10-11 | SO₃H | H | SO₃H | H | S(CH₂)₁₋₆CO—OSU |
| T10-12 | H | H | SO₃H | SO₃H | S(CH₂)₁₋₆CO—OSU |
| T10-13 | SO₃H | SO₃H | H | H | S(CH₂)₁₋₆CO—OSU |
| T10-14 | SO₃H | SO₃H | SO₃H | SO₃H | S(CH₂)₁₋₆CO—OSU |
| T10-15 | H | SO₃H | H | SO₃H | S(CH₂)₁₋₆CO—OSU |
| T10-16 | SO₃H | H | SO₃H | H | S(CH₂)₁₋₆CO—MAL |
| T10-17 | H | H | SO₃H | SO₃H | S(CH₂)₁₋₆CO—MAL |
| T10-18 | SO₃H | SO₃H | H | H | S(CH₂)₁₋₆CO—MAL |
| T10-19 | SO₃H | SO₃H | SO₃H | SO₃H | S(CH₂)₁₋₆CO—MAL |
| T10-20 | H | SO₃H | H | SO₃H | S(CH₂)₁₋₆CO—MAL |
| T10-21 | SO₃H | H | SO₃H | H | SPh(CH₂)₀₋₆COOH |
| T10-22 | H | H | SO₃H | SO₃H | Sph(CH₂)₀₋₆COOH |
| T10-23 | SO₃H | SO₃H | H | H | SPh(CH₂)₀₋₆COOH |
| T10-24 | SO₃H | SO₃H | SO₃H | SO₃H | SPh(CH₂)₀₋₆COOH |
| T10-25 | H | SO₃H | H | SO₃H | SPh(CH₂)₀₋₆COOH |
| T10-26 | SO₃H | H | SO₃H | H | O-Ph(CH₂)₀₋₆COOH |
| T10-27 | H | H | SO₃H | SO₃H | O-Ph(CH₂)₀₋₆COOH |
| T10-28 | SO₃H | SO₃H | H | H | O-Ph(CH₂)₀₋₆COOH |
| T10-29 | SO₃H | SO₃H | SO₃H | SO₃H | O-Ph(CH₂)₀₋₆COOH |
| T10-30 | H | SO₃H | H | SO₃H | O-Ph(CH₂)₀₋₆COOH |
| T10-31 | SO₃H | H | SO₃H | H | SPh(CH₂)₀₋₆CO—OSU |
| T10-32 | H | H | SO₃H | SO₃H | SPh(CH₂)₀₋₆CO—OSU |
| T10-33 | SO₃H | SO₃H | H | H | SPh(CH₂)₀₋₆CO—OSU |
| T10-34 | SO₃H | SO₃H | SO₃H | SO₃H | SPh(CH₂)₀₋₆CO—OSU |
| T10-35 | H | SO₃H | H | SO₃H | SPh(CH₂)₀₋₆CO—OSU |
| T10-36 | SO₃H | H | SO₃H | H | O-Ph(CH₂)₀₋₆CO—OSU |
| T10-37 | H | H | SO₃H | SO₃H | O-Ph(CH₂)₀₋₆CO—OSU |
| T10-38 | SO₃H | SO₃H | H | H | O-Ph(CH₂)₀₋₆CO—OSU |
| T10-39 | SO₃H | SO₃H | SO₃H | SO₃H | O-Ph(CH₂)₀₋₆CO—OSU |
| T10-40 | H | SO₃H | H | SO₃H | O-Ph(CH₂)₀₋₆CO—OSU |
| T10-41 | SO₃H | H | SO₃H | H | SPh(CH₂)₀₋₆CO—MAL |
| T10-42 | H | H | SO₃H | SO₃H | SPh(CH₂)₀₋₆CO—MAL |
| T10-43 | SO₃H | SO₃H | H | H | SPh(CH₂)₀₋₆CO—MAL |
| T10-44 | SO₃H | SO₃H | SO₃H | SO₃H | SPh(CH₂)₀₋₆CO—MAL |
| T10-45 | H | SO₃H | H | SO₃H | SPh(CH₂)₀₋₆CO—MAL |

| | | | | | |
|---|---|---|---|---|---|
| T10-46 | SO₃H | H | SO₃H | H | O-Ph(CH₂)₀₋₆CO—MAL |
| T10-47 | H | H | SO₃H | SO₃H | O-Ph(CH₂)₀₋₆CO—MAL |
| T10-48 | SO₃H | SO₃H | H | H | O-Ph(CH₂)₀₋₆CO—MAL |
| T10-49 | SO₃H | SO₃H | SO₃H | SO₃H | O-Ph(CH₂)₀₋₆CO—MAL |
| T10-50 | H | SO₃H | H | SO₃H | O-Ph(CH₂)₀₋₆CO—MAL |

OSu = N-Hydroxysuccinimidyl; MAL = N-(2-(N-maleimido)-ethyl)-amide

III. Synthesis

Also provided are methods for the synthesis of fluorochromes and key intermediates (bridges, B, and functionalized polycyclic compounds $P_1$ or $P_2$). In particular, methods are described that allow the use of functional groups that impart water solubility to the resulting fluorochrome, but present significant challenges during synthesis due to incompatibility with solvents or reagents required. The new procedures allow synthesis of commercially useful quantities of the intermediates required to make the fluorochromes of the present disclosure.

Generally, the fluorochrome compounds of the present disclosure can be synthesized in the following manner. Two equivalents of a suitably substituted heterocyclic moiety ($P_1$ and $P_2$, wherein $P_1 = P_2$) are reacted with a bridge precursor B bearing two reactive aldehyde groups, each protected in the form of an imine, such as an anilinium imine, in a mixture of acetic acid, acetic anhydride with the addition of a suitable base, such as potassium acetate, at a temperature of about 100° C. for about two hours to form a symmetrical fluorochrome, followed by purification by HPLC as shown in the exemplary scheme below.

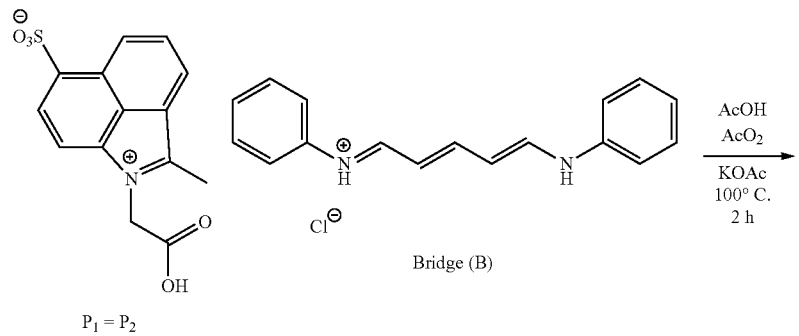

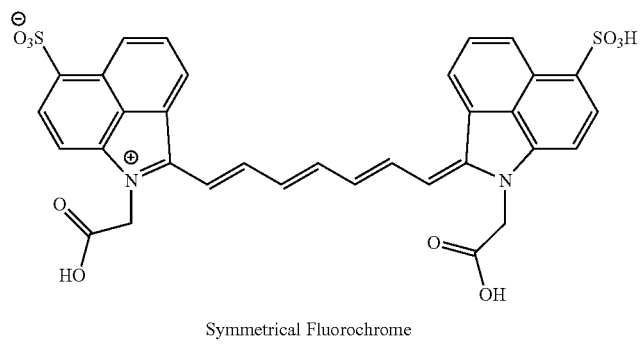

Symmetrical Fluorochrome

In certain embodiments, the fluorochrome compounds are unsymmetrical optionally where $P_1$ is not identical to $P_2$. Such unsymmetrical fluorochrome compounds can be synthesized as follows. One equivalent of a suitably substituted heterocyclic moiety ($P_1$, wherein $P_1 \neq P_2$) is reacted with a bridge precursor B bearing two reactive aldehyde groups, each protected in the form of an imine, such as an anilinium imine, in a mixture of acetic acid, acetic anhydride in the absence of base, at a temperature of about 100° C. for about two hours to form a mono-substituted bridge intermediate (I), after which one equivalent of a different suitably substituted heterocyclic moiety ($P_2$) is added along with a suitable base, such as potassium acetate, and heating to 100° C. is resumed for about two hours to form the unsymmetrical fluorochrome, which can be purified by HPLC, according to the following scheme:

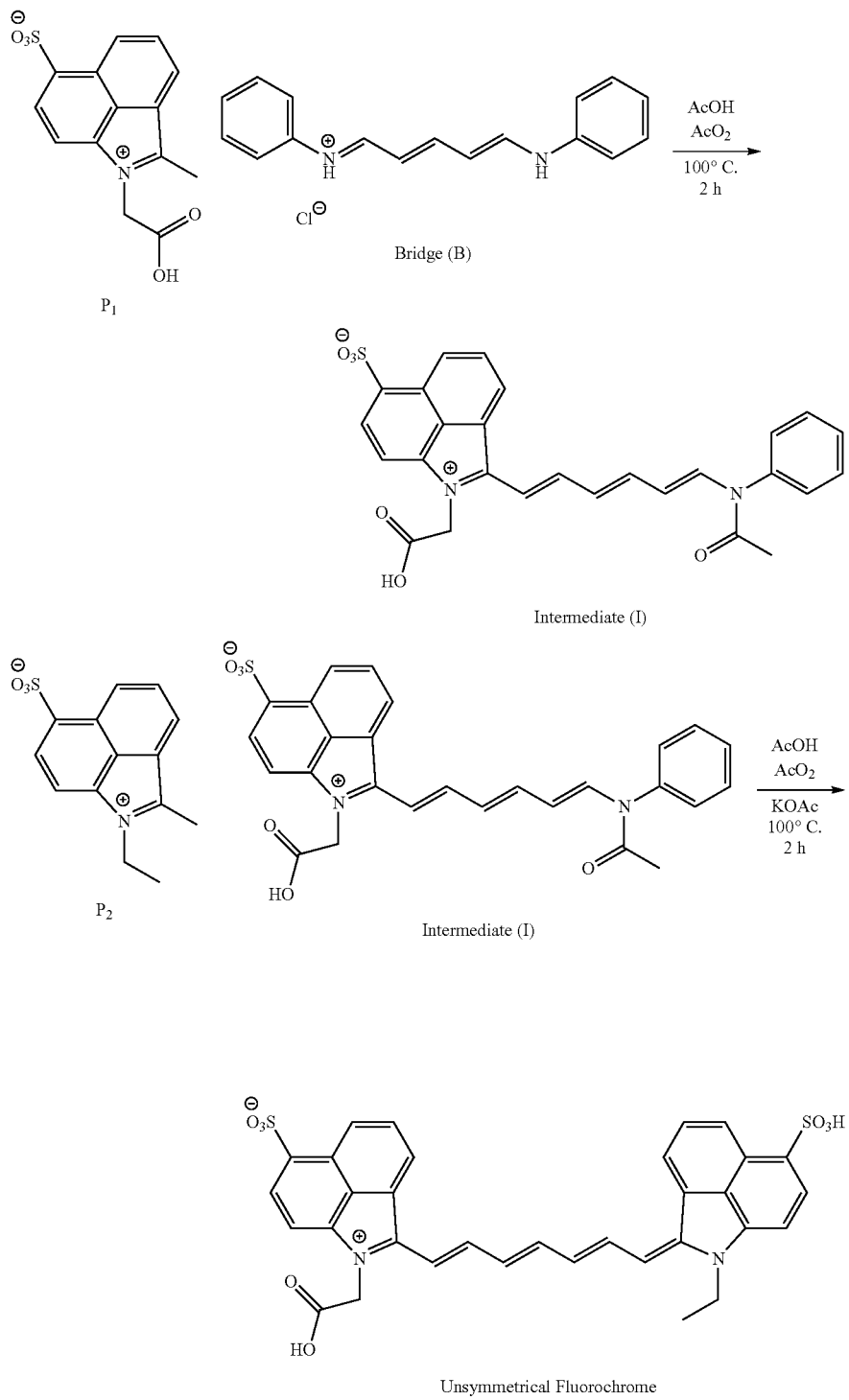

In some embodiments, a suitably substituted bridge B can further react with other molecules to form a linker L. As an illustration, a linker substitution can be performed on a chloride substituted bridge as follows. One equivalent of chloro-substituted bridge fluorochrome is reacted with 2 equivalents of 2-(4-mercaptophenyl) acetic acid in DMF with 2% pyridine for 15 minutes at room temperature. The resulting linker (L) substituted fluorochrome is then purified by HPLC.

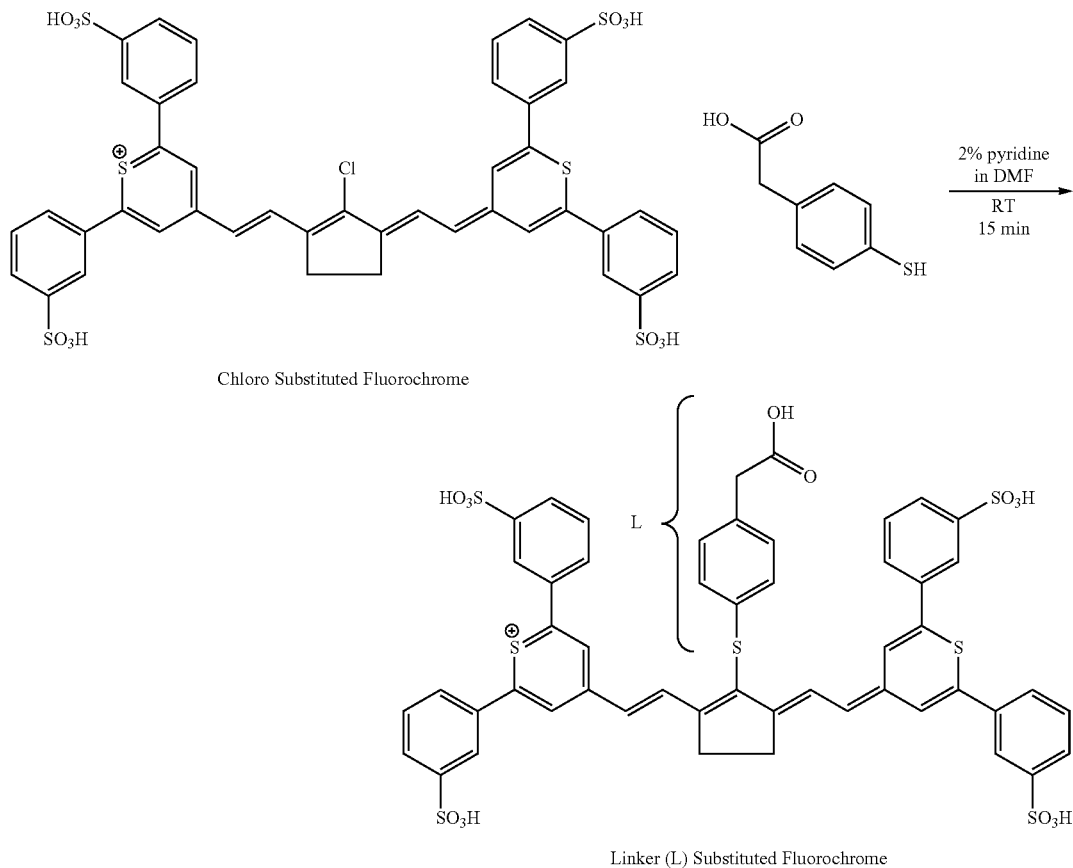

In some embodiments, methods are provided for the synthesis of suitably substituted aromatic heterocycles, such as benz[c,d]indolium, thiopyrylium or acridinium salts. Optionally, sulfonate groups are introduced to a suitably activated benz[c,d]indolinone, acridone, or thiopyranone, through reaction with chlorosulfonic acid followed by hydrolysis and conversion to the to the corresponding benz[c,d]indolium, thiopyrylium or acridinium salts.

In some embodiments, the starting material is benz[c,d]indolin-2-one.

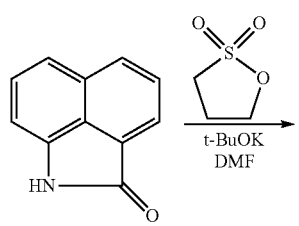

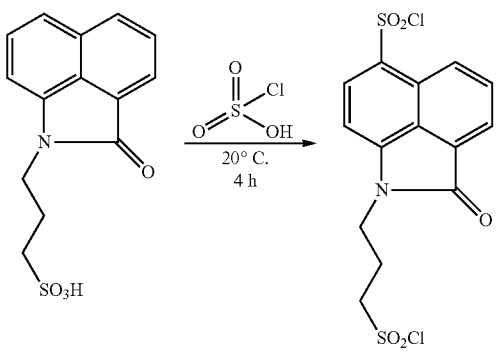

-continued

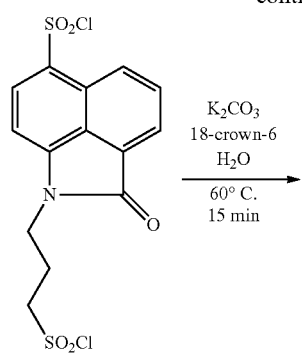
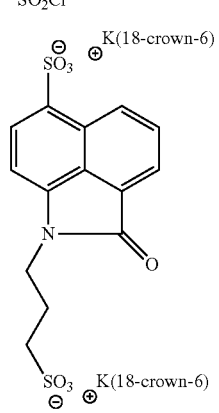
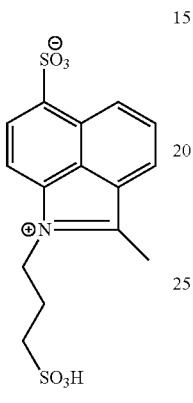
In some embodiments, the starting material is 2,6-diphenylthiopyran-4-one.
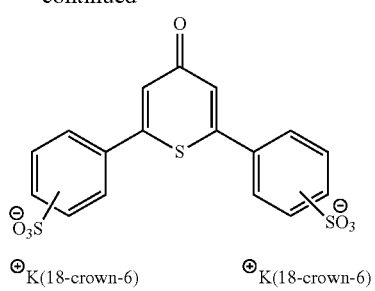
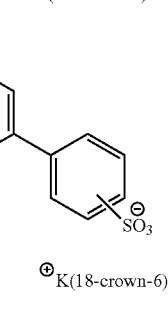
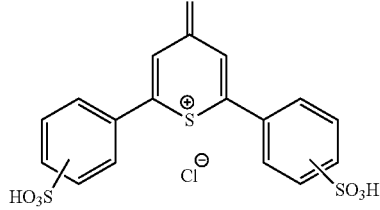
In some embodiments, the starting material is 10-methylacridin-9-one.
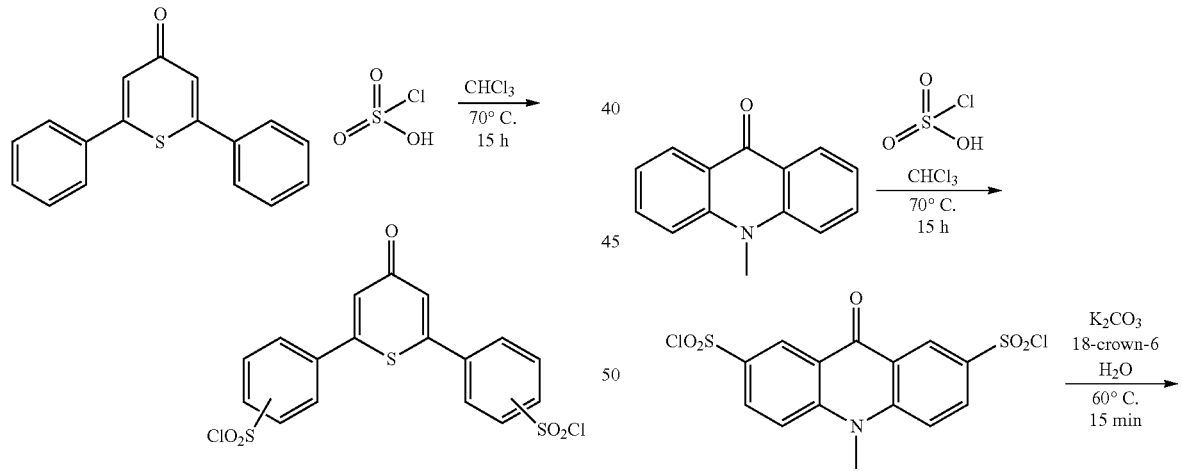
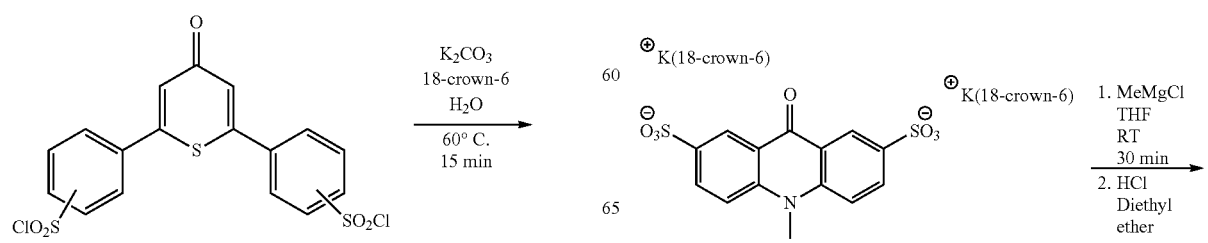

-continued

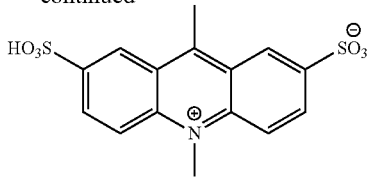

Dyes having absorption max in the SWIR window (1000-1300 nm) are suitable for exciting with 980 nm laser. However, existing dyes are very difficult to solubilize in aqueous or most organic solvents, and thus are practically not suitable for use in biological applications. As such, these molecules are optionally excluded from the present disclosure. Lack of a functional group for conjugating to other moieties and lack of polar substituents that enable aqueous solubility further complicate their direct use in any biologically important detection systems.

IR-1061

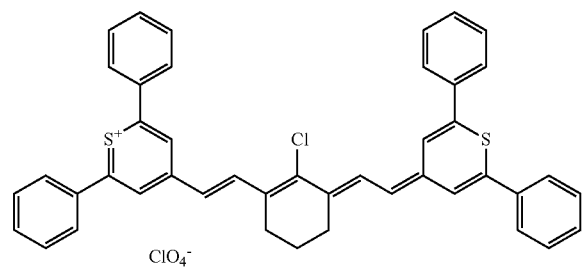

IR-1048

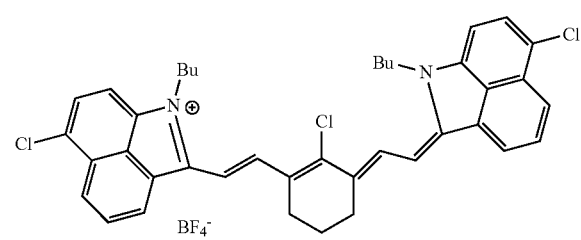

CAS # 155613-98-2

-continued

IR-26

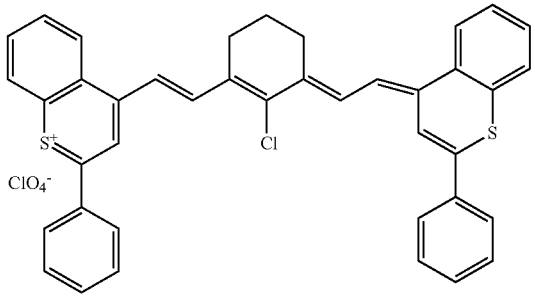

Compound 23

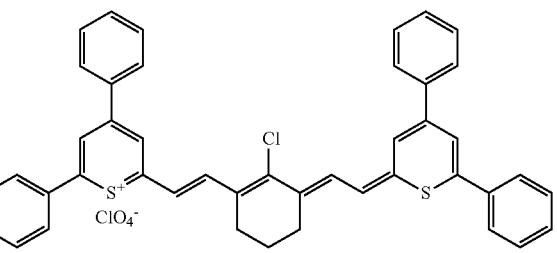

(herein referred to as "Dye 23")
as reported in *J. Org. Chem.*, 42 (5), p887 (1977)

Addressing this issue, some methods as provided herein may be used to synthesize heterocycles bearing one or more aqueous soluble substituents such as sulfonates or "sulfonic acid" groups as in the table below for synthesizing water soluble SWIR dyes; wherein, R is an alklyl-X (with X=H or $SO_3H$ or COOH or $NH_2$, or OH or halide), and one or more of $R_1$, $R_2$, and $R_3$ being a $SO_3^-$ or $SO_3H$ group.

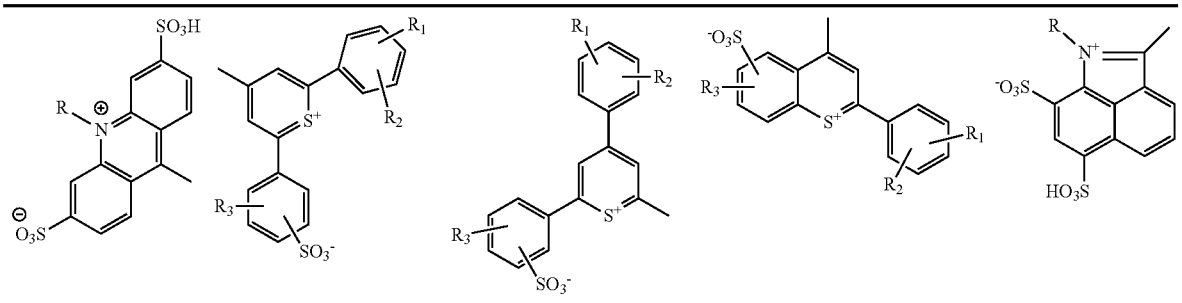

IV. Properties and Uses

Fluorochrome compounds with low solubility in water frequently undergo aggregation or conformationally induced hypsochromic shifts in optical properties. In some embodiments, the fluorochrome compounds are solubilized by incorporation of one or more solubilizing groups. The solubilizing groups are optionally sulfonates. Optionally, the water soluble fluorochrome compounds substantially retain their SWIR optical properties when in solution in water without undergoing a hypsochromic shift in absorbance or emission relative to the optical properties in an organic solvent such as methanol. As used herein, the term water soluble with respect to SWIR dyes means full soluble in water to a concentration of 1 µM or greater, optionally 10 µM or greater, optionally to 100 µM.

It is contemplated that the fluorochrome compounds as provided herein are particularly useful for photon mediated imaging and detection applications. In some aspects, the fluorochrome compounds are linked, conjugated or otherwise bound to targeting ligands, such as peptides, drugs, proteins, antibodies or nucleic acids that bind with specificity to a particular biological target, for example in a biological sample, on a cell, on a tissue, or in a living animal or patient. In this way, the SWIR optical properties can be used to detect, visualize, or image the presence, absence or spatial distribution of the biological target in the sample, cell, tissue, animal or patient.

In other aspects, the fluorochrome compounds are linked, conjugated or otherwise bound to one or more carrier molecules, illustratively but not limited to 3,3-diphenylpropylamine, pamidronate, alendronate, bisphosphonates, polyethylene glycol, polyvinylpyrrolidone, N-(2-hydroxypropyl) methacrylamide, polymers, copolymers, proteins, protamine, poly-L-arginine, poly-D-arginine, liposomes, or nanoparticles. In other aspects, the conjugates of the fluorochrome compounds direct the localization of the fluorochrome compounds in cells, tissues, animals or patients, to, for example, a cell nucleus, cytoplasm, lysosomes, mitochondria, vasculature, bone, lung, kidney, liver, heart, brain, or tumor tissue.

In some aspects, the fluorochrome compounds are useful for microscopy, flow cytometry, or tissue imaging.

In some aspects, the fluorochrome compounds are useful for in vivo fluorescence optical imaging.

In some aspects the fluorochrome compounds are useful for ex vivo fluorescence optical imaging.

In some aspects, the fluorochrome compounds are useful for photoacoustic imaging.

In some aspects, the fluorochrome compounds act as photosensitizers to generate singlet oxygen upon excitation with light. Optionally, fluorochrome compounds are useful for photodynamic therapy. Optionally, fluorochrome compounds may be used as a sensitizer in a luminescent singlet oxygen channeling assay.

Another aspect of this disclosure includes a peptide, protein or other biomolecule that presents a proteolytic or enzymolytic scissile bond, and two or more fluorochrome compounds as provided herein that are chemically linked to the peptide, protein or biomolecule such that their fluorescence is significantly quenched. Upon the action of an enzyme by e.g. enzymatic cleavage upon the peptide, protein or biomolecule scissile bond, the fluorochrome compounds are separated and the agent emits a fluorescent signal when excited by electromagnetic radiation of appropriate wavelength and frequency. As used herein, the term "quenched" is understood to mean the process of partially or completely reducing the fluorescent signal from a fluorophore. For example, a fluorescent signal from the fluorochrome compound can be reduced inter- or intra-molecularly through the placement of a second fluorochrome (either the same or a different compound) in close proximity to the first fluorochrome or the placement of a non-fluorogenic quenching chromophore molecule, e.g., quencher, in close proximity to the first fluorophore. The agent is de-quenched (or activated), for example, through the enzymatic cleavage of a peptide, protein or biomolecule proteolytic or enzymolytic scissile bond.

In some embodiments, the fluorochrome compounds may have very low intrinsic fluorescence (quantum yield less than about 0.01%) but retain high absorption (molar extinction coefficient higher than about 50,000 $M^{-1}cm^{-1}$) in the NIR to SWIR region of the electromagnetic spectrum. It is contemplated that such fluorochrome compounds could be used as quencher compounds when in close proximity to another fluorescent compound that emits fluorescence at wavelengths close to the absorption wavelengths. Such compounds, containing one fluorescent compound and a complementary quencher compound with low intrinsic fluorescence could be activatable if, for example, the fluorescent compound and the quencher compound are separated by a peptide, protein or biomolecule enzymolytic scissile bond that is recognized and cleaved by a particular enzyme or protease. It is further contemplated that the intramolecularly quenched fluorochrome and quencher compounds could be activated through chemical means as well, such as an oxidation or reduction with or without the aid of an enzyme.

(a) Imaging Methods

The present disclosure provides methods for in vitro and in vivo imaging using the compounds disclosed herein. For a review of optical imaging techniques, see, e.g., Alfano et al., ANN. NY ACAD. SCI. 820:248-270 (1997); Weissleder, *Nature Biotechnology* 19, 316-317 (2001); Ntziachristos et al., *Eur. Radiol.* 13:195-208 (2003); Graves et al., *Curr. Mol. Med.* 4:419-430 (2004); Citrin et al., *Expert Rev. Anticancer Ther.* 4:857-864 (2004); Ntziachristos, *Ann. Rev. Biomed. Eng.* 8:1-33 (2006); Koo et al., *Cell Oncol.* 28:127-139 (2006); and Rao et al., *Curr. Opin. Biotechnol.* 18:17-25 (2007).

Optical imaging includes all methods from direct visualization without use of any device and use of devices such as various scopes, catheters and optical imaging equipment, for example computer based hardware for tomographic presentations. The imaging agents are useful with optical imaging modalities and measurement techniques including, but not limited to: endoscopy; fluorescence endoscopy; luminescence imaging; time resolved transmittance imaging; transmittance imaging; nonlinear microscopy; confocal imaging; acousto-optical imaging; photoacoustic imaging; reflectance spectroscopy; spectroscopy; coherence interferometry; interferometry; optical coherence tomography; diffuse optical tomography and fluorescence mediated molecular tomography (continuous wave, time domain frequency domain systems and early photon), and measurement of light scattering, absorption, polarization, luminescence, fluorescence lifetime, quantum yield, and quenching.

An imaging system useful in the practice of the imaging methods as provided herein typically includes three basic components: (1) an appropriate light source for inducing excitation of the compound, (2) a system for separating or distinguishing emissions from light used for fluorophore excitation, and (3) a detection system. The detection system can be hand-held or incorporated into other useful imaging devices, such as intraoperative microscopes. Exemplary detection systems include an endoscope, catheter, tomographic system, hand-held imaging system, or a intraoperative microscope.

Optionally, the light source provides monochromatic (or substantially monochromatic) light. The light source can be a suitably filtered light, i.e., bandpass light from a broadband source. For example, light from a 150-watt halogen lamp can be passed through a suitable bandpass filter commercially available from Omega Optical (Brattleboro, Vt.). Depending upon the system, the light source can be a laser. See, e.g., Boas et al., PROC. NATL. ACAD. SCI. USA 91:4887-4891, 1994; Ntziachristos et al., PROC. NATL. ACAD. SCI. USA 97:2767-2772, 2000; and Alexander, J. CLIN. LASER MED. SURG. 9:416-418, 1991. Information on lasers for imaging can be found, for example, at Imaging Diagnostic Systems, Inc., Plantation, Fla. and various other sources. A high pass or bandpass filter can be used to separate optical emissions from excitation light. A suitable high pass or bandpass filter is commercially available from Omega Optical, Burlington, Vt.

In general, the light detection system can be viewed as including a light gathering/image forming component and a light/signal detection/image recording component. Although the light detection system can be a single integrated device that incorporates both components, the light gathering/image forming component and light detection/image recording component are discussed separately.

A particularly useful light gathering/image forming component is an endoscope. Endoscopic devices and techniques which have been used for in vivo optical imaging of numerous tissues and organs, including peritoneum (Gahlen et al., J. PHOTOCHEM. PHOTOBIOL. B 52:131-135, 1999), ovarian cancer (Major et al., Gynecol. Oncol. 66:122-132, 1997), colon and rectum (Mycek et al., GASTROINTEST. ENDOSC. 48:390-394, 1998; and Stepp et al., ENDOSCOPY 30:379-386, 1998), bile ducts (Izuishi et al., HEPATOGASTROENTEROLOGY 46:804-807, 1999), stomach (Abe et al., ENDOSCOPY 32:281-286, 2000), bladder (Kriegmair et al., UROL. INT. 63:27-31, 1999; and Riedl et al., J. ENDOUROL. 13:755-759, 1999), lung (Hirsch et al., CLIN CANCER RES 7:5-220, 2001), brain (Ward, J. LASER APPL. 10:224-228, 1998), esophagus, and head and neck regions can be employed.

Other types of light gathering components are catheter-based devices, including fiber optics devices. Such devices are particularly suitable for intravascular imaging. See, e.g., Tearney et al., SCIENCE 276:2037-2039, 1997; and CIRCULATION 94:3013, 1996.

Still other imaging technologies, including phased array technology (Boas et al., PROC. NATL. ACAD. SCI. USA 91:4887-4891, 1994; Chance, ANN. NY ACAD. SCI. 838:29-45, 1998), optical tomography (Cheng et al., OPTICS EXPRESS 3:118-123, 1998; and Siegel et al., OPTICS EXPRESS 4:287-298, 1999), intravital microscopy (Dellian et al., BR. J. CANCER 82:1513-1518, 2000; Monsky et al., CANCER RES. 59:4129-4135, 1999; and Fukumura et al., CELL 94:715-725, 1998), confocal imaging (Korlach et al., PROC. NATL. ACAD. SCI. USA 96:8461-8466, 1999; Rajadhyaksha et al., J. INVEST. DERMATOL. 104:946-952, 1995; and Gonzalez et al., J. MED. 30:337-356, 1999) and fluorescence molecular tomography (FMT) (Nziachristos et al., NATURE MEDICINE 8:757-760, 2002; U.S. Pat. No. 6,615,063, PCT WO 03/102558, and PCT WO 03/079015) can be used with the imaging agents of this disclosure. Similarly, the imaging agents can be used in a variety of imaging systems, for example, (1) the IVIS® Imaging Systems: 100 Series, 200 Series (Xenogen, Alameda, Calif.), (2) SPECTRUM and LUMINA (Xenogen, Alameda, Calif.), (3) the SoftScan® or the eXplore Optix™ (GE Healthcare, United Kingdom), (4) Maestro™ and Nuance™-2 Systems (CRi, Woburn, Mass.), (5) Image Station In-Vivo FX from Carestream Molecular Imaging, Rochester, N.Y. (formerly Kodak Molecular Imaging Systems), (6) OV100, IV100 (Olympus Corporation, Japan), (7) Cellvizio Mauna Kea Technologies, France), (8)] Nano-SPECT/CT or HiSPECT (Bioscan, Washington, D.C.), (9) CTLM® or LILA™ (Imaging Diagnostic Systems, Plantation, Fla.), (10) DYNOT™ (NIRx Medical Technologies, Glen Head, N.Y.), and (11) NightOWL Imaging Systems by Berthold Technologies, Germany.

A variety of light detection/image recording components, e.g., charge coupled device (CCD) systems or photographic film, can be used in such systems. The choice of light detection/image recording depends on factors including the type of light gathering/image forming component being used. It is understood, however, that the selection of suitable components, assembling them into an optical imaging system, and operating the system is within ordinary skill in the art.

(i) In Vivo Imaging Methods

With respect to optical in vivo imaging, such a method comprises (a) administering to a subject one or more of the compounds as described herein, (b) allowing sufficient time to permit the compound to distribute or localize within the subject, and (c) detecting a signal emitted by the compound. The signal emitted by the compound can be used to construct an image, for example, a tomographic image. The foregoing steps can be repeated at predetermined time intervals thereby to permit evaluation of the emitted signals of the imaging compounds in the subject over time.

In another in vivo imaging method, the method comprises the steps of (a) administering to a subject one or more of the compounds described herein that contains a fluorochrome; (b) allowing sufficient time to permit the compound to distribute or localize within the subject; (c) exposing the subject to light of a wavelength absorbable by the fluorochrome, and (d) detecting a signal emitted by the compound. The foregoing steps can be repeated at predetermined time intervals thereby to permit evaluation of the emitted signals of the compounds in the subject over time. The illuminating and/or detecting steps (steps (c) and (d), respectively) can be performed using an endoscope, catheter, tomographic system, planar system, hand-held imaging system, goggles, an intraoperative microscope, or other suitable device.

Before or during the method steps, a detection system can be positioned around or in the vicinity of a subject (for example, an animal (e.g., human) to detect signals emitted from the subject. The emitted signals can be processed to construct an image, for example, a tomographic image. In addition, the processed signals can be displayed as images either alone or as fused (combined) images.

In addition, it is possible to practice an in vivo imaging method that selectively detects and images one, two or more molecular imaging probes, optionally including the currently provided compounds simultaneously. In such an approach, for example, in step (a) noted above, two or more imaging probes whose signal properties are distinguishable from one another are administered to the subject, either at the same time or sequentially, wherein at least one of the molecular imaging probes is a compound as provided herein. The use of multiple probes permits the recording of multiple biological processes, functions or targets.

The subject may be a vertebrate, for example, a mammal, for example, a human. The subject may also be a non-vertebrate (for example, C. elegans, drosophila, or another model research organism, etc.) used in laboratory research.

Information provided by such in vivo imaging approaches, for example, the presence, absence, or level of emitted signal can optionally be used to detect and/or monitor a health condition in the subject. Exemplary health conditions include, without limitation, autoimmune disease, bone disease, cancer, cardiovascular disease, environmental disease, dermatological disease, immunologic disease, inherited disease, infectious disease, metabolic disease, neurodegenerative disease, ophthalmic disease, respiratory disease, early stages of such diseases, and progression or remission of disease (e.g. tumor size changes). In addition, in vivo imaging can be used to assess the effect of a compound or therapy by using the imaging agents, wherein the subject is imaged prior to and after treatment with the compound or therapy, and the corresponding signal/images are compared.

The compounds as provided herein also can be used in in vivo imaging method where cells labeled with the compound are administered to the recipient. The cells can be labeled with the compounds either in vivo or ex vivo. In the ex vivo approach, cells can be derived directly from a subject or from another source (e.g., from another subject, cell culture, etc.). The compounds can be mixed with the cells to effectively label the cells and the resulting labeled cells administered to the subject into a subject in step (a). Any of steps (b)-(d) then are followed as described above. This method can be used for monitoring trafficking and localization of certain cell types, including T-cells, tumor cells, immune cells and stem cells, and other cell types. In particular, this method may be used to monitor cell-based therapies.

It is understood that the formulation of the compounds, the choice of mode of administration, the dosages of compounds administered to the subject, and the timing between administration of the imaging compounds and imaging may be selected by one of ordinary skill in the art.

The foregoing methods can be used to determine a number of indicia, optionally including tracking the localization of the imaging compound(s) in the subject over time or assessing changes or alterations in the metabolism and/or excretion of the imaging compounds in the subject over time. The methods can also be used to follow therapy for health conditions by imaging molecular events and biological pathways modulated by such therapy, including but not limited to determining efficacy, optimal timing, optimal dosing levels (including for individual patients or test subjects), and synergistic effects of combinations of therapy.

The methods and compositions of this disclosure can be used to help a physician or surgeon to identify and characterize areas of interest or disease, such as arthritis, cancers and specifically colon polyps, or vulnerable or unstable plaque, to distinguish diseased and normal tissue, such as detecting tumor margins that are difficult to detect using an ordinary operating microscope, e.g., in brain surgery, to help dictate a therapeutic or surgical intervention, e.g., by determining whether a lesion is cancerous and should be removed or non-cancerous and left alone, or in surgically staging a disease, e.g., intraoperative lymph node staging, sentinel lymph node mapping, or assessing intraoperative bleeding.

The methods and compositions of this disclosure can also be used in the detection, characterization and/or determination of the localization of a health condition, especially early disease, the severity of a disease or a disease-associated condition, the staging of a disease, and/or monitoring a disease. The presence, absence, or level of an emitted signal can be indicative of a disease state.

The methods and compositions of this disclosure can also be used to monitor and/or guide various therapeutic interventions, such as surgical procedures, and monitoring drug therapy, including cell based therapies. The methods of this disclosure can also be used in prognosis of a health condition.

With respect to each of the foregoing, examples of such health conditions that can be detected or monitored (before, during or after therapy) include but are not limited to inflammation (for example, inflammation caused by arthritis, for example, rheumatoid arthritis), cancer (for example, colorectal, ovarian, lung, breast, prostate, cervical, testicular, skin, brain, gastrointestinal, pancreatic, liver, kidney, bladder, stomach, leukemia, mouth, esophageal, bone), cardiovascular disease (for example, atherosclerosis and inflammatory conditions of blood vessels, ischemia, stroke, thrombosis, disseminated intravascular coagulation), dermatologic disease (for example, Kaposi's Sarcoma, psoriasis, allergic dermatitis), ophthalmic disease (for example, macular degeneration, diabetic retinopathy), infectious disease (for example, bacterial, viral, fungal and parasitic infections, including Acquired Immunodeficiency Syndrome, malaria, Chagas Disease, Schistosomiasis), immunologic disease (for example, an autoimmune disorder, lymphoma, multiple sclerosis, rheumatoid arthritis, diabetes mellitus, lupus erythematosis, myasthenia gravis, Graves disease), central nervous system disease (for example, a neurodegenerative disease, such as Parkinson's disease or Alzheimer's disease, Huntington's Disease, amyotrophic lateral sclerosis, prion disease), inherited diseases, metabolic diseases, environmental diseases (for example, lead, mercury and radioactive poisoning, skin cancer), bone-related disease (for example, osteoporosis, primary and metastatic bone tumors, osteoarthritis), neurodegenerative disease, and surgery-related complications (such as graft rejection, organ rejection, alterations in wound healing, fibrosis or other complications related to surgical implants).

The methods and compositions described herein can, therefore, be used, for example, to determine the presence and/or localization of tumor cells, the presence and/or localization of inflammation, including the presence of activated macrophages, for instance in atherosclerosis or arthritis, the presence and in localization of vascular disease including areas at risk for acute occlusion (i.e., vulnerable plaques) in coronary and peripheral arteries, regions of expanding aneurysms, unstable plaque in carotid arteries, and ischemic areas. The methods and compositions of this disclosure can also be used in identification and evaluation of cell death, injury, apoptosis, necrosis, hypoxia and angiogenesis. The methods and compositions can also be used for drug delivery and to monitor drug delivery, especially when drugs or drug-like molecules are chemically attached to one or more of the compounds as provided herein. Exemplary drug molecules include chemotherapeutic and cytostatic agents and photodynamic agents including but not limited to porfimer sodium, motexafin lutetium, cetirizine dihydrochloride, aminolevulinic acid, hypericin, benzoporphyrin derivative, and porphyrins.

In addition, the methods and compositions described herein can be used to image angiogenesis (new blood vessel formation) in a subject. The method comprises administering to a subject (for example, a human or animal) an amount of one or more of the imaging compounds described herein sufficient to facilitate angiogenesis imaging. After sufficient time to permit the agent to distribute within the animal or distribute within the area to be imaged, the presence and/or amount of the agent is determined. The presence and/or amount of the agent can then be used to create an image, for example, a tomographic image, representative of new blood vessel formation in the subject.

(ii) In Vitro Imaging Methods

With respect to in vitro imaging, the imaging compounds can be used in a variety of in vitro assays. For example, an exemplary in vitro imaging method comprises: (a) contacting a sample, for example, a biological sample, with one or more of the imaging compounds described herein; (b) allowing the agent(s) to interact with a biological target in the sample; (c) optionally, removing unbound agent; and (d) detecting a signal emitted from the agent thereby to determine whether the imaging compounds has been activated by or bound to the biological target. When the imaging compound comprises a fluorochrome, step (d) may further include illuminating the sample with light of a wavelength absorbable by the fluorochrome to produce the emitted signal.

After an imaging compound has been designed, synthesized, and optionally formulated, it can be tested in vitro to assess its biological and performance characteristics. For instance, different types of cells grown in culture can be used to assess the biological and performance characteristics of the imaging compound. Cellular uptake, binding or cellular localization of the agent can be assessed using techniques known in the art, including, for example, fluorescent microscopy, FACS analysis, immunohistochemistry, immunoprecipitation, in situ hybridization and Forster resonance energy transfer (FRET) or fluorescence resonance energy transfer. By way of example, the imaging compounds can be contacted with a sample for a period of time and then washed to remove any free imaging compounds. The sample can then be viewed using an appropriate detection device such as a fluorescent microscope equipped with appropriate filters matched to the optical properties of a fluorescent agent. Fluorescence microscopy of cells in culture or scintillation counting is also a convenient means for determining whether uptake and binding has occurred. Tissues, tissue sections and other types of samples such as cytospin samples can also be used in a similar manner to assess the biological and performance characteristics of the compounds. Other detection methods include, but are not limited to flow cytometry, immunoassays, hybridization assays, and microarray analysis, can also be used in the practice of this disclosure.

(b) Therapeutic Applications

Certain of the imaging compounds as described herein, for example, imaging compounds containing a fluorochrome and/or a drug molecule, can be used to ameliorate a symptom of, or treat, a particular health condition, such as a disease or disorder. The method comprises (a) administering to a subject an amount of one or more the imaging compounds described herein sufficient to impart a therapeutic effect in the subject; and (b) permitting sufficient time for the agent to distribute within the subject or otherwise localize in a region of the subject to be treated and then, (c) depending upon the therapeutic agent, optionally activating the imaging compound to impart a therapeutic effect. For example, when the therapeutic agent is a radiolabel, no subsequent activation is required. However, when the therapeutic agent is a photoreactive agent, for example, a dye used in photodynamic therapy, the agent may be activated by exposing the agent to light having a wavelength that activates the agent. As a result, the agents can be used to treat a condition of interest, for example, a cancer, immune disorder, inflammatory disorder, vascular disorder and the like. Furthermore, the agents can be used to prevent, ameliorate, or reverse angiogenesis in a region of interest in the subject.

Various aspects of the present disclosure are illustrated by the following non-limiting examples. The examples are for illustrative purposes and are not a limitation on any practice of the present invention. It will be understood that variations and modifications can be made without departing from the spirit and scope of the invention.

EXAMPLES

Example 1: Synthesis of Fluorochrome Compound D65 (15 in Scheme 1)

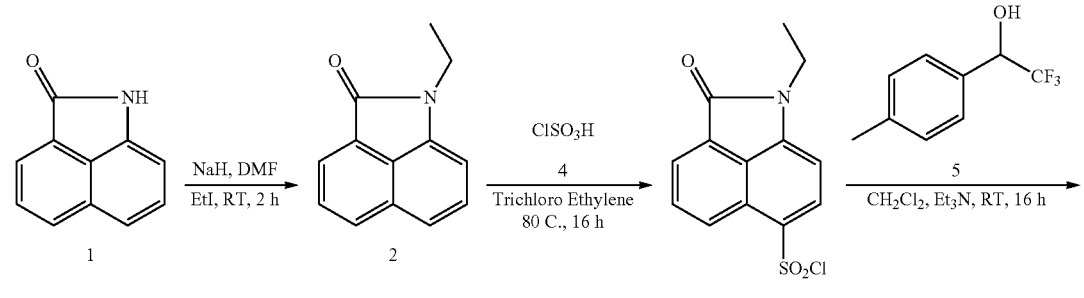

Scheme 1

-continued
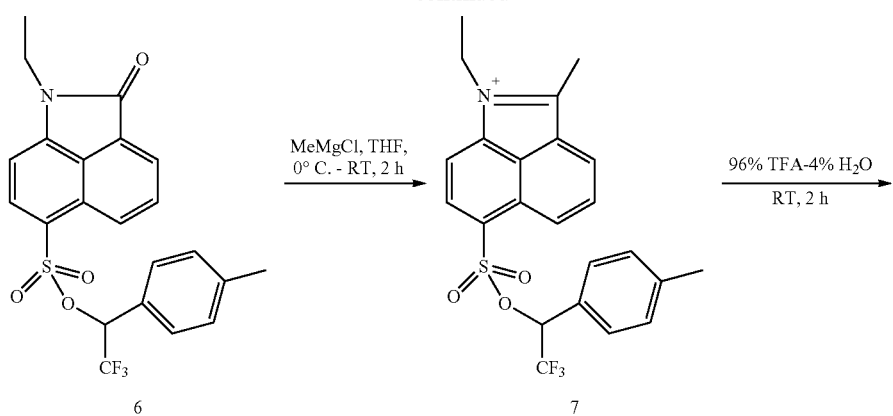
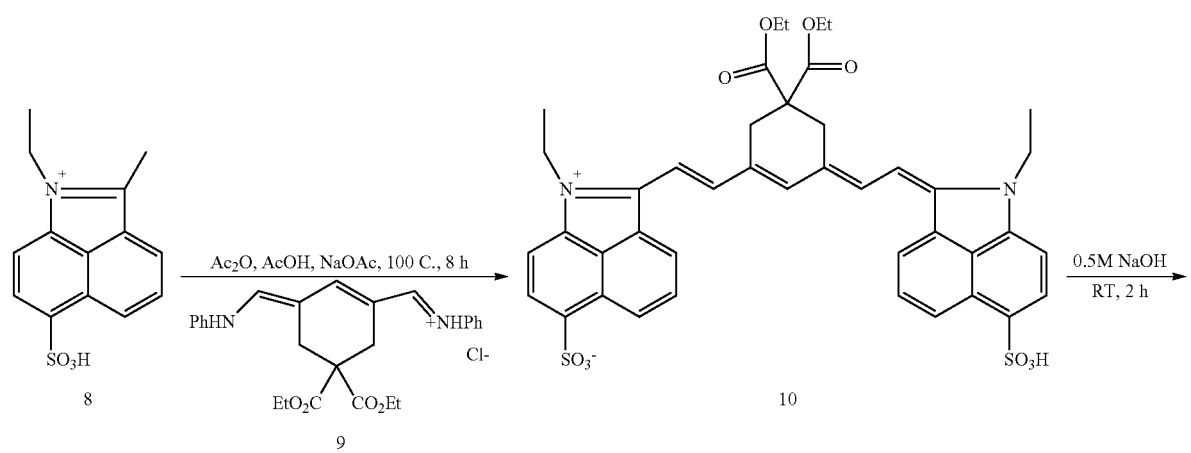

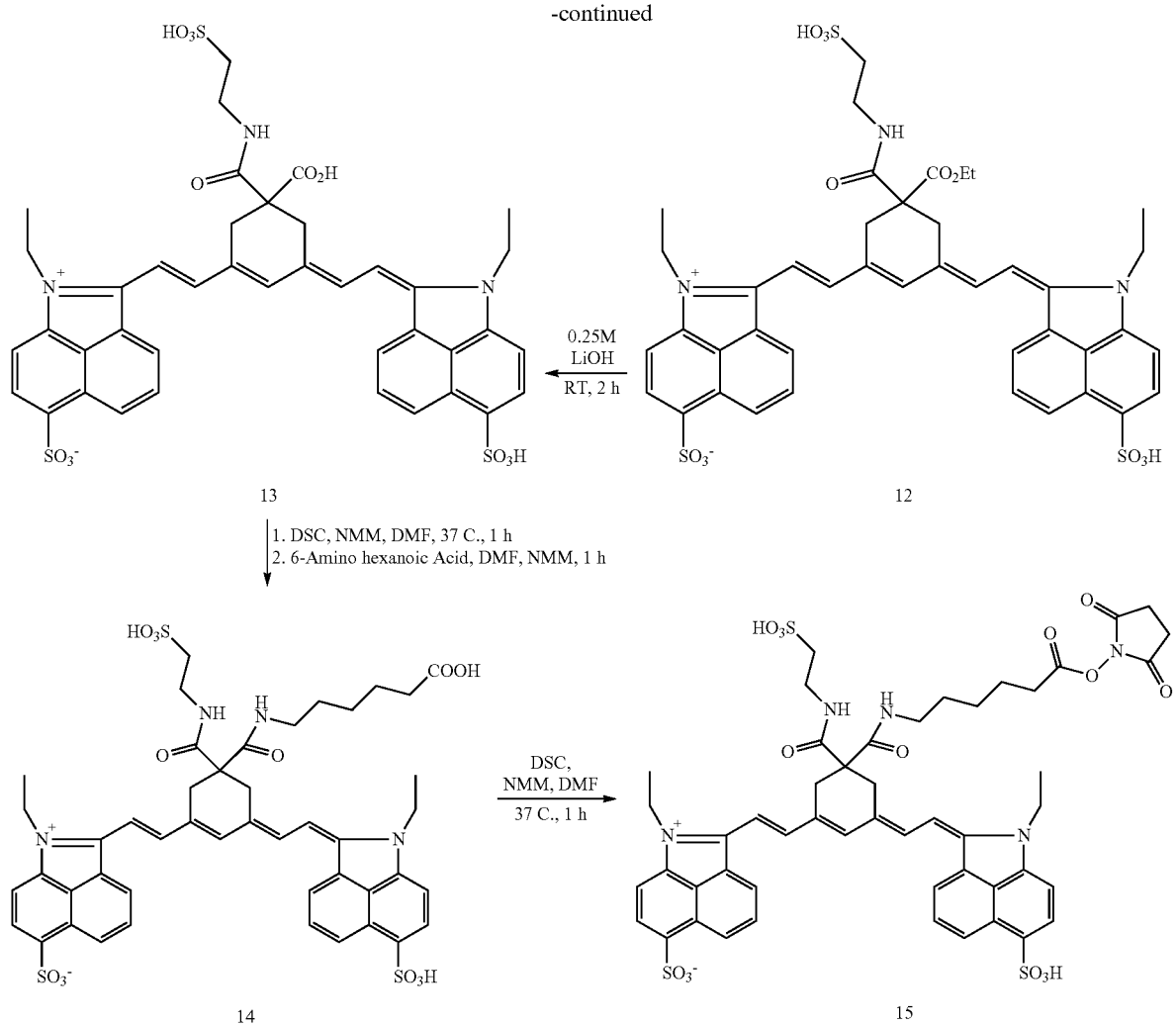

1-ethylbenzo[cd]indol-2(1H)-one (2)

2.5 g Benz[cd]indol-2(1H)-one (1, from TCI America) was dissolved in 20 mL of dry DMF, to which was added 2 equivalents of sodium hydride (60% in mineral oil) after washing with dry hexanes under nitrogen cooled to 0-5° C. with stirring. After 5 minutes, three equivalents of ethyl iodide were added in drops over 2 min. Cooling was removed and was allowed to warm up to room temp; stirring was continued for 2 hrs. The reaction was monitored by TLC (Silica, Hexane-EtOAc 3:1) as well as by RP HPLC on C18 column (Gradient: 10%-85% B; B=Acetonitrile and A=25 mM Ammonium Formate with 5% methanol). Reaction mixture was poured into ice water, and the product was extracted with ethyl acetate followed by washings, drying over anhydrous sodium sulfate, filtration and rotary evaporation which afforded a yellow solid in 90% yield.

Sulfonyl Chloride of 1-ethylbenzo[cd]indol-2(1H)-one (3)

To 1-ethylbenzo[cd]indol-2(1H)-one (2, 2 g) in an RBF was added 20 mL of trichloroethylene (TCE) and was fitted with a reflux condenser. Three equivalents of chlorosulfonic acid (ClSO$_3$H) was added in drops over 2 min with magnetic stirring. Reaction mixture was heated to 80° C. After 16 hrs, the contents were concentrated on a rotovap and then poured into water. Extraction with ethyl acetate and washings with water several times, followed by rotovap drying yielded the sulfonyl chloride as the exclusive monosulfonyl chloride product, which was confirmed LCMS as the sulfonic acid MW 277 and by proton NMR (300 Mhz) as K salt of sulfonic acid in DMSO-d$_6$: δ (ppm) (JJ coupling constants in Hz): 1.254 (t, 3H), 3.921 (q, 2H), 7.084 (d, 1H, JJ=7.44), 7.789 (t, 1J, JJ=7.14), 7.785 (d, 1H, JJ=7.41), 8.024 (d, 1H, 7.14), 8.722 (d, 1H, JJ=8.52)

2,2,2-Trifluoro-1-p-tolyl-ethanol Protection of Sulfonyl Chloride (6)

(Ref.: Pauff, S. M., et. al., J. Org. Chem. 2013, 78, 711-716) 1-ethylbenzo[cd]indol-2(1H)-one-6-sulfonylchloride (3) as obtained above was treated with 2,2,2-Trifluoro-1-p-tolyl-ethanol (at 5% excess) in dichloromethane and two equivalents of triethylamine at RT, with stirring for 16 hrs. The product was monitored by TLC, and confirmed by LCMS. Aqueous extraction and washings with 0.1M NaOH followed by rotovap drying the sulonate ester was isolated as thick oil.

Grignard Reaction to 7:

The sulfonate ester was cooled to 0° C. in dry THF under nitrogen. Two equivalents of 3.0 Molar THF solution of methyl magnesium chloride (MeMgCl) was added through a syringe and then allowed to warm up to room temp. After 2 hrs, 1M HCl was added, and rotovap dried to remove THF. The resulting mass was extracted into ethyl acetate, washed with water and 7 was isolated as greenish blue solid.

The quaternary salt 7 obtained as above was immediately deprotected with 4% aqueous FTA at room temp for 2 hrs, which was confirmed by LCMS. The resulting deprotected quaternary salt was extracted into water, and the organic materials were removed by washing with ethyl acetate. Thorough drying by rotovap and then speed vac overnight afforded the dry quaternary salt 8.

Preparation of Schiff's base (9) was carried out as described in the U.S. Pat. No. 9,798,604.

Preparation of diester 10 was carried out using 100 mg of the quaternary salt 8 dissolved in 5 mL of acetic acid, 10 mL acetic anhydride in a 50 mL RBF to which was added 0.5 equivalent of bisanil 9. Two equivalents of sodium acetate were added and the reaction mixture was heated at 100° C. for 8 hrs. The reaction mixture was concentrated on rotovap, and the residue was precipitated in ethyl acetate, which was then centrifuged in a 50 mL polypropylene tube, washed 1× with ethyl acetate, and then speed vac dried. The solid was dissolved in water and purified on C18 column by HPLC (Gradient: 10-60% B; Mobile phases B=Acetonitrile and Mobile Phase A=25 mM Triethyl ammonium acetate, pH 6.7 with 5% acetonitrile). Pure product was obtained in 25% yield of the dye reaction.

Preparation of 11: The diester 10 was dissolved in water and 5M NaOH solution was added so that the final net conc. being 500 mM. After 2 hrs, the saponification was completed as indicated by LCMS and the mono acid ester was purified by RP HPLC on C18 column (Gradient: 10-50% B; Mobile phases B=Acetonitrile and Mobile Phase A=25 mM Triethyl ammonium acetate, pH 6.7 with 5% acetonitrile). The collected fractions from multiple runs were combined and rotovap dired. The residue was dissolved in minimal amount of DMF and precipitated with ethyl acetate, centrifuged and then the solid was speed vac dried at 30 C for 1 h.

Preparation of 12: To dry mono acid ester 11 in 1 mL of dry DMF was added 2 equivalents of HATU (Aldrich, N-[(Dimethylamino)-1H-1,2,3-triazolo-[4,5-b]pyridin-1-yl-methylene]-N-methylmethanaminium hexafluorophosphate N-oxide, CAS #148893-10-1), three equivalents of taurine, and three equivalents of DIPEA (N,N-di-isopropyl ethyl amine), and incubated at 37° C. for 1 h. After the completion of coupling reaction was revealed by LCMS, it was diluted into water and immediately purified on C18 column as above with a gradient of 05-40% B. The resulting pure fractions were combined, rotovap dried followed by EtOAc precipitation.

Preparation of 13: Compound 12 was treated with 0.25 M solution of lithium hydroxide at room temp for two hours. The saponification was confirmed by LCMS. Acetic acid was added to neutralize the reaction mixture, and was purified on C18 column with a gradient of 05-30% B. The pure fractions were combined and rotovap dried. Dry dark brown powder was isolated by precipitation in DMF-ethyl acetate (1:20).

Preparation of 14: It was carried out in two steps. Compound 13 was mixed with 2 equivalents of DSC (disuccinimidyl dicarbonate) in dry DMF (500 μL), and 2 equivalents of N-methyl morpholine (NMM) was added. Mixed and incubated at 37° C. for 1 h. The NHSE formation was confirmed by LCMS as butylamine product (a small aliquot (1 uL) of the reaction mix was added to 50 μL of 0.1M butylamine-HCl, pH 9, and analyzed by LCMS). The DMF solution was precipitated with ethyl acetate and centrifuged to isolate the NHSE. It was immediately used as such in the next reaction, by redissolving in dry DMF and reacting with five equivalents of 6-amino hexanoic acid, 2 equivalents of NMM and incubating at 37° C. for 1 h. The product formation and the completion of the reaction were confirmed by LCMS, after which the reaction mixture was acidified with acetic acid and diluted with water followed by purification on C18 column using a gradient of 05-30% B. The collected fractions were dried by rotovap and the residue was precipitated by DMF and ethyl acetate (1:20). Centrifuging the precipitate and then during the residue in speed vac at 30° C. for 30 minutes, afforded the dark powder.

Preparation of 15: Compound 14 (5 mg) was mixed with 2 equivalents of DSC (disuccinimidyl dicarbonate) in dry DMF (500 μL), and 2 equivalents of N-methyl morpholine (NMM) was added. Mixed and incubated at 37° C. for 1 h. The NHSE formation was confirmed by LCMS as butylamine product (a small aliquot (1 uL) of the reaction mix was added to 50 μL of 0.1M butylamine-HCl, pH 9, and analyzed by LCMS). The DMF solution was precipitated with ethyl acetate and centrifuged to isolate the NHSE. It is stored at −20° C. and can be used for labeling reactions.

Example 2: Synthesis of Fluorochrome Compound D66 (24 in Scheme 2)

Scheme 2

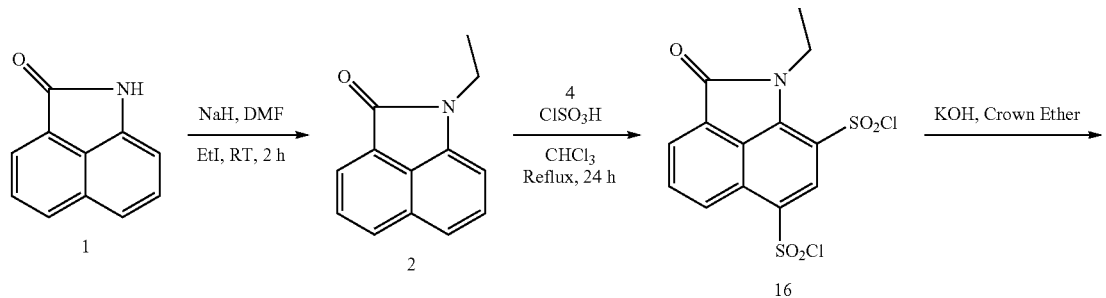

16

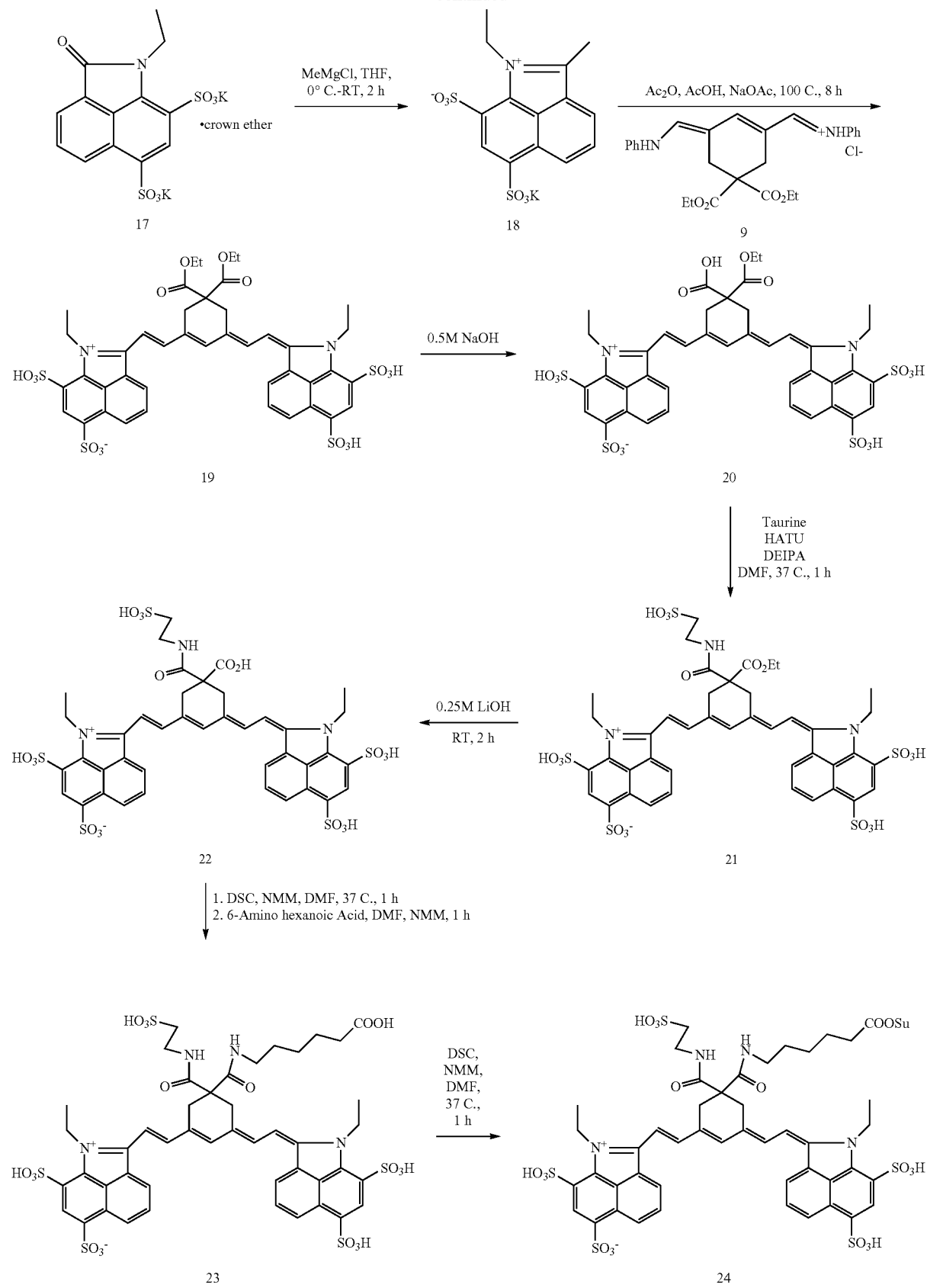

1-ethylbenzo[cd]indol-2(1H)-one 2.5 g Benz[cd]indol-2(1H)-one (1, from TCI America) was dissolved in 20 mL of dry DMF, to which was added 2 equivalents of sodium hydride (60% in mineral oil) after washing with dry hexanes under nitrogen cooled to 0-5° C. with stirring. After 5 minutes, three equivalents of ethyl iodide was added in drops over 2 min. Cooling was removed and was allowed to warm up to room temp; stirring was continued for 2 hrs. The reaction was monitored by TLC (Silica, Hexane-EtOAc 3:1) as well as by RP HPLC on C18 column (Gradient: 10%-85% B; B=Acetonitrile and A=25 mM Ammonium Formate with 5% methanol). Reaction mixture was poured into ice water, and the product was extracted with ethyl acetate followed by washings, drying over anhydrous sodium sulfate, filtration and rotary evaporation which afforded a yellow solid in 90% yield.

5,6-Di-sulfonyl Chloride of 1-ethylbenzo[cd]indol-2 (1H)-one (16)

To 1-ethylbenzo[cd]indol-2(1H)-one (2) in an RBF was added 25 mL of chloroform ($CHCl_3$) and was fitted with a reflux condenser. Five equivalents of chlorosulfonic acid ($ClSO_3H$) was added in drops over 2 min with magnetic stirring. Reaction mixture was heated to reflux for 24 hrs. The contents were concentrated on rotovap and then poured into water and was washed with ethyl acetate. Aqueous layer on analysis by LCMS confirmed only one product whose molecular weight of 357 corresponded to the di-sulfonic acid form of the product 16. It was converted to potassium salt by treating with 1.05 equivalent of KOH. One equivalent of 18-crown-6 was further added to the mixture and stirred well, to make it soluble in organic solvents to be suitable for use in the next step. The resulting mass was dried by rotovap thoroughly.

The positions of sulfonate substitutions in 17 to be ortho and para to N were confirmed by proton NMR (300 MHz) in DMSO-$d_6$ (as K salt of sulfonic acid) δ (ppm) (JJ coupling constants in Hz): 1.225 (t, 3H), 4.489 (q, 2H), 7.758 (t, 1H, JJ=8.2), 7.976 (d, 1H, JJ=6.9), 8.338 (s, 1H), 8.722 (d, 1H, JJ=8.5)

Grignard Reaction to 18:

The di-sulfonated benz[c,d]-indole-one-K-crown ether complex was cooled to 0° C. in dry THF under nitrogen. Two equivalents of 3.0 Molar THF solution of methyl magnesium chloride (MeMgCl) was added through a syringe and then allowed to warm up to room temp. After 2 hrs, 1M HCl was added, and rotovap dried to remove THF. The resulting mass was extracted into ethyl acetate, washed with water and crude 18 isolated as bluish green solid was thoroughly dried by rotovap and speed vac.

Preparation of Schiff's base (9) was carried out as described in the U.S. Pat. No. 9,798,604.

Preparation of diester 19 was carried out in the same manner as described for compound 10 in Scheme 1. Purification was carried out on RP-C18 column by HPLC (Gradient: 10-50% B; Mobile phases B=Acetonitrile and Mobile Phase A=25 mM Triethyl ammonium acetate, pH 6.7 with 5% acetonitrile).

Preparation of 20: The diester 19 was dissolved in water and 5M NaOH solution was added so that the final net conc. being 500 mM. After 2 hrs, the saponification was completed as indicated by LCMS and the mono acid ester was purified by RP HPLC on C18 column (Gradient: 5-40% B; Mobile phases B=Acetonitrile and Mobile Phase A=25 mM Triethyl ammonium acetate, pH 6.7 with 5% acetonitrile). The collected fractions from multiple runs were combined and rotovap dired. The residue was dissolved in minimal amount of DMF and precipitated with ethyl acetate, centrifuged and then the solid was speed vac dried at 30 C for 1 h.

Preparation of 21: To dry mono acid ester 20 in 1 mL of dry DMF was added 2 equivalents of HATU (Aldrich, N-[(Dimethylamino)-1H-1,2,3-triazolo-[4,5-b]pyridin-1-yl-methylene]-N-methylmethanaminium hexafluorophosphate N-oxide, CAS #148893-10-1), three equivalents of taurine, and three equivalents of DIPEA (N,N-di-isopropyl ethyl amine), and incubated at 37° C. for 1 h. After the completion of coupling reaction was revealed by LCMS, it was diluted into water and immediately purified on C18 column as above with a gradient of 00-30% B. The resulting pure fractions were combined, rotovap dried followed by EtOAc precipitation.

Preparation of 22: Compound 21 was treated with 0.25 M solution of lithium hydroxide at room temp for two hours. The saponification was confirmed by LCMS. Acetic acid was added to neutralize the reaction mixture, and was purified on C18 column with a gradient of 00-30% B. The pure fractions were combined and rotovap dried. Dry dark brown powder was isolated by precipitation in DMF-ethyl acetate (1:20).

Preparation of 23 was carried out in two steps. Compound 22 was mixed with 2 equivalents of DSC (disuccinimidyl dicarbonate) in dry DMF (500 µL), and 2 equivalents of N-methyl morpholine (NMM) was added. Mixed and incubated at 37° C. for 1 h. The NHSE formation was confirmed by LCMS as butylamine product (a small aliquot (1 uL) of the reaction mix was added to 50 µL of 0.1M butylamine-HCl, pH 9, and analyzed by LCMS). The DMF solution was precipitated with ethyl acetate and centrifuged to isolate the NHSE. It was immediately used as such in the next reaction, by redissolving in dry DMF and reacting with five equivalents of 6-amino hexanoic acid, 2 equivalents of NMM and incubating at 37° C. for 1 h. The product formation and the completion of the reaction were confirmed by LCMS, after which the reaction mixture was acidified with acetic acid and diluted with water followed by purification on C18 column using a gradient of 00-30% B. The collected fractions were dried by rotovap and the residue was precipitated by DMF and ethyl acetate (1:20). Centrifuging the precipitate and then drying the residue in speed vac at 30° C. for 30 minutes, afforded the dark powder.

Preparation of 24: Compound 23 was mixed with 2 equivalents of DSC (disuccinimidyl dicarbonate) in dry DMF (500 µL), and 2 equivalents of N-methyl morpholine (NMM) was added, and mixed well. It was incubated at 37° C. for 1 h. The NHSE formation was confirmed by LCMS as butylamine product (a small aliquot~1 uL of the reaction mix was added to 50 µL of a solution of 0.1M butylamine-HCl (pH~9) and analyzed by LCMS). The DMF solution was precipitated with ethyl acetate and centrifuged to isolate the NHSE. It was stored at −20° C. and was used for labeling reactions later.

Example 3: Synthesis of Fluorochrome Compound D67 (28 in Scheme 3)

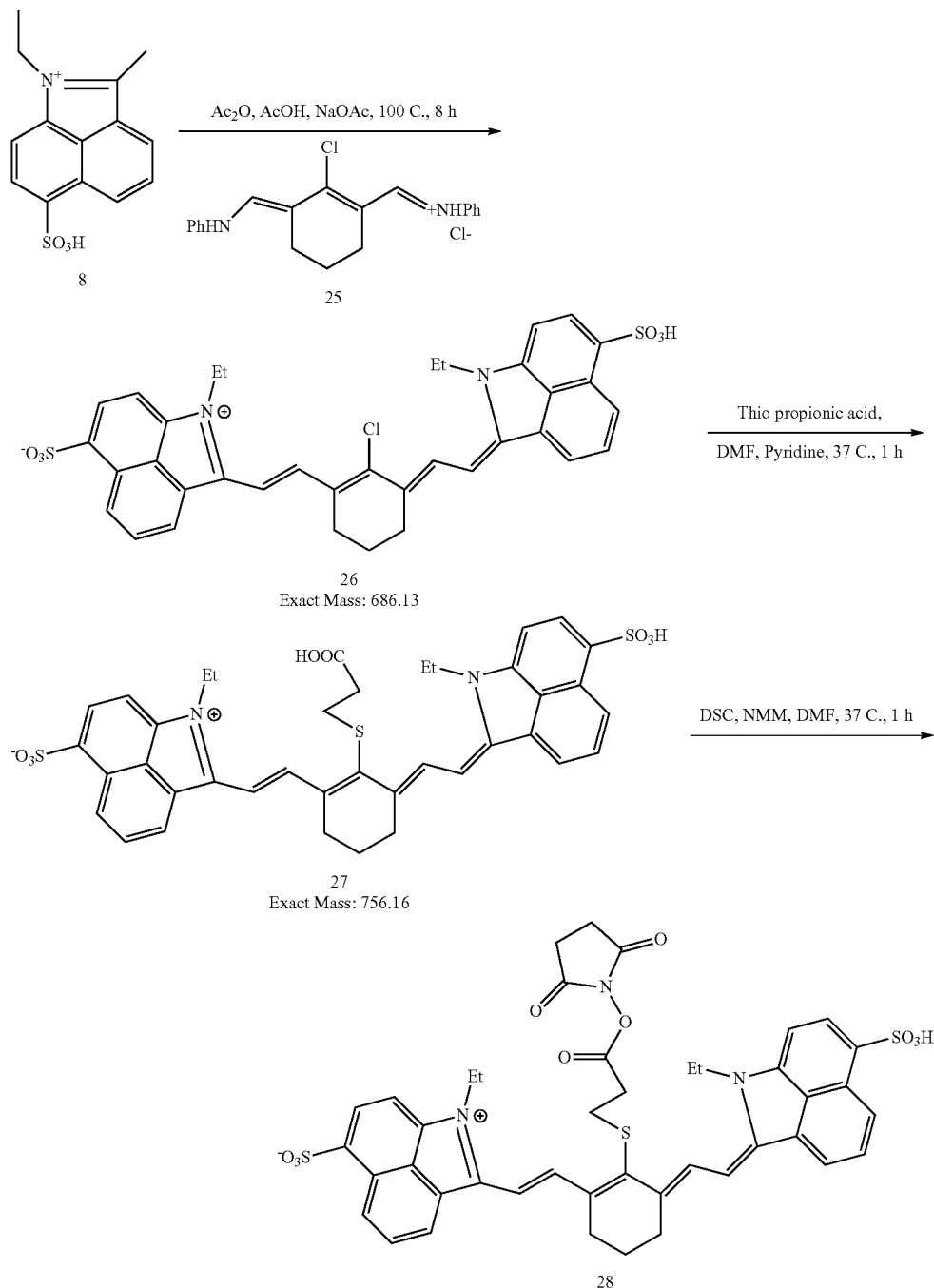

Preparation of Compound 26: The same method used for synthesizing compound 10 was followed and the synthesis confirmed by mass spectroscopy as 687.13 Da.

Preparation of Compound 27: A mixture of 10 mg of chloro dye 26 dissolved in 200 μL of anhydrous DMF, five equivalents of mercapto propionic acid (MpA) and five equivalents of pyridine (dried over KOH) in a 2 mL tube was incubated at 37° C. for 1 hr. It was quenched with 25 μL acetic acid, diluted in water and purified on C18 column (gradient 10-65% B) to get 40% yield. The LCMS for 27 confirmed the MW of 756 Da.

Preparation of Compound 28: It was prepared following the same method used for compound 15.

Chloro dye 26 exhibits a significantly different absorption property in various solvents, with its abs.max ranging from 810 nm in dichloromethane (DCM) to 1069 nm in DMSO as shown in Table 11 below.

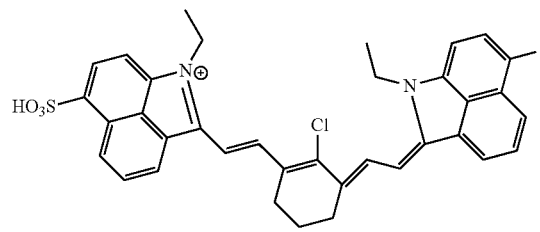

26

The large shifting of abs. max to lower wavelengths, especially in water is noteworthy because it is desirable that such "blue shifts" are minimal to be useful in biological applications such as in vivo imaging. Such shifts are common to cyanine dyes and are attributable to aggregation or stacking of the dye molecules with each other. The higher degree of aggregation is reflected in the larger "nm" shifts towards blue spectrum.

TABLE 11

Absorbance maxima of 26 in various solvents

| No | Solvent | Absorption max (nm) |
|----|---------|---------------------|
| 1 | Methanol | 1022 |
| 2 | Ethanol | 1032 |
| 3 | DMSO | 1065 |
| 4 | Dichloromethane | 810 |
| 5 | Chloroform | 820 |
| 6 | Acetone | 833, 1033 |
| 7 | Acetonitrile | 1019 |
| 8 | Water | 829 |

Example 4: Synthesis of Fluorochrome Compound D68 (34 in Scheme 4)

Scheme 4

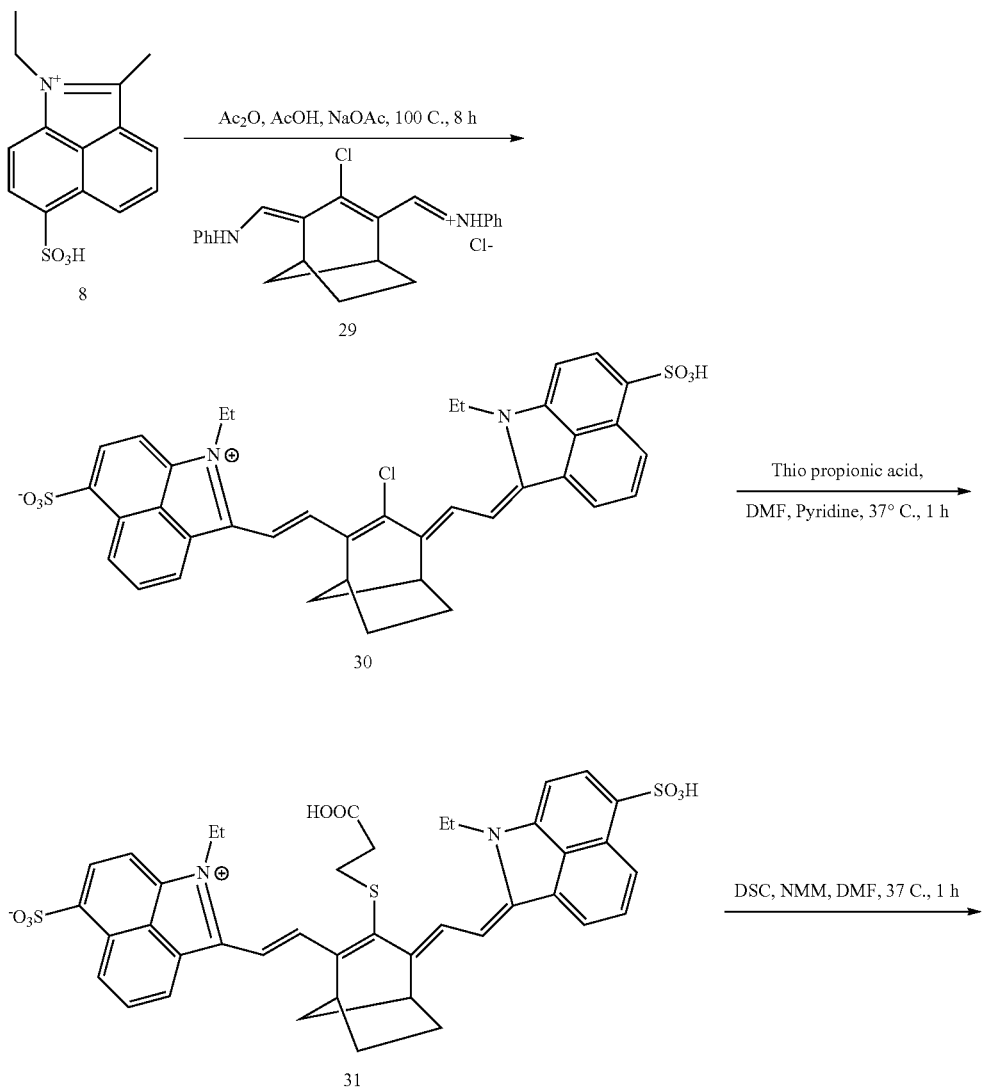

-continued
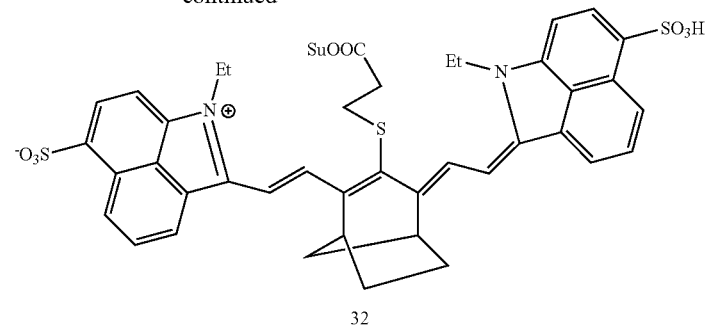
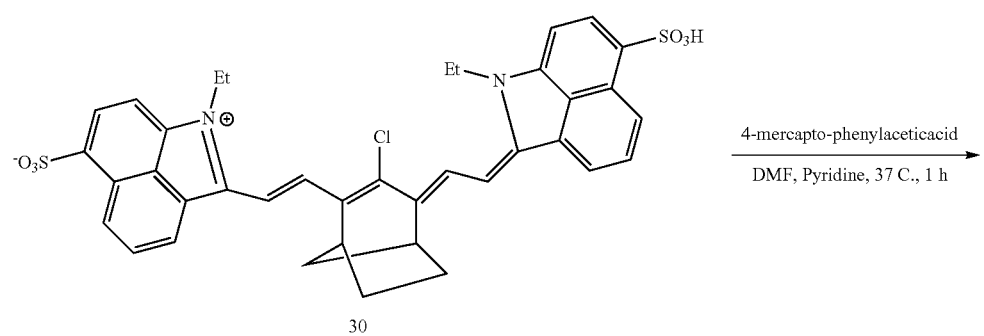
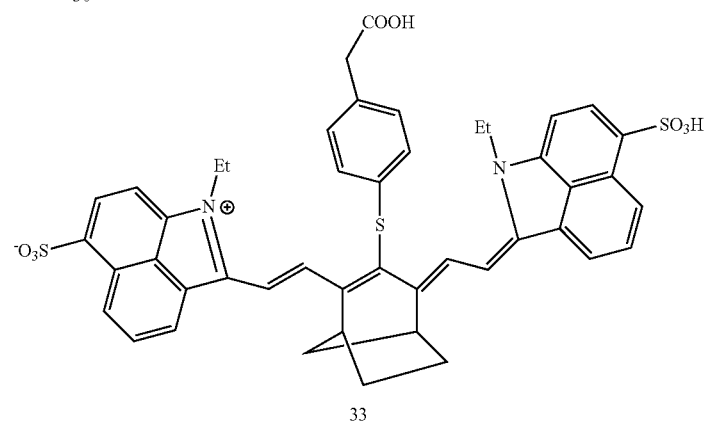
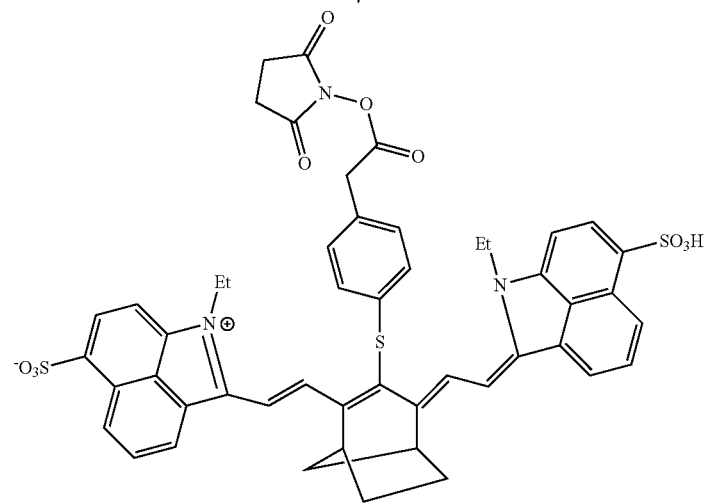

The compounds 30 to 34 were prepared in a similar manner as that of compounds 26 to 28 described in Scheme 3.
Compound 18 (Potassium disulfo-1-ethyl-2-methyl benz[c,d]-indolinone inner salt) is used in place of 8 in Schemes 3 and 4 for the synthesis of tetra sulfonated analogs.
Example 5: Synthesis of Fluorochrome Compound D29 (39 in Scheme 5)
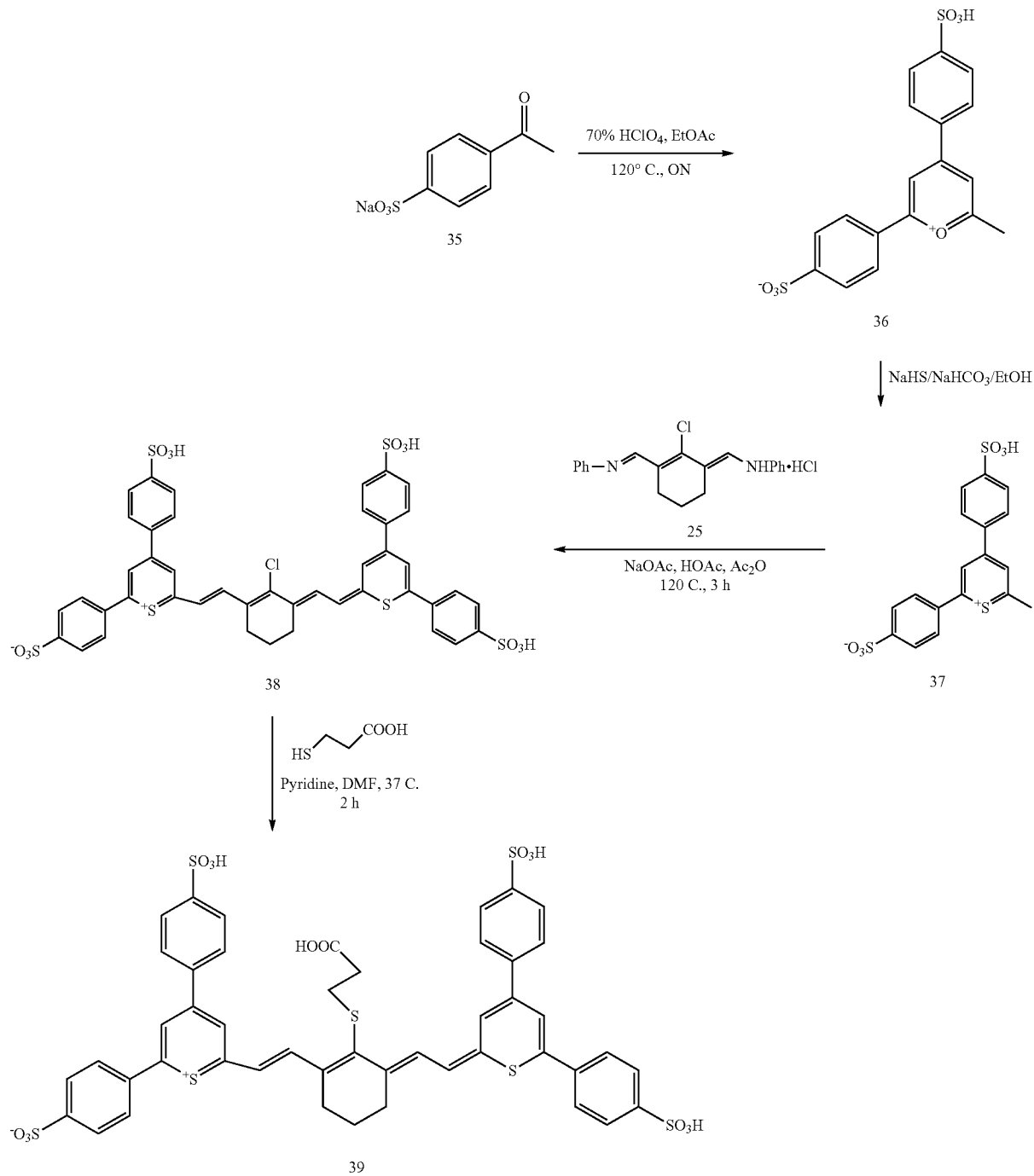

Compound 36

To 0.5 mmol of commercially available sodium (4-acetylbenzene)sulfonate in a pressure tube was added 1 mL of 70% perchloric acid and 0.2 mL of ethyl acetate. The air tightly closed tube was heated on an oil bath at 120° C. for 16 hrs. A large amount of cold acetone (50 mL) was added to the cooled tube, and the precipitated product was collected and dried. LCMS confirmed the product of MW 407 Da, and was purified on PhenyHexyl (X-Bridge) column with a gradient of 5-40% B. A 25% yield was realized.

Compound 37

0.5 mmol of compound 36 was dissolved in a pressure tube containing 5 mL of a solution prepared as below: 2 g of sodium sulfide (as nano hydrate) in 5 mL water and 2 mL ethanol to which was added 0.75 g of sodium bicarbonate (NaHCO$_3$) was added and the tube was quickly screw capped and left stirring at room temp for 12 hrs. The contents were concentrated by rotovap and the residue was dissolved in water and purified on RPC18 column (10-65% B).

Compounds 38 and 39

They were prepared by following the same procedure described for compounds 26 and 27 respectively.

Example 6: Synthesis of Fluorochrome Compounds D37 and D38 (Compounds 50 and 51 in Scheme 6)

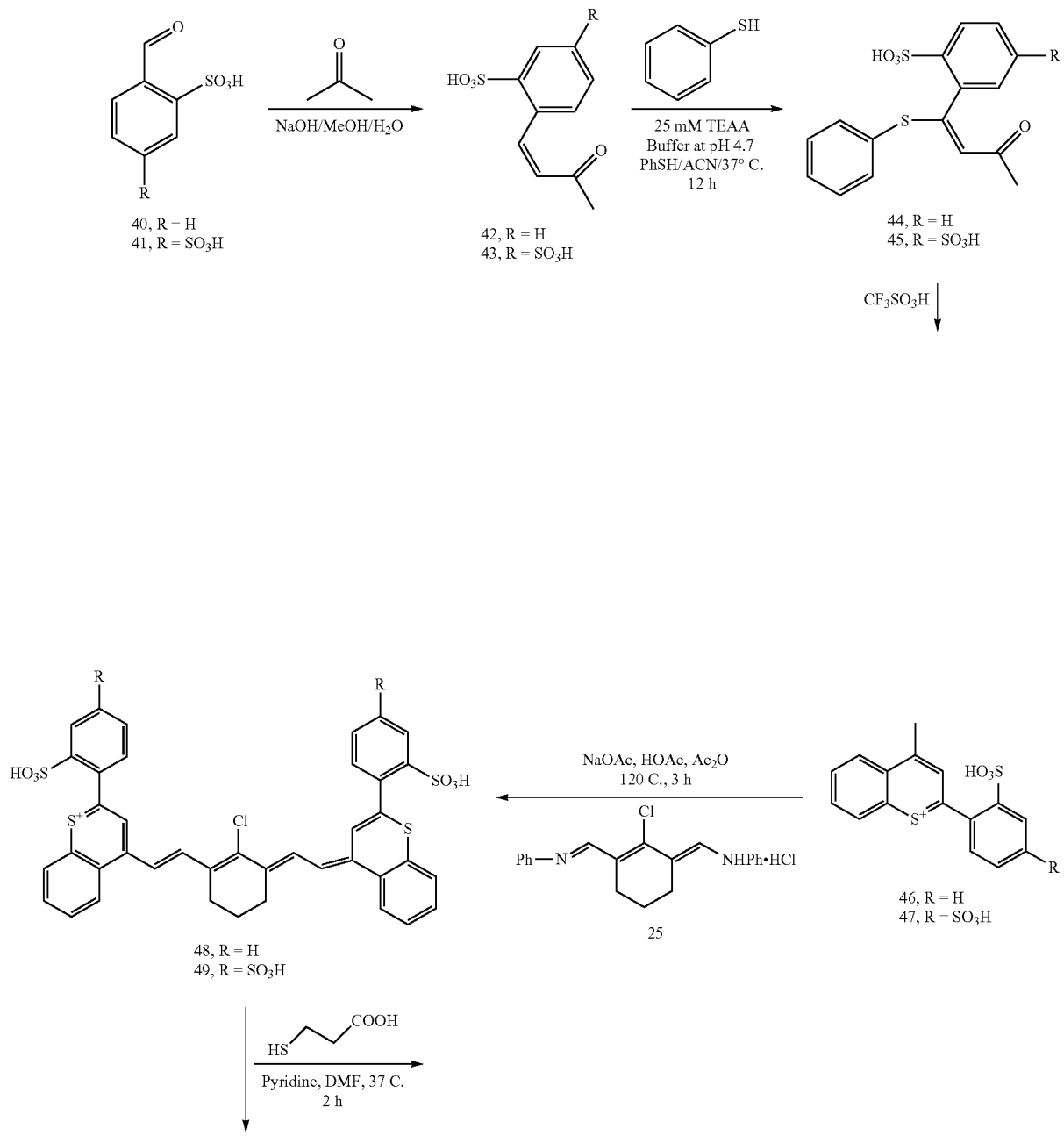

-continued

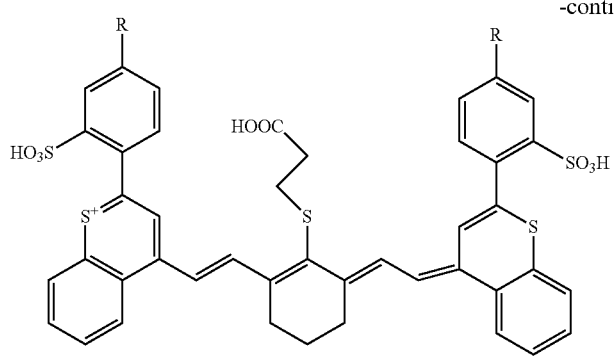

50, R = H
51, R = SO₃H

Compound 42

Compound 40 (TCI America), 1.08 g was mixed with 5 mL of acetone and 15 mL of methanol in an RBF. 1.04 mL of 50% sodium hydroxide was diluted with 1.6 mL of water and then added to the flask with vigorous stirring. With in 10 min, 90% product was realized by HPLC analysis (00-50% B, PhenyHexyl column, 25 mM ammonium formate and acetonitrile). It was purified after quenching with dil HCl and concentrating on rotovap. 60% yield. In the same manner compound 43 can be synthesized from commercially available 41.

Compound 44

0.17 g of compound 42 was dissolved in 1 mL of 25 mM triethylammonium acetate buffer (TEAAc, pH4.7) in a 50 mL poly proylene tube, to which was added 4.1 mL of acetonitrile and 0.35 mL of thiophenol. The homogeneous solution was incubated at 37° C. for 16 hrs. The reaction mixture was diluted with water and extracted with dichloromethane to remove thiophenol. The aqueous layer was subjected to purification by RP-HPLC on PhenylHexyl column, using 25 mM TEAAc (A) at pH4.7 and acetonitrile (B) as mobile phases with a gradient of 00-50% B. The pure fractions were collected and dried on speed vac. LCMS confirmed the mass of 337. In the same manner compound 45 can be synthesized from 43.

Compound 46

To 16 mg of dried compound 44 in a 2 mL glass vial, was added 0.15 mL of trifluoromethane sulfonic acid inside a fume hood. The capped vial was left at 37° C. for 12 hrs. The reaction mixture was diluted with water which formed pink solution leaving insoluble gummy precipitate. Aqueous layer was separated by centrifuging and subjected to HPLC purification and the peak that corresponded to mass 317 Da was isolated (20% yield). Compound 47 can be synthesized from 45 in the same manner.

Compound 48

Prepared by following the procedure described for the preparation of compound 26. Compound 49 can be prepared from compound 47 in the same way.

Compound 50 was prepared by following the procedure described for the preparation of compound 27.

Compound 51 can be made in a similar manner.

Example 7: Synthesis of Fluorochrome Compounds D69 and D70 (64 and 65 in Scheme 7)

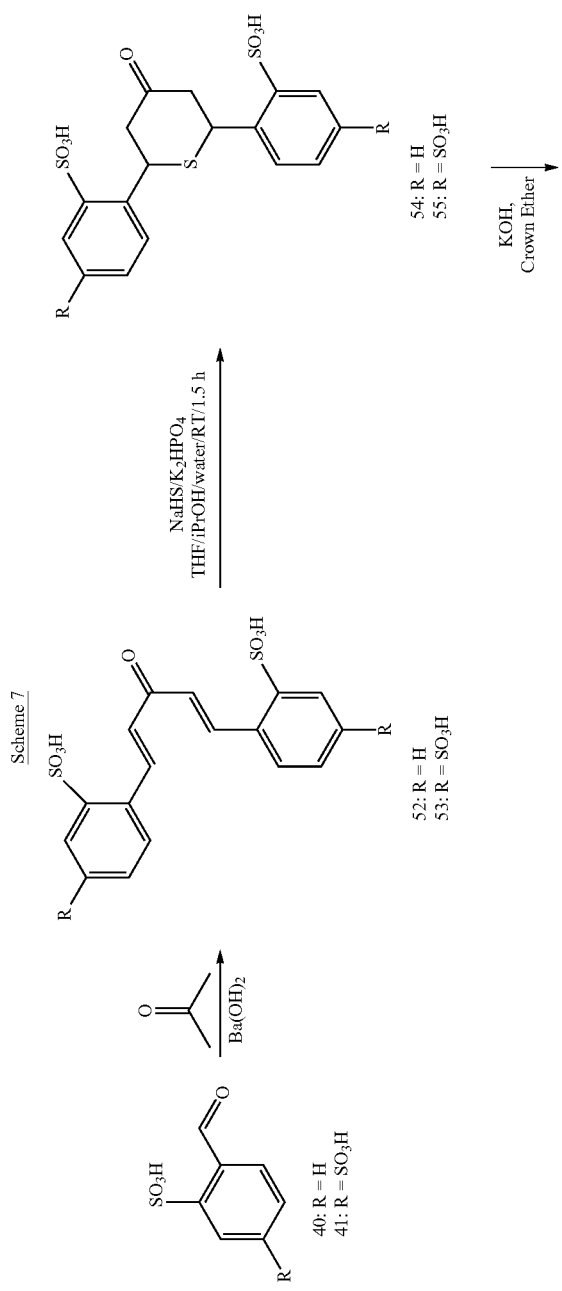

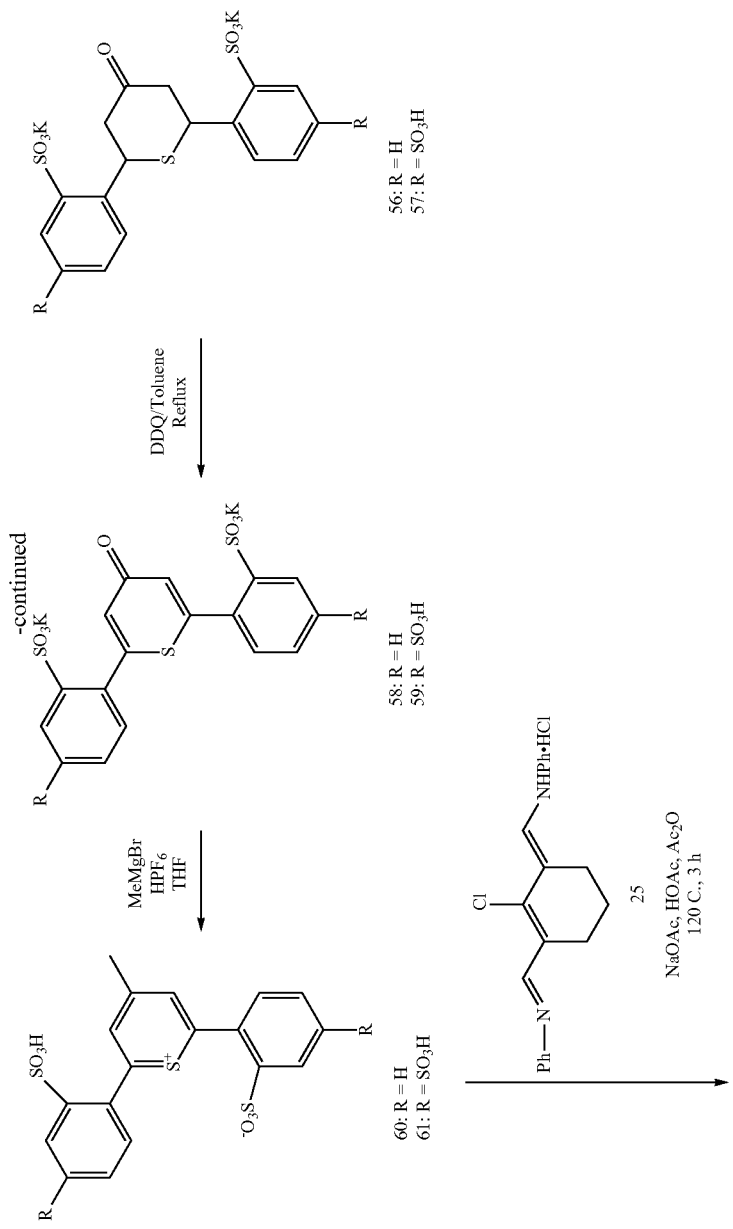

-continued
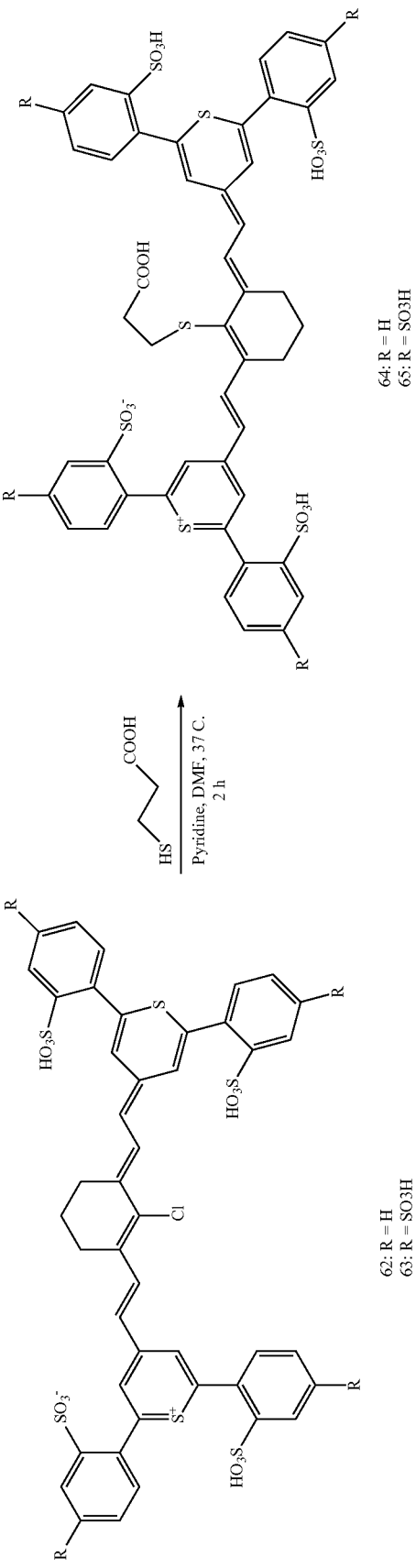
62: R = H
63: R = SO3H
64: R = H
65: R = SO3H

Compound 52

Ten mmoles of 2-formylbenzenesulfonic acid (as sodium salt, TCI) is mixed with five mmoles of acetone in 96% ethanol (20 mL) and Ba(OH)$_2$ (2 mmoles) is added as catalyst, and the mixture is refluxed for 2 hrs (Ref. Sinistierra, J. V., et al., Synthesis (6), 502-4 (1984)). The reaction mixture is neutralized with dilute HCl, and is purified by RP-HPLC on C18 column (gradient 05-50% B, A=95% 25 mM TEAAc+5% acetonitrile, pH 6.7, B=100% acetonitrile). The product is identified by LCMS corresponding to MW 394 Da.

Compound 54

Compound 54 is prepared by following the procedure described in WO2016/081813 on page 41 (Detty, et.al.), and the product is purified by RP-HPLC on C18 column with a gradient of 10-60% B. Compound 54 is then converted to potassium salt by mixing with 1.05 equivalent of 1 M KOH followed by adding 1.05 equivalent of 18-Crown-6. It is concentrated by rotovap and then dried under vacuum for an over night at 37° C. resulting in compound 56.

Compound 58

Compound 56 is oxidized to 58 by DDQ in toluene and refluxing for 2 hrs (Detty, et.al., WO2016/081813, page 42), followed by filtration through celite and rotovap drying.

The resulting 58 is reacted with a THF solution of 3.0 M MeMgCl in THF under nitrogen at room temp, followed by quenching with an aqueous solution of 10% HPF$_6$. THF and water are removed by rotovap. The residue is redissolved in ethyl acetate, and washed gently with water to remove inorganic salts. Rotovap drying afford the crude 4-methyl pyrylium salt 60 which is used in the synthesis of dyes as such.

Compound 62 is synthesized by the procedure described for compound 10.

Compound 64 is made as per the procedure for compound 27.

Compound 65: The synthesis of compound 65 from compound 41 (4-formyl, 1,3 benzene sulfonic acid, di sodium slat, TCI) is carried out in the same way as described above for compound 64.

Example 8: Synthesis of Fluorochrome Compound D23 (76 in Scheme 8)

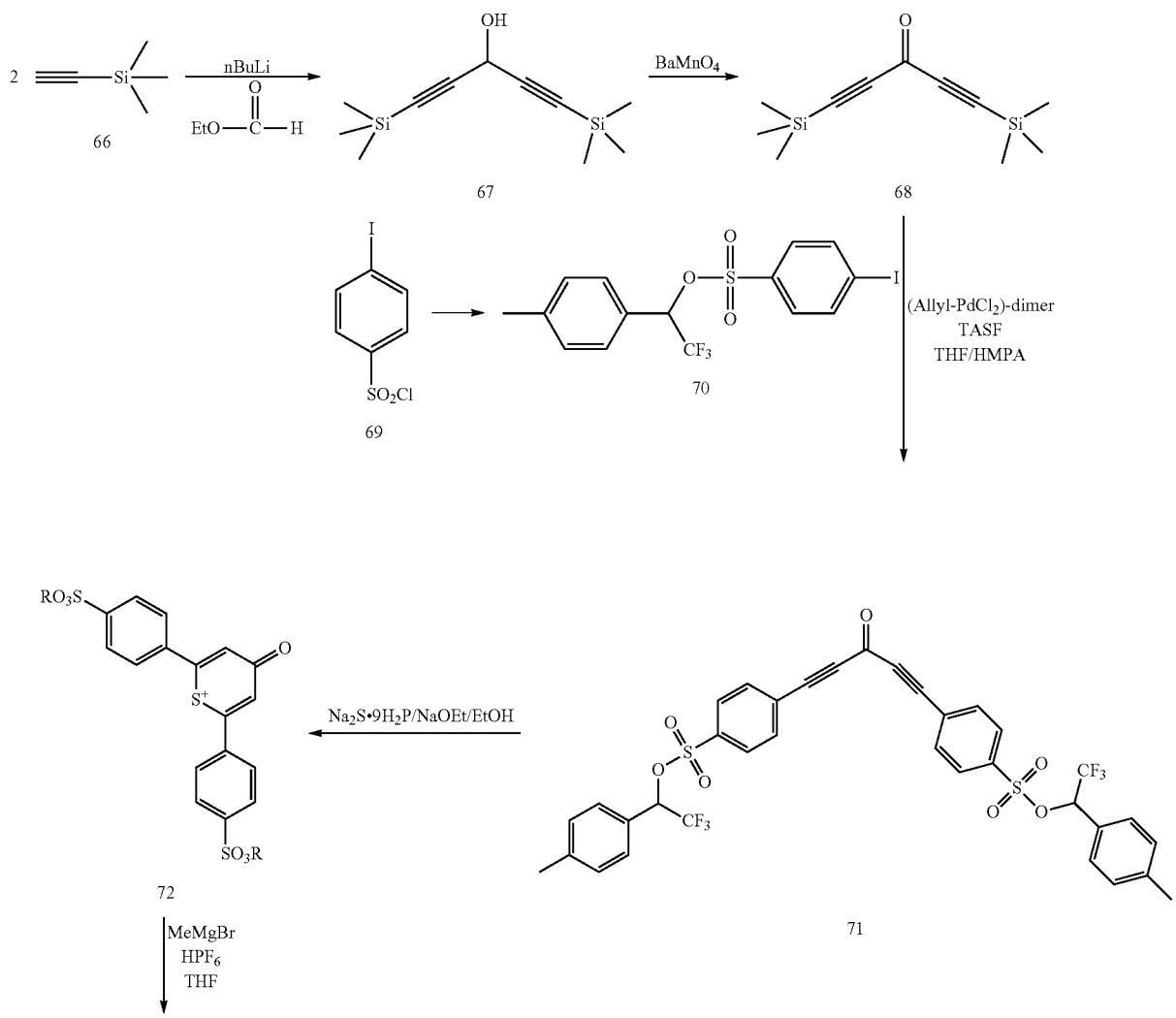

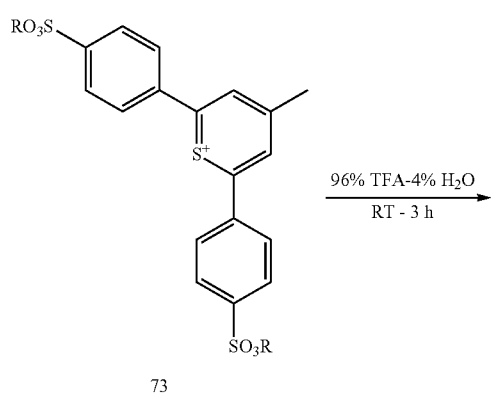

73
R = Protecting Group

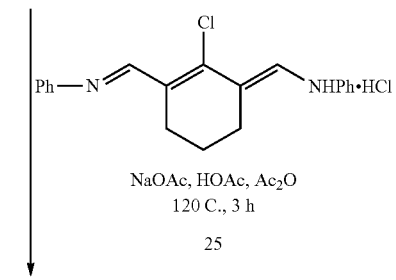

74

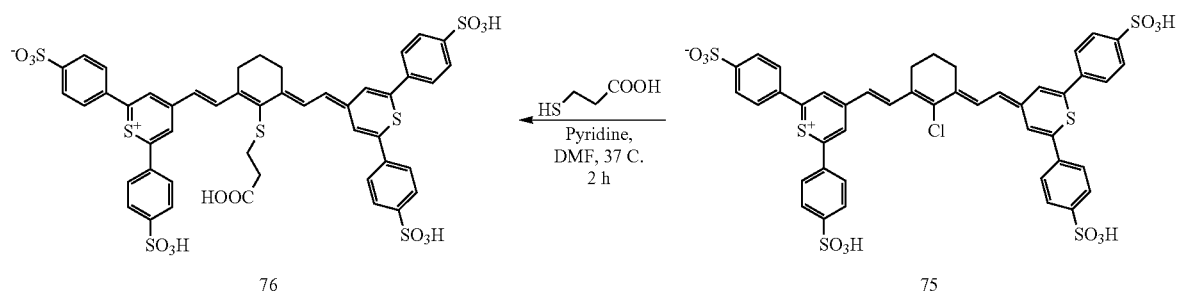

TASF=tris(diethylamino)sulfonium difluorotrimethylsilicate; Ref.: Hatanaka, Y., and Hiyama, T., J. Org Chem., (1988), 53, 920-923; Aldrichimica Acta, 36 (3), 2003, 75-85 (for 70 to 71 conversion); JP2001-011070A (Eng Translation, for the preparation of 67, 72 and 73); Bowling, N. P. et.al, J. Org Chem., 71, 5841-5847 (2006) for BaMnO4 oxidation (scheme 3, step d);

Compound 67

Trimethyl silyl acetylene (66) is cooled at −78° C. in THF under nitrogen, to which is added ethyl formate slowly with stirring. After 10 min, it is warmed up to room temp and stirred for an additional 2 hrs. Reaction is quenched with saturated ammonium chloride solution, and THF is removed by rotovap. The aqueous solution is extracted with ethyl acetate, concentrated and dried by rotovap (Ref.: Bowling, N. P. et.al, J. Org Chem., 71, 5841-5847 (2006)).

Compound 68: Compound 67 is treated with Ba manganate in methylene chloride and isolated as described in the above ref. (Bowling, N. P. et.al, J. Org Chem., 71, 5841-5847 (2006)).

Compound 70 is prepared from 4-iodobenzenesulfonylchloride in the same way as described for compound 6 previously.

Compound 71: The procedure reported in ref. Hatanaka, Y., and Hiyama, T., J. Org Chem.,(1988), 53, 920-923 is followed for making compound 71 from 68 and 70.

Compound 72: Compound 71 is treated with a solution of sodium sulfide in ethanol water along with sodium hydroxide as described in ref. JP2001-011070A.

Compound 73: Compound 72 is subjected Grignard's reaction with MeMgCl in THF and quenched with dil HPF$_6$ solution, by following the procedure describe earlier for compound 60.

Compound 74: Deprotection of compound 73 is carried out in 96% TFA-4% water in the same way as done for the compound 8.

Compound 75: Synthesis of compound 10 procedure was followed using 74 and bisanil 25.

Compound 76: Chloro dye 75 is converted to a vinyl thio ether 76 in DMF with pyridine as catalyst as per the procedure previously described for compound 27.

Example 9: Synthesis of Fluorochrome Compound D71 (78 in Scheme 9)

Scheme 9

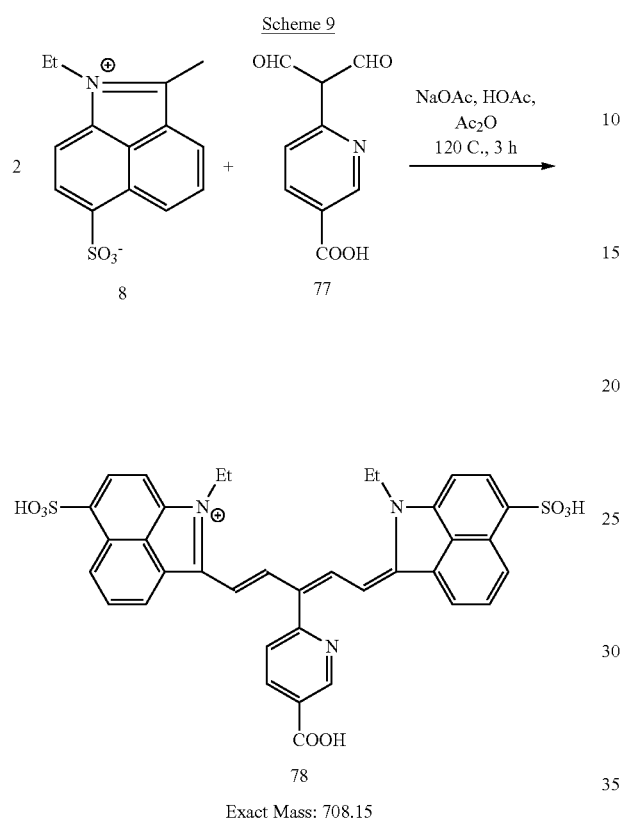

Exact Mass: 708.15 abs max: 851 nm in methanol.

Synthesis of compound 78 was carried out using 2 equivalents of compound 8 (10 mg) and compound 77 in a mixture of 2.5 mL acetic acid, 5 mL acetic anhydride and 2 equivalents of sodium acetate and heating at 120° C. for 3 hrs. After removing the solvents by rotovap the residue was dissolved in water and purified by RP-HPLC (using C18 column and a gradient of 10-60% B (Mobile phase A=95% 25 mM TEAAc+5% acetonitrile, pH 6.7, mobile phase B=100% acetonitrile). The product was identified by LCMS corresponding to MW 709 Da (as M+1). The absorption max of compound 78 in methanol is determined to be 851 nm.

Example 10: Synthesis of Fluorochrome Compound D72

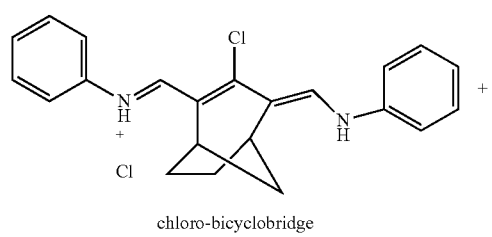

chloro-bicyclobridge

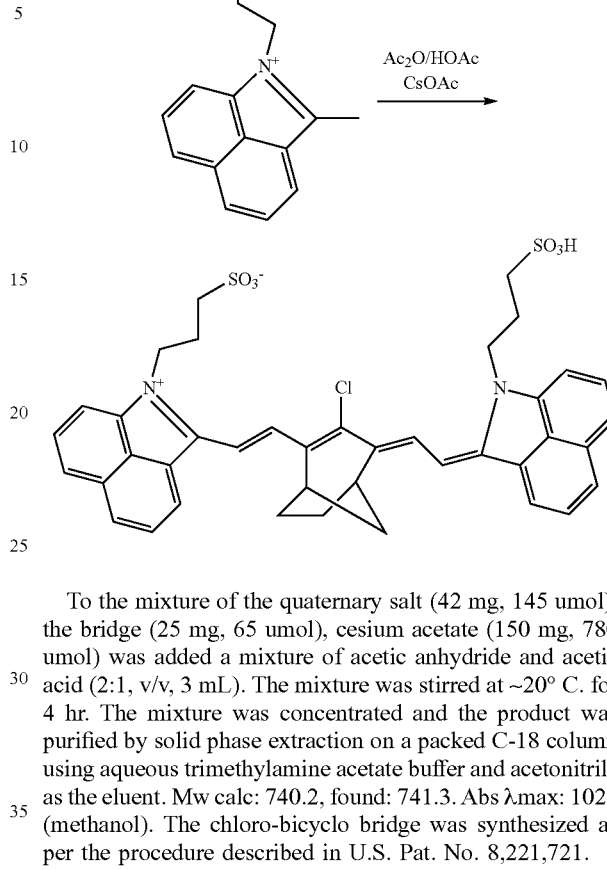

To the mixture of the quaternary salt (42 mg, 145 umol), the bridge (25 mg, 65 umol), cesium acetate (150 mg, 780 umol) was added a mixture of acetic anhydride and acetic acid (2:1, v/v, 3 mL). The mixture was stirred at ~20° C. for 4 hr. The mixture was concentrated and the product was purified by solid phase extraction on a packed C-18 column using aqueous trimethylamine acetate buffer and acetonitrile as the eluent. Mw calc: 740.2, found: 741.3. Abs λmax: 1026 (methanol). The chloro-bicyclo bridge was synthesized as per the procedure described in U.S. Pat. No. 8,221,721.

Example 10: Synthesis of Fluorochrome Compound D73

To the mixture of the quaternary salt (18 mg, 69 mol), the bridge (12 mg, 34 mol), cesium acetate (120 mg, 625 mol) was added a mixture of acetic anhydride and acetic acid (2:1, v/v, 3 mL). The mixture was stirred at ~20° C. for 16 hr. The mixture was concentrated and the product was purified by solid phase extraction on a packed C-18 column using aqueous trimethylamine acetate buffer and acetonitrile as the eluent. Mw calc: 684.1 Da, found: 684.2 Da. Abs λmax: 1050 nm (methanol).

Example 11: Synthesis of Fluorochrome Compound D74

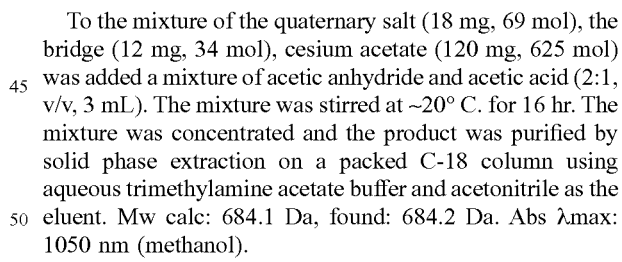

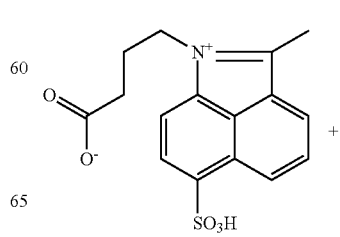

-continued

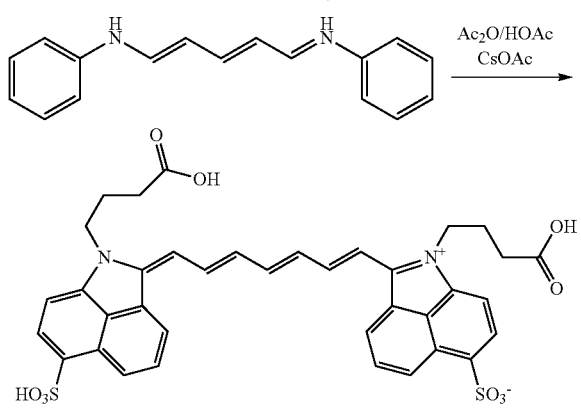

To the mixture of the quaternary salt (15 mg, 45 mol), the bridge (TCI, 6 mg, 21 mol), cesium acetate (90 mg, 470 mol) was added a mixture of acetic anhydride and acetic acid (2:1, v/v, 3 mL). The mixture was stirred at ~20° C. for 5 hr. The mixture was concentrated and the product was purified by solid phase extraction on a packed C-18 column using aqueous trimethylamine acetate buffer and acetonitrile as the eluent. mw calc: 728.2 Da, found: 729.2 Da. Abs λmax: 980 nm (methanol).

Example 12: Synthesis of Fluorochrome Compound D19

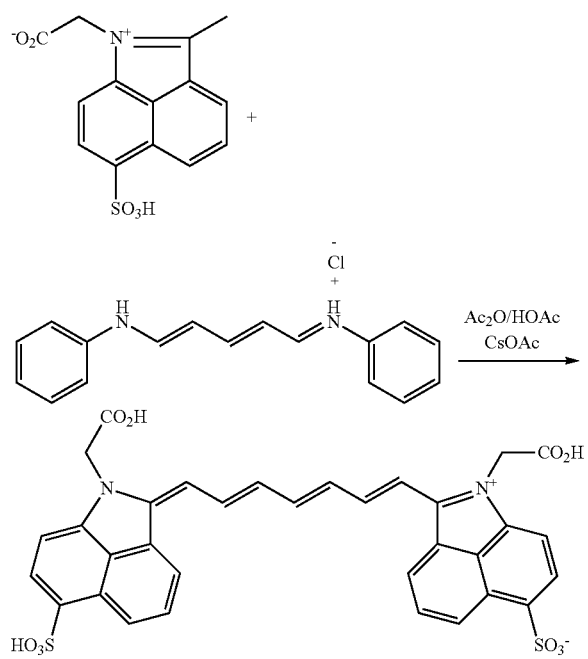

using aqueous trimethylamine acetate buffer and acetonitrile as the eluent. mw calc: 672.0 Da, found: 671.1 Da. Abs λmax: 980 nm (methanol).

Example 13: Synthesis of Fluorochrome Compound D18

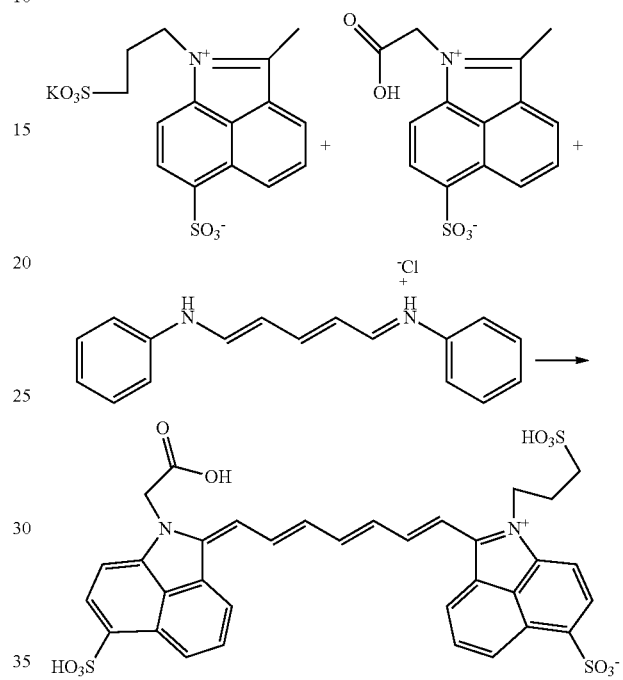

To the mixture of the disulfonate quaternary salt (17 mg, 42 mol), the sulfonate acetic acid quaternary salt (13 mg, 42 mol), the bridge (10 mg, 35 mol), cesium acetate (150 mg, 781 mol) was added a mixture of acetic anhydride and acetic acid (2:1, v/v, 3 mL). The mixture was stirred at ~20° C. for 18 hr. The mixture was concentrated and the product was purified by preparative HPLC using aqueous trimethylamine acetate buffer and acetonitrile as the eluent. mw calc: 736.8 Da, found: 737.7 Da. Abs λmax: 970 nm (methanol).

Example 14: Synthesis of Fluorochrome Compound D75

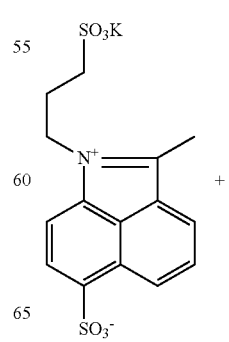

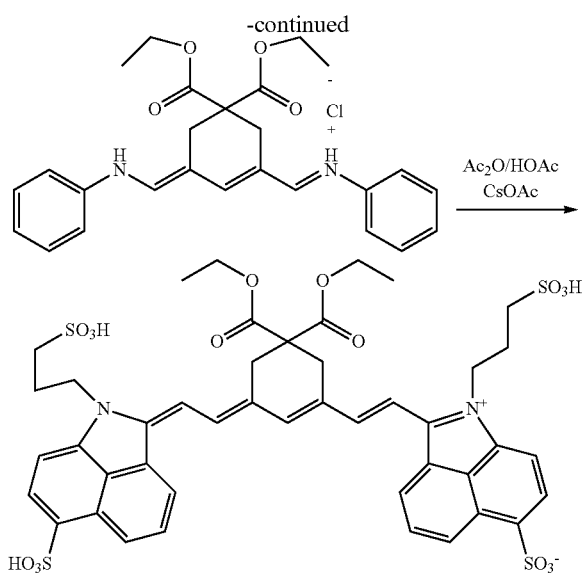

To the mixture of the quaternary salt (25 mg, 61 umol), the bridge (13 mg, 28 umol), cesium acetate (120 mg, 625 umol) was added a mixture of acetic anhydride and acetic acid (2:1, v/v, 3 mL). The mixture was stirred at ~40° C. for 4 hr. The mixture was concentrated and the product was purified by solid phase extraction on a packed C-18 column using aqueous trimethylamine acetate buffer and acetonitrile as the eluent. mw calc: 984.2, found: 985.1. Abs λmax: 990 nm (methanol)

Example 15: Synthesis of 4-methyl-2,6-bis(3-sulfophenyl)thiopyrylium chloride 2,6-Diphenyl-4H-thiopyran-4-one (0.5 g) The thiopyranone was dissolved in 5 mL of chloroform and stirred in a 250 mL round bottom flask. Chlorosulfonic acid (1.25 mL) was then added slowly. A reflux condenser was attached and the solution was heated to 70° C. overnight. The reaction mixture was then poured over ice and the solid precipitate isolated by filtration, washed with ice water and dried under vacuum to give 2,6-di(chlorosulfophenyl)-4H-thiopyran-4-one. ESI MS calculated [M+H]=460.9 for $C_{17}H_{11}C_{12}O_5S_3^+$, found 461.1.

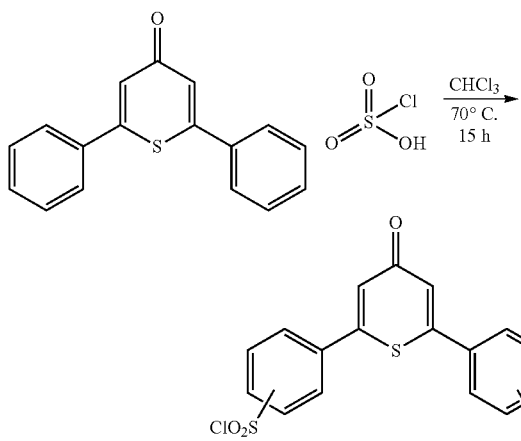

2,6-di(chlorosulfophenyl)-4H-thiopyran-4-one (200 mg), potassium carbonate (120 mg) and 18-crown-6 (230 mg) were combined in 2 mL of water and 1 mL of acetonitrile and heated to 60° C. for 15 minutes. The solution was diluted to 5 mL with water and passed through a 2 g column of C18 reverse phase silica gel eluting the product with 20% acetonitrile in water. The first 5 mL of eluent were combined and dried under vacuum to give 405 mg of 2,6-di(sulfophenyl)-4H-thiopyran-4-one, potassium/18-crown-6 salt. ESI MS calculated [M+H]=425.0 for $C_{17}H_{13}O_7S_3^+$, found 425.2.

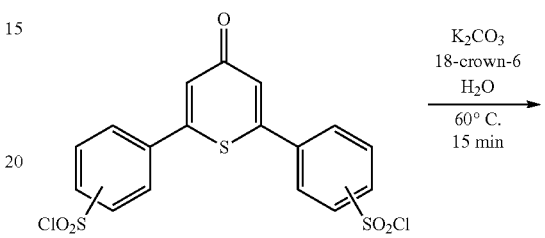

2,6-di(sulfophenyl)-4H-thiopyran-4-one, potassium/18-crown-6 salt (480 mg) was dispersed in 5 mL of anhydrous THF in a 250 mL round bottom flask flushed with nitrogen.

Methylmagnesium chloride (0.94 mL of a 3 M solution in THF) was added dropwise, and the mixture stirred at room temperature overnight. The solution was then cooled in an ice bath and quenched by slow addition of 4 mL of 1 M hydrogen chloride in diethyl ether. The resulting yellow, solid precipitate of 4-methyl-2,6-bis(3-sulfophenyl)thiopyrylium chloride was filtered, washed with ether and dried in vacuum. ESI MS calculated [M+H]=423.0 for $C_{18}H_{15}O_6S_3^+$, found 423.2.

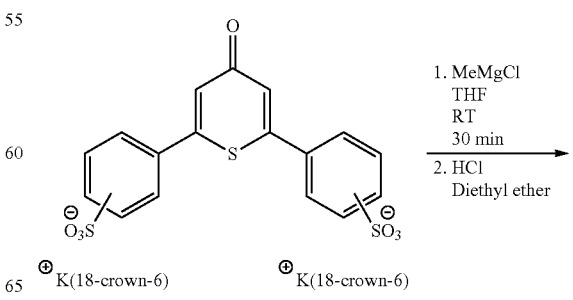

-continued

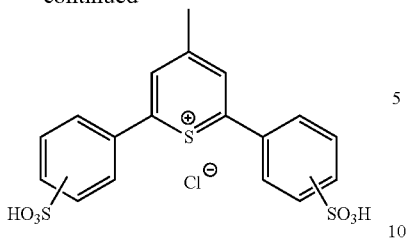

Example 16: Synthesis of Fluorochrome Compound D60

4-methyl-2,6-bis(3-sulfophenyl)thiopyrylium chloride (12 mg), and N-[(3-(Anilinomethylene)-2-chloro-1-cyclohexen-1-yl)methylene]aniline monohydrochloride (5 mg) were combined in 0.5 mL of acetic anhydride and 0.5 mL of acetic acid. Triethylamine (TEA) (0.1 mL) was added and the mixture was heated to 95° C. for 1.5 h. The crude product was precipitated with 25 mL of diethyl ether, filtered and purified by HPLC to give dye D60. ESI MS calculated [M+H]=981.0 for $C_{44}H_{34}ClO_{12}S_6^+$, found 981.5. Absorbance max (MeOH) 1062 nm.

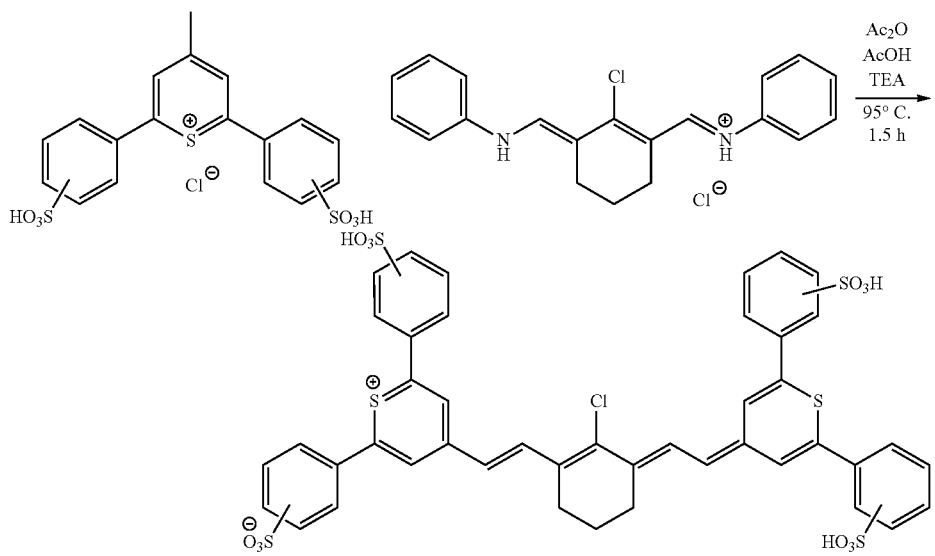

Example 17: Synthesis of Fluorochrome Compound D64

4-methyl-2,6-bis(3-sulfophenyl)thiopyrylium chloride (12 mg), and 2-chlorocyclopent-1-ene-1,3-dialdehyde (2.2 mg) were combined in 0.5 mL of acetic anhydride and 0.5 mL of acetic acid. Triethylamine (TEA) (0.1 mL) was added and the solution was stirred at room temperature for 4 h. The crude product was precipitated with 25 mL of diethyl ether, filtered and purified by HPLC to give dye D64. ESI MS calculated [M+H]=967.0 for $C_{43}H_{32}ClO_{12}S_6^+$, found 967.4. Absorbance max (MeOH) 1068 nm.

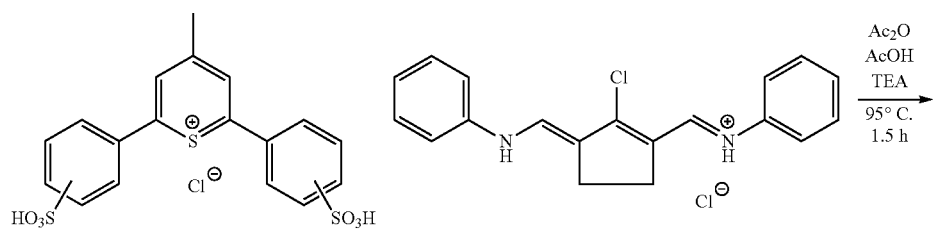

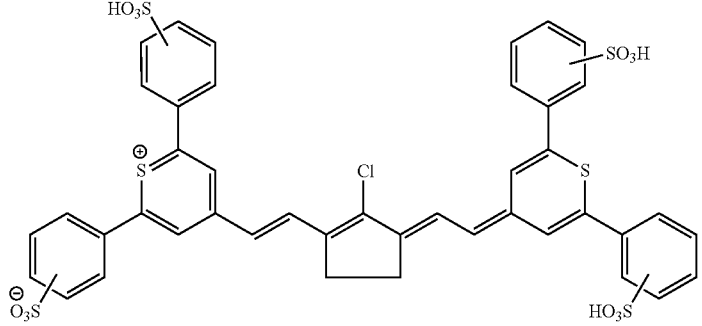

Example 18: Synthesis of Fluorochrome Compound D61

4-methyl-2,6-bis(3-sulfophenyl)thiopyrylium chloride (12 mg), and N-3-chloro-4-((phenylamino)methylene)bicyclo[3.2.1]oct-2-en-2-yl)methylene)benzenaminium chloride (5.4 mg) were combined in 0.5 mL of acetic anhydride and 0.5 mL of acetic acid. Triethylamine (TEA) (0.1 mL) was added and the mixture was heated to 95° C. for 1.5 h. The crude product was precipitated with 25 mL of diethyl ether, filtered and purified by HPLC to give compound D61. ESI MS calculated [M+H]=1007.0 Da for $C_{46}H_{36}ClO_{12}S_6^+$, found 1007.4 Da. Absorbance max (MeOH) 1063 nm.

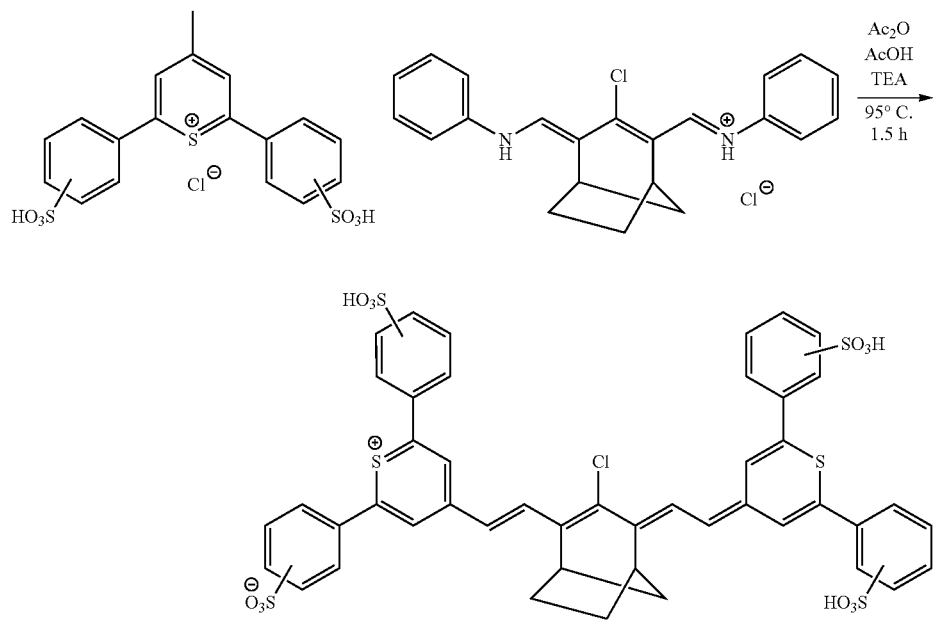

Example 19. Synthesis of Fluorochrome Compound D62

The chloro-substituted thiopyrylium dye D64 (14 mg) and 4-mercaptophenylacetic acid (4.4 mg) were combined and dissolved in 0.5 mL of anhydrous DMF to which 0.01 mL of pyridine was added. The mixture was stirred at room temperature for 30 minutes, then the product compound D56 was precipitated with ether, isolated by filtration and purified by HPLC. ESI MS calculated [M+H]=1099.0 Da for $C_{51}H_{39}O_{14}S_7^+$, found 1099.4 Da. Absorbance max (MeOH) 1061 nm.

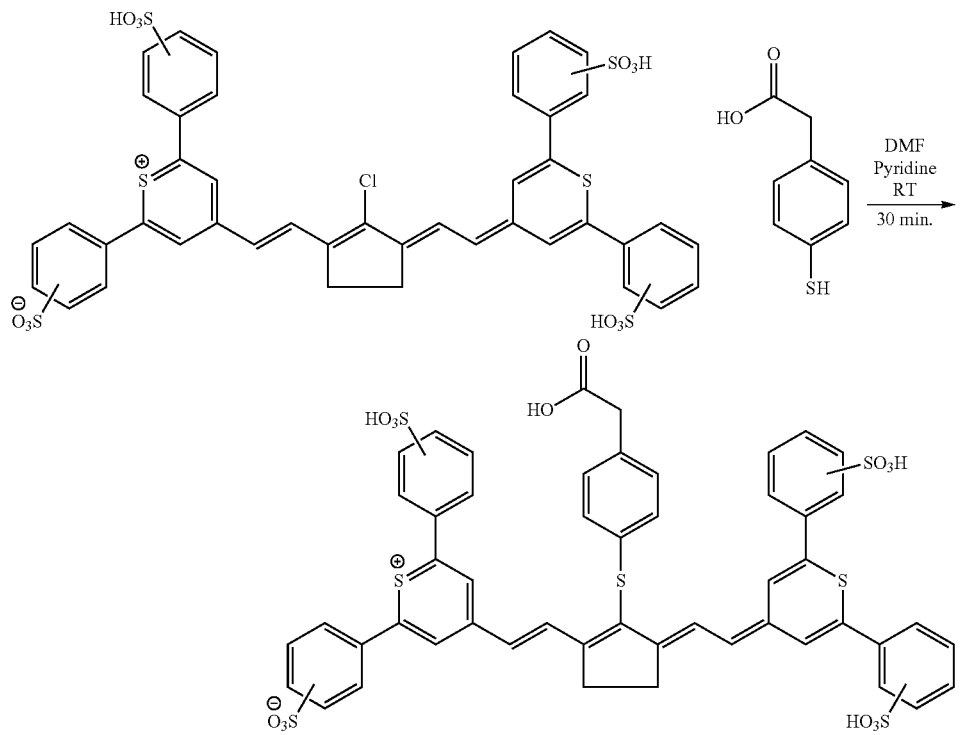

Example 20: Synthesis of Fluorochrome Compound D63

4-methyl-2,6-bis(3-sulfophenyl)thiopyrylium chloride (3 mg), and N-5,5-bis(ethoxycarbonyl)-3-((phenylamino)methylene)cyclohex-1-en-1-yl)methylene)benzenaminium chloride (1.7 mg) were combined in 0.5 mL of acetic anhydride and 0.5 mL of acetic acid. Triethylamine (TEA) (0.1 mL) was added and the mixture was heated to 95° C. for 1.5 h. The crude product was precipitated with 25 mL of diethyl ether, filtered and purified by HPLC to give dye D63. ESI MS calculated [M+H]=1091.1 Da for $C_{50}H_{43}O_{16}S_6^+$, found 1091.6 Da. Absorbance max (MeOH) 1016 nm.

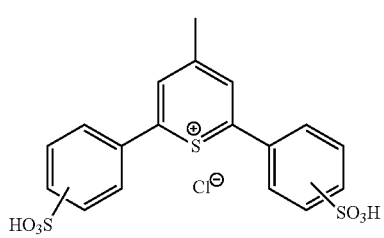

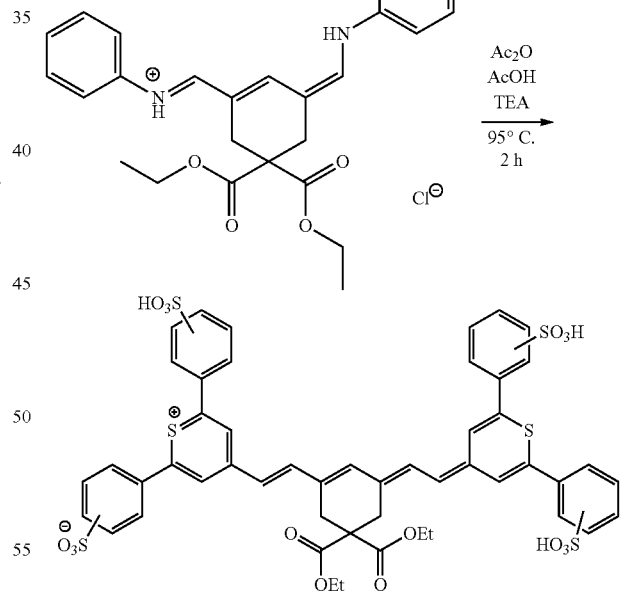

Example 21: Synthesis of 9,10-dimethyl-3,6-disulfoacridin-10-ium 9-methylacridine (0.5 g) was placed in a 250 mL flask and immersed in an ice bath. 1.2 mL of chlorosulfonic acid (1.2 mL) was added dropwise and the mixture was stirred to obtain a clear, orange-brown solution. A reflux condenser was attached and the flask was heated to 100° C. for 12 h.

The mixture was then cooled in an ice bath and quenched by addition of 25 g of crushed ice. The mixture was filtered, and the solid precipitate washed on the filter with 25 mL of ice water. The solid was collected and transferred to a flask with 25 mL of 200 mM sodium carbonate, then heated to 70° C. with stirring for 1 h forming a clear, brown solution. The water was removed by evaporation, and the solid purified by HPLC eluting with 25 mM triethylammonium acetate and acetonitrile which was evaporated to yield 0.9 g of the triethylammonium salt of 9-methyl-3,6-disulfoacridine. ESI MS calculated [M+H]=354.1 Da for $C_{14}H_{12}NO_6S_2^+$, found 354.3 Da.

9-methyl-3,6-disulfoacridine triethylammonium salt (0.5 g) and iodomethane (800 mg) are dissolved in 10 mL of anhydrous DMF in a pressure vessel. The vessel is sealed tightly and heated to 60° C. for 8 h. The product is precipitated by addition of 25 mL of ethyl acetate, filtered and washed with 25 additional mL to yield 9,10-dimethyl-3,6-disulfoacridin-10-ium as a triethylammonium salt.

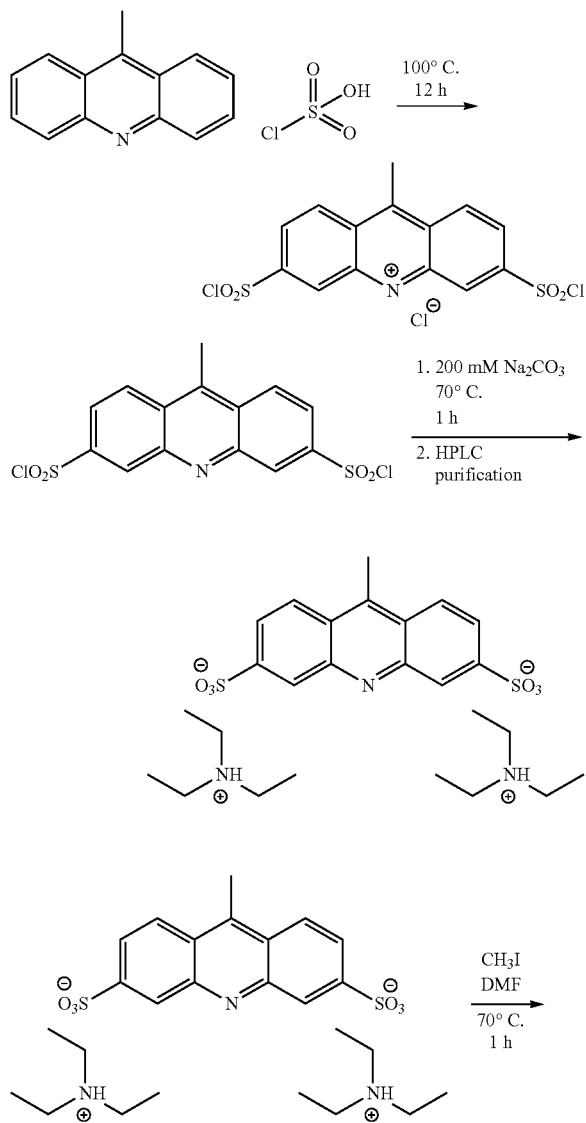

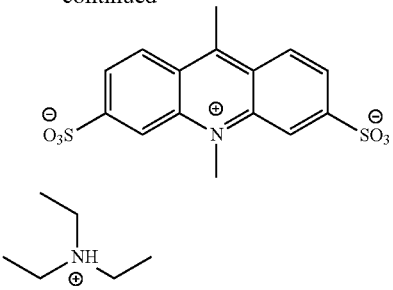

Example 22: Synthesis of 9,10-dimethyl-2,7-disulfoacridin-10-ium 10-methylacridin-9-one (1.0 g) was dispersed in 10 mL of anhydrous chloroform in a 100 mL round bottom flask and cooled in an ice bath. Chloropsulfonic acid (1.9 mL) was added dropwise. After the addition, the flask was fitted with a condenser and heated to reflux for 6 h. The reaction was quenched by addition of 25 g of crushed ice and solid product isolated by filtration, washed with three portions of ice water and dried in vacuum to give 10-methylacridin-9-one-2,7-disulfonyl chloride.

10-methylacridin-9-one-2,7-disulfonyl chloride (0.5 g) was dissolved in 10 mL of dichloromethane in a 100 mL round bottom flask and cooled in an ice bath. 2,2,2-trifluoro-1-(p-tolyl)ethanol (0.58 g) dissolved in 3 mL of dichloromethane was then added followed by 0.52 mL of anhydrous triethylamine was added and the mixture was stirred for 10 minutes then allowed to warm to room temperature. The solution was stirred for 3 h, then 15 mL of saturated sodium bicarbonate and the product was extracted with three 25 mL portions of dichloromethane. The dichloromethane extracts were combined, washed with saturated brine, dried over sodium sulfate and evaporated to dryness to yield 0.553 g of 2,2,2-trifluoro-1-(p-tolyl)ethanol protected 10-methyl-acridin-9-one-2,7-disulfonate. ESI MS calculated [M+H]=714.1 Da for $C_{32}H_{26}F_6NO_7S_2^+$, found 714.2 Da.

2,2,2-trifluoro-1-(p-tolyl)ethanol protected 10-methyl-acridin-9-one-2,7-disulfonate (0.4 g) was placed in an oven-dried 3-neck round bottom flask flushed with nitrogen. 10 mL of anhydrous THF was added to the flask and mixture was stirred. Methylmagnesium chloride, 3 M in THF was added dropwise. The clear, red solution was stirred at RT for 30 minutes, then cooled in an ice bath. 2.4 mL of 1 M HCl was added dropwise then the solution was allowed to warm to room temperature. The THF was removed by rotary evaporation and 25 mL of saturated sodium bicarbonate added to the solid residue that was then extracted into three portions of 25 mL of dichloromethane. The dichloromethane extracts were washed with brine, dried over sodium sulfate and the solvent removed under vacuum to give 0.39 g of 2,2,2-trifluoro-1-(p-tolyl)ethanol protected 9,10-dimethyl-acridinium-2,7-disulfonate. ESI MS calculated [M+H]=712.1 Da for $C_{33}H_{28}F_6NO_6S_2^+$, found 712.3 Da.

2,2,2-trifluoro-1-(p-tolyl)ethanol protected 9,10-dimethylacridinium-2,7-disulfonate (0.39 g) was dissolved in 2.5 mL of trifluoroacetic acid (TFA) and 25 μL of water. The solution was stirred at room temperature for 2 h. The deprotected product was isolated by precipitation with ether to give the 9,10-dimethyl-2,7-disulfoacridin-10-ium inner salt.

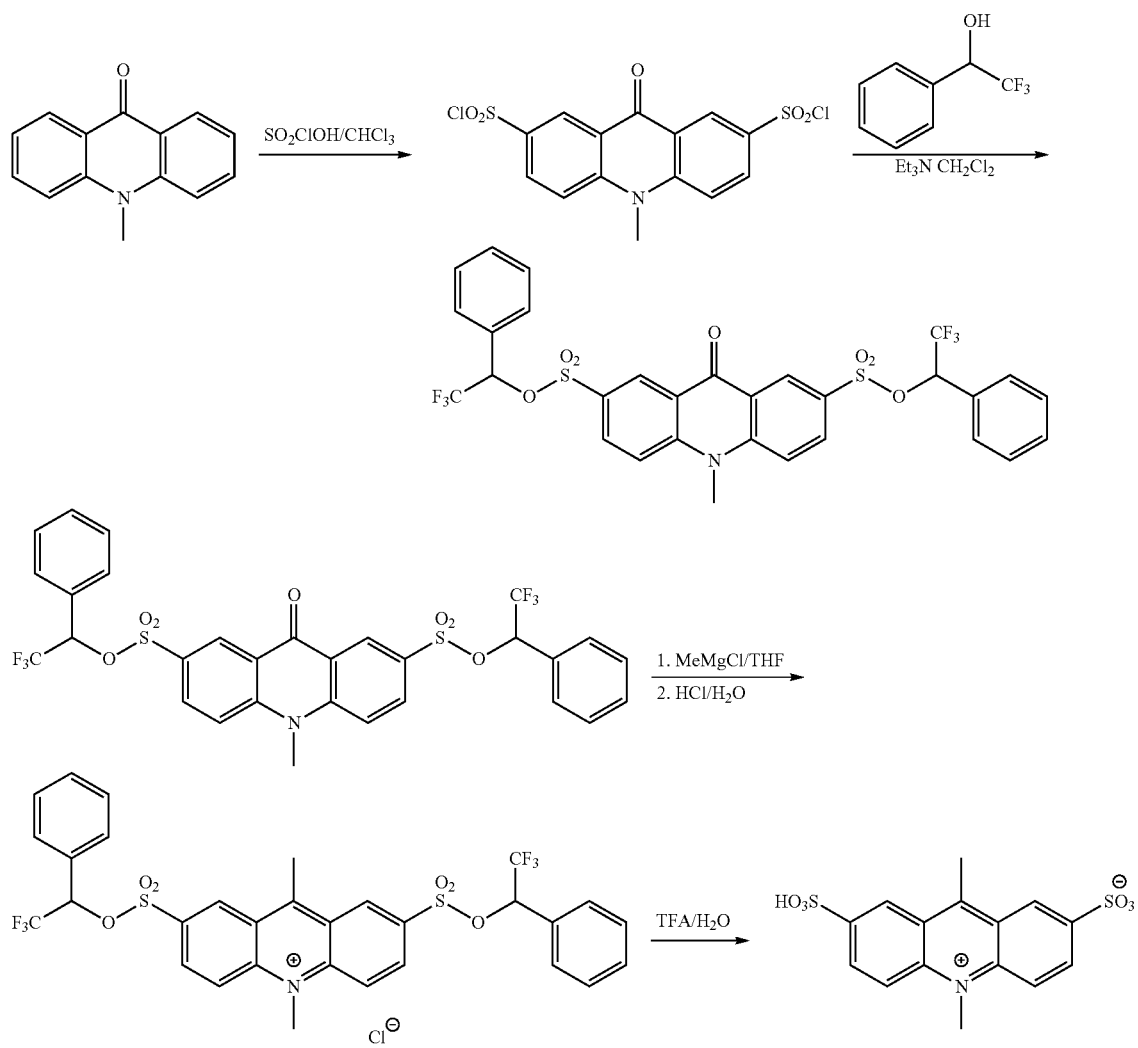

Example 23: Synthesis of Fluorochrome Compound D56

9,10-dimethyl-3,6-disulfoacridin-10-ium, triethylammonium salt (25 mg), and N-[(3-(Anilinomethylene)-2-chloro-1-cyclohexen-1-yl)methylene]aniline monohydrochloride (10 mg) are combined in 0.5 mL of acetic anhydride and 0.2 mL of acetic acid. Triethylamine (TEA) (0.02 mL) is added and the mixture is heated to 80° C. for 8 h. The crude product is precipitated with 5 mL of ethyl acetate, filtered and purified by HPLC to give the chloro-substituted acridinium dye.

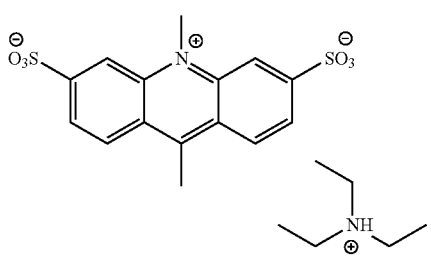

-continued

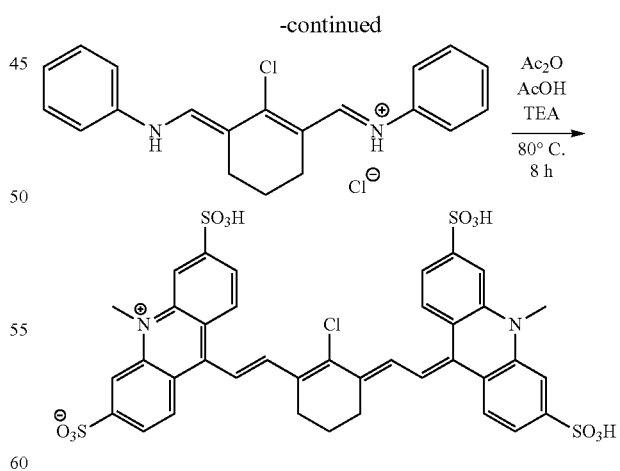

The chloro-substituted acridinium dye (15 mg) and 4-mercaptophenylacetic acid (5 mg) are combined and dissolved in 0.5 mL of anhydrous DMF to which 0.01 mL of Pyridine is added. The mixture is stirred at room temperature for 30 minutes, then the product dye D56 is precipitated with ether, isolated by filtration and purified by HPLC.

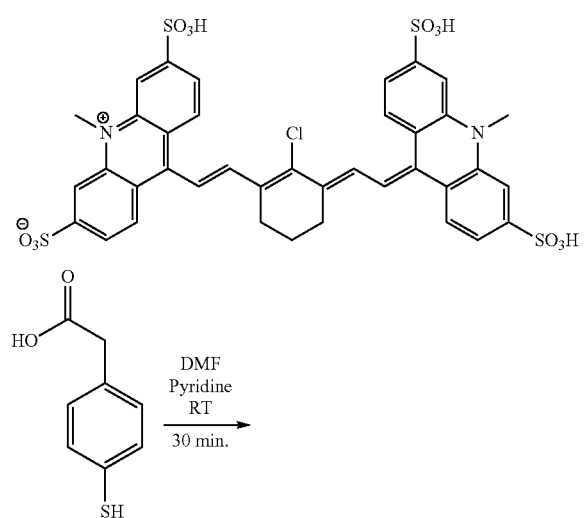

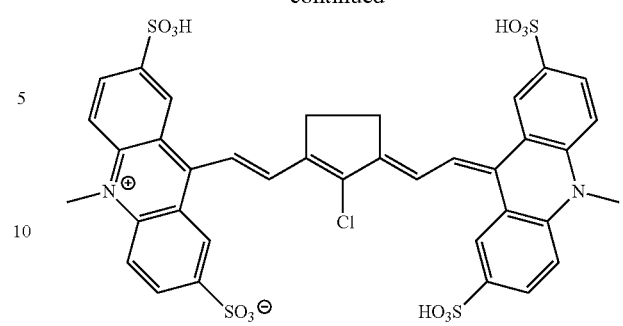

The chloro-substituted acridinium dye (15 mg) and 3-mercaptopropionic acid (5 mg) are combined and dissolved in 0.5 mL of anhydrous DMF to which 0.01 mL of triethylamine (TEA) is added. The mixture is heated to 60° C. for 2 h, then the product dye D59 is precipitated with ether, isolated by filtration and purified by HPLC.

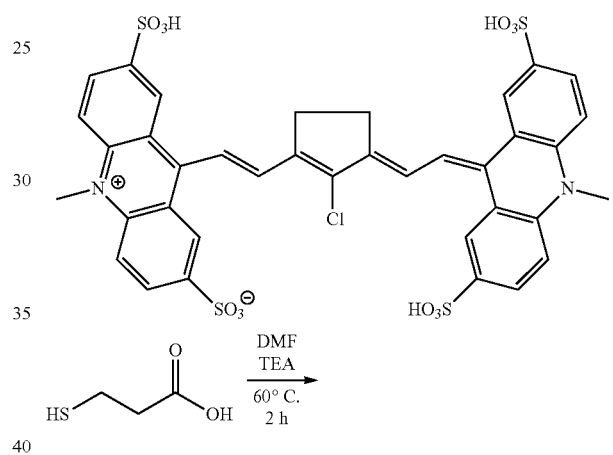

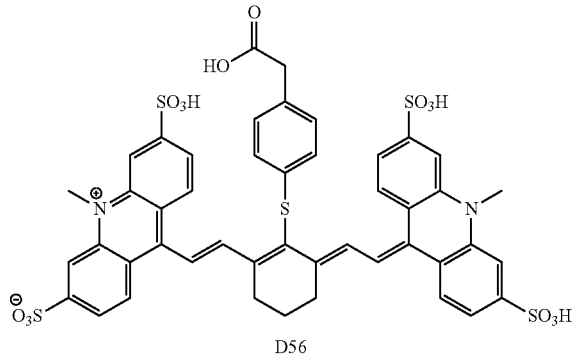

Example 24: Synthesis of Fluorochrome Compound D59

9,10-dimethyl-2,7-disulfoacridin-10-ium inner salt (25 mg), and 2-chlorocyclopent-1-ene-1,3-dialdehyde (5 mg) are combined in 0.5 mL of acetic anhydride and 0.2 mL of acetic acid. Triethylamine (TEA) (0.02 mL) is added and the mixture is heated to 50° C. for 4 h. The crude product is precipitated with 5 mL of ethyl acetate, filtered and purified by HPLC to give the chloro-substituted acridinium dye.

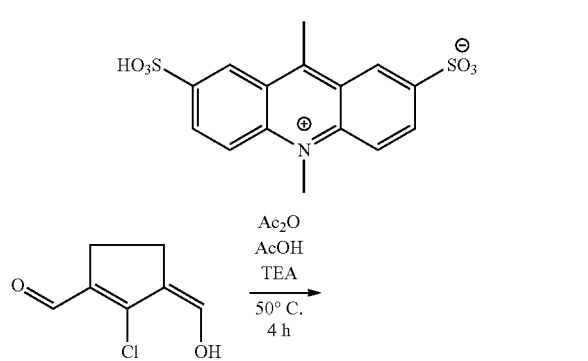

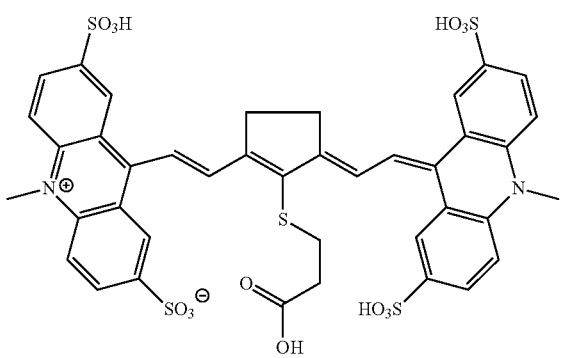

Example 25: The Synthesis of 2H-naphtho[1,8-bc]thiophen-2-one

The only known cyanine dyes based on napthothiophenium salts found in the literature were disclosed by Vasilenko, N. P.; Mikhailenko, F. A.; Maidannik, A. G.Khimiya Geterotsiklicheskikh Soedinenii (1987), (3), 418-19 as the following:

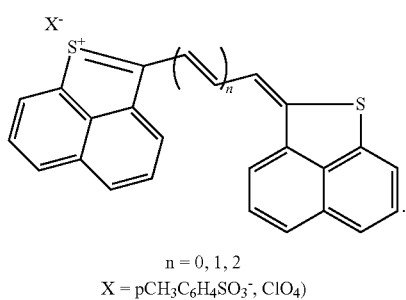

n = 0, 1, 2
X = pCH₃C₆H₄SO₃⁻, ClO₄)

However, such dyes are water insoluble and unsuitable for use in biological applications. Hence, the following procedure describes the synthesis of water soluble analogs of napthothiphenium derived symmetric cyanine dyes.

The synthesis of 2H-naphtho[1,8-bc]thiophen-2-one is carried out starting from commercially available thionaphthol and trichloroacetic anhydride, substantially as described by Mitsuduo et.al in Synlett, 27 (16), 2327-32 (2016). The resulting thio lactone is treated with 5-6 fold excess of chlorosulfonic acid in chloroform for 24 hrs and hydrolyzed the sulfonyl chloride in water forming disulfonated-2H-naphtho[1,8-bc]thiophen-2-one. It is converted to bis-tetrabutyl ammonium salt by treating with tetrabutyl ammonium hydroxide. Grignard reaction is carried out with 3 molar THF solution of MeMgCl under nitrogen in dry THF followed by acidic workup with HCl in diethylether yielding 2-methyl-6,8-disulfonaphtho[1,8-bc]thiophen-1-ium chloride, which is isolated by filtration and thorough drying under vacuum. It is reacted with bridge 9 in a mixture of acetic acid and acetic anhydride along with sodium acetate at 100° C. for about 8 hrs to realize the formation of tetra sulfonated napthothiophenium dye. It is subsequently subjected to a series of reactions as shown in the scheme below to obtain the final product T8-8.

Scheme for the Synthesis of Dyes Based on P18

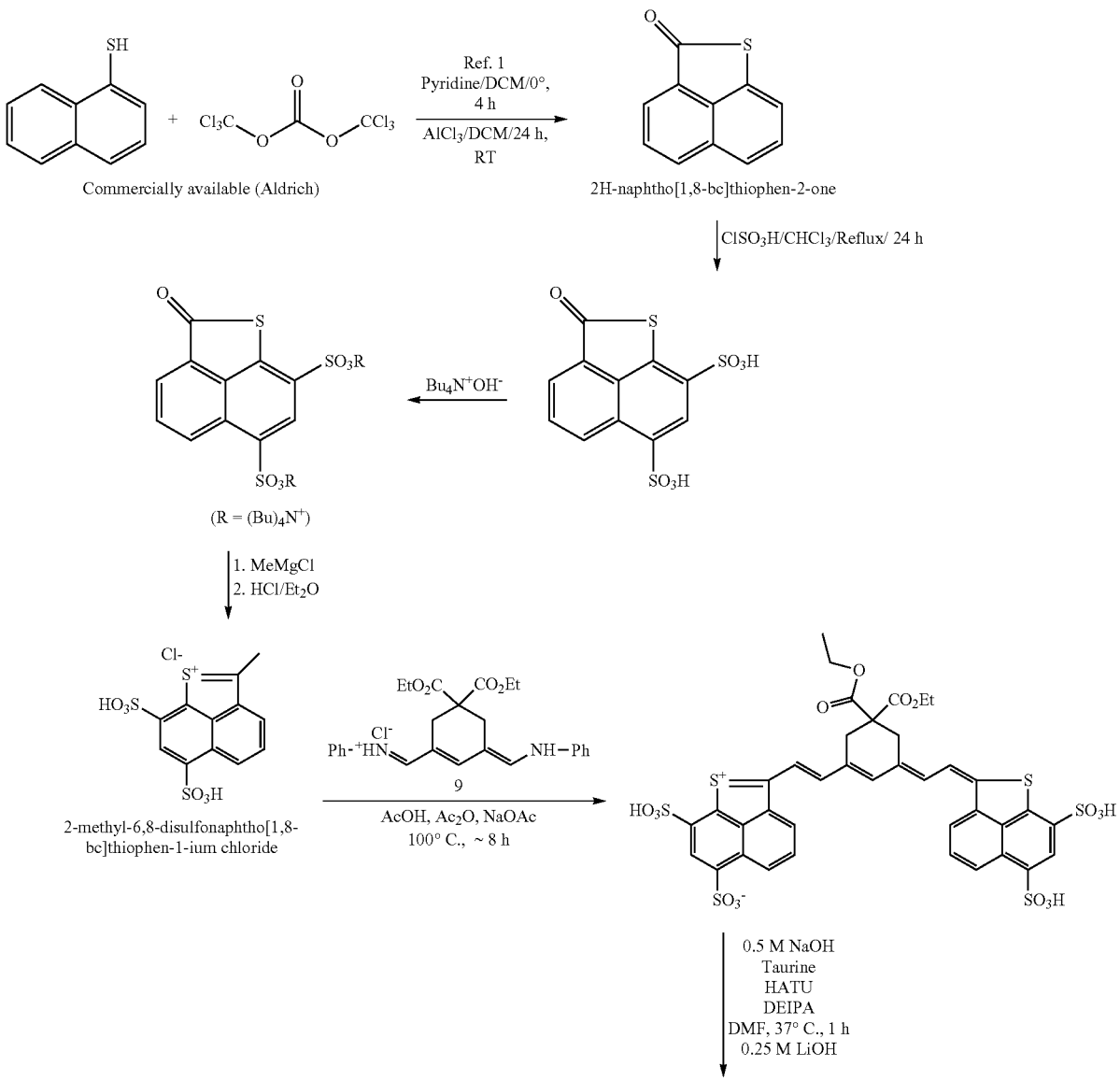

-continued

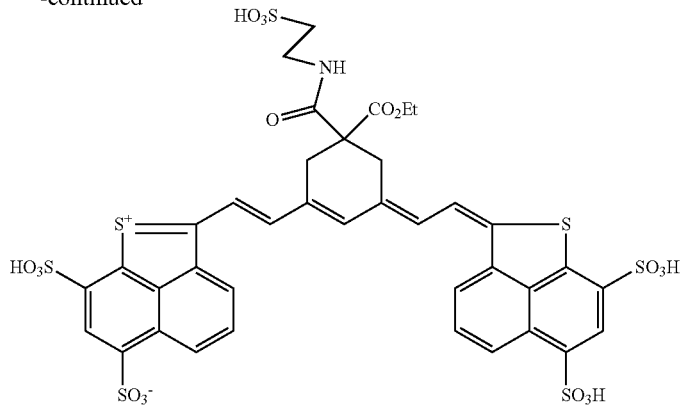

T8-8

Ref. 1: Mitsuduo, Koichi, et. al
Synlett, 27 (16), 2327-32 (2016)

Example 26: Synthesis of Quaternary Salt Intermediates QS1 to QS6 Used for the Synthesis of Dyes with Endgroups P50, P32 and P51 to P54, Respectively Several quaternary salts isolated by addition of HCl in ether are hygroscopic and decompose when exposed to moisture. In addition to the desired quaternary salt, the isolated solid also contained other salts, i.e., potassium 18-crown-6 salt and magnesium salt from the Grignard reagent. Thus, the weight % purities were estimated based on the amount of starting amide used in the reaction and the materials were used without further purification. Several exemplary quaternary salt intermediates are shown in Table 12.

TABLE 12

Quaternary Salts QS1 to QS6 used for the sysnthesis of dyes
D81, D82, D72, D84, D85, D17, D19, D15, D13, D86, D20, D18

| Quaternary Salts P | Structure |
| --- | --- |
| QS1 | 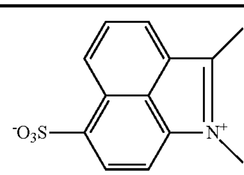 |
| QS2 | 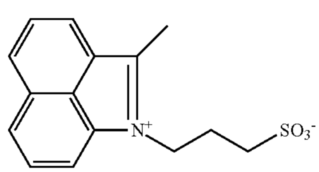 |
| QS3 | 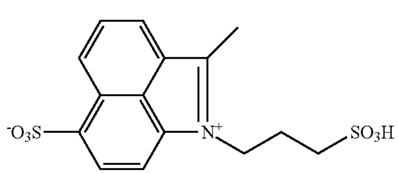 |

TABLE 12-continued

Quaternary Salts QS1 to QS6 used for the sysnthesis of dyes
D81, D82, D72, D84, D85, D17, D19, D15, D13, D86, D20, D18

| Quaternary Salts P | Structure |
| --- | --- |
| QS4 | |
| QS5 | |
| QS6 | |

Synthesis of Quaternary Salt QS1

CH$_3$I/tBuOK

-continued

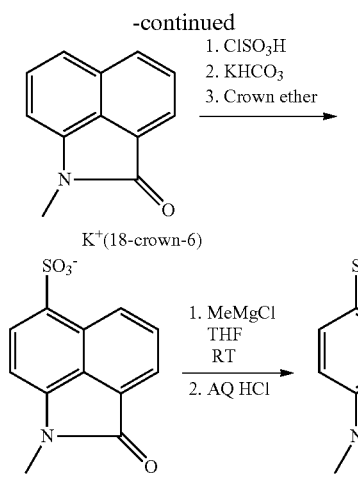

Alkylation.

To the solution of benz[c,d] indol-2(1H) one (338 mg, 2.0 mmol) and iodomethane (424 mg, 3.0 mmol) in dry DMF (5 mL) was added potassium t-butoxide (404 mg, 3.6 mmol) in portions over 10 min. After 1 h at ambient temperature, the reaction was quenched by addition of 0.2 mL of acetic acid. The solution was concentrated to ~2 mL, and partitioned with ethyl acetate (15 mL) and water (10 mL). The ethyl acetate solution was washed with 2×10 mL of water and 10 mL of brine. After dried over anhydrous sodium sulfate, the solution was concentrated to dryness.

Weight: 330 mg, 91%. The structure was confirmed by LC/MS, m/z=184.4 Da, M+1.

Sulfonation.

To starting material (184 mg, 1.0 mmol) was added chlorosulfonic acid (500 µL) and the mixture was stirred at ambient temperature for 16 h. The solution was carefully diluted with 2 mL of water and then quenched into a mixture of water/acetonitrile (2:1, v/v, 30 mL) containing 6.0 g of triethylamine. The mixture was stirred at ambient temperature for 16 h. The solution was concentrated to ~10 mL and pH was adjusted to 4-5 with acetic acid. The mixture was loaded onto a C18 packed column, 10 g resin and eluted with water. The column was eluted with a gradient mixture of aqueous buffer of triethylamine (12.5 mM) and acetic acid (25 mM), TEAA buffer, and acetonitrile. The volume was 20 mL each of the following TEAA/MeCN ratio (v/v): 95/5, 90/10, 85/15, 80/20, and 75/25.

The yellow solution was collected and analyzed by LC/MS, m/z=263.5 Da. Concentration of the solution provided the product as a yellow solid as triethylamine salt with obtained weight: 296 mg, 81%.

Crown Ether Salt Formation.

To the solution of the triethylamine salt (183 mg, 0.50 mmol) in 5 mL of water was added potassium bicarbonate (50 mg, 0.50 mmol) and 18-crown-6 (132 mg, 0.50 mmol), and the solution was concentrated to dryness. The solid was sonicated in 5 mL of MTBE and a fine slurry resulted. The supernatant was removed after centrifugation. The solid was dried under vacuum to constant weight. Obtained weight of compound: 280 mg.

Grignard Reaction.

To the suspension of the crown ether salt (164 mg, 0.29 mmol) in dry THF (5 mL) was added CH₃—MgCl (3 M in THF, 165 µL, 0.5 mmol) and the resulting mixture was stirred at ambient temperature for 6 h. To the mixture was added 2 mL of 1 M HCl in ether. The mixture was stirred at ambient temperature for 30 min and collected by centrifugation. The obtained solid was washed with 5 mL of ether and 2×2 mL of 1 M aqueous HCl, and dried under vacuum. Obtained weight: 58 mg, 76%. The structure was confirmed by LC/MS m/z=262.1 Da, M+1.

Synthesis of Quaternary Salt QS2

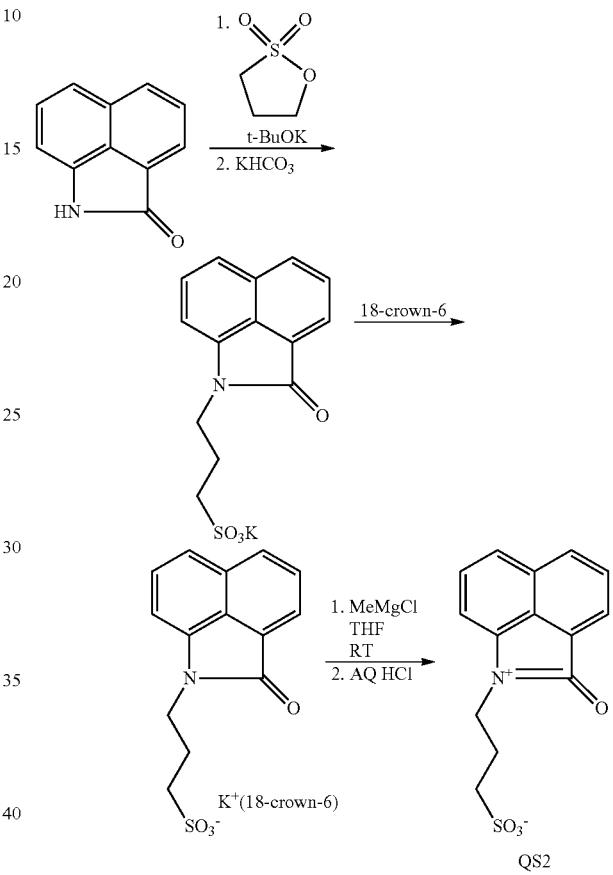

Alkylation.

To the solution of benz[c,d] indol-2(1H)one (169 mg, 1.0 mmol) and 1,3-propanesultone (183 mg, 1.5 mmol) in dry DMF (3.5 mL) was added potassium t-butoxide (202 mg, 1.8 mmol) in portions over 10 min. After 2 h at ambient temperature, the reaction was quenched by addition of 0.1 mL of acetic acid. The solution was concentrated to ~1 mL by rotavap and diluted to 10 mL with water. The solution was loaded onto a C18 resin short column of 10 mL bed volume. The column was eluted with a gradient mixture of aqueous TEAA and acetonitrile. The volume was 20 mL each of the following TEAA/MeCN ratio (v/v): 95/5, 90/10, 85/15, 80/20, and 75/25. The yellow fractions were analyzed by LC/MS, m/z=292.4 Da, M+1. The appropriate fractions were combined and concentrated to dryness to a final obtained weight: 342 mg as the triethylamine salt, 87%. The solid was dissolved in 5 mL of water and solid potassium bicarbonate (88 mg, 0.88 mmol) was added. The solution was concentrated to dryness to provide the product as a yellow solid. The final obtained weight: 328 mg.

Crown Ether Salt Formation.

To the solution of the potassium salt (66 mg, 0.20 mmol) in 5 mL of water was added 18-crown-6 (53 mg, 0.20 mmol)

and the solution was concentrated to dryness. The solid was sonicated in 5 mL of MTBE and a fine slurry was resulted. The supernatant was removed after centrifugation. The solid was dried under vacuum to constant weight. The obtained weight: 117 mg.

Grignard Reaction.

To the suspension of the crown ether salt (60 mg, 0.10 mmol) in dry THF (3 mL) was added CH$_3$MgCl (3 M in THF, 60 µL, 0.18 mmol) and the resulting mixture was stirred at ambient temperature for 4 h. To the mixture was added a mixture of 1 M aqueous HCl (3 mL) and methanol (1 mL). The mixture was stirred at ambient temperature for 30 min and collected by centrifugation. The solid was washed with 2×5 mL of dry ether and dried under vacuum. The obtained weight: 21 mg, 72%. The structure was confirmed by LC/MS, m/z=290.5 Da, M+1.

Synthesis of Quaternary Salt QS3

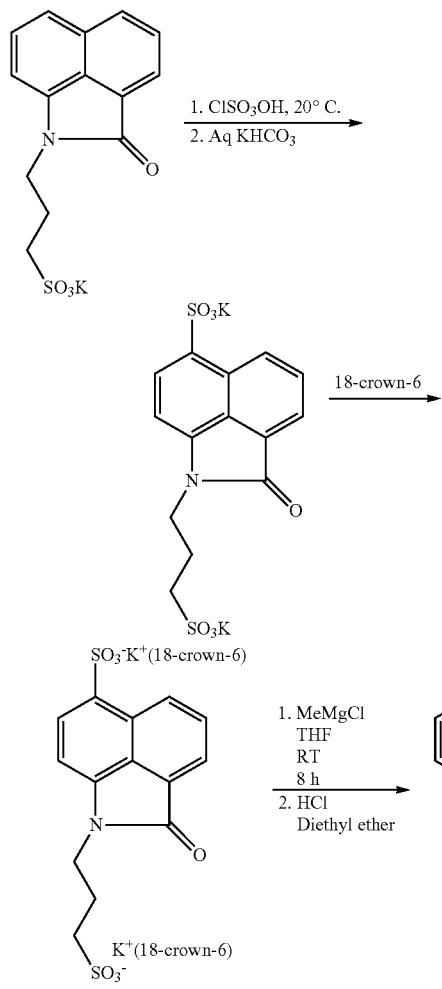

Sulfonation.

To starting material (102 mg, 0.31 mmol) was added chlorosulfonic acid (360 µL) and the mixture was stirred at ambient temperature for 2 h. The solution was carefully diluted with 2 mL of water and then quenched into a mixture of water/acetonitrile (2:1, v/v, 30 mL) containing 1.0 g of potassium carbonate. The mixture was stirred at ambient temperature for 16 h. The solution was concentrated to ~10 mL and pH was adjusted to 4-5 with acetic acid. The mixture was loaded onto a C18 packed column, 10 g resin and eluted with water. Two yellow bands developed and the first one was collected, while the second one was retained in the column. The first yellow fraction was analyzed by LC/MS, m/z=372.5 Da, M+1. Concentration of the solution provided the product as a yellow solid, 108 mg, 78%.

Crown Ether Salt Formation.

To the solution of the di-potassium salt (50 mg, 0.11 mmol) in 5 mL of water was added 18-crown-6 (58 mg, 0.22 mmol) and the solution was concentrated to dryness. The solid was sonicated in 5 mL of MTBE and a fine slurry was resulted. The supernatant was removed after centrifugation. The solid was dried under vacuum to an obtained weight: 107 mg.

Grignard Reaction.

To the suspension of the crown ether salt (107 mg, 0.11 mmol) in dry THF (3 mL) was added CH$_3$MgCl (3 M in THF, 60 µL, 0.18 mmol) and the resulting mixture was stirred at ambient temperature for 4 h. To the mixture was added HCl in ether (2 M, 300 µL) and ether (3 mL). The solid was washed with 2×5 mL of dry ether and dried under vacuum. The obtained weight: 167 mg, 27 w % based on 0.11 mmol of starting material. Product not stable when analyzed by RP-HPLC and was used without further purification.

Synthesis of Quaternary Salt QS4

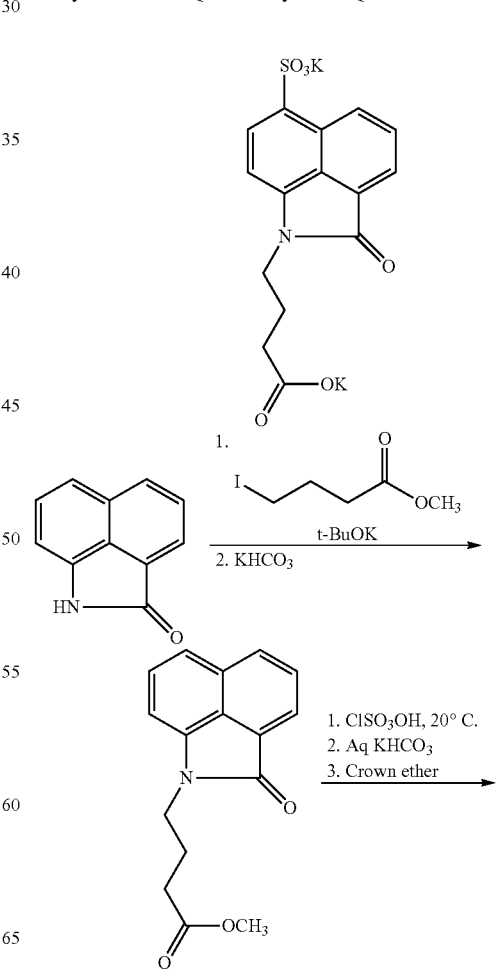

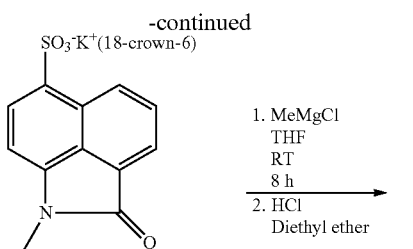

were combined and concentrated to dryness, providing the product as the triethylamine salt, 256 mg, 80%, LC/MS m/z=336.5 Da, M+1

The solid was dissolved in 10 mL of water and potassium bicarbonate (118 mg, 1.18 mmol) was added, followed by 18-crown-6 (312 mg, 1.18 mmol). The solution was concentrated to dryness. The solid was sonicated in 5 mL of MTBE for 15 min. A fine slurry was obtained. The supernatant was removed after centrifugation. The solid was dried under vacuum to constant weight, 550 mg.

Grignard Reaction.

To the suspension of the crown ether salt (190 mg, 0.20 mmol) in dry THF (3 mL) was added $CH_3MgCl$ (3 M in THF, 100 μL, 0.30 mmol) and the resulting mixture was stirred at ambient temperature for 4 h. To the mixture was added HCl in ether (2 M, 200 μL) and ether (3 mL). The solid was washed with 2×5 mL of dry ether and dried under vacuum. The obtained weight: 230 mg, 29% based on 0.20 mmol of starting material. Product was used without further purification.

Synthesis of Quaternary Salt QS5

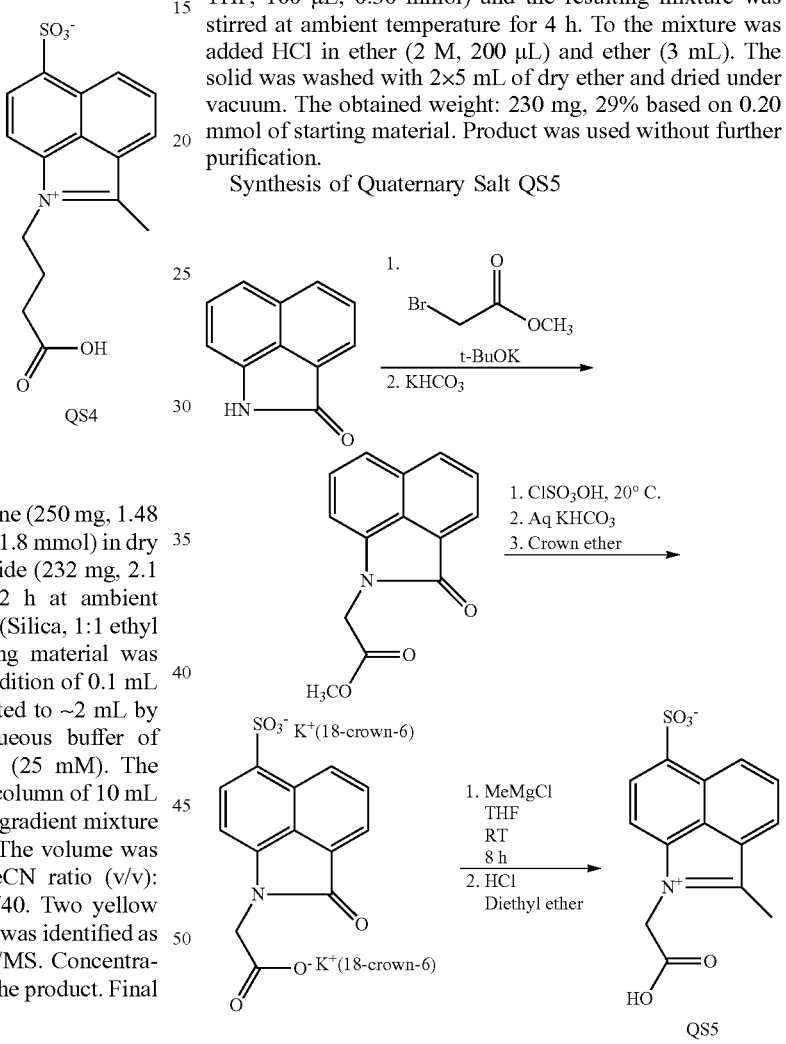

Alkylation.

To the solution of benz[c,d] indol-2(1H)one (250 mg, 1.48 mmol) and methyl 4-iodobutylate (404 mg, 1.8 mmol) in dry DMF (5 mL) was added potassium t-butoxide (232 mg, 2.1 mmol) in portions over 10 min. After 2 h at ambient temperature, the reaction analyzed by TLC (Silica, 1:1 ethyl acetate/hexane). A small amount of stating material was detected. The reaction was quenched by addition of 0.1 mL of acetic acid. The solution was concentrated to ~2 mL by rotavap and diluted to 10 mL with aqueous buffer of triethylamine (12.5 mM) and acetic acid (25 mM). The solution was loaded onto a C18 resin short column of 10 mL bed volume. The column was eluted with a gradient mixture of aqueous TEAA buffer and acetonitrile. The volume was 10 mL each of the following TEAA/MeCN ratio (v/v): 90/10, 80/20, 70/30, 60/40,50/50, and 60/40. Two yellow fractions were collected and the second one was identified as the desired product, m/z=270.3 Da by LC/MS. Concentration of the second yellow fraction afforded the product. Final obtained weight: 291 mg, 73%.

Sulfonation/Crown Ether Salt.

To starting material (200 mg, 0.74 mmol) was added chlorosulfonic acid (500 μL) and the mixture was stirred at ambient temperature for 2 h. The solution was carefully diluted with 2 mL of water and then quenched into a mixture of water/acetonitrile (2:1, v/v, 30 mL) containing 6 g of triethylamine. The mixture was stirred at ambient temperature for 16 h. The solution was concentrated to ~10 mL and pH was adjusted to 4-5 with acetic acid. The mixture was loaded onto a C18 packed column, 10 g resin and eluted with water. The column was eluted with a gradient mixture of aqueous TEAA buffer and acetonitrile. The volume was 20 mL each of the following TEAA/MeCN ratio (v/v): 95/5, 90/10, 85/15, 80/20, and 75/25. The appropriate fractions To the solution of benz[c,d] indol-2(1H)one (540 mg, 3.2 mmol) and methyl bromoacetate (684 mg, 4.4 mmol) in dry DMF (10 mL) was added potassium carbonate (662 mg, 4.8 mmol). The mixture was stirred at ambient temperature for 16 h. The reaction was quenched by addition of 0.5 mL of acetic acid. The mixture was concentrated to ~4 mL and partitioned with ethyl acetate (30 mL) and water (20 mL). The ethyl acetate solution was washed with 2×10 mL of water and 10 mL of brine. After drying over anhydrous sodium sulfate, the solution was concentrated to dryness. Obtained weight: 720 mg, 93%. The structure was confirmed by LC/MS, m/z=242.3 Da, M+1.

Sulfonation/Crown Ether Salt.

To starting material (483 mg, 2.0 mmol) was added chlorosulfonic acid (1.0 mL) and the mixture was stirred at ambient temperature for 16 h. The solution was carefully diluted with 2 mL of water and then quenched into a mixture of water/acetonitrile (2:1, v/v, 50 mL) containing 3.0 g of potassium carbonate. The mixture was stirred at ambient temperature for 16 h. The solution was concentrated to ~10 mL and pH was adjusted to 4-5 with acetic acid. The mixture was loaded onto a C18 packed column, 50 g resin and eluted with 20 mL of water, a gradient mixture of aqueous TEAA buffer and acetonitrile. The volume was 20 mL each of the following TEAA/MeCN ratio (v/v): 95/5, 90/10, 85/15, 80/20, and 75/25. The appropriate fractions were combined and concentrated to dryness, providing the product as the triethylamine salt, 557 mg, 68%, LC/MS, m/z=308.4 Da, M+1

The solid (557 mg, 1.36 mmol as triethylamine salt) was dissolved in 10 mL of water and potassium bicarbonate (272 mg, 2.72 mmol) was added, followed by 18-crown-6 (718 mg, 2.72 mmol). The solution was concentrated to dryness. The solid was sonicated in 5 mL of MTBE for 15 min. A fine slurry was obtained. The supernatant was removed after centrifugation. The solid was dried under vacuum to constant weight, 1.21 g.

Grignard Reaction.

To the suspension of the crown ether salt (365 mg, 0.40 mmol) in dry THF (5 mL) was added CH3MgCl (3 M in THF, 200 µL, 0.60 mmol) and the resulting mixture was stirred at ambient temperature for 16 h. To the mixture was added HCl in ether (2 M, 0.6 mL) and ether (3 mL). The solid was washed with 2×5 mL of dry ether and dried under vacuum.

Weight: 490 mg, 25% based on 0.40 mmol of starting material. Product was used without further purification.

Example 27: Dye Synthesis General Procedures

The dyes, Table 14, were synthesized by condensation of the quaternary salt (Table 12) with the bridge (Table 13) in a mixture of acetic anhydride/acetic acid using cesium acetate as the base.

TABLE 13

Bridge Intermediates B

| Intermediate B | Structure |
|---|---|
| B$_1$ | Ph-NH-CH=CH-CH=CH-CH=N-Ph · HCl |
| B$_2$ | Ph-NH-CH=C(cyclohexene with Cl)-CH=N-Ph · HCl |
| B$_3$ | Ph-N=CH-C(=C(Cl)-bicyclic)-CH=NH-Ph · HCl |

Symmetric Dyes

To the mixture of the quaternary salt QS (48 mol), bridge B (20 mol), cesium acetate (480 µmol) was added 5 mL of a mixture of acetic anhydride/acetic acid (2:1, v/v). The mixture was heated at 40-50° C. for 4-8 h. After concentrating under vacuum to ~1 mL, water (~10 mL) was added and the mixture was purified using a packed C18 short column (~12 mL bed volume), eluted with a gradient mixture of aqueous TEAA buffer and acetonitrile The volume was 20 mL each of the following TEAA/MeCN ratio (v/v): 95/5, 90/10, 85/15, 80/20, and 75/25.

D81 was synthesized by condensation of QS1 with B$_3$, LC/MS m/z=685.2 Da and 687.2 Da, M+1, UV-Vis $\lambda_{max}$~1026 nm (methanol).

D82 was synthesized by condensation of QS1 with B$_2$, LC/MS m/z=659.2 Da and 671.2 Da M+1, UV-Vis $\lambda_{max}$~1020 nm (methanol).

D72 was synthesized by condensation of QS2 with B$_3$, LC/MS m/z=741.3 Da and 743 Da. UV-Vis $\lambda_{max}$~1030 nm (methanol).

D84 was synthesized by condensation of QS2 with B$_2$, LC/MS m/z=715.3 Da and 717.3 Da, M+1, UV-Vis $\lambda_{max}$~1020 nm (methanol).

D85 was synthesized by condensation of QS3 with B$_2$, LC/MS m/z=875.4 Da and 877.4 Da, UV-Vis $\lambda_{max}$~1030 nm (methanol).

D17 was synthesized by condensation of QS4 with B$_1$, LC/MS m/z=729.3 Da M+1, UV-Vis $\lambda_{max}$~990 nm (methanol).

D19 was synthesized by condensation of QS5 with B$_1$, LC/MS m/z=673.3 Da, M+1, UV-Vis $\lambda_{max}$~1010 nm (methanol).

D15 was synthesized by condensation of QS5 with B$_3$, LC/MS m/z=901.3 Da, 903.1 Da, M+1, UV-Vis $\lambda_{max}$~1030 nm (methanol).

Asymmetric Dyes

To the mixture of two different quaternary salts QS and QS' (both ~24 µmol) and the bridge B (20 mol), cesium acetate (480 µmol) was added 5 mL of a mixture of acetic anhydride/acetic acid (2:1, v/v). The mixture was heated at 40-50° C. for 4-8 h. After concentrated under vacuum to ~1 mL, water (~10 mL) was added and the mixture was purified using preparative HPLC with a C18 column (Gradient: 5-50% A/B; A=aqueous TEAA buffer, triethylamine (12.5 mM), acetic acid (25 mM), acetonitrile 2.5%; B=acetonitrile)

D13 was synthesized by condensation of QS3 and QS4 with B$_1$. LC/MS m/z=765.3 Da, M+1, UV-Vis $\lambda_{max}$~980 nm (methanol).

D86 was synthesized by reaction of QS4 (24 mol) with B$_1$ (20 mol), cesium acetate (480 mol) in 5 mL of acetic anhydride/acetic acid (2:1, v/v) at ambient temperature for 2 h. To the mixture was added QS6 (22 µmol) and the reaction continued at 40° C. for 2 h. LC/MS m/z=887.3 Da, M+1, UV-Vis $\lambda_{max}$~890 nm (methanol).

D20 was synthesized by condensation of QS1 and QS4 with B$_1$. LC/MS m/z=657.3 Da, M+1, UV-Vis $\lambda_{max}$~980 nm (methanol).

D18 was synthesized by condensation of QS3 and QS5 with B$_1$. LC/MS m/z=737.3 Da, M+1, UV-Vis $\lambda_{max}$~990 nm (methanol).

TABLE 14
Exemplary dyes
| Dye | Structure |
|---|---|
| D81 | 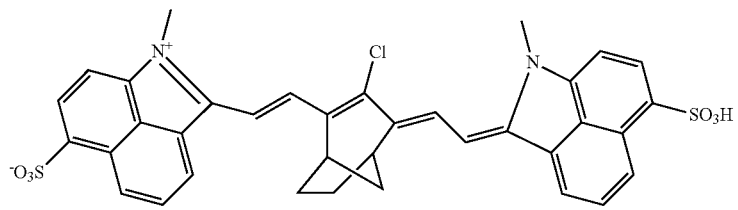 |
| D82 | 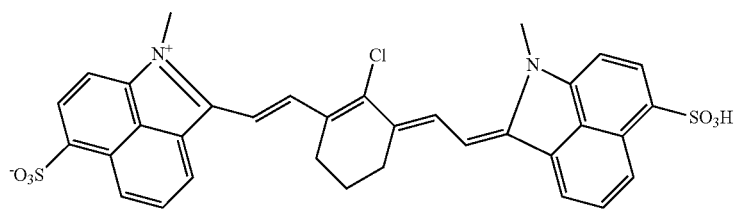 |
| D72 | 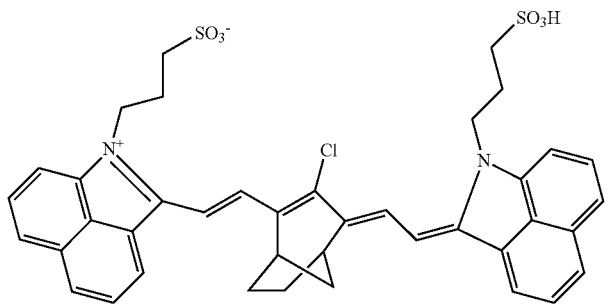 |
| D84 | 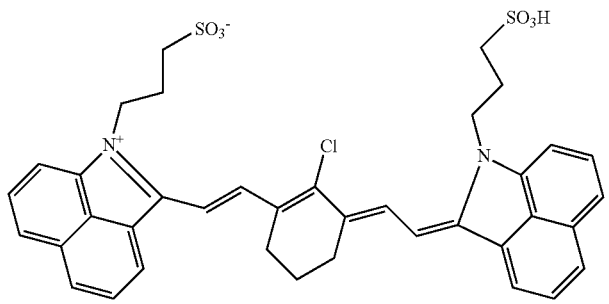 |
| D85 | 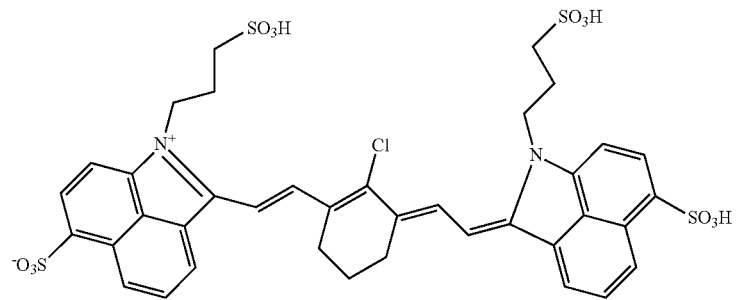 |

TABLE 14-continued

Exemplary dyes

| Dye | Structure |
| --- | --- |
| D17 | 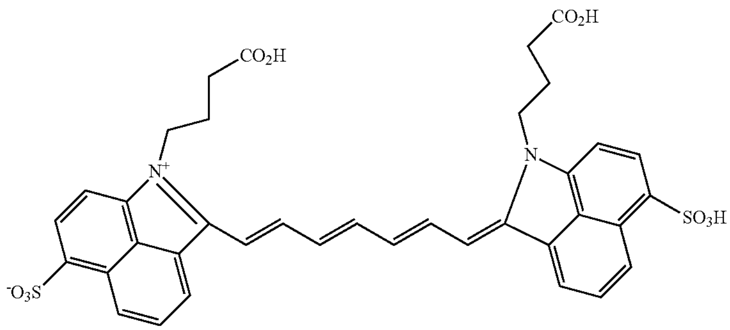 |
| D19 | 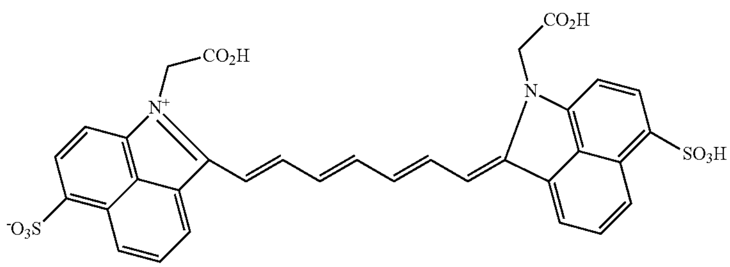 |
| D15 | 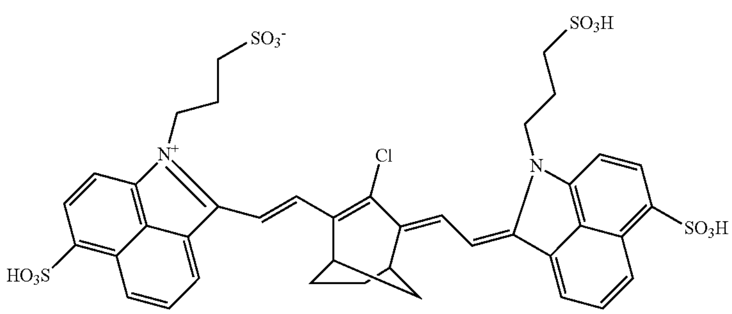 |
| D13 | 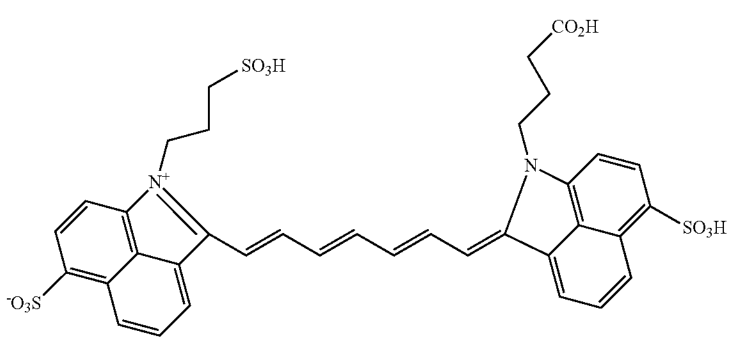 |

TABLE 14-continued

Exemplary dyes

| Dye | Structure |
| --- | --- |
| D86 | 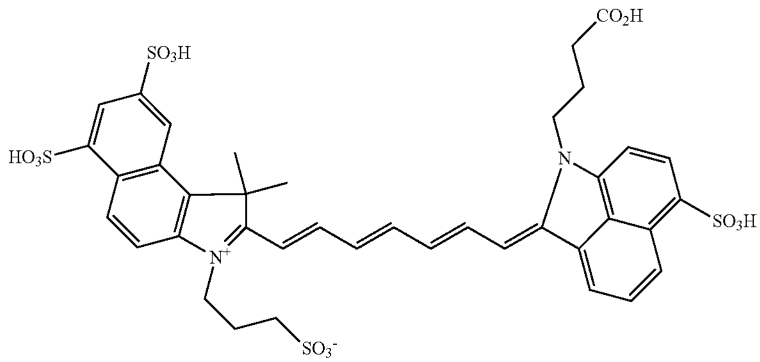 |
| D20 | 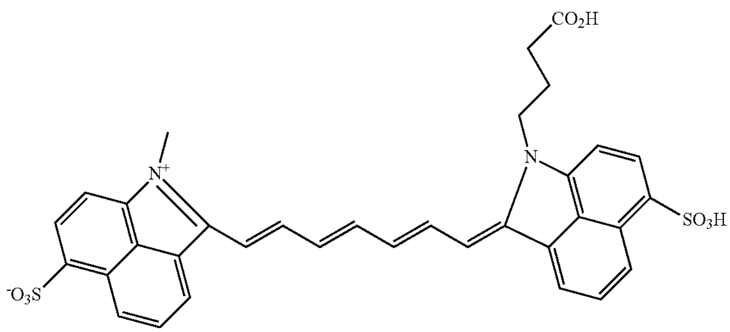 |
| D18 | 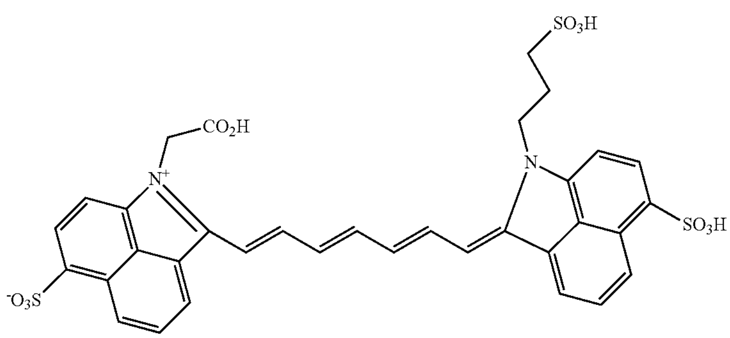 |

Example 28: Absorbance Spectra of Fluorochrome Compounds in Methanol and Water Equimolar concentrations of the fluorochrome compounds D3, D19 and D2 were dissolved in methanol or water in a 1 mL cuvette and the absorbance measured against a methanol or water blank sample on a Cary 50 absorbance spectrophotometer. Normalized spectra thus obtained are shown in FIG. 1 for each fluorochrome compound.

Figure 2:
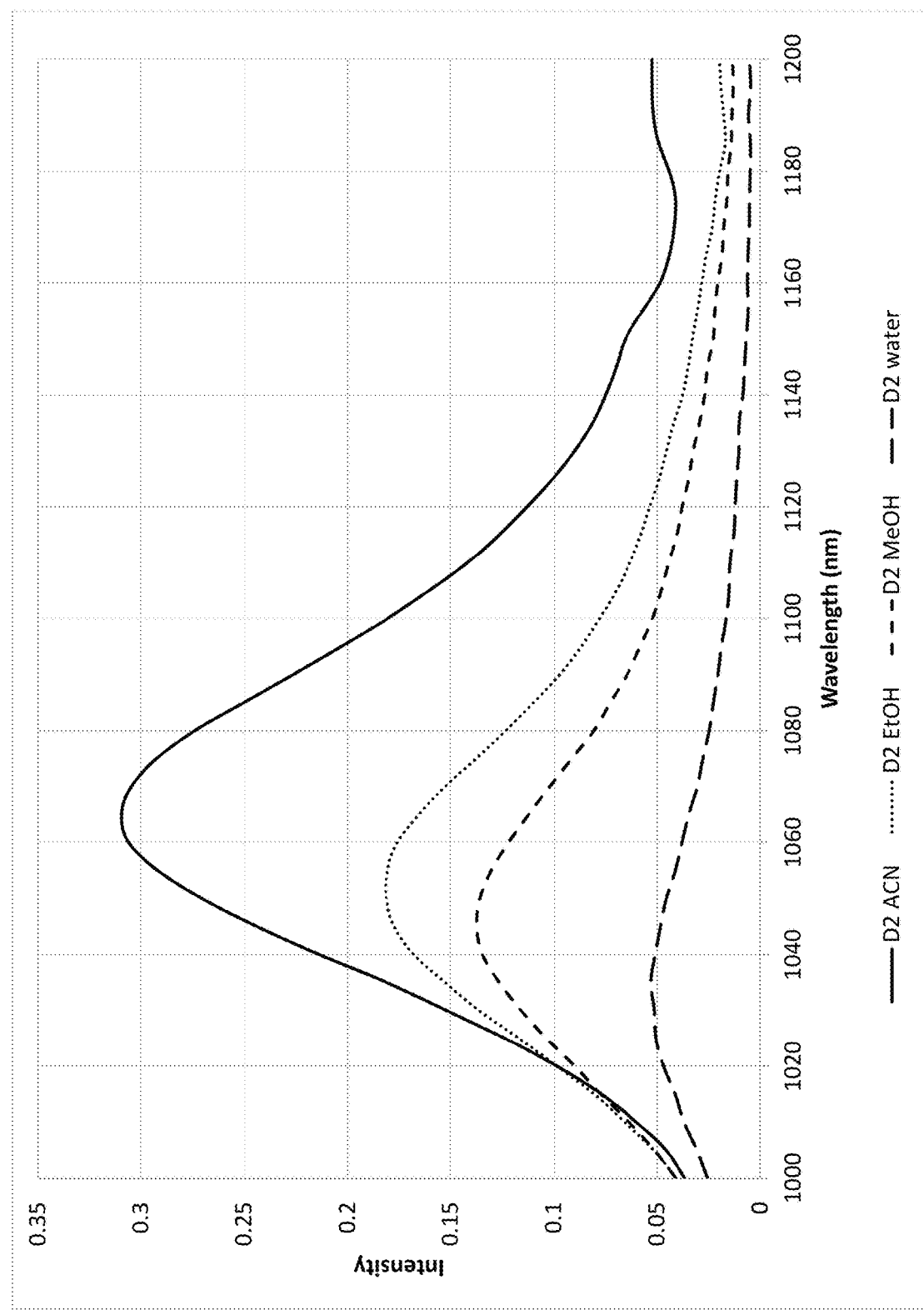
FIG. 2 illustrates the fluorescence spectra of exemplary compound D2 in various solvents.

Example 29: Emission Spectra of Representative Water Soluble Fluorochrome D2 in Various Solvents The emission of D2 was measured in acetonitrile (ACN), ethanol (EtOH), methanol (MeOH). Spectra were recorded on a Quantamaster 8075-21 fluorescence spectrophotometer equipped with a liquid nitrogen cooled cooled DSS-IGA020L/CUS InGaAs NIR detector with excitation at 980 nm and emission recorded from 1000 nm to 1200 nm. The emission spectra as illustrated in FIG. 2 are at equal absorbance at 980 nm for each solvent.

Example 30: Imaging Fluorescence Emission of D2

A 100 µL solution of fluorochrome compound D2 in water (approximately 4 µM concentration) was placed in a FMT phantom and excited with a 976 nm laser. The fluorescent light was then imaged with an InGaAs camera using a 980 nm long pass filter.

Example 31: Fluorescence of DiSulfonated Chloro Dyes Based on Benz[cd]indoles and Comparison with IR-26 in Dichloroethane

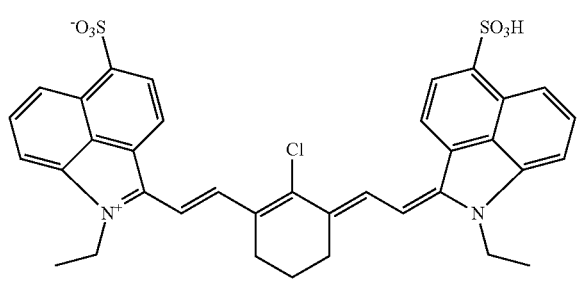

A

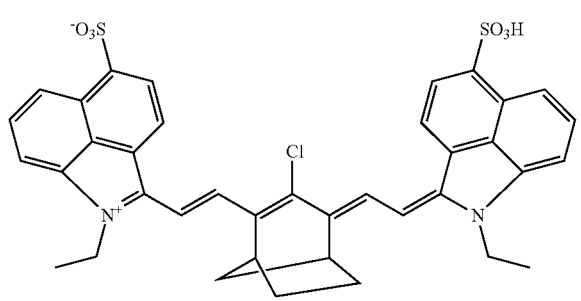

B

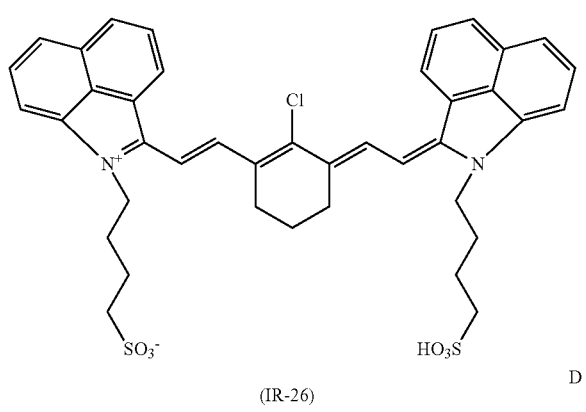

C (IR-26) D

Figure 3:
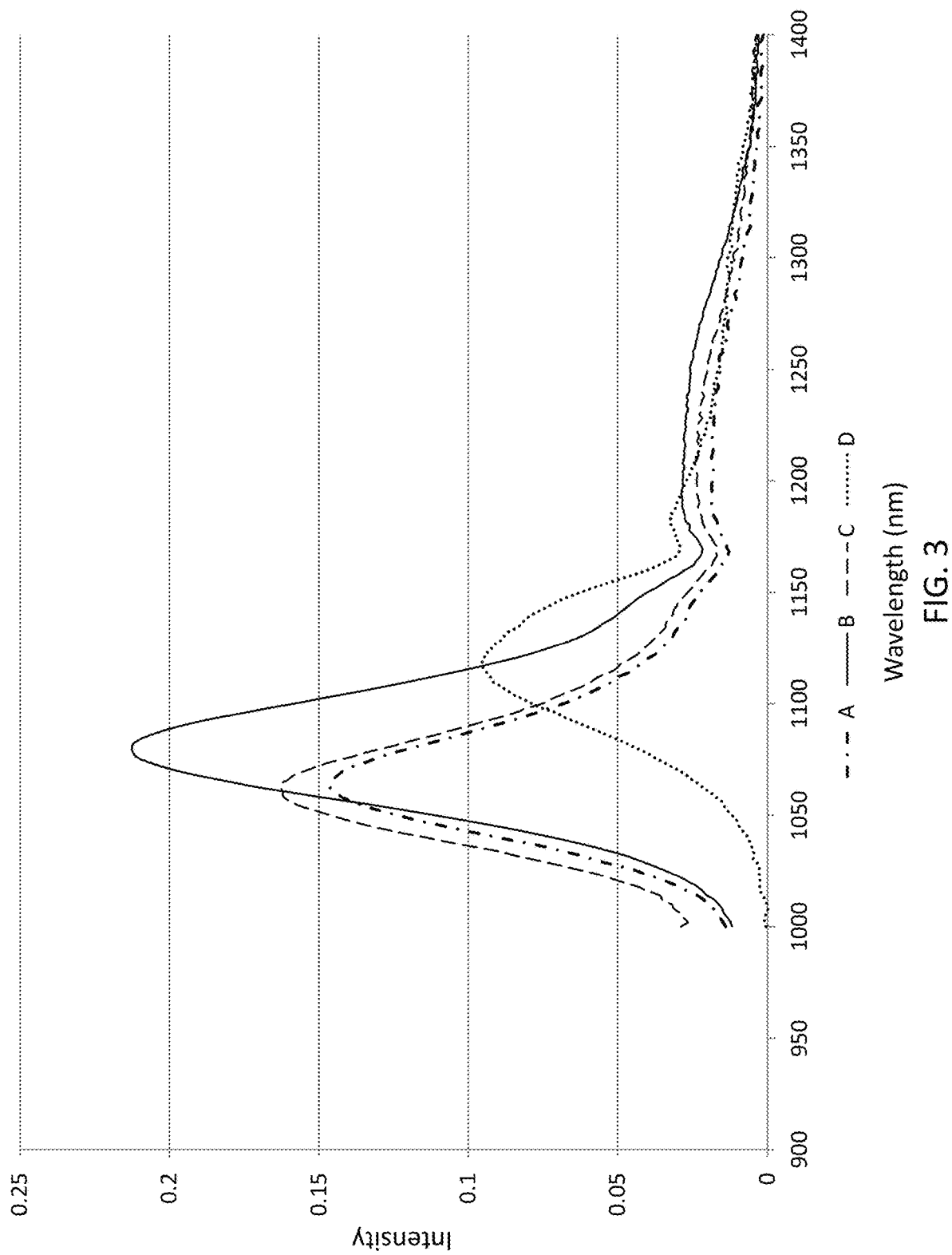
FIG. 3 illustrates fluorescence spectra of various compounds according to aspects as provided herein relative to a reference compound IR-26.

The fluorescence spectra for an equal absorbance ~0.13 solution of dyes A, B, C in dichloroethane were determined by exciting at 980 nm (Horiba (Quantamaster 8075-21), nitrogen cooled InGaAs detector) and compared them with a commercially available dye, IR-26 (obtained from Exciton) D as reference. Dye B is more than 2 fold brighter than the reference IR-26 in DCE as illustrated in FIG. 3.

The fluorescence of dyes A, B and C were also determined in other solvents viz., methanol, ethanol, DMSO and water. Results are illustrated in Table 15.

TABLE 15

| | Fluorescence Max (nm) | | | |
|---|---|---|---|---|
| Solvents | A | B | C | D |
| MeOH | 1046 | 1056 | 1042 | |
| EtOH | 1050 | 1062 | 1046 | |
| DMSO | 1080 | 1092 | 1074 | |
| DCE | 1064 | 1080 | 1062 | 1118 |
| Water | | | | |

| | % Fluorescence Relative to C | | | |
|---|---|---|---|---|
| Solvents | A | B | C | D (IR-26) |
| MeOH | 86.00 | 94.80 | 1.00 | |
| EtOH | 92.92 | 76.31 | 1.00 | |
| DMSO | 29.46 | 80.53 | 1.00 | |
| DCE | 90.11 | 130.82 | 1.00 | 58.89 |
| Water | | | | |

Figure 4:
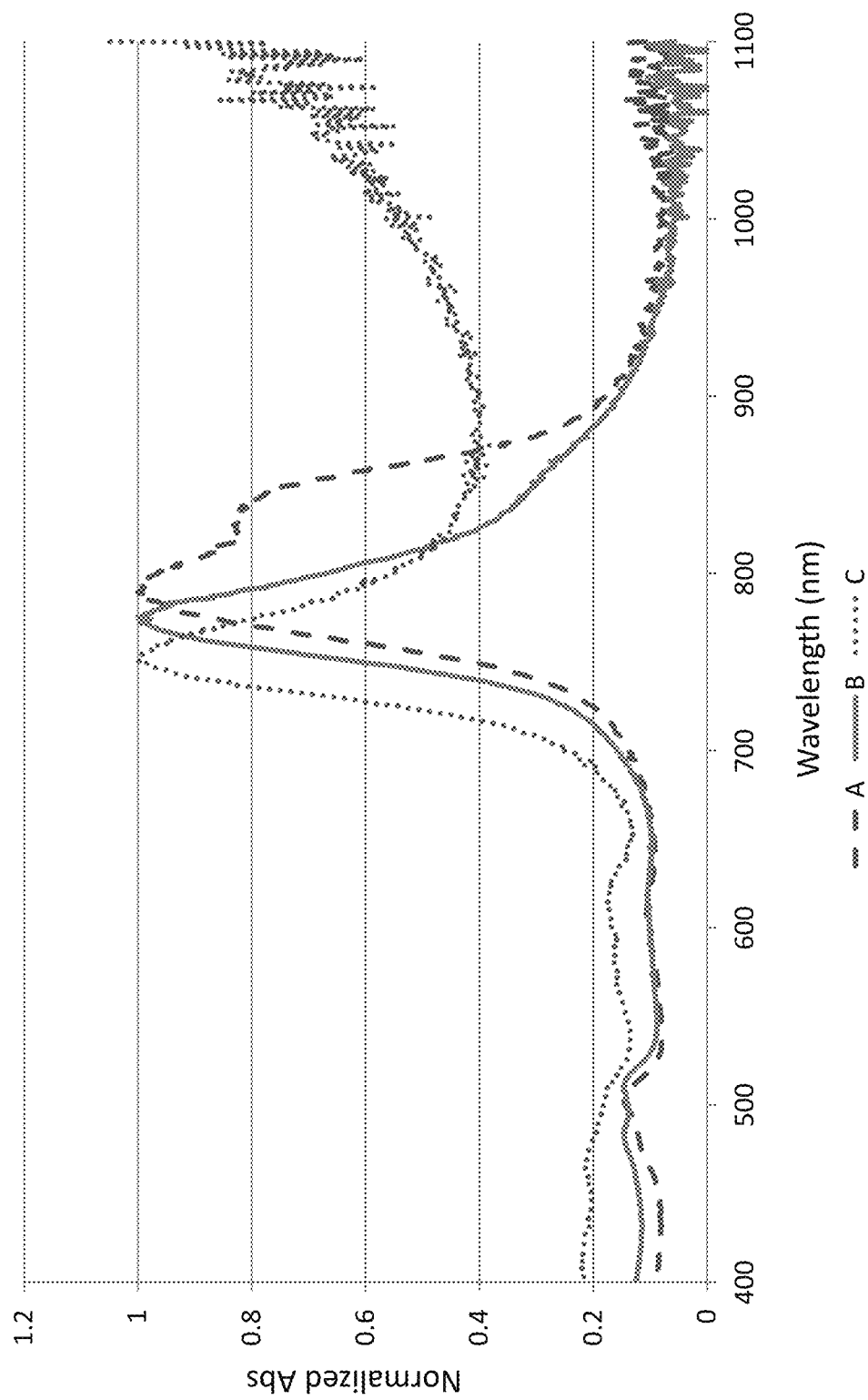
FIG. 4 illustrates the normalized absorbance spectra of various compounds according to aspects as provided herein.

Dyes A, B and C have their emission highly quenched in water. Very little residual fluorescence is observed for an aqueous solution. Their absorption spectra are consistent with the blue shifted absorbance max resulting from high degree of aggregation. Results are illustrated in FIG. 4. From the abs and emission spectra of the disulfonated benz[c,d]-indole dyes, it is clear that the presence of two sulfonate groups on the fluorophores are not sufficient to have good fluorescence, which still undergo strong aggregation in aqueous solutions and result in quenching, and require 4 or more such water solubilizing groups.

Example 32: Conjugation of Fluorophore D2 with Cyclo-(RGDyK) Peptide

The fluorophores as described herein are capable of being conjugated to an organic small molecule or a biomolecule, and the optical properties of the resulting conjugate are unaltered and thus may be useful for biological applications including in vivo imaging.

An RGD peptide, cyclo-(RGDyK) was obtained from AnaSpec (Cat # AS-6113-5). It is one the most widely used imaging agents that has hight affinity to αvβ3-integrins which are highly expressed in tumors. About one mg of compound D2 was first activated using 2 mg disuccinikidyl carbonate (DSC) in 100 μL DMF along with 1 μL N-methyl morpholine (NMM), and incubated at 37° C. for 1 hr yielding NHSE. The DMF solution was diluted with dry ethyl acetate (EA, 1.8 mL) and the precipitate was centrifuged. The pellet was washed with 250 μL EA, and the residue was speed vac dried for 20 min. The resulting NHSE was reconstituted in 100 μL DMF and is stored at −20° C., which is stable for weeks. 0.1 mg of D2-NHSE was reacted with 3 fold excess of RGD peptide in 100 μL DMF and 1 μL NMM, at 37° C. After 90 min, the LCMS analysis showed >99% conversion of the dye to the product. It was purified on PhenylHexyl (X-Bridge) column over a gradient of 00-35% B, using 100% acetonitrile as buffer B, and 25 mM triethylammonium acetate as buffer A (pH~6.5).

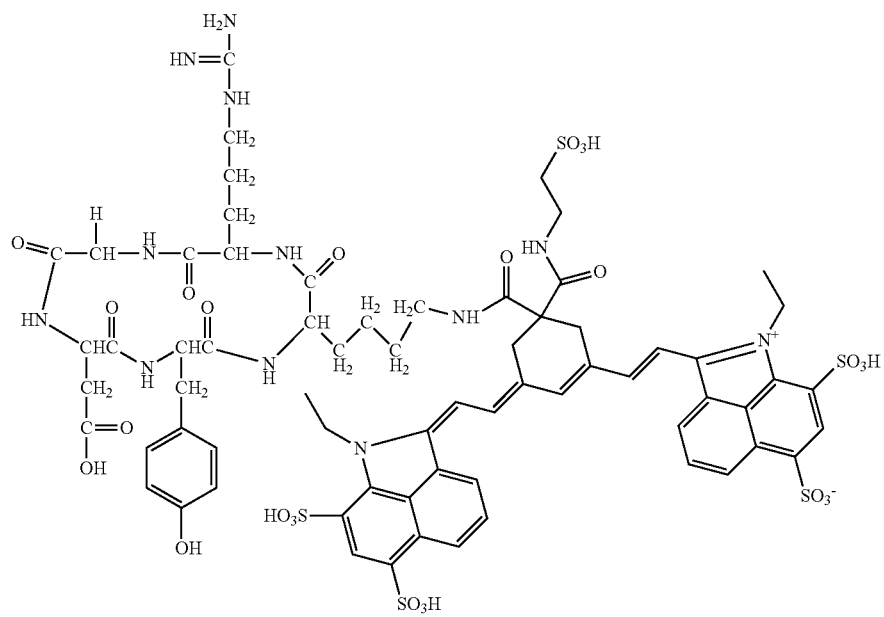

cyclo(RGDyK) labelled with a SWIR dye

Figure 5:
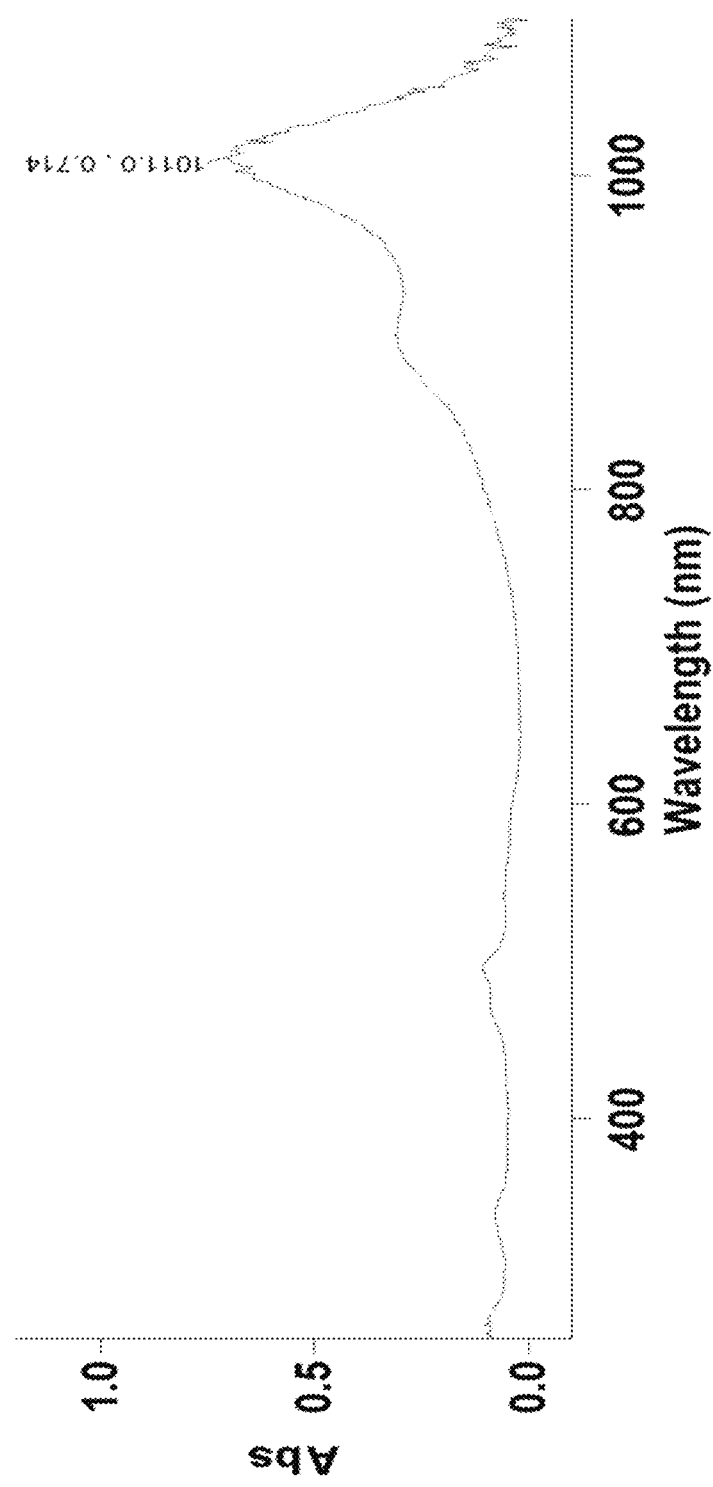
FIG. 5 illustrates the absorbance spectrum of an exemplary D2-cyclo-(RGDyK) conjugate.
Figure 6:
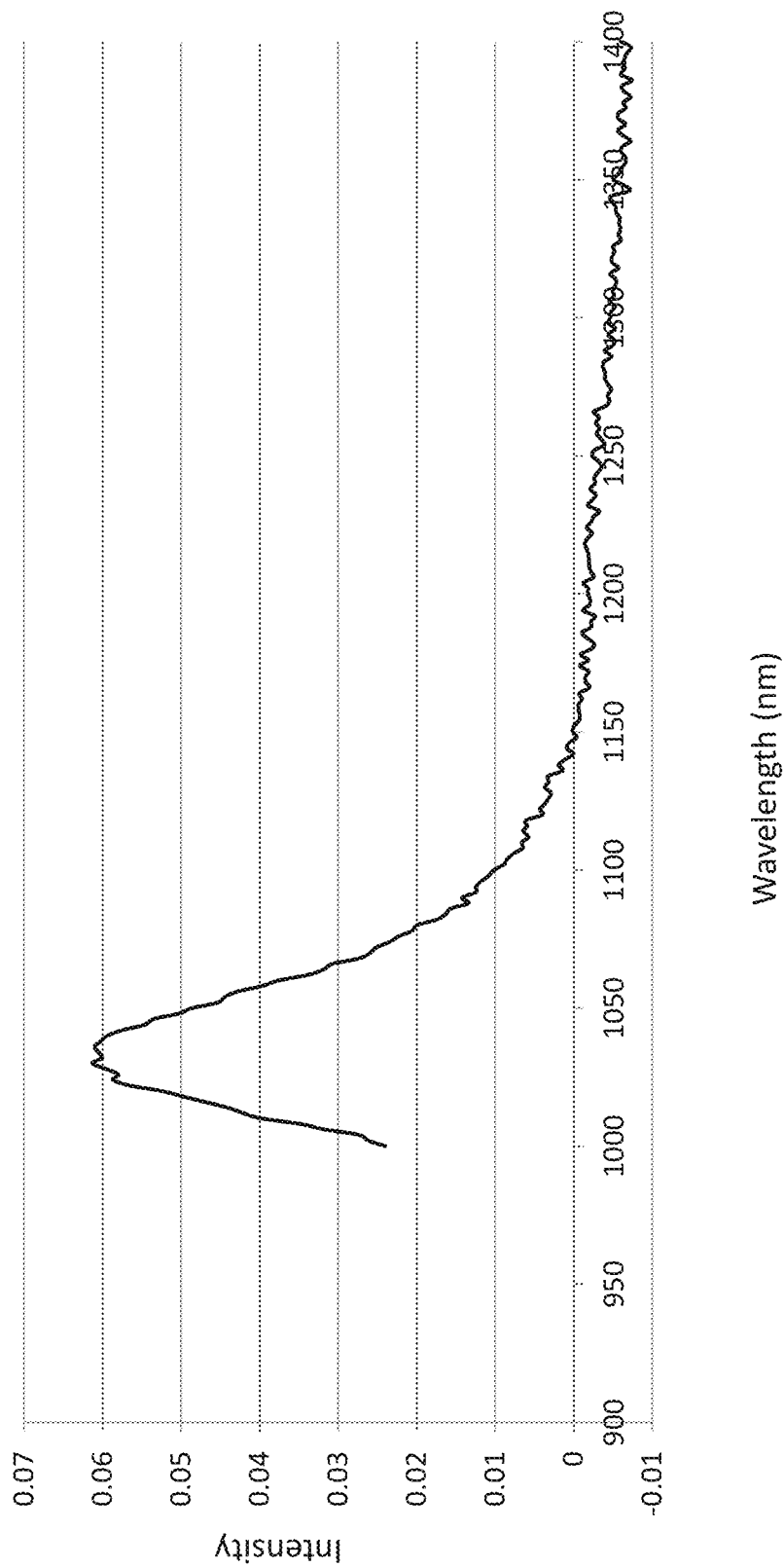
FIG. 6 illustrates the fluorescence spectrum of an exemplary D2-cyclo-(RGDyK) conjugate in 1×PBS upon excitation at 980 nm illustrating an emission maximum of 1036 nm.

The resulting compound was analyzed and further characterized. Purity of D2-cyclo-(RGDyK) after HPLC purification (detection at 800 nm) illustrated no observable contamination. The calculated mass is 1610 Da ($C_{67}H_{76}N_{12}O_{25}S_5$) and observed mass is 806.3 Da (as half mass (M+2/2)). D2-cyclo-(RGDyK) conjugate in 1×PBS has an absorbance max at 1011 nm, and shows no "blue shift" of the absorbance peak due to aggregation in aqueous solution that is observed for the fluorophores with less solubilizing groups such as sulfonates. (FIG. 5) The fluorescence spectrum of the D2-cyclo-(RGDyK) conjugate determined on Horiba with $N_2$ cooled InGaAs detector is illustrated in FIG. 6.

Example 33: Activation of Fluorochrome D2 to Succinimidyl Ester D80

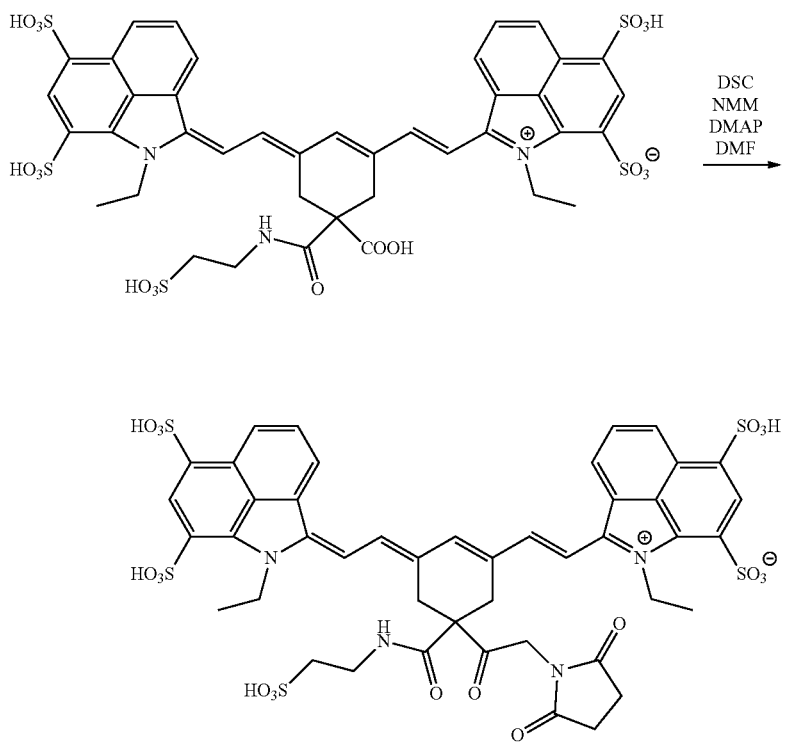

D2 (5.5 mg) was dissolved in 100 µL of anhydrous DMF in a 2.0 mL polypropylene centrifuge tube. DSC (disuccinimidyl carbonate, 7 mg) was added along with DMAP (4-dimethylaminopyridine, 0.4 mg) and NMM (N-methylmorpholine, 3 µL) and the solution was rotated at room temperature in the dark overnight. The material was then precipitated by addition of 1.5 mL of ethyl acetate and centrifuged at 10,000×g for 5 minutes. The ethyl acetate was decanted and the solid dispersed in 1.5 mL additional ethyl acetate followed by centrifugation at 10,000 g for 5 minutes and again decanting the ethyl acetate from the precipitate. The solid was dissolved in 100 µL of anhydrous DMF and 20 µL aliquoted into each of 5 centrifuge tubes containing 1.5 mL of ethyl acetate. The 5 tubes were centrifuged at 10,000×g for 5 minutes then the ethyl acetate decanted off. The precipitated solid in the tubes was dried under vacuum and the tubes containing activated N-hydroxysuccinimidyl ester D80 stored at −20° C. prior to use.

Example 34: Conjugation of Succinimidyl Ester D80 to Polyethylene Glycol Amine gation at 1500×g for 120 seconds eluted the labeled mPEG-NH$_2$-40 k while the unconjugated dye was retained on the column.

Example 35: Optical Properties of D80 Conjugated to Polyethylene Glycol

Figure 7:
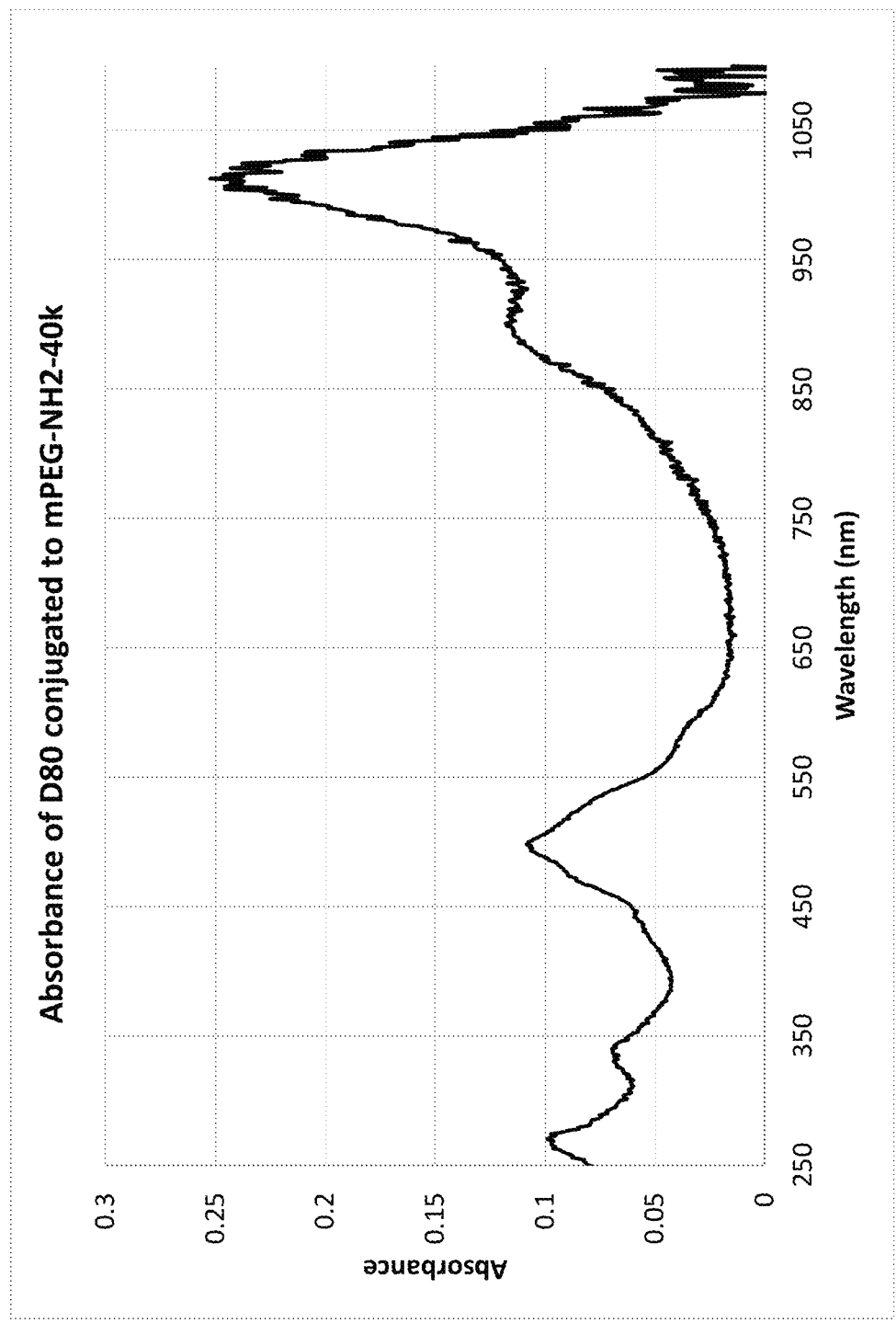
FIG. 7 illustrates a absorbance spectrum of compound D80 conjugated to polyethylene glycol.
Figure 8:
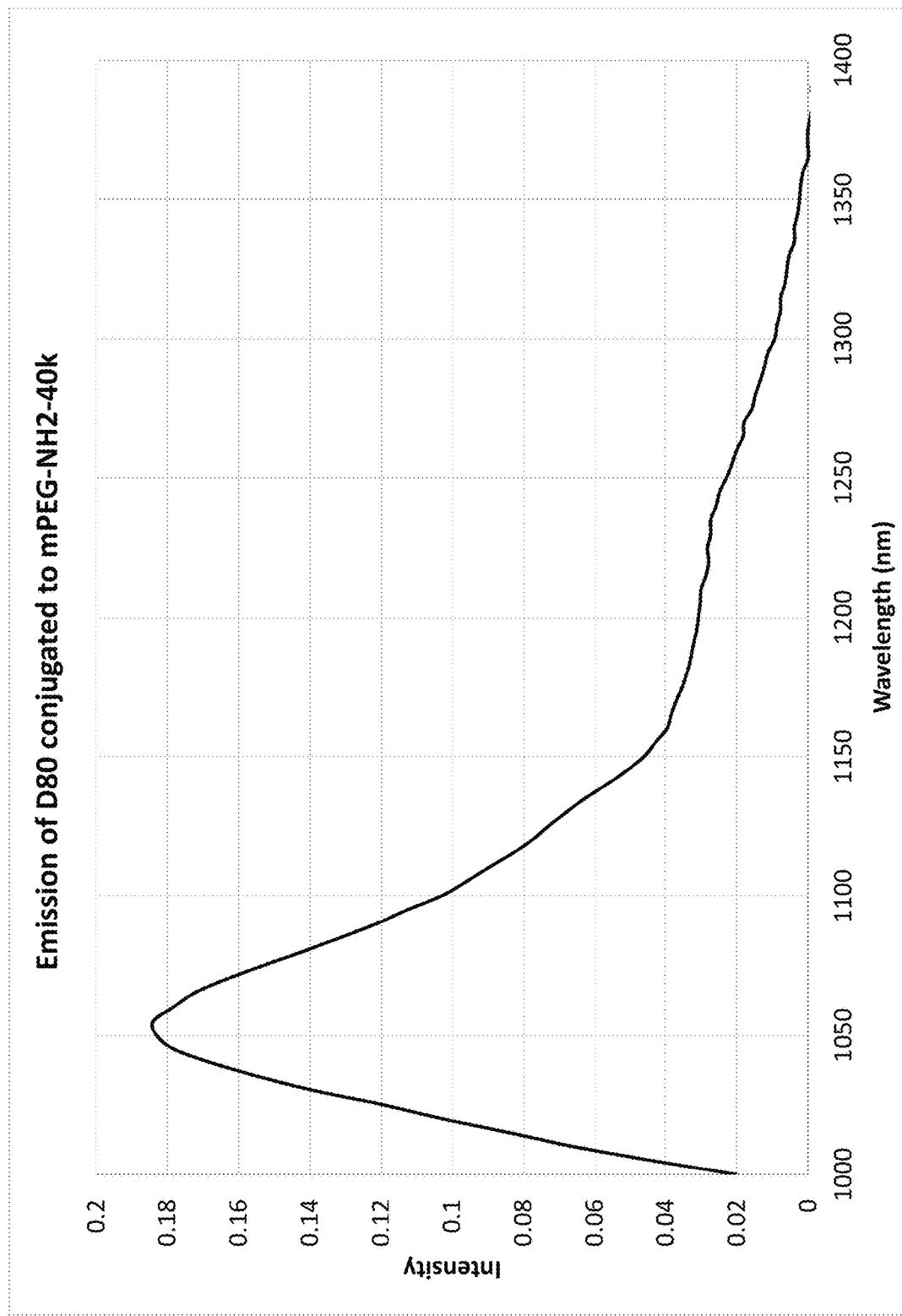
FIG. 8 illustrates a fluorescence spectrum of compound D80 conjugated to polyethylene glycol.

The absorbance of purified conjugate of D80 with methoxypolyethylene glycol amine, 40 kDa, was measured in 1×PBS solution on a Cary 50 UV/vis absorbance spectrophotometer from 250 nm to 1100 nm. Results are illustrated in FIG. 7. The emission of the conjugate was measured in 1×PBS solution on a Quantamaster 8075-21 fluorescence spectrophotometer equipped with a liquid nitrogen cooled cooled DSS-IGA020L/CUS InGaAs NIR detector with excitation at 980 nm and emission recorded from 1000 nm to 1400 nm. Results are illustrated in FIG. 8.

Example 36: Conjugation of Succinimidyl Ester D80 to an Antibody (Mouse Anti-Human IgG)

Mouse anti-human IgG was obtained from Jackson ImmunoResearch in 0.01 M phosphate, 0.25 M NaCl, pH

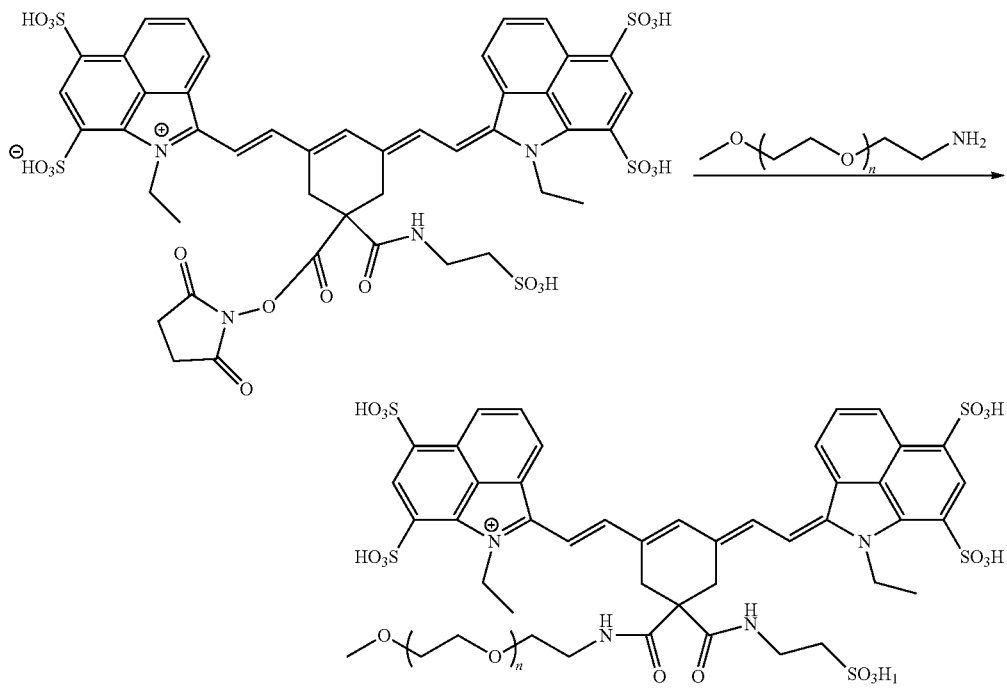

Figure 9:
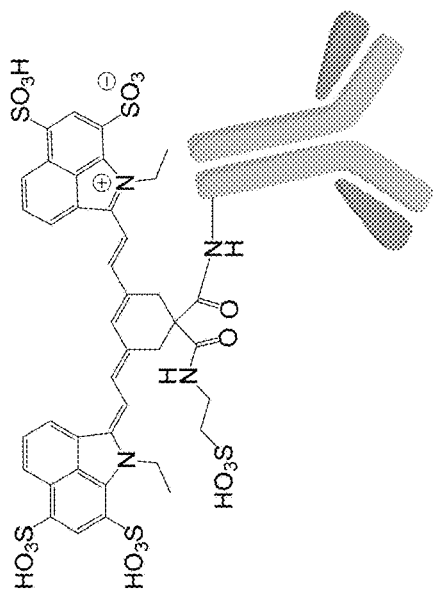
FIG. 9 is a schematic illustration of compound D80 conjugated to an antibody.
Figure 9:
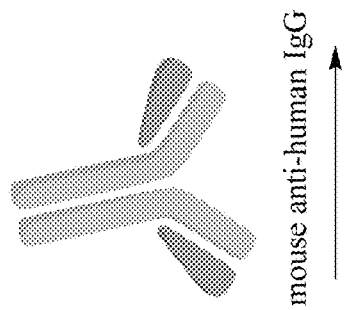
Figure 9:
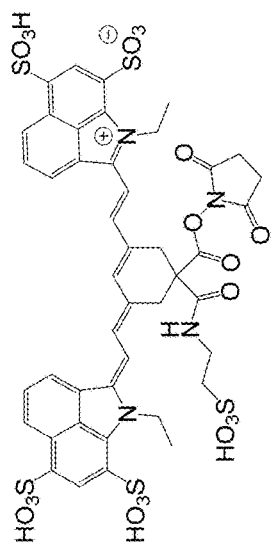

Methoxypolyethylene glycol amine, 40 kDa molecular weight (mPEG-NH$_2$-40 k), was obtained from JenKemUSA (P/N M-NH2-40 k) and dissolved in 1×PBS to a concentration of 5 mg/mL. 60 µL of the mPEG-NH2-40 k solution was placed in a vial with 30 µL of 1×PBS. N-hydroxysuccinimidyl ester D80 was dissolved in DMF to a final concentration of 10 mM and the 2.5 µL was added to the mPEG-NH2-40 k solution followed by 10 µL of 0.1 M sodium bicarbonate, pH 8.3. The mixture was allowed to react at 23° C. for 2 hours with rotation. The labeled mPEG-NH$_2$-40 k was purified from unconjugated dye and buffer components on 0.5 mL Zeba columns with 7 kDa MWCO (Thermo Fisher) according to the manufacturer's protocol after equilibrating the columns with four 300 µL portions of 1×PBS. After loading the crude samples on the Zeba columns, centrifu- 7.6 at 1.7 mg/mL. 100 µL of the mouse anti-human IgG solution was placed in each of 4 vials. The conjugation of D80 to an exemplary antibody is schematically illustrated in FIG. 9. Briefly, N-hydroxysuccinimidyl ester D80 was dissolved in DMF to a final concentration of 10 mM and the solution was added to the each of the four vials (1 µL, 2 µL, 4 µL and 8 µL, respectively). The solutions were allowed to react at 23° C. for 2 hours with rotation. The labeled antibodies were purified from unconjugated dye and buffer components on 0.5 mL Zeba columns with 40 kDa MWCO (Thermo Fisher) according to the manufactures protocol after equilibrating the columns with four 300 µL portions of 1×PBS. After loading the crude samples on the Zeba columns, centrifugation at 1500×g for 120 seconds eluted the labeled antibody while the unconjugated dye was retained on the column. Dye loading (dyes per antibody) were calculated from absorbance at 280 nm (antibody and dye) and 1030 nm (dye) by subtracting 55% of the absorbance of the dye at 1030 nm from the total absorbance of the sample at 280 nm (to remove the contribution of the dye to the absorbance at 280 nm) and taking the ratio of the absorbance at 1030 nm to the corrected absorbance at 280 nm. It was assumed that the extinction coefficients of the antibody at 280 nm and the dye at 1030 nm are approximately equivalent, or about 200,000 $M^{-1}cm^{-1}$. Dye loadings calculated in this manner for each of the four samples were found to be 0.4, 0.6, 0.8 and 1.0, dyes per antibody, respectively.

Example 37: Optical Properties of D80 Conjugated to Mouse Anti-Human IgG

Purified mouse anti-human IgG conjugated to D2 from example 36 in 1×PBS solution was placed in a 2 mm path length cuvette (Eppendorf UVette) and the absorbance measured on a Cary 50 UV/vis absorbance spectrophotometer from 250 nm to 1100 nm. Dye loading (dyes per antibody) were calculated from absorbance at 280 nm (antibody and dye) and 1030 nm (dye) by subtracting 55% of the absorbance of the dye at 1030 nm from the total absorbance of the sample at 280 nm (to remove the contribution of the dye to the absorbance at 280 nm) and taking the ratio of the absorbance at 1030 nm to the corrected absorbance at 280 nm. It was assumed that the extinction coefficients of the antibody at 280 nm and the dye at 1030 nm are approximately equivalent, or about 200,000 $M^{-1}cm^{-1}$. Dye loadings calculated in this manner for each of the four samples were found to be 0.4, 0.6, 0.8 and 1.0, D2 dyes per antibody, respectively.

Figure 10:
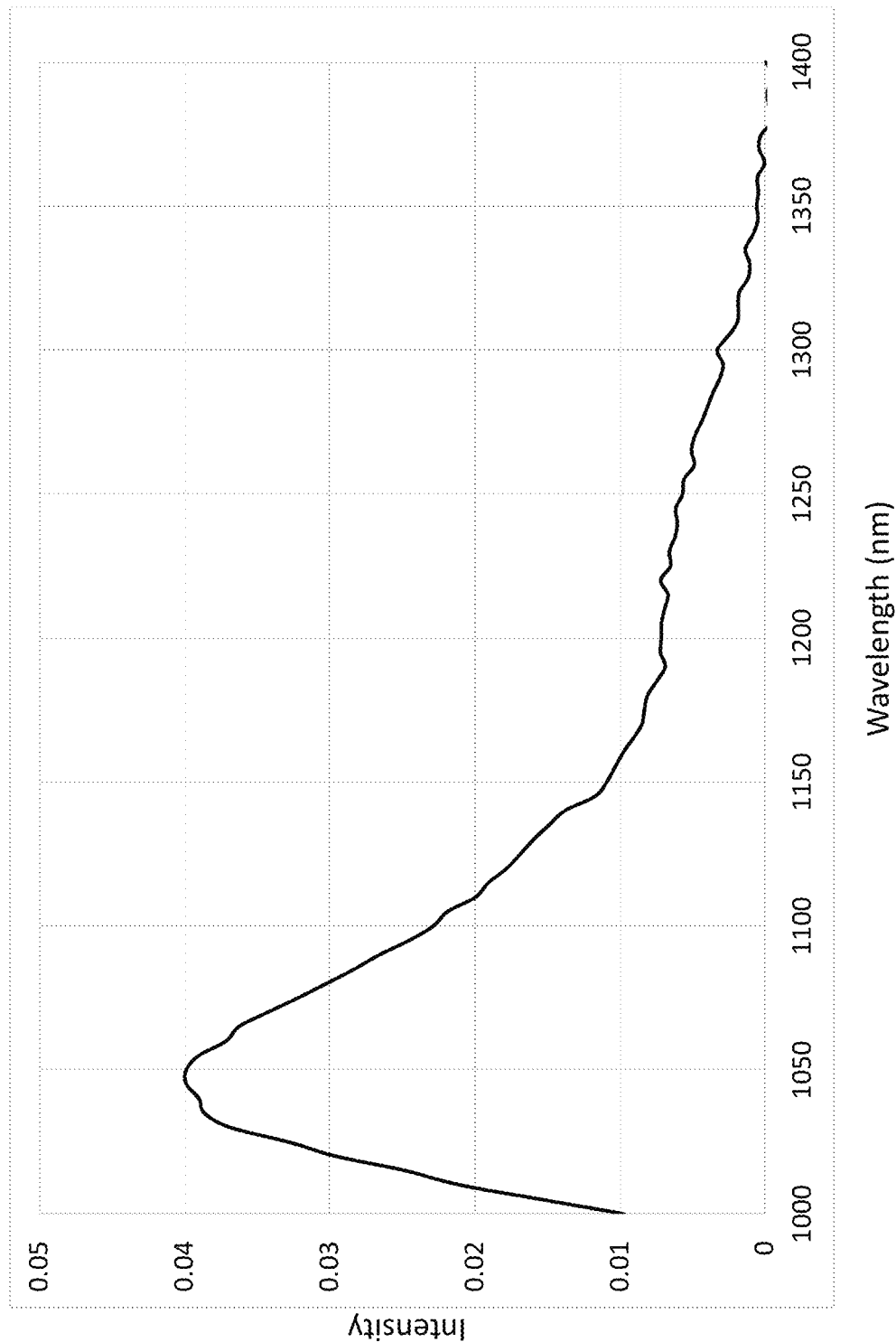
FIG. 10 illustrates a fluorescence spectrum of exemplary compound D80 conjugated to an antibody.

Emission spectra of the D80 conjugated mouse anti-human IgG antibody solutions in 1×PBS were recorded on a Quantamaster 8075-21 fluorescence spectrophotometer equipped with a liquid nitrogen cooled DSS-IGA020L/CUS InGaAs NIR detector with excitation at 980 nm. The representative emission spectrum of the labeled antibody (2 µL dye solution) is illustrated in FIG. 10.

Example 38: Conjugation of Succinimidyl Ester D80 to an Antibody (Atezolizumab)

Atezolizumab was obtained from Selleck Chemicals in 1×PBS at a concentration of 5 mg/mL. 60 µL of the Atezolizumab antibody solution (0.3 mg, 2.1 nmol) placed in each of 3 vials, along with 30 µL of 1×PBS. N-hydroxysuccinimidyl ester D80 was dissolved in DMF to a final concentration of 10 mM and the solution was added to the each of the three vials (1.25 µL, 2.5 µL and 5 µL, respectively). A solution of 0.1 M sodium bicarbonate, pH 8.3 (10 µL) was then added to each of the vials to raise the pH and the solutions were rotated at 23° C. for 2 hours. The labeled antibodies were purified from unconjugated dye and buffer components on 0.5 mL Zeba columns with 40 kDa MWCO (Thermo Fisher) according to the manufacturer's protocol after equilibrating the columns with four 300 µL portions of 1×PBS. After loading the crude samples on the Zeba columns, centrifugation at 1500×g for 120 seconds eluted the labeled antibody while the unconjugated dye was retained on the column. The eluted sample was obtained in 1×PBS solution and filtered through a 0.2 micron centrifugal filter.

Example 39: Optical Properties of D80 Conjugated to an Atezolizumab

Figure 11:
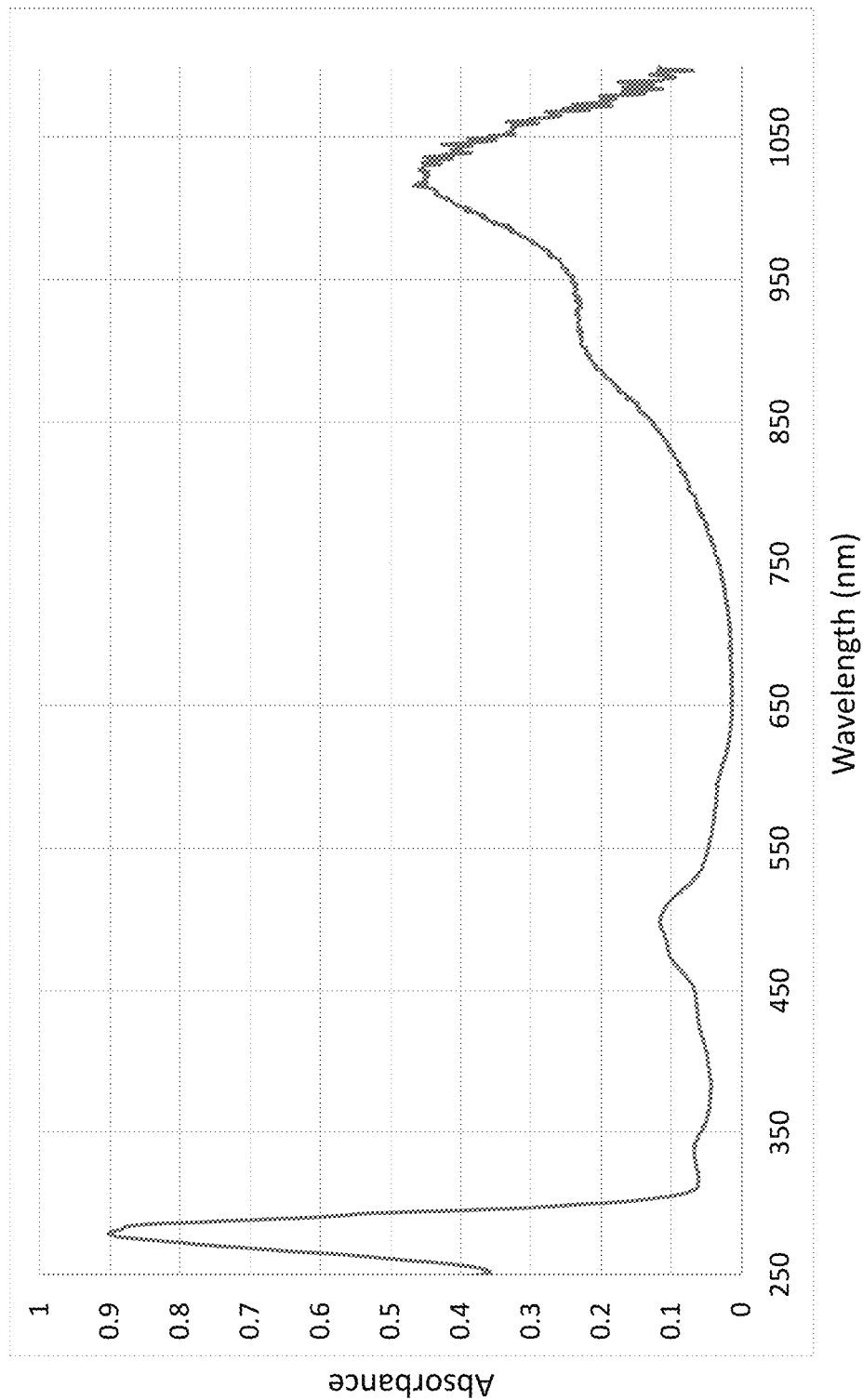
FIG. 11 illustrates an absorbance spectrum of exemplary compound D80 conjugated atezolizumab.

Purified Atezolizumab conjugated to D80 from example 38 in 1×PBS solution was placed in a 2 mm path length cuvette (Eppendorf UVette) and the absorbance measured on a Cary 50 UV/vis absorbance spectrophotometer from 250 nm to 1100 nm. Dye loading (dyes per antibody) were calculated from absorbance at 280 nm (antibody and dye) and 1030 nm (dye) by subtracting 55% of the absorbance of the dye at 1030 nm from the total absorbance of the sample at 280 nm (to remove the contribution of the dye to the absorbance at 280 nm) and taking the ratio of the absorbance at 1030 nm to the corrected absorbance at 280 nm. It was assumed that the extinction coefficients of the antibody at 280 nm and the dye at 1030 nm are approximately equivalent, or about 200,000 $M^{-1}cm^{-1}$. Dye loading calculated in this manner for a representative sample was found to be approximately 0.7 dyes per antibody. The resulting spectrum is illustrated in FIG. 11.

Figure 12:
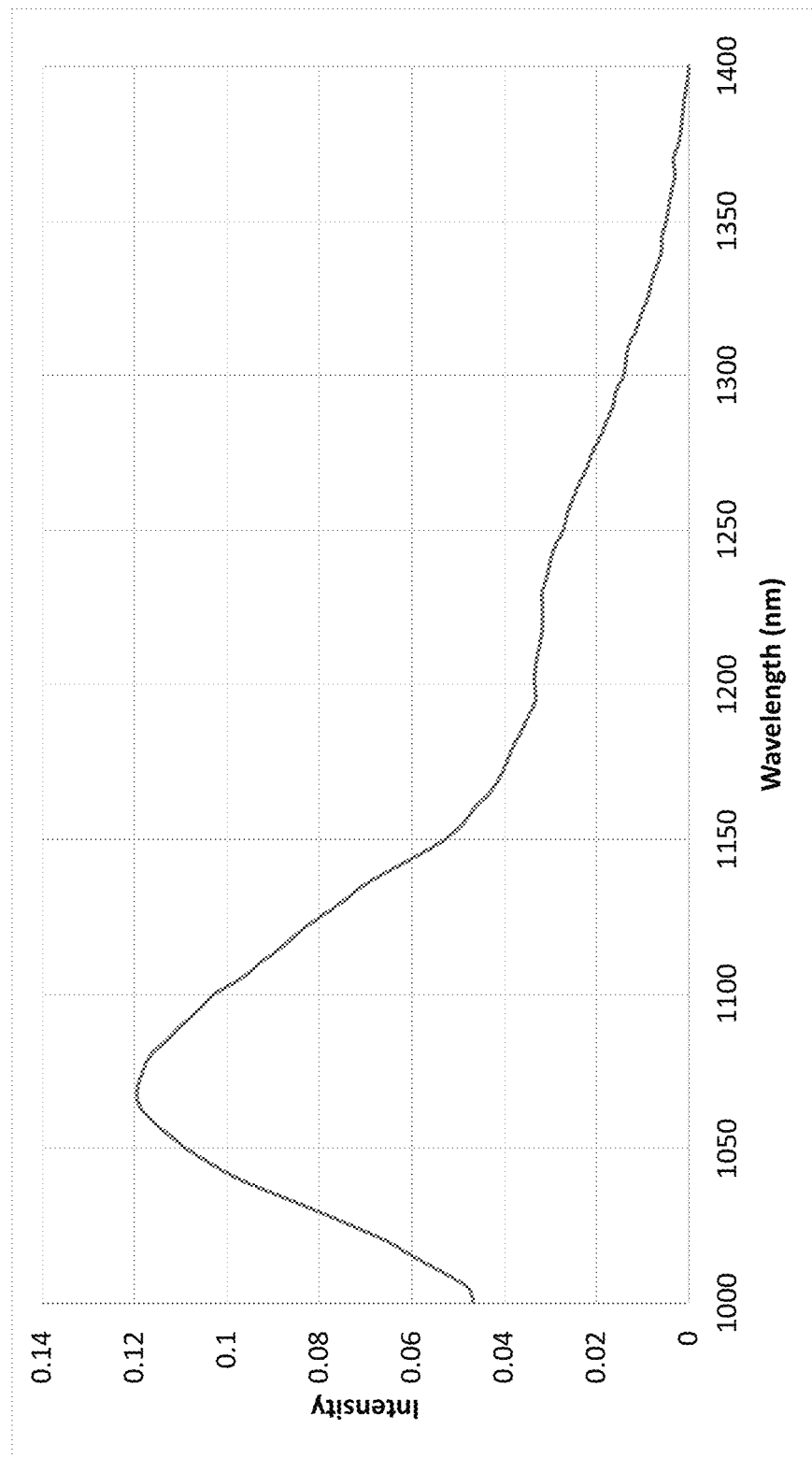
FIG. 12 illustrates a fluorescence spectrum of exemplary compound D80 conjugated atezolizumab.

The emission spectrum of the D80 conjugated atezolizumab solution was recorded in 1×PBS solution on a Quantamaster 8075-21 fluorescence spectrophotometer equipped with a liquid nitrogen cooled cooled DSS-IGA020L/CUS InGaAs NIR detector with excitation at 980 nm. The representative emission spectrum of the labeled antibody is illustrated in FIG. 12.

Example 40: Imaging of D2 in a Mouse

Mice were injected retro-orbitally with 2 nmol of D2 in 1×PBS. The mice were subsequently sacrificed to stop blood circulation and imaged in the heart region using an InGaAs short-wave infrared camera with 976 nm laser excitation and a 980 nm long pass filter. Fluorescent signal from D2 was observed in the heart and carotid arteries.

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified. Methods of nucleotide amplification, cell transfection, and protein expression and purification are similarly within the level of skill in the art.

Patents, publications, and applications mentioned in the specification are indicative of the levels of those skilled in the art to which the invention pertains. These patents, publications, and applications are incorporated herein by reference to the same extent as if each individual patent, publication, or application was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A compound represented by the following structural formula:

(Formula I)

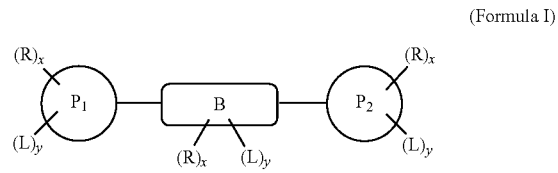

or a salt thereof, wherein:

$P_1$ and $P_2$ are, independently, a substituted or unsubstituted acridine or acridinium moiety, a substituted or unsubstituted pyrylium or thiopyrylium moiety, or a benz[c,d]indole;

B is a substituted or unsubstituted polymethine, substituted or unsubstituted cyclic alkene or cyclic polyalkene, substituted or unsubstituted polycyclic alkene or polycyclic polyalkene, substituted or unsubstituted aryl or heteroaryl, substituted or unsubstituted alkenylaryl, thiadiazole, benzothiadiazole, or bisbenzothiadiazole;

L is absent or is a linker moiety, optionally bearing a functional group or reactive group selected from the group consisting of a carboxylate, carboxyalkyl, maleimide, succinimidyl ester, succinimidyl ester, carboxamide, propargyl, azidoalkyl, alkyne, isothiocyanate, of —$NH_2$ —OH, —SH, —$SO_3H$, carboxyl, —COCl, —$CONHNH_2$, acetoxymethyl esters, substituted and unsubstituted N-hydroxysuccinimidyl esters, substituted and unsubstituted N-hydroxysulfosuccinimido esters, nitro- or fluoro or phenol esters, azide, —$COCH_2I$, phosphoramidite, phthalamido, acyl fluoride, acyl chloride, acyl azide, tyramide, cinnamamide, hydroxycinnamamide, aldehyde, ketone, phosphoramidite, isocyanate, isothiocyanate, sulfonyl chloride, maleimide, and biotin;

R is, independently for each occurrence, hydrogen, substituted or unsubstituted $C_1$ to $C_{24}$ alkyl, substituted or unsubstituted alkylaryl, substituted or unsubstituted aryl, substituted or unsubstituted heteroaryl, substituted or unsubstituted alkenyl, substituted or unsubstituted alkynyl, sulfonate, aryl sulfonate, $C_1$ to $C_{24}$ alkyl sulfonate, taurine, carboxylate, amine, alkylamine, arylamine, alkylammonium, arylammonium, sulfonamide, halogen, hydroxy, amide, nitro, cyano, azide, O-alkyl, S-alkyl, silyl, trialkylsilyl, O-silyl, haloalkyl, alkylsulfhydryl, trifluoromethyl, hydrazide, substituted or unsubstituted aryl, heteroaryl, or heterocyclic alkynyl, carboxyalkyl, aminoalkyl, haloalkyl, azidoalkyl, amide, amino acid, peptide, or L, with the proviso that in at least one instance R in said compound comprises a sulfonate, aryl sulfonate, or $C_1$ to $C_{24}$ alkyl sulfonate;

wherein said compound comprises at least four sulfonates, alkyl sulfonates, arylsulfonates, taurines or a combination thereof, is water soluble, and absorbs and/or emits light between 950 nm and 1350 nm.

2. A compound represented by the following structural formula:

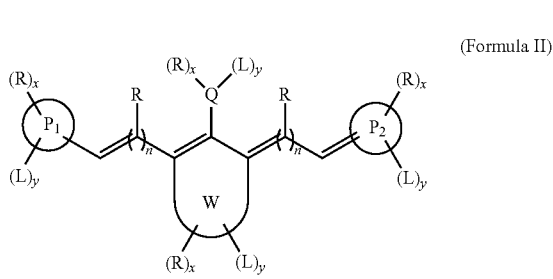

(Formula II)

or a salt thereof, wherein:

$P_1$ and $P_2$ are a benz[c,d]indole moiety;

Q is a hydrogen, $C_1$-$C_{24}$ alkyl, aryl, heteroaryl, polyaryl, phenyl, thienyl, furanyl, pyridyl, pyridinium, halogen, substituted or unsubstituted S-alkyl, substituted or unsubstituted S-aryl, substituted or unsubstituted O-alkyl, substituted or unsubstituted O-aryl, substituted or unsubstituted N-alkyl, substituted or unsubstituted N-aryl, cyano, trifluoromethyl, azidoaryl, boronic acid, boronic ester, hydroxyl, alkoxy, aryloxy, alkylthio, arylthio, nitrogen, silicon, boron, carboxy, cyano, ester, amine, amide, amino acid, peptide or L, W is absent or a substituted or unsubstituted cyclic or polycyclic group containing aliphatic or aromatic carbon, nitrogen, oxygen, sulfur, or silicon forming a 4 to 9 membered ring;

L is absent or is a linker moiety, optionally bearing a functional group or reactive group, such as selected from the group consisting of a carboxylate, carboxyalkyl, maleimide, succinimidyl ester, carboxamide, propargyl, azidoalkyl, alkyne, isothiocyanate, of —$NH_2$ —OH, —SH, —$SO_3H$, carboxyl, —COCl, —$CONHNH_2$, acetoxymethyl esters, substituted and unsubstituted N-hydroxysuccinimidyl esters, substituted and unsubstituted N-hydroxysulfosuccinimido esters, nitro- or fluoro or phenol esters, azide, —$COCH_2I$, phosphoramidite, phthalamido, acyl fluoride, acyl chloride, acyl azide, tyramide, cinnamamide, hydroxycinnamamide, aldehyde, ketone, phosphoramidite, isocyanate, isothiocyanate, sulfonyl chloride, maleimide and biotin;

R is, independently for each occurrence, hydrogen, substituted or unsubstituted $C_1$ to $C_{24}$ alkyl, substituted or unsubstituted alkylaryl, substituted or unsubstituted aryl, substituted or unsubstituted heteroaryl, substituted or unsubstituted alkenyl, substituted or unsubstituted alkynyl, sulfonate, aryl sulfonate, $C_1$ to $C_{24}$ alkyl sulfonate, taurine, carboxylate, amine, alkylamine, arylamine, alkylammonium, arylammonium, sulfonamide, halogen, hydroxy, amide, nitro, cyano, azide, O-alkyl, S-alkyl, silyl, trialkylsilyl, O-silyl, haloalkyl, alkylsulfhydryl, trifluoromethyl, hydrazide, substituted or unsubstituted aryl, heteroaryl, or heterocyclic alkynyl, carboxyalkyl, aminoalkyl, haloalkyl, azidoalkyl, amide, amino acid, peptide or L, with the proviso that in at least one instance R in said compound comprises a sulfonate, aryl sulfonate, or $C_1$ to $C_{24}$ alkyl sulfonate;

x and y are, independently for each occurrence, integers from 0 to 15; and wherein said compound comprises at least four sulfonates, alkyl sulfonates, arylsulfonates, taurines or a combination thereof, is water soluble, and absorbs and/or emits light between 950 nm and 1350 nm.

3. The compound of claim 1, wherein the molecule absorbs and/or emits light between 1000 nm and 1250 nm.

4. The compound of claim 1, wherein the optical absorbance and fluorescent emission properties are substantially similar in organic solvents, aqueous environments, and biological environments.

5. The compound of claim 1, comprising a molecule selected from the group consisting of
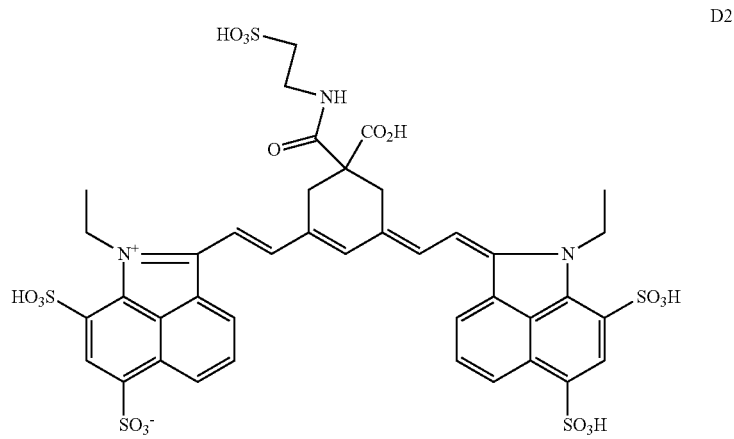
D2
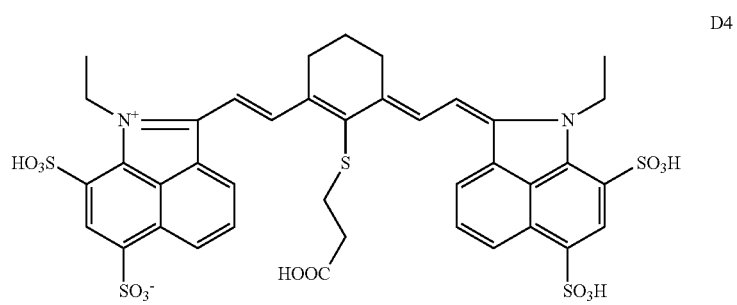
D4
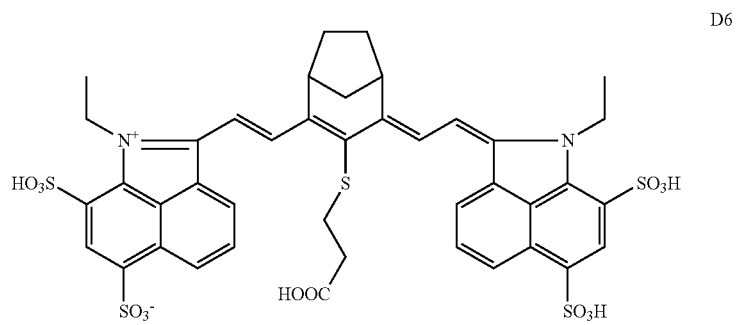
D6
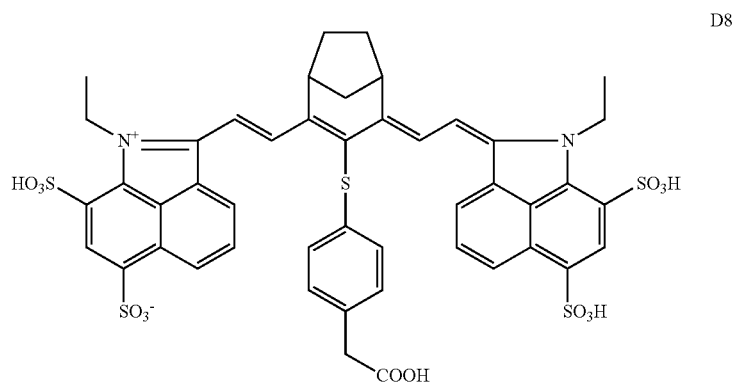
D8

-continued
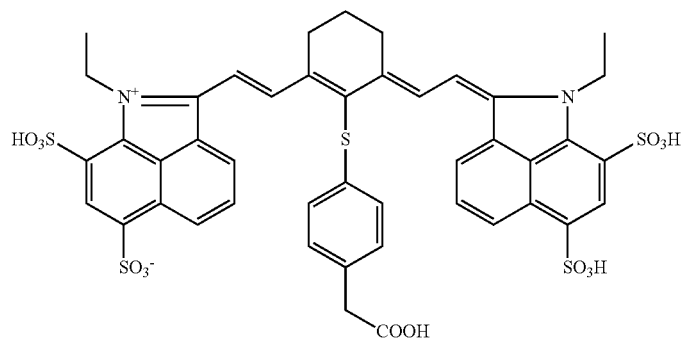
D10
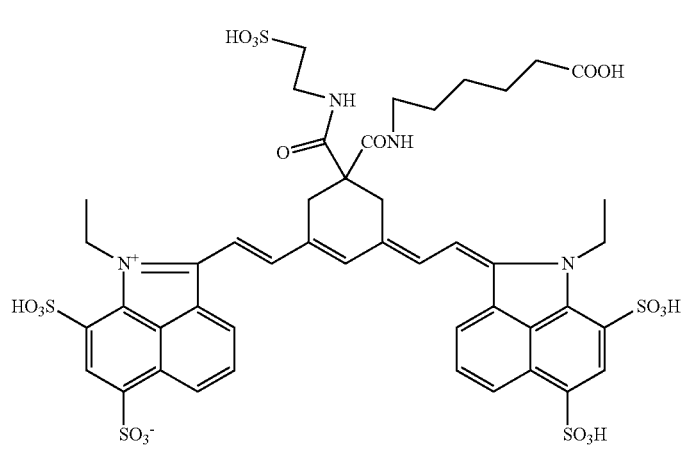
D12
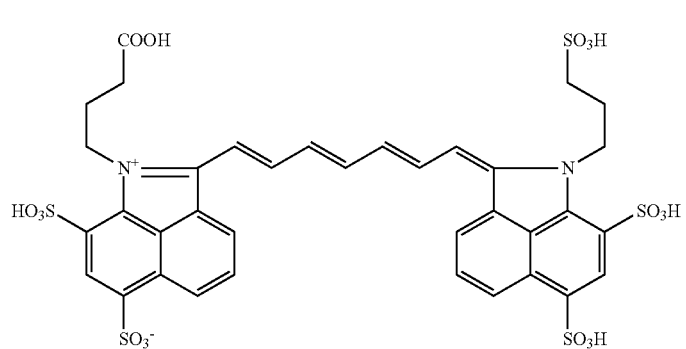
D14
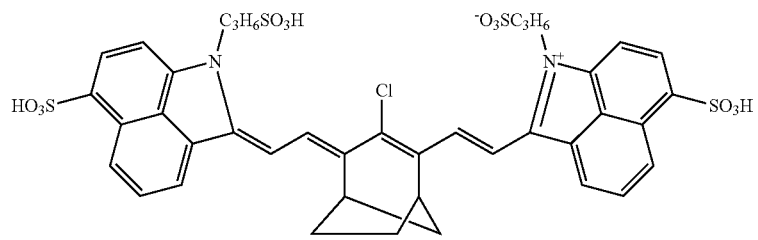
D15
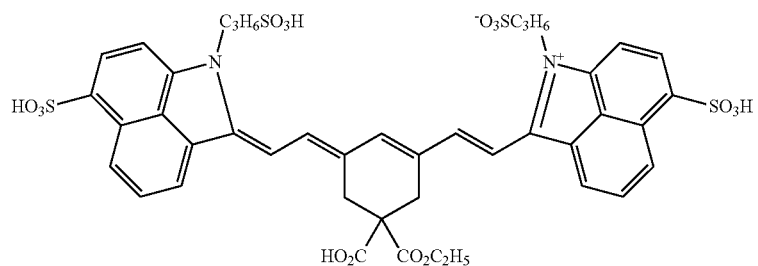
D16

-continued
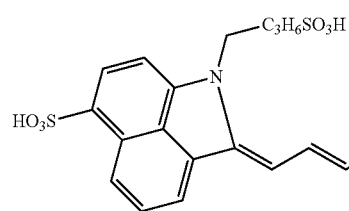
D18
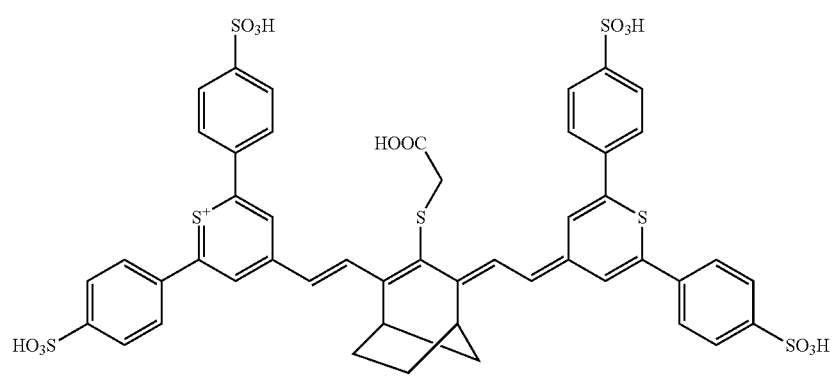
D21
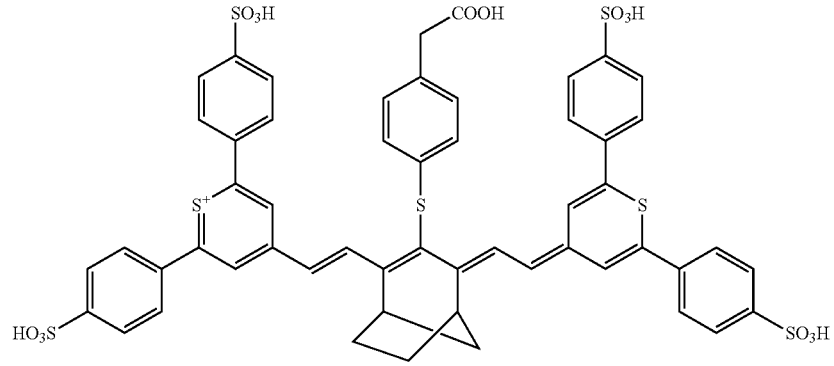
D22
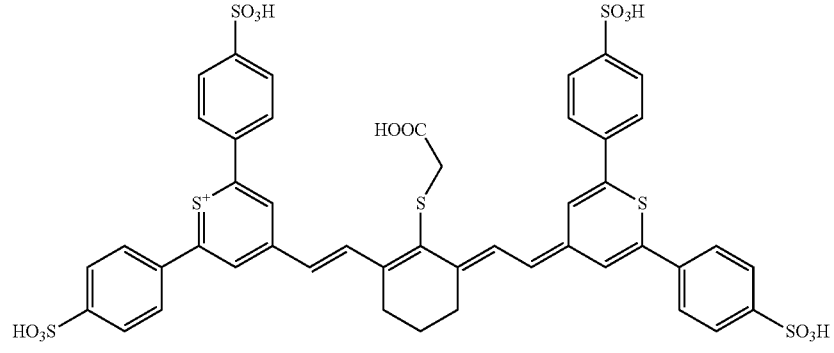
D23
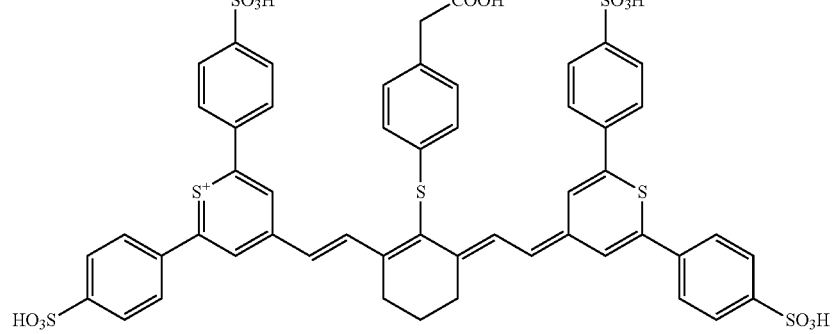
D24

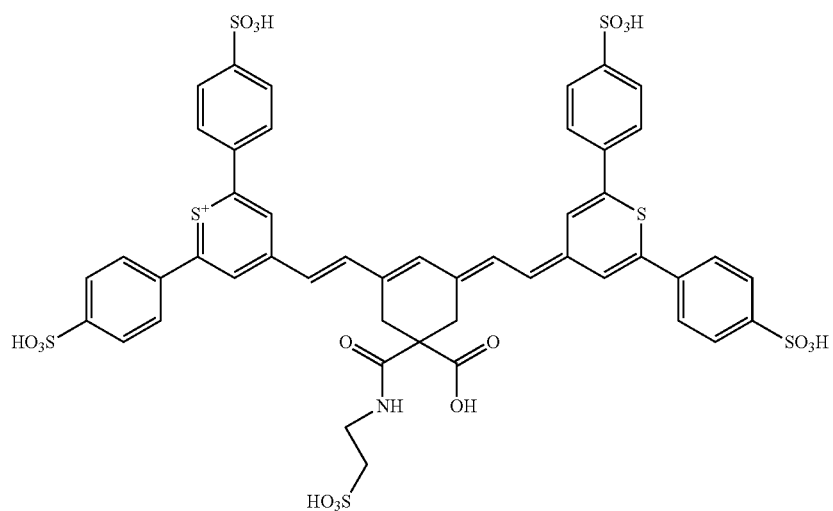
D25
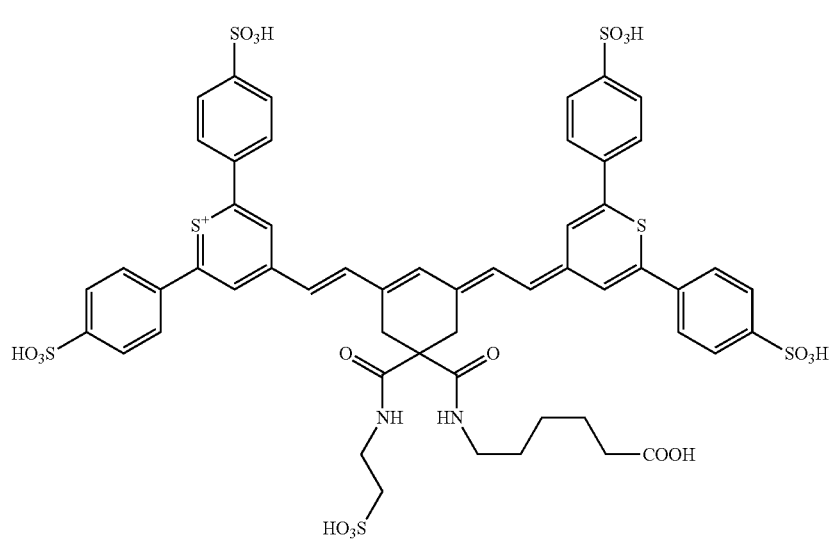
D26
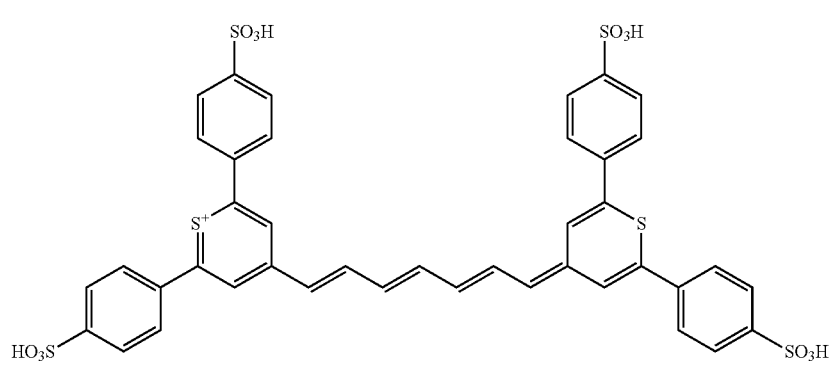
D27

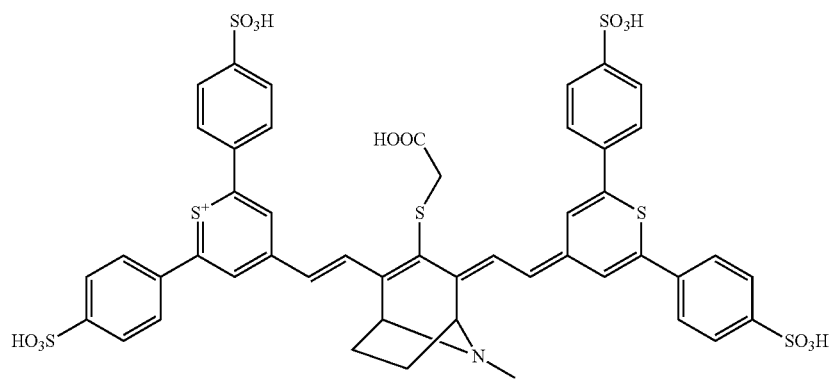
D28
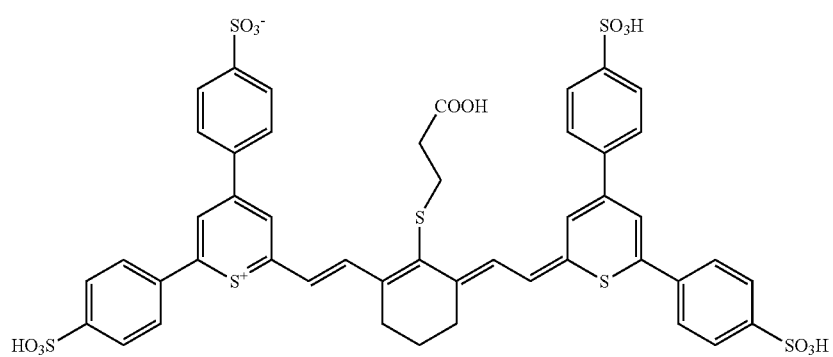
D29
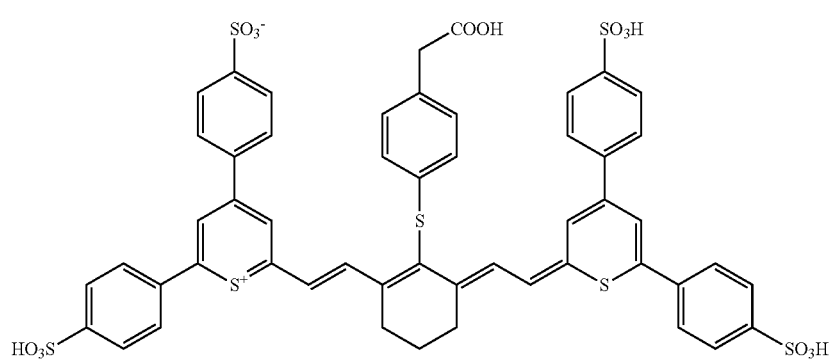
D30
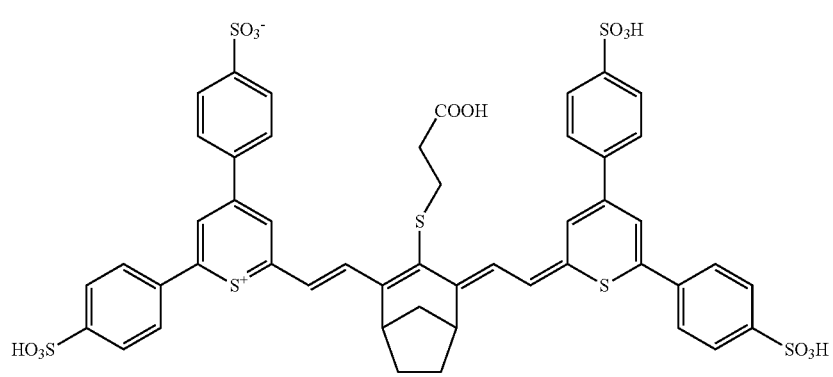
D31

-continued
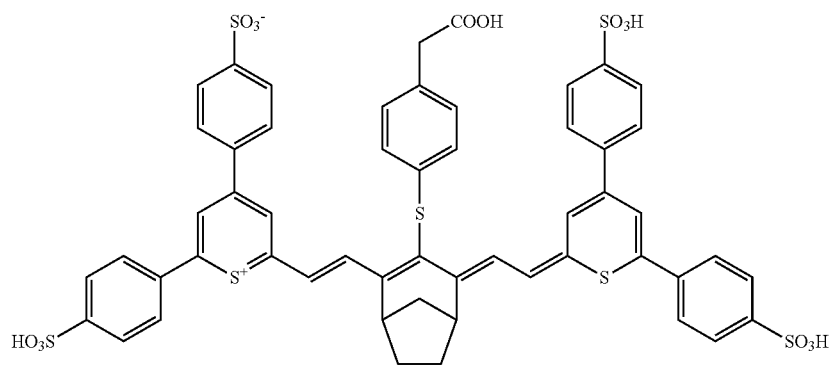
D32
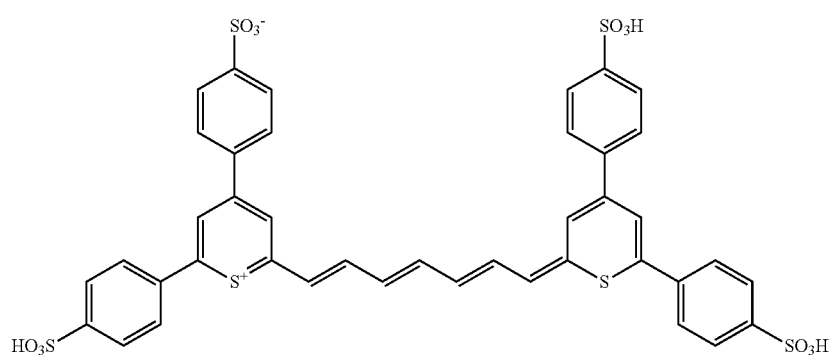
D33
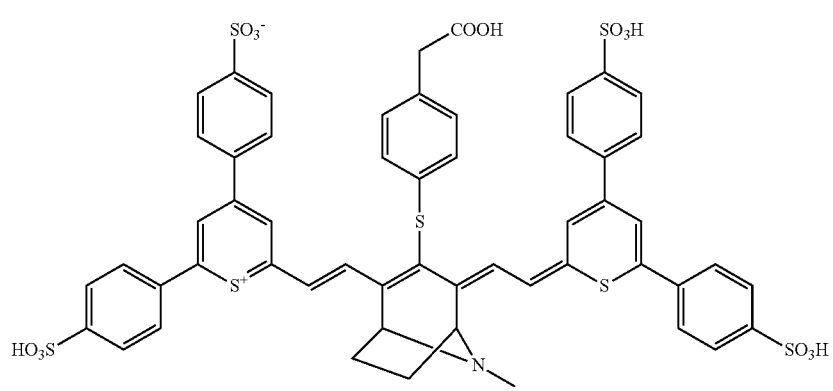
D34
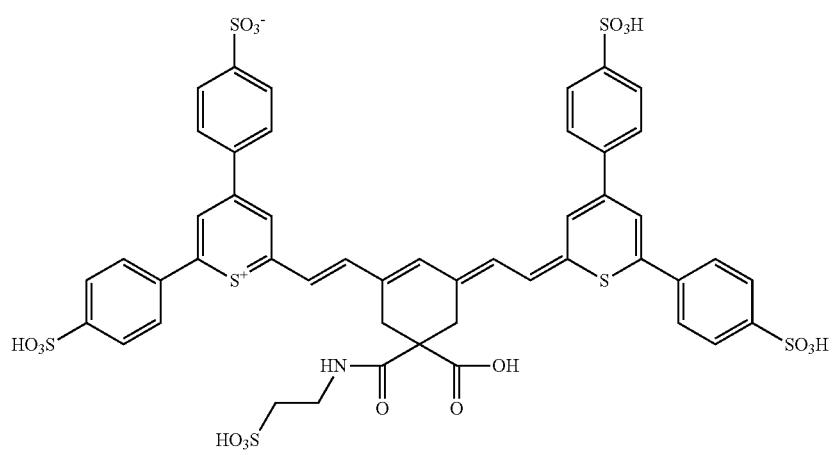
D35

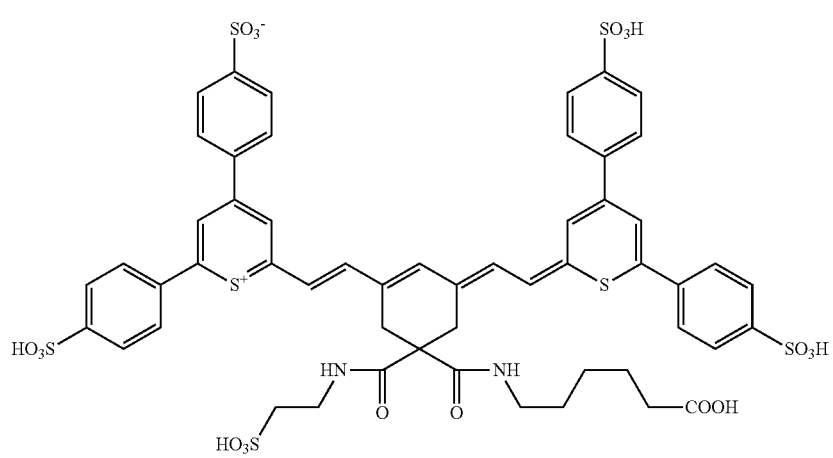
D36
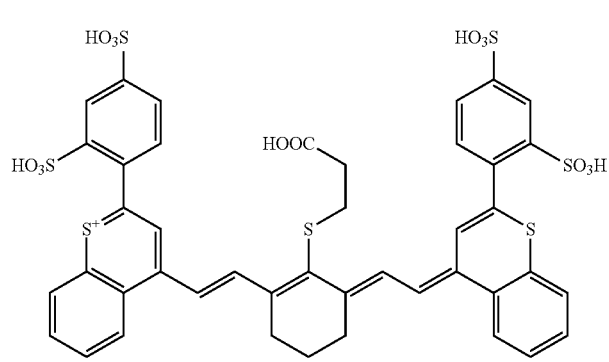
D38
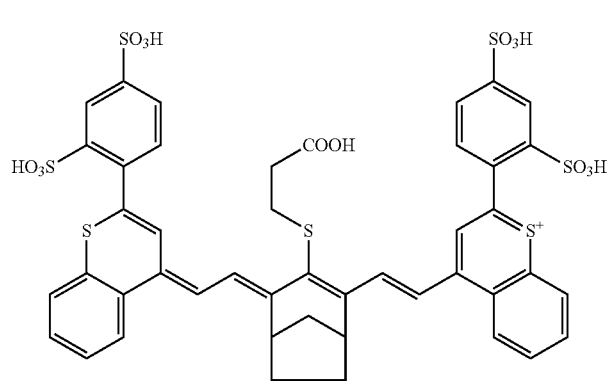
D40
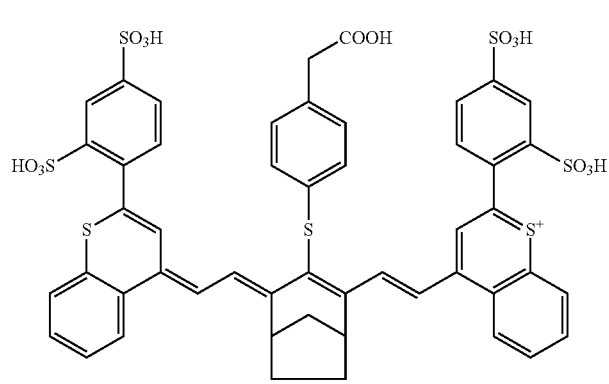
D42

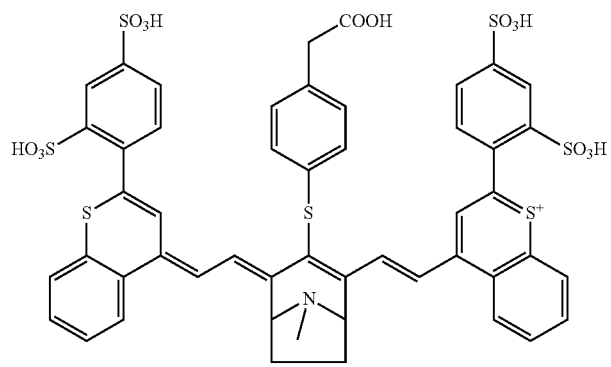
D44
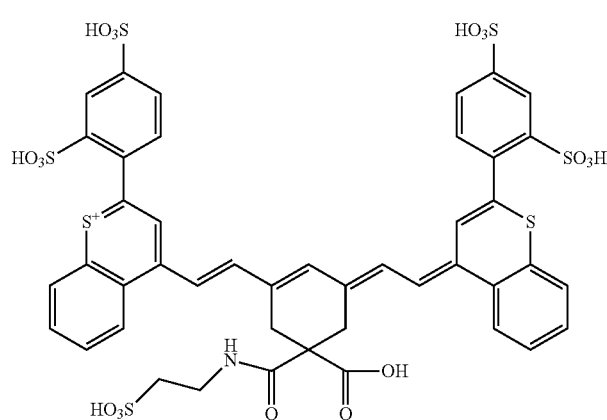
D46
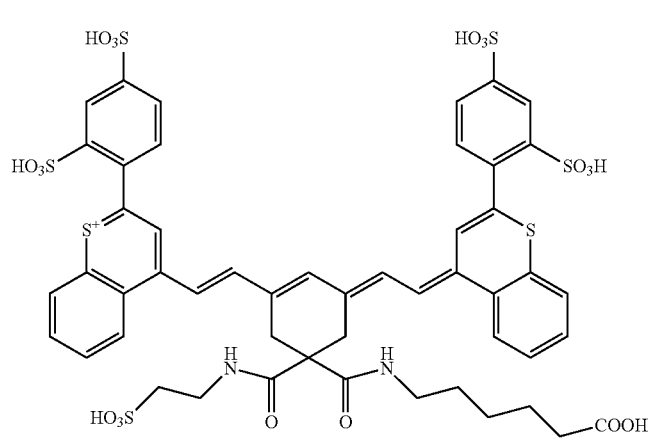
D48
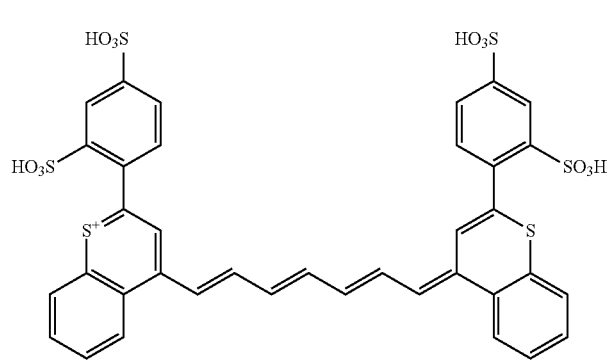
D50

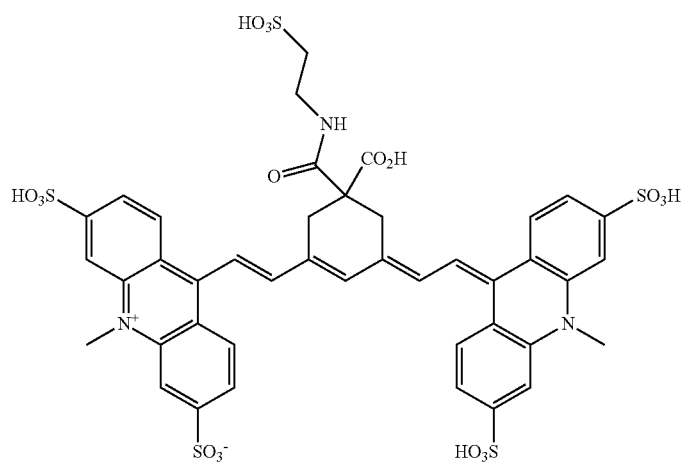
D51
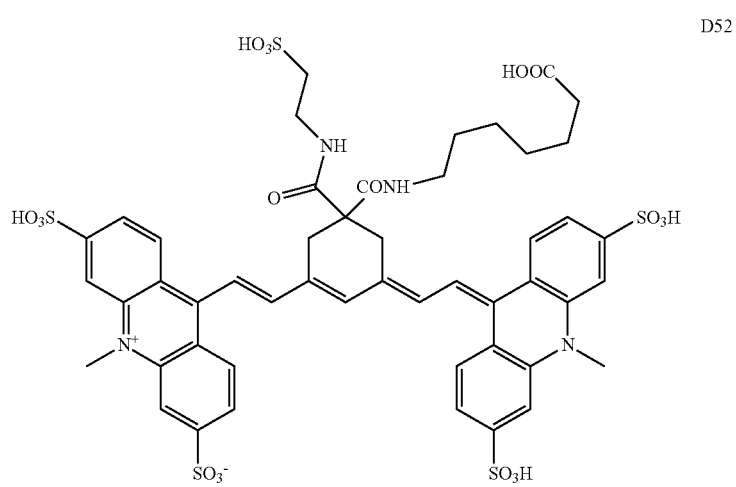
D52
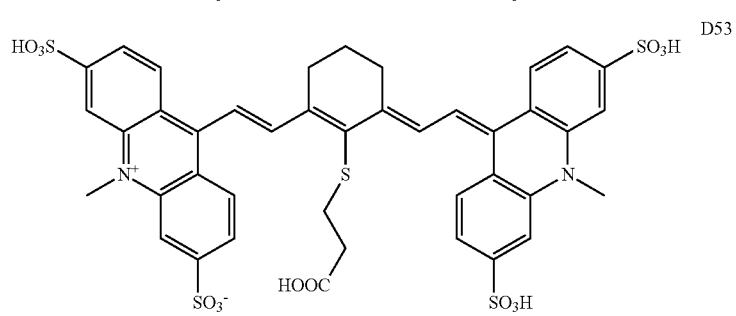
D53
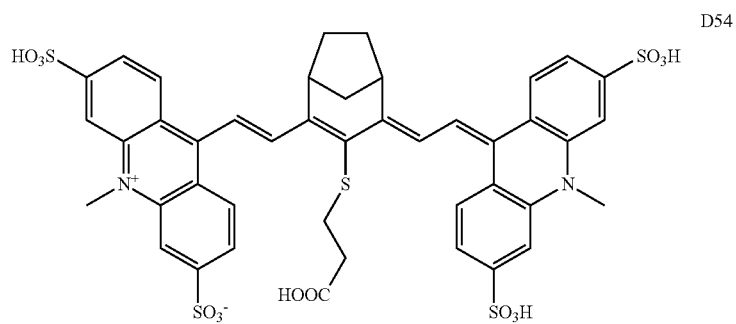
D54

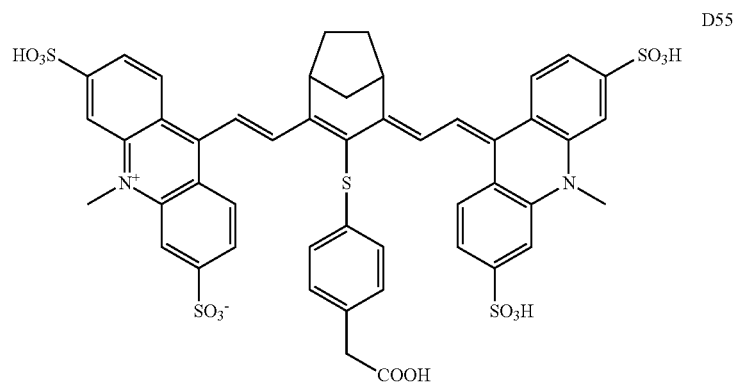
D55
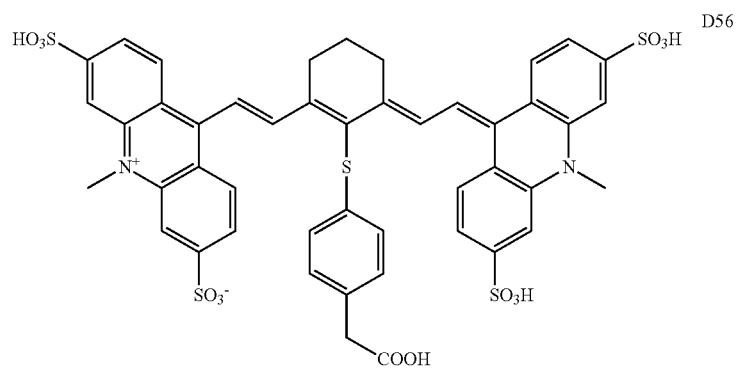
D56
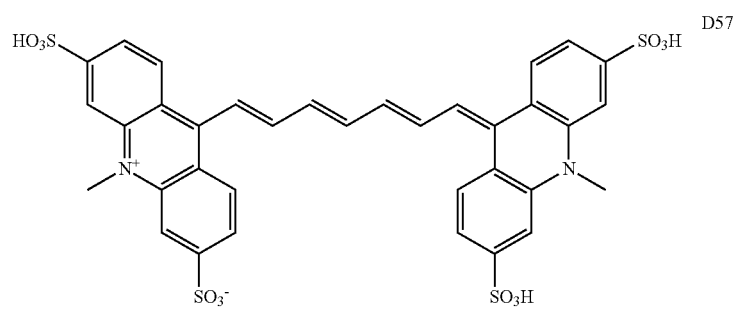
D57
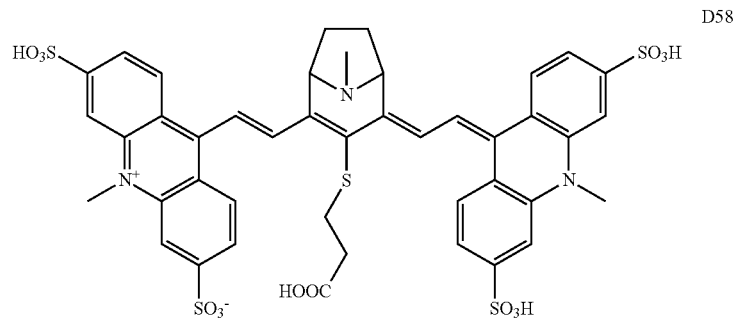
D58

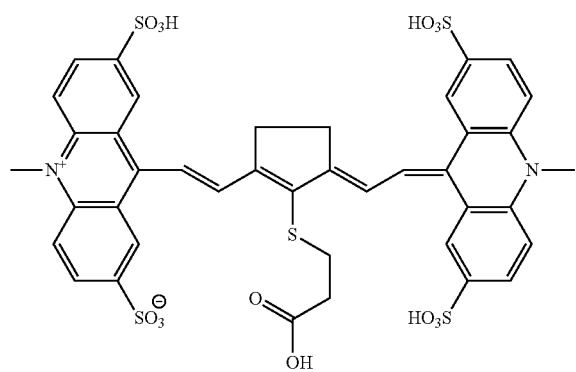
D59
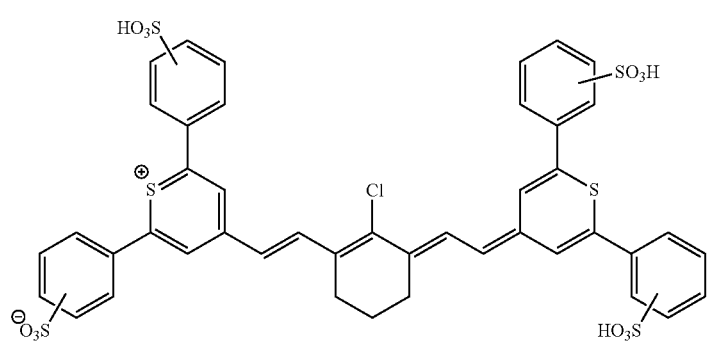
D60
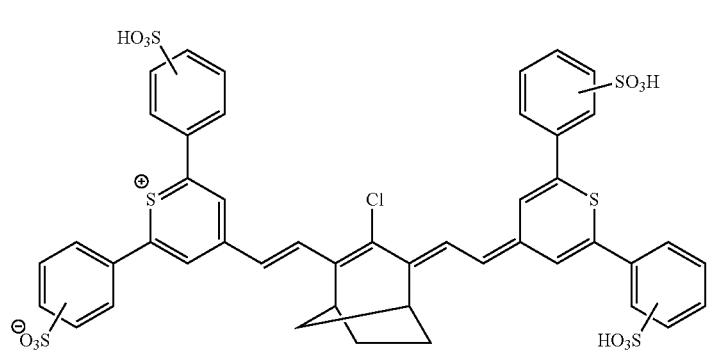
D61
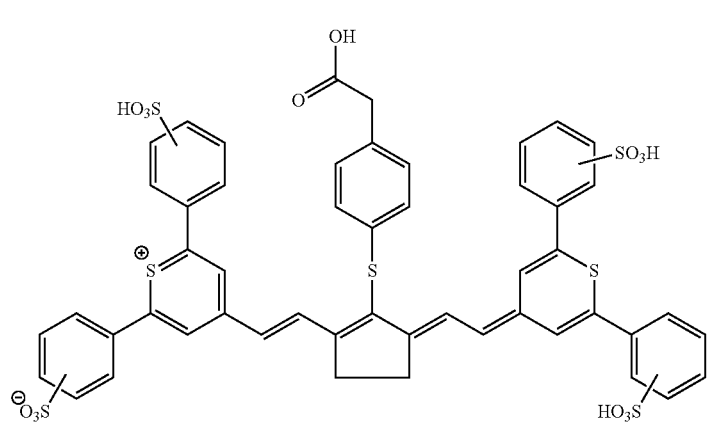
D62

-continued
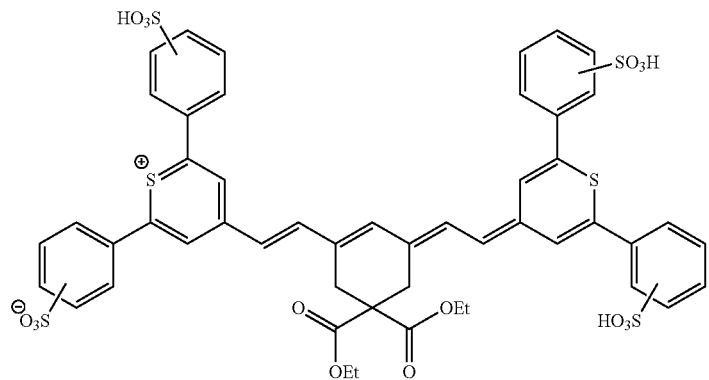
D63
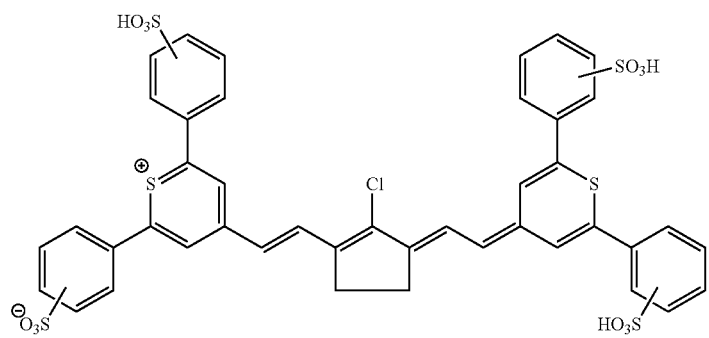
D64
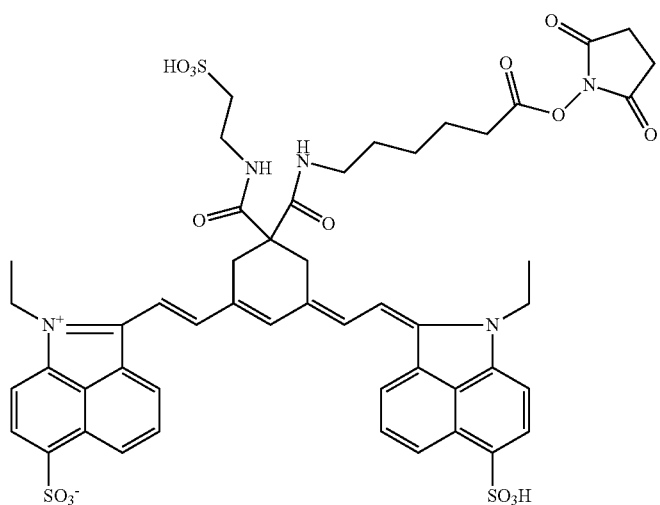
D66
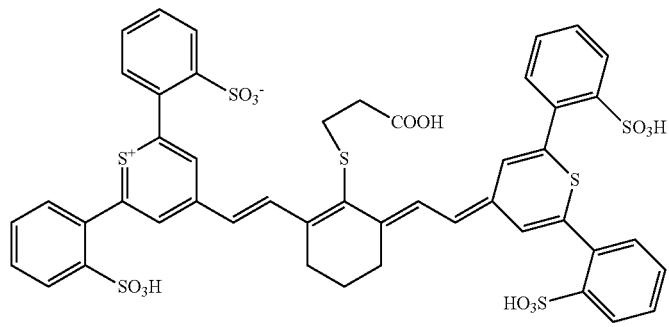
D69

-continued
D70
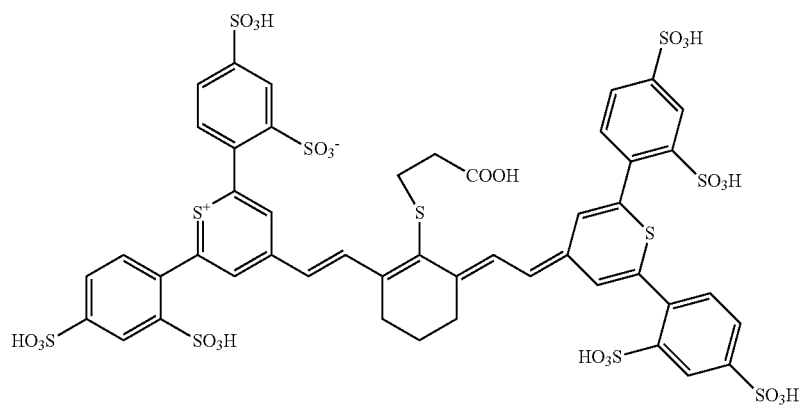
D75
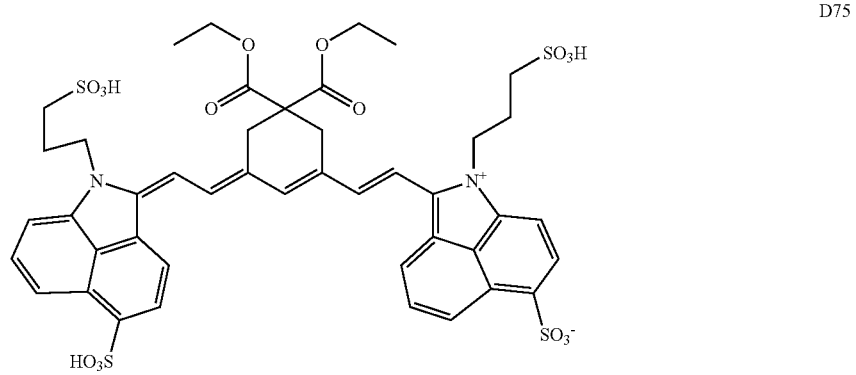
D77
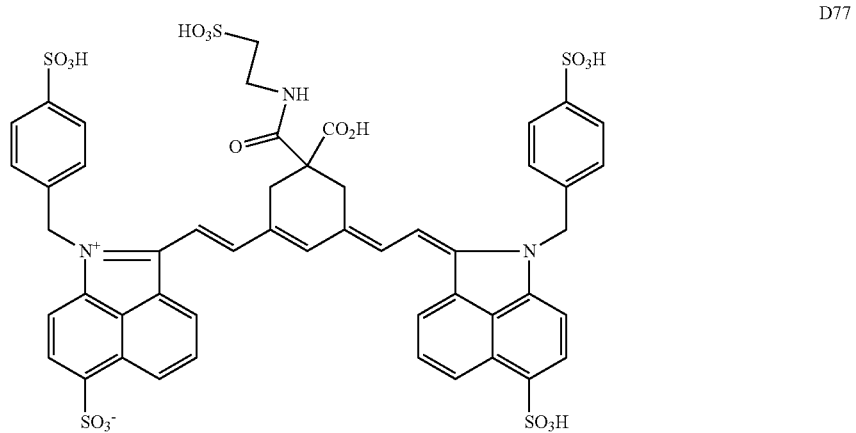
D76
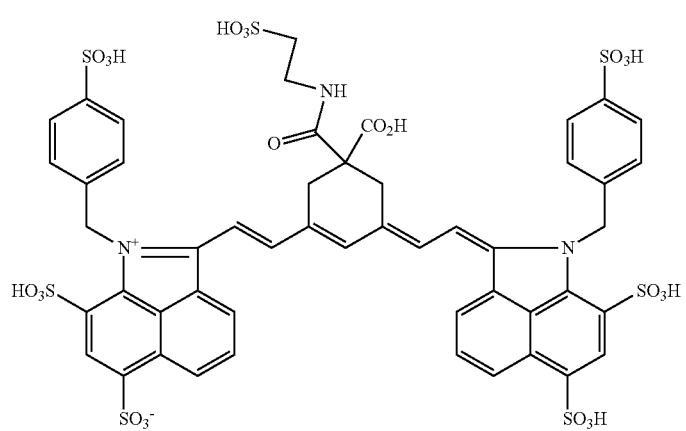

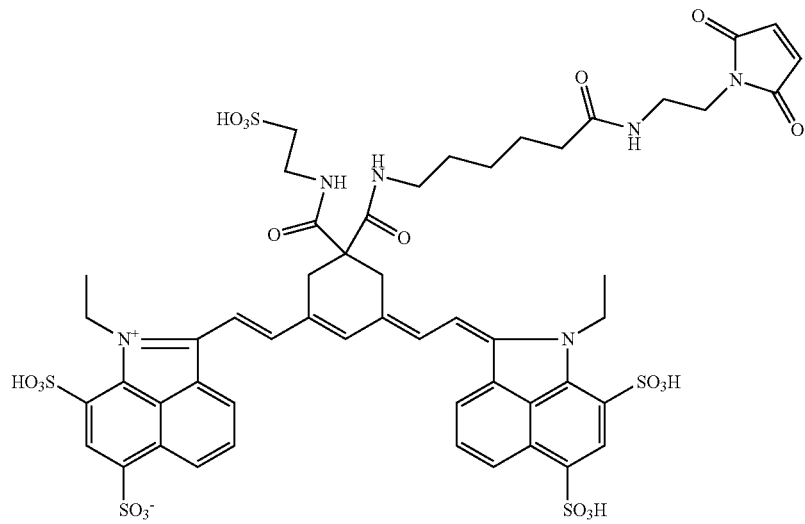

D79

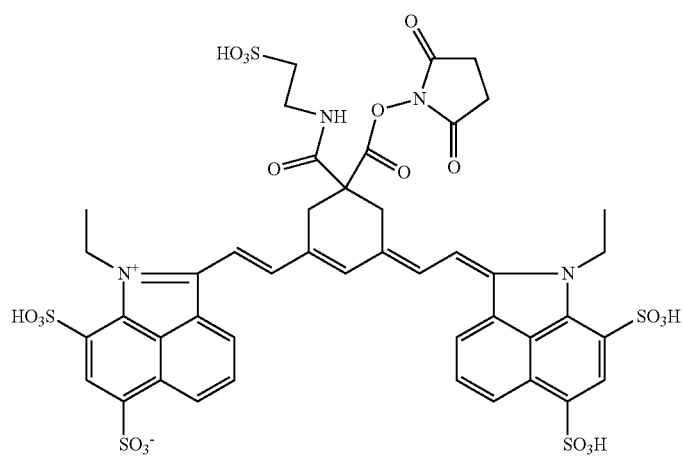

D80 and pharmaceutically acceptable salts thereof.

6. The compound of claim 1, wherein $P_1$ and $P_2$ are a polysulfonated benz[c,d]indole.

7. The compound of claim 1, wherein $P_1$ and $P_2$ are a polysulfonated thiopyrylium.

8. The compound of claim 1, wherein $P_1$ and $P_2$ are a polysulfonated acridinium.

9. The compound of claim 1, wherein the linking group, L, is bound, covalently or non-covalently, to biological material comprising a drug, peptide, protein, antibody, nucleic acid, carbohydrate, lipid, biomolecule, nanoparticle, membrane, cell or tissue.

10. A compound of Formula III or Formula IV where:

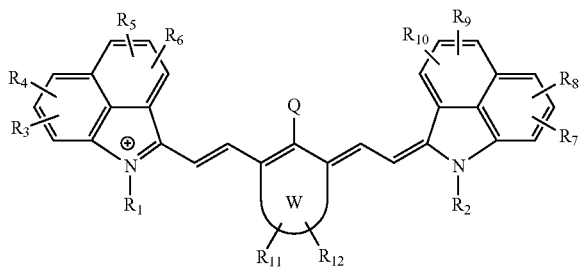

III

-continued

IV

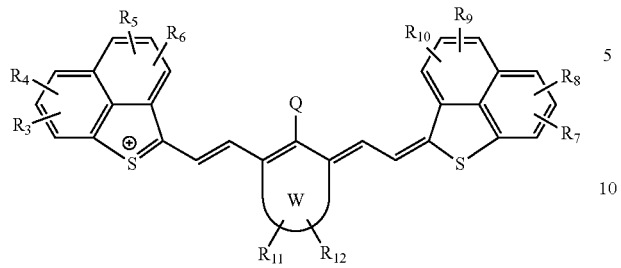

or a salt thereof, wherein:

Q is a hydrogen, $C_1$-$C_{24}$ alkyl, aryl, heteroaryl, polyaryl, phenyl, thienyl, furanyl, pyridyl, pyridinium, halogen, substituted or unsubstituted S-alkyl, substituted or unsubstituted S-aryl, substituted or unsubstituted O-alkyl, substituted or unsubstituted O-aryl, substituted or unsubstituted N-alkyl, substituted or unsubstituted N-aryl, cyano, trifluoromethyl, azidoaryl, boronic acid, boronic ester, hydroxyl, alkoxy, aryloxy, alkylthio, arylthio, nitrogen, silicon, boron, carboxy, cyano, ester, amine, amide, amino acid, peptide or L;

W is absent or a substituted or unsubstituted cyclic or polycyclic group containing aliphatic or aromatic carbon, nitrogen, oxygen, sulfur, or silicon forming a 4 to 9 membered ring;

$R_1$-$R_{12}$ are, independently for each occurrence, hydrogen, substituted or unsubstituted $C_1$ to $C_{24}$ alkyl, substituted or unsubstituted alkylaryl, substituted or unsubstituted aryl, substituted or unsubstituted heteroaryl, substituted or unsubstituted alkenyl, substituted or unsubstituted alkynyl, sulfonate, aryl sulfonate, $C_1$ to $C_{24}$ alkyl sulfonate, taurine, carboxylate, amine, alkylamine, arylamine, alkylammonium, arylammonium, sulfonamide, halogen, hydroxy, amide, nitro, cyano, azide, O-alkyl, S-alkyl, silyl, trialkylsilyl, O-silyl, haloalkyl, alkylsulfhydryl, trifluoromethyl, hydrazide, substituted or unsubstituted aryl, heteroaryl, or heterocyclic alkynyl, carboxyalkyl, aminoalkyl, haloalkyl, azidoalkyl, amide, amino acid, peptide or L, with the proviso that in at least one instance R in said compound comprises a sulfonate, aryl sulfonate, or $C_1$ to $C_{24}$ alkyl sulfonate;

L is absent or is a linker moiety, optionally bearing a functional group or reactive group, such as selected from the group consisting of a carboxylate, carboxyalkyl, maleimide, succinimidyl ester, carboxamide, propargyl, azidoalkyl, alkyne, isothiocyanate, of —NH$_2$ —OH, —SH, —SO$_3$H, carboxyl, —COCl, —CONHNH$_2$, acetoxymethyl esters, substituted and unsubstituted N-hydroxysuccinimidyl esters, substituted and unsubstituted N-hydroxysulfosuccinimido esters, nitro- or fluoro or phenol esters, azide, —COCH$_2$I, phosphoramidite, phthalamido, acyl fluoride, acyl chloride, acyl azide, tyramide, cinnamamide, hydroxycinnamamide, aldehyde, ketone, phosphoramidite, isocyanate, isothiocyanate, sulfonyl chloride, maleimide and biotin; and wherein said compound comprises at least four sulfonates, alkyl sulfonates, arylsulfonates, taurines or a combination thereof, is water soluble, and absorbs and/or emits light between 950 nm and 1350 nm.

11. The compound of claim 1 wherein $P_1$ and $P_2$ are:

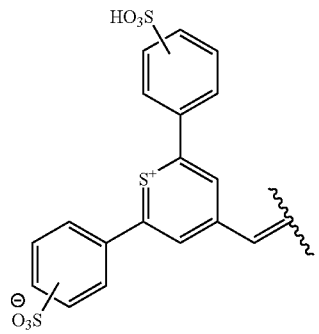

or a salt thereof.

12. The compound of claim 1, wherein $P_1$ and $P_2$ are:

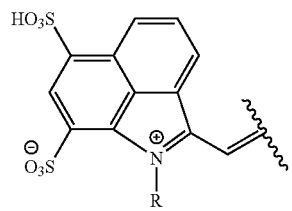

or a salt thereof, wherein:

R is substituted or unsubstituted $C_1$ to $C_{24}$ alkyl, substituted or unsubstituted alkylaryl, substituted or unsubstituted aryl, substituted or unsubstituted heteroaryl, substituted or unsubstituted alkenyl, substituted or unsubstituted alkynyl, aryl sulfonate, $C_1$ to $C_{24}$ alkyl sulfonate, $C_1$-$C_{24}$ alkyl carboxylate, aryl carboxylate, $C_1$-$C_{24}$ alkylamine, arylamine, $C_1$-$C_{24}$ alkylammonium, arylammonium, or substituted or unsubstituted polyethylene glycol.

13. The compound of claim 1 wherein $P_1$ and $P_2$ are:

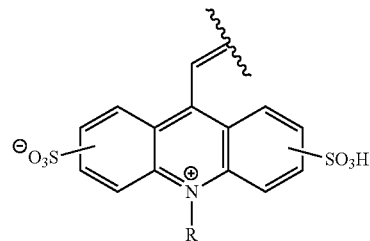

or a salt thereof, wherein:

R is substituted or unsubstituted $C_1$ to $C_{24}$ alkyl, substituted or unsubstituted alkylaryl, substituted or unsubstituted aryl, substituted or unsubstituted heteroaryl, substituted or unsubstituted alkenyl, substituted or unsubstituted alkynyl, aryl sulfonate, $C_1$ to $C_{24}$ alkyl sulfonate, $C_1$-$C_{24}$ alkyl carboxylate, aryl carboxylate, $C_1$-$C_{24}$ alkylamine, arylamine, $C_1$-$C_{24}$ alkylammonium, arylammonium, or substituted or unsubstituted polyethylene glycol.

14. A compound of any of the following formulae:

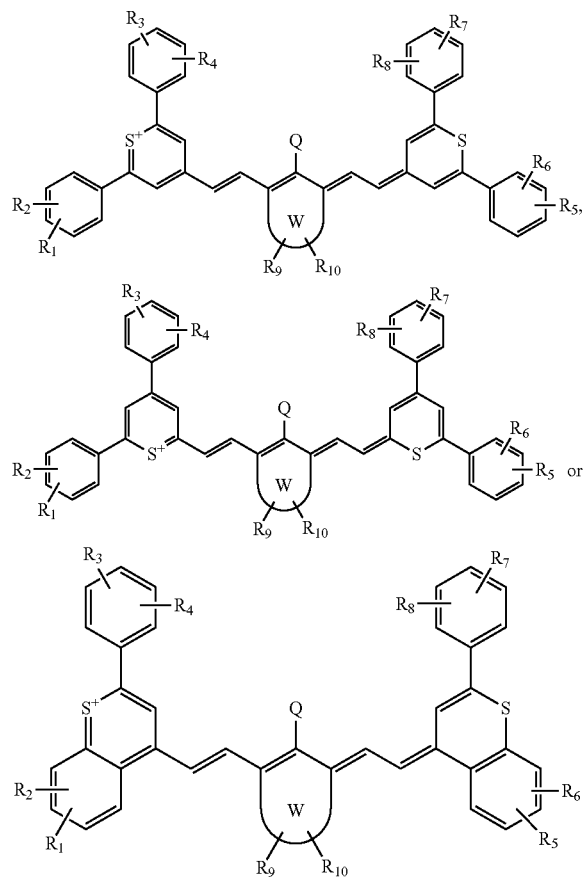

or a salt thereof, wherein:

Q is a hydrogen, $C_1$-$C_{24}$ alkyl, aryl, heteroaryl, polyaryl, phenyl, thienyl, furanyl, pyridyl, pyridinium, halogen, substituted or unsubstituted S-alkyl, substituted or unsubstituted S-aryl, substituted or unsubstituted O-alkyl, substituted or unsubstituted O-aryl, substituted or unsubstituted N-alkyl, substituted or unsubstituted N-aryl, cyano, trifluoromethyl, azidoaryl, boronic acid, boronic ester, hydroxyl, alkoxy, aryloxy, alkylthio, arylthio, nitrogen, silicon, boron, carboxy, cyano, ester, amine, amide, amino acid, peptide or L, W is absent or a substituted or unsubstituted cyclic or polycyclic group containing aliphatic or aromatic carbon, nitrogen, oxygen, sulfur, or silicon forming a 4 to 9 membered ring;

$R_1$-$R_{10}$ are, independently for each occurrence, hydrogen, substituted or unsubstituted $C_1$ to $C_{24}$ alkyl, substituted or unsubstituted alkylaryl, substituted or unsubstituted aryl, substituted or unsubstituted heteroaryl, substituted or unsubstituted alkenyl, substituted or unsubstituted alkynyl, sulfonate, aryl sulfonate, $C_1$ to $C_{24}$ alkyl sulfonate, taurine, carboxylate, amine, alkylamine, arylamine, alkylammonium, arylammonium, sulfonamide, halogen, hydroxy, amide, nitro, cyano, azide, O-alkyl, S-alkyl, silyl, trialkylsilyl, O-silyl, haloalkyl, alkylsulfhydryl, trifluoromethyl, hydrazide, substituted or unsubstituted aryl, heteroaryl, or heterocyclic alkynyl, carboxyalkyl, aminoalkyl, haloalkyl, azidoalkyl, amide, amino acid, peptide or L, wherein at least four of $R_1$-$R_8$ are sulfonates, alkyl sulfonates, arylsulfonates or taurine;

L is absent or is a linker moiety, optionally bearing a functional group or reactive group selected from the group consisting of a carboxylate, carboxyalkyl, maleimide, succinimidyl ester, carboxamide, propargyl, azidoalkyl, alkyne, isothiocyanate, of —NH$_2$ —OH, —SH, —SO$_3$H, carboxyl, —COCl, —CONHNH$_2$, acetoxymethyl esters, substituted and unsubstituted N-hydroxysuccinimidyl esters, substituted and unsubstituted N-hydroxysulfosuccinimido esters, nitro- or fluoro or phenol esters, azide, —COCH$_2$I, phosphoramidite, phthalamido, acyl fluoride, acyl chloride, acyl azide, tyramide, cinnamamide, hydroxycinnamamide, aldehyde, ketone, phosphoramidite, isocyanate, isothiocyanate, sulfonyl chloride, maleimide and biotin.

15. A compound represented by the following formula:

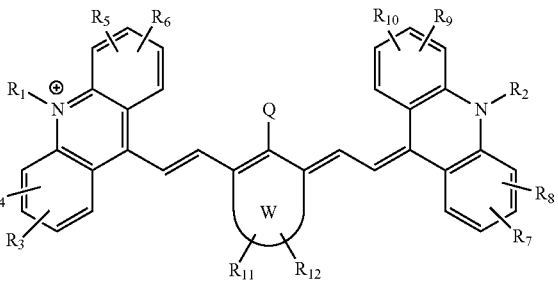

or a salt thereof, wherein:

Q is a hydrogen, $C_1$-$C_{24}$ alkyl, aryl, heteroaryl, polyaryl, phenyl, thienyl, furanyl, pyridyl, pyridinium, halogen, substituted or unsubstituted S-alkyl, substituted or unsubstituted S-aryl, substituted or unsubstituted O-alkyl, substituted or unsubstituted O-aryl, substituted or unsubstituted N-alkyl, substituted or unsubstituted N-aryl, cyano, trifluoromethyl, azidoaryl, boronic acid, boronic ester, hydroxyl, alkoxy, aryloxy, alkylthio, arylthio, nitrogen, silicon, boron, carboxy, cyano, ester, amine, amide, amino acid, peptide or L, W is absent or a substituted or unsubstituted cyclic or polycyclic group containing aliphatic or aromatic carbon, nitrogen, oxygen, sulfur, or silicon forming a 4 to 9 membered ring;

$R_1$-$R_{12}$ are, independently for each occurrence, hydrogen, substituted or unsubstituted $C_1$ to $C_{24}$ alkyl, substituted or unsubstituted alkylaryl, substituted or unsubstituted aryl, substituted or unsubstituted heteroaryl, substituted or unsubstituted alkenyl, substituted or unsubstituted alkynyl, sulfonate, aryl sulfonate, $C_1$ to $C_{24}$ alkyl sulfonate, taurine, carboxylate, amine, alkylamine, arylamine, alkylammonium, arylammonium, sulfonamide, halogen, hydroxy, amide, nitro, cyano, azide, O-alkyl, S-alkyl, silyl, trialkylsilyl, O-silyl, haloalkyl, alkylsulfhydryl, trifluoromethyl, hydrazide, substituted or unsubstituted aryl, heteroaryl, or heterocyclic alkynyl, carboxyalkyl, aminoalkyl, haloalkyl, azidoalkyl, amide, amino acid, peptide or L, wherein at least four of $R_1$-$R_8$ are sulfonates, alkyl sulfonates, arylsulfonates or taurine;

L is absent or is a linker moiety, optionally bearing a functional group or reactive group selected from the group consisting of a carboxylate, carboxyalkyl, maleimide, succinimidyl ester, carboxamide, propargyl, azidoalkyl, alkyne, isothiocyanate, of —NH$_2$ —OH, —SH, —SO$_3$H, carboxyl, —COCl, —CONHNH$_2$, acetoxymethyl esters, substituted and unsubstituted N-hydroxysuccinimidyl esters, substituted and unsubstituted N-hydroxysulfosuccinimido esters, nitro- or fluoro or phenol esters, azide, —COCH$_2$I, phosphoramidite, phthalamido, acyl fluoride, acyl chloride, acyl azide, tyramide, cinnamamide, hydroxycinnamamide, aldehyde, ketone, phosphoramidite, isocyanate, isothiocyanate, sulfonyl chloride, maleimide and biotin.

16. The compound of claim 1 wherein the compound is linked, coupled or otherwise bound to a biomolecule comprising a drug, ligand peptide, protein, antibody, nucleic acid, carbohydrate, lipid, nanoparticle, virus, membrane, cell, or tissue.

17. A pharmaceutically acceptable composition suitable for administration to a subject comprising a compound of claim 1 and a pharmaceutically acceptable excipient.

18. A method of in vivo imaging, the method comprising:
(a) administering to a subject an agent of claim 1;
(b) allowing the agent to distribute within the subject; and
(c) detecting a signal emitted by the protein labeling agent.

19. A method of in vivo optical imaging, the method comprising:
(a) administering to a subject an agent of claim 1, wherein the agent comprises a fluorochome;
(b) allowing the agent to distribute within the subject;
(c) exposing the subject to light of a wavelength absorbable by the fluorochrome; and
(d) detecting a signal emitted by the agent.

20. An in vitro imaging method, the method comprising:
(a) contacting a sample with an agent of claim 1;
(b) allowing the agent to bind to a biological target;
(c) optionally removing unbound agent; and
(d) detecting signal emitted from the agent thereby to determine whether the agent has been activated by or bound to the biological target.

21. The method of claim 20, wherein the sample is a biological sample.

22. An ex vivo imaging method, the method comprising:
(a) contacting a sample with an agent of claim 1;
(b) allowing the agent to bind to a biological target;
(c) optionally removing unbound agent; and
(d) detecting signal emitted from the agent thereby to determine whether the agent has been activated by or bound to the biological target.

23. The method of claim 22, wherein the sample is a biological sample.

24. The method of claim 18, wherein the signal emitted by the agent is used to construct an image.

25. The method of claim 24, wherein the image is a tomographic image.

26. The method of claim 18, wherein steps (a)-(c) are repeated at predetermined time intervals thereby to permit evaluation of the emitted signals in the subject over time.

27. The method of claim 19 wherein steps (a)-(d) are repeated at predetermined time intervals thereby to permit evaluation of the emitted signals in the subject over time.

28. The method of claim 18, wherein the subject is an animal or a human.

29. The method of claim 18, wherein in step (a) two or more imaging probes whose signal properties are distinguishable from one another are administered to a subject, wherein at least one of the imaging probes is fluorescent in the SWIR region of 900 nm to 1700 nm.

30. The method of claim 18, wherein the illuminating and detecting steps are performed using an endoscope, catheter, tomographic system, hand-held optical imaging system, or an intraoperative microscope.

31. The method of claim 18, wherein the presence, absence, or level of emitted signal is indicative of a heath condition.

32. The method of claim 18, wherein the method is used to detect and/or monitor a health condition.

33. The method of claim 32, wherein the health condition is selected from bone disease, cancer, cardiovascular disease, atherosclerosis, restinosis, cardiac ischemia, myocardial reperfusion injury, environmental disease, dermatological disease, immunologic disease, inherited disease, infectious disease, inflammatory disease, metabolic disease, neurodegenerative disease, ophthalmic disease, and respiratory disease.

34. The method of claim 18, wherein, in step (a), cells labeled with the compound are administered to the subject.

35. The method of claim 34, wherein the signal emitted by the fluorescent compound is used to monitor trafficking and localization of the cells.

36. A method of treating a health condition in a subject comprising administering to a subject, either systemically or locally, an agent of claim 1, wherein the agent comprises a radiolabel that localizes in the area to be treated and delivers an effective dose of radiation.

37. The methods of claim 18, wherein an Indium Gallium Arsenide (InGaAs) photodetector is used for imaging or measurement of the fluorescent emission signal.

38. A compound comprising a molecule selected from the group consisting of

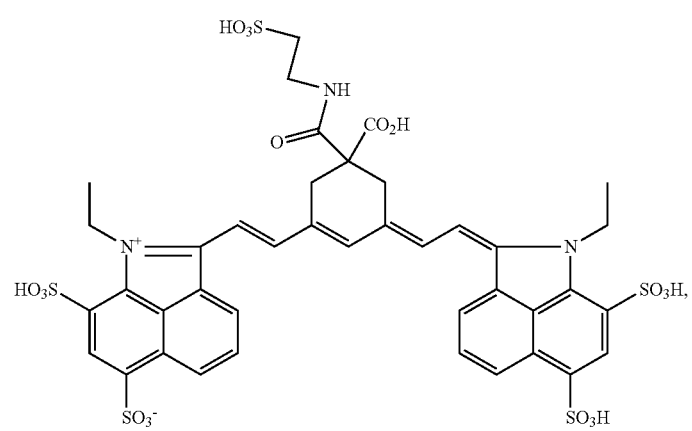

D2

-continued
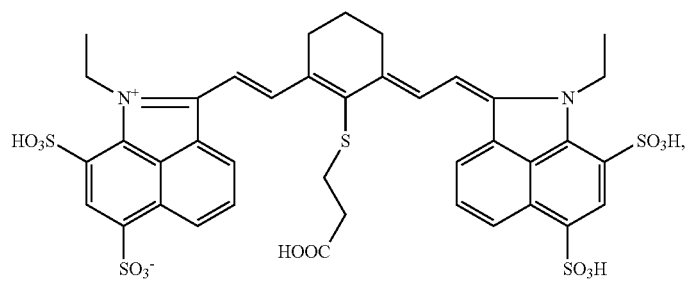
D4
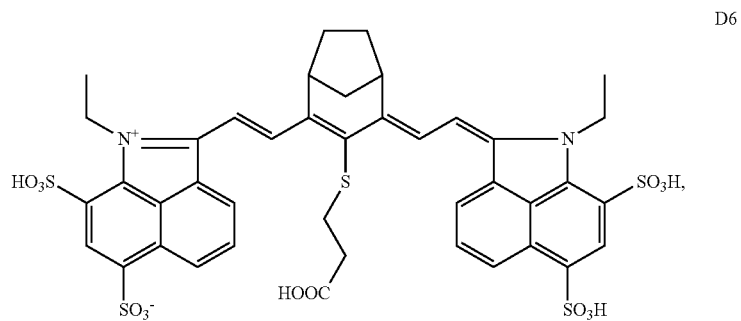
D6
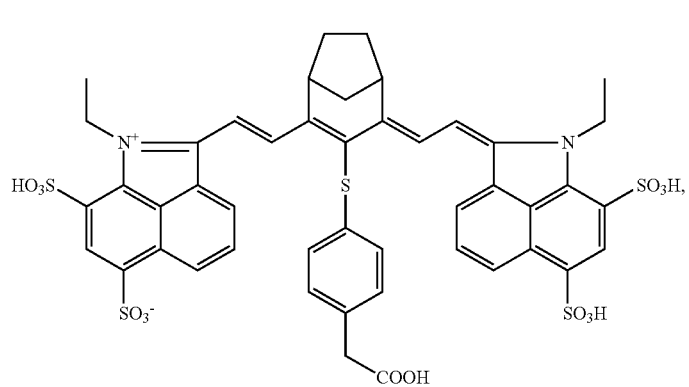
D8
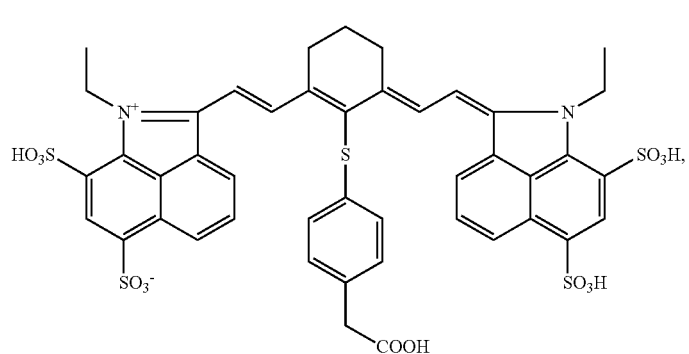
D10

-continued
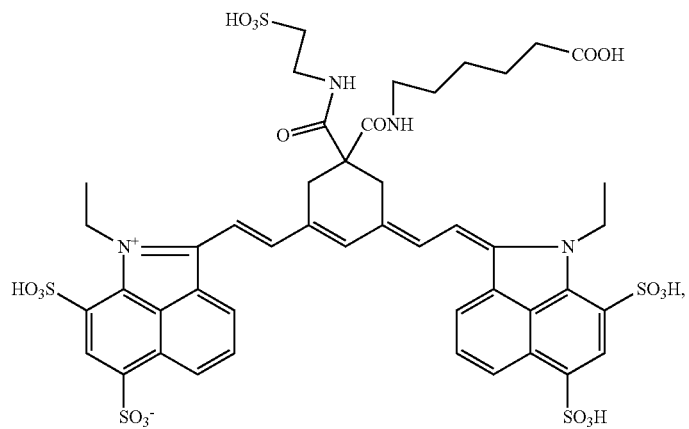
D12
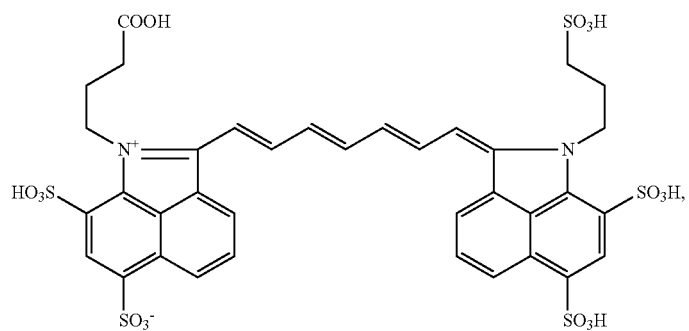
D14
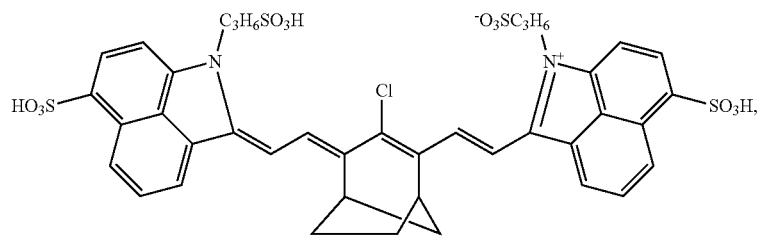
D15
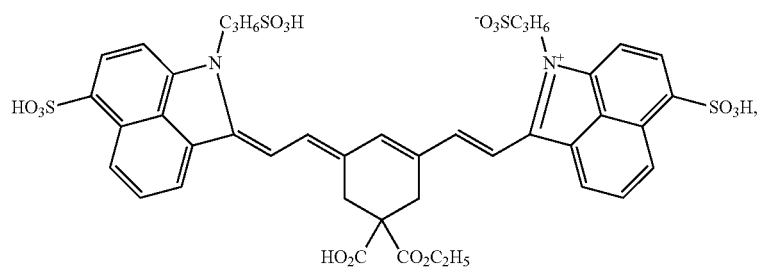
D16
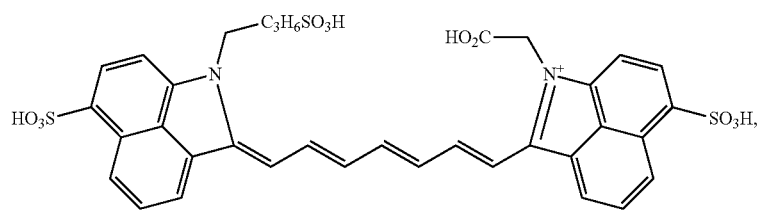
D18

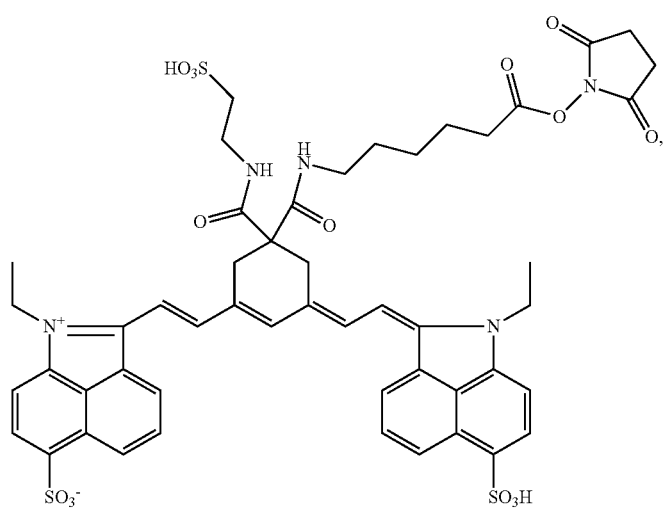
D66
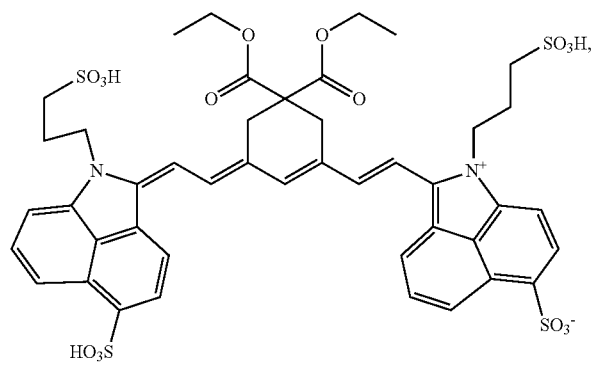
D75
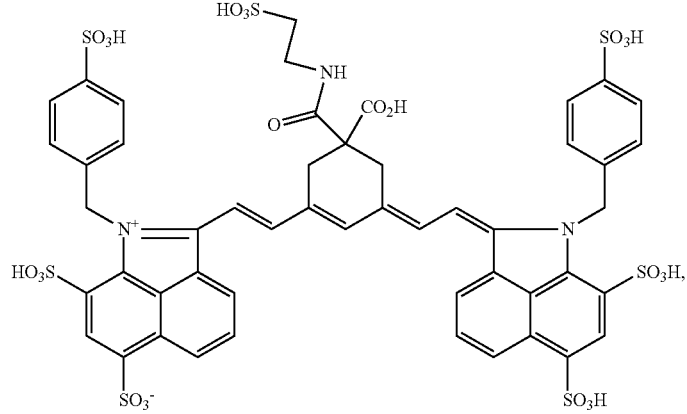
D76

-continued

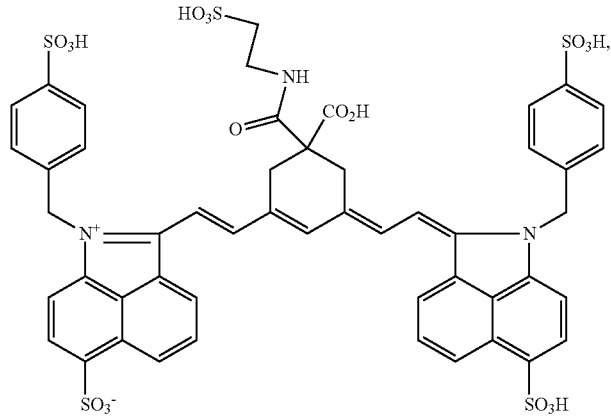

D77

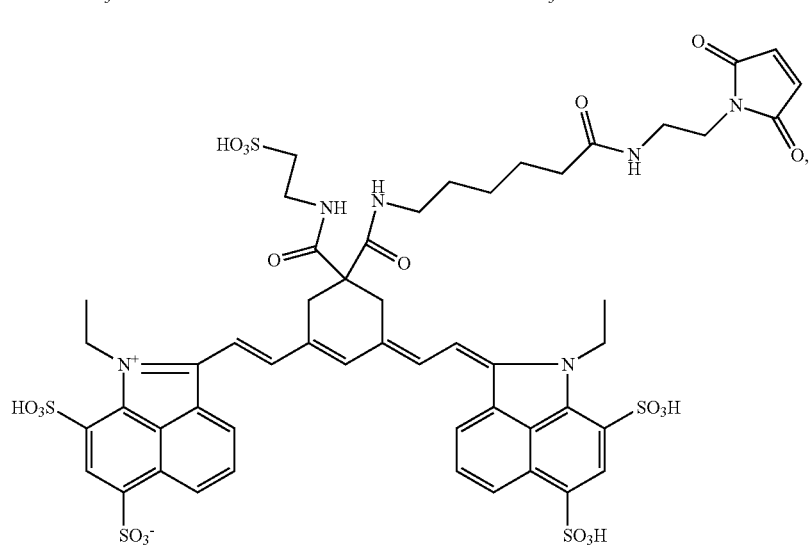

D79

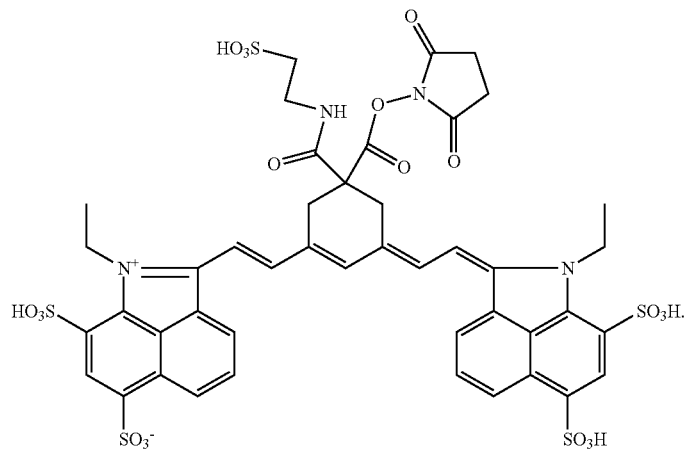

D80 and pharmaceutically acceptable salts thereof.

39. The compound of claim 10, wherein both of $R_1$ and $R_2$ are alkyl sulfonates or alkyl carboxylates.

40. The compound of claim 10, wherein at least one of $R_3$-$R_6$ are sulfonates and at least one of $R_7$-$R_{10}$ are sulfonates.

41. The compound of claim 10, wherein the compound is Formula III and Q is a hydrogen, $C_1$-$C_{24}$ alkyl, aryl, heteroaryl, polyaryl, phenyl, thienyl, furanyl, pyridyl, pyridinium, substituted or unsubstituted S-alkyl, substituted or unsubstituted S-aryl, substituted or unsubstituted O-alkyl, substituted or unsubstituted O-aryl, substituted or unsubstituted N-alkyl, substituted or unsubstituted N-aryl, cyano, trifluoromethyl, azidoaryl, boronic acid, boronic ester, hydroxyl, alkoxy, aryloxy, alkylthio, arylthio, nitrogen, silicon, boron, carboxy, cyano, ester, amine, amide, amino acid, peptide or L.

42. The compound of claim 41, wherein W is a substituted or unsubstituted cyclic or polycyclic group containing aliphatic or aromatic carbon, nitrogen, oxygen, sulfur, or silicon forming a 4 to 9 membered ring.

* * * * *